US009045524B2

(12) United States Patent
Ahlfors et al.

(10) Patent No.: US 9,045,524 B2
(45) Date of Patent: *Jun. 2, 2015

(54) SELECTIVE CASPASE INHIBITORS AND USES THEREOF

(75) Inventors: Jan-Eric Ahlfors, Laval (CA); Khalid Mekouar, Laval (CA)

(73) Assignee: NOVAGENESIS FOUNDATION (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/321,681

(22) PCT Filed: May 21, 2010

(86) PCT No.: PCT/CA2010/000783
§ 371 (c)(1),
(2), (4) Date: Feb. 29, 2012

(87) PCT Pub. No.: WO2010/133000
PCT Pub. Date: Nov. 25, 2010

(65) Prior Publication Data
US 2012/0157394 A1  Jun. 21, 2012

Related U.S. Application Data

(60) Provisional application No. 61/263,314, filed on Nov. 20, 2009.

(30) Foreign Application Priority Data

May 21, 2009 (WO) ................ PCT/CA2009/000696

(51) Int. Cl.
| C07K 5/08 | (2006.01) |
| C07K 5/10 | (2006.01) |
| A61K 38/00 | (2006.01) |
| C07K 5/02 | (2006.01) |
| C07K 5/093 | (2006.01) |
| C07K 14/81 | (2006.01) |

(52) U.S. Cl.
CPC .............. *C07K 5/0202* (2013.01); *A61K 38/00* (2013.01); *C07K 5/0819* (2013.01); *C07K 14/8139* (2013.01)

(58) Field of Classification Search
CPC .. A61K 38/00; C07K 14/8139; C07K 5/0819; C07K 5/0202
See application file for complete search history.

(56) References Cited

U.S. PATENT DOCUMENTS

| 3,341,331 A | 9/1967 | Kimura et al. |
| 3,640,716 A | 2/1972 | Nagae et al. |
| 4,269,936 A | 5/1981 | Arai et al. |
| 5,278,148 A * | 1/1994 | Branca et al. ................ 514/15.7 |
| 5,976,858 A * | 11/1999 | Palmer et al. ................ 435/219 |
| 6,287,840 B1 | 9/2001 | Palmer et al. |
| 7,256,198 B2 | 8/2007 | Dollings et al. |
| 7,589,066 B2 | 9/2009 | Orlowski et al. |
| 2008/0220416 A1 | 9/2008 | Miele et al. |
| 2008/0227976 A1 | 9/2008 | Mortimore et al. |
| 2011/0077190 A1 | 3/2011 | Ahlfors et al. |
| 2012/0157394 A1 | 6/2012 | Ahlfors et al. |
| 2014/0038903 A1 | 2/2014 | Ahlfors et al. |

FOREIGN PATENT DOCUMENTS

| CN | 1513871 A | 7/2004 |
| CN | 101161672 A | 4/2008 |
| JP | 2002-145848 A | 5/2002 |
| WO | 95/23222 A1 | 8/1995 |
| WO | 96/30395 A2 | 10/1996 |
| WO | WO 96/30353 A1 | 10/1996 |
| WO | WO 96/30395 A2 | 10/1996 |
| WO | 97/43305 A1 | 11/1997 |
| WO | 98/42342 A1 | 10/1998 |
| WO | WO 99/31122 A1 | 6/1999 |
| WO | WO 99/48910 A1 | 9/1999 |
| WO | WO 99/57135 A1 | 11/1999 |
| WO | 01/42216 A2 | 6/2001 |
| WO | 01/90070 A2 | 11/2001 |
| WO | 01/94351 A1 | 12/2001 |
| WO | 02/22611 A2 | 3/2002 |
| WO | 02/42278 A2 | 5/2002 |
| WO | WO 03/016335 A2 | 2/2003 |

(Continued)

OTHER PUBLICATIONS

Definition of derivative, from http://cancerweb.ncl.ac.uk/cgi-bin/omd?query=derivative, pp. 1-5, accessed Jul. 7, 2005.*
Muller, Prodrug Approaches for Enhancing the Bioavailability of Drugs eith Low Solubility, Chemistry & Biodiversity, 2009, 6, pp. 2071-2083.*
Beaumont, et, al, Design of Ester Prodrugs to Enhance Oral Absorption of Poorly Permeable Compounds: Challenges to the Discovery Scientist, Current Drug Metabolism, 2003, 4, 461-485.*
Hyo-Kyung Han, Targeted Prodrug Design to Optimize Drug Delivery, AAPS Pharmsci 2000; 2 (1) article 6 pp. 1-11.*
Yashveer Singh et al, Recent Trends in Targeted Anticancer Prodrug and Conjugate Design, Curr Med Chem. 2008 ; 15(18): 1802-1826.*
Testa B., Prodrug Research: Futile or Fertile?, Biochem. Pharm., 2004, 68, pp. 2097-2106.*

(Continued)

*Primary Examiner* — Julie Ha
*Assistant Examiner* — Li Ni Komatsu
(74) *Attorney, Agent, or Firm* — Knobbe, Martens, Olson & Bear LLP

(57) ABSTRACT

The present invention relates to compounds of Formula I, II, IVC, VIIIC, IXC, or XC and their pharmaceutical uses. Particular aspects of the invention relate to the use of those compounds for the selective inhibition of one or more caspases. Also described are methods where the compounds of Formula I, II, IVC, VIIIC, IXC, or XC are used in the prevention and/or treatment of various diseases and conditions in subjects, including caspase-mediated diseases such as sepsis, myocardial infarction, ischemic stroke, spinal cord injury (SCI), traumatic brain injury (TBI) and neurodegenerative disease (e.g. multiple sclerosis (MS) and Alzheimer's, Parkinson's, and Huntington's diseases). Processes for synthesizing tripeptides are provided.

4 Claims, 14 Drawing Sheets

(56) References Cited

FOREIGN PATENT DOCUMENTS

| WO | 2008/008264 A2 | 1/2008 |
| WO | WO 2008/008264 A2 | 1/2008 |
| WO | 2009/140765 A1 | 11/2009 |
| WO | WO 2010/133000 A1 | 11/2010 |
| WO | 2012/140500 A1 | 10/2012 |

OTHER PUBLICATIONS

Ettmayer, P. et al, Lessons Learned from Marketed and Investigational Prodrugs, J. Med. Chem., 2004, 47 (10), pp. 2393-2404.*

Definition of peptidomimetic, from http://www.chemicool.com/definition/peptidomimetic, p. 1, accessed Oct. 20, 2013.*

Adessi et al, Converting a Peptide into a Drug: Strategies to Improve Stability and Bioavailability, Current Medicinal Chemistry, 2002, 9, pp. 963-978.*

Han et al., Papain-Like Protease 2 (PLP2) from Severe Acute Respiratory Syndrome Coronavirus (SARS-CoV): Expression, Purification, Characterization, and Inhibition, Biochemistry, 44: 10349-10359 (2005).

Tong, Liang, Viral Proteases, Chem. Rev., 102: 4609-4626 (2002).

Berdowska, Izabela, Cysteine proteases as disease markers, Clinica Chimica Acta, 342: 41-69 (2004).

Vyas, et al., Formulation and Physiological Factors Influencing CNS Delivery upon Intranasal Administration, Critical Reviews in Therapeutic Drug Carrier Systems, 23: 319-347 (2006).

Grzonka et al., Cysteine Proteases, Industrial Enzymes, 181-195 (2007).

Newton et al., Synthesis and evaluation of vinyl sulfones as caspase-3 inhibitors: A structure-activity study, European Journal of Medicinal Chemistry, 45: 3858-3863 (2010).

Gloria et al., Aspartic vinyl sulfones: Inhibitors of a caspase-3-dependent pathyway, European Journal of Medicinal Chemistry, 46: 2141-2146 (2011).

Thompson et al., Carboxyl-Modified Amino Acids and Peptides as Protease Inhibitors, J. Med. Chem., 29: 104-111 (1986).

Rodriguez et al., Systemic Injection of a Tripeptide Inhibits the Intracellular Activation of CPP32-like Proteases In Vivo and Fully Protects Mice against Fas-mediated Fulminant Liver Destruction and Death, J. Exp. Med., 184: 2067-2072 (1996).

Ewing et al., Design and Structure-Activity Relationships of Potent and Selective Inhibitors of Blood Coagulation Factor Xa, J. Med. Chem., 42: 3557-3571 (1999).

Hanzlik et al., Communications to the Editor, Journal of Medicinal Chemistry, 27: 711-712 (1984).

Merrifield, R.B., Solid Phase Peptide Synthesis. I. The Synthesis of a Tetrapeptide, J. Am. Chem. Soc., 85: 2149-2154 (1963).

Nazif et al., Global analysis of proteasomal substrate specificity using positional-scanning libraries of covalent inhibitors, Proceedings of the National Academy of Sciences U.S.A., 98: 2967-2972 (2001).

Ng et al., "Click" synthesis of small-molecule inhibitors targeting caspases, Organic & Biomolecular Chemistry, 6: 844-847 (2008).

Uttamchandani et al., Activity-based fingerprinting and inhibitor discovery of cysteine proteases in a microarray, Chem. Commun., 1518-1520 (2007).

Santos et al., Michael Acceptors as Cysteine Protease Inhibitors, Mini-Reviews in Medicinal Chemistry, 7: 1040-1050 (2007).

Yaoita et al., Attenuation of Ischemia/Reperfusion Injury in Rats by a Caspase Inhibitor, Circulation, 97: 276-281 (1998).

Bavikar et al., Pd-catalyzed one-pot chemoselective hydrogenation protocol for the preparation of carboxamides directly from azides, Tetrahedron Letters, 51: 3815-3819 (2010).

Wagh et al., Allylic amination of internal alkynes with aromatic and aliphatic amines using polymer-supported triphenylphosphane-palladium complex as a heterogeneous recyclable catalyst, European Journal of Organic Chemistry, 26: 5071-5076 (2010).

Han et al., Targeted prodrug design to optimize drug delivery, AAPS Pharmsci., 2(1):1-11 (2000).

Liu et al., "Structure-Activity Relationships for Inhibition of Papain by Peptide Michael Acceptors," J. Med. Chem. 35:1067-1075, 1992.

Rawlings et al., "Evolutionary Families of Peptidases," Biochem. J. 290:205-218, 1993.

Testa, Prodrug research: futile or ferrile, Biochem Pharma., 68:2097-2106 (2004).

Winssinger et al., Profiling protein function with small molecule microarrays, Proc. Natl. Acad. Sci. 99(17), 11139-11144, 2002.

Ng, Su Ling, et al., "Click" synthesis of small-molecule inhibitors targeting caspases, Organic and Biomecular Chemistry, 2008, 6, pp. 844-847.

Uttamchandani, Mahesh, et al., Activity-based fingerprinting and inhibitor discovery of cysteine proteases in a microarray, Chemical Communications, 2007, pp. 1518-1520.

Friedrich-Bochnitschek, et al., Allyl Esters as Carboxy Protecting Groups in the Synthesis of O-Glycopeptide, J. Org. Chem., 1989, 54, 751-756.

Götz, et al., Aza-peptidyl Michael Acceptors. A New Class of Potent and Selective Inhibitors of Asparaginyl Endopeptidases (Legumains) from Evolutionarily Diverse Pathogens, J. Med. Chem., 2008, 51, 2816-2832.

Isaacs et al, Structure-based design of novel groups for use in the P1 position of thrombin inhibitor scaffolds. Part 1: Weakly basic azoles, Bioorganic & Medicinal Chemistry Letters, 2006, 16, pp. 338-342.

O'Donnell et al., Serine-threonine protein phosphatase inhibitors derived from nodularin: role of the 2-methyl and 3-diene groups in the Adda residue and the effect of macrocyclic conformational restraint, Journal of the Chemical Society, Perkin Transactions 1, No. 14, Jan. 1, 2001, pp. 1696-1708.

* cited by examiner

SELECTIVE CASPASE INHIBITORS AND USES THEREOF

CROSS REFERENCE TO RELATED APPLICATIONS

This application is the U.S. National Stage Application under 35 U.S.C. §371 of International Application No. PCT/CA2010/000783, with an international filing date of May 21, 2010, which claims the benefit of U.S. Appl. No. 61/263,314, filed Nov. 20, 2009.

FIELD OF INVENTION

The present invention relates to chemical compounds and their pharmaceutical uses. More particularly, the invention relates to selective inhibitors of caspases and their uses for the prevention and/or treatment of various diseases and conditions in subjects.

BACKGROUND OF INVENTION

Caspases comprise a family of cysteine protease enzymes with a well-known role as key mediators in apoptosis signaling pathways and cell disassembly. Interleukin converting enzyme (ICE), also known as Caspase-1, was the first identified caspase. In humans, 11 other known caspases have been further identified. Caspases have been classified in two general groups according to their effects: proapoptotic (caspase-2, 3, 6, 7, 8, 9, 10) and proinflammatory (caspase-1, 4, 5, 11, 12) caspases. The proapoptotic caspases have been divided in initiators (caspase-2, 8, 9, 10) also known as group II, and executioners (caspase-3, 6, 7) of the apoptotic process or group III. The Interleukin converting enzyme (ICE) also known as Caspase-1 has a proinflammatory role only.

There is growing evidence demonstrating the role of caspases in very diverse pathologies. For instance it is known that proapoptotic caspases are involved in the pathogenesis of many cardiovascular disorders. Some proapoptotic caspases such as caspase-8 also possess non-apoptotic function that may contribute to tumor progression. Caspase-1 plays an important role in response to pathogenic infection as well as in inflammatory and autoimmune disorders. In addition, caspase-1 activity is increased in retinas of diabetic patients and it constitutes a critical regulator of cardiomyocyte programmed cell death in the mammalian heart. Caspases also plays a role in neurodegenerative diseases and trauma. For instance, it has been shown that the caspase-3 cascade is highly activated due to the traumatic spinal cord injury. Finally, the activation of caspase-1 and caspase-3 in Amyotrophic Lateral Sclerosis (ALS) patients and the activation of caspase-7, -8, and -9 in a mouse model at end stage of ALS have been reported. Increased levels of apoptosis and caspase activity (especially caspase-3) are reported to be frequently observed at sites of cellular damage in both acute (e.g. Sepsis, myocardial infarction (MI), Ischemic Stroke, Spinal cord injury (SCI), traumatic Brain Injury (TBI)) and neurodegenerative disease (e.g. Alzheimer's, Parkinson's and Huntington's diseases, and multiple sclerosis (MS)).

Since caspases are involved in a number of diseases, several compounds and methods have been developed to inactivate them. For example, the broad irreversible caspase inhibitor benzyloxycarbonyl-Val-Ala-Asp-fluoromethylketone (z-VAD-fmk) was protective and efficiently blocked death receptor-mediated liver injury in animal models (Rodriguez et al. (1996), J Exp Med. 1996 Nov. 1; 184(5):2067-72). Myocardial infarction and the resulting death of myocytes was ameliorated by z-VAD-fmk and related peptide inhibitors in animal models (Yaoita et al., 91998) *Circulation* 97: 276-281). There have been also a lot of efforts for identifying inhibitors of peptidase. For instance, Hanzlik and Thompson (J. Med. Chem. (1984), 27(6), 711-712) describe vinylogous amino acid esters for inactivating thiol proteases. Thompson et al. (J. Med. Chem. (1986), 29(1), 104-111) describe carboxyl-modified amino acids and peptides as protease inhibitors. Liu and Hanzlik have prepared a series of peptidyl Michael acceptors with different electron withdrawing groups with different recognition and binding groups as inactivators against papain, a member of the cysteine proteinase family. Similarly, U.S. Pat. No. 5,976,858 and U.S. Pat. No. 6,287,840 to Palmer wt et al. describes irreversible cysteine protease inhibitors containing vinyl groups conjugated to electron withdrawing groups. However, these and other compounds are not effective against caspases, because caspases are among the most specific endopeptidases.

Given their role in several diseases and conditions, there is a need for compounds capable of selectively targeting either a specific caspase or a group of caspases. There is also a need for effective pharmaceutical compositions and method of treatment for caspase-mediated diseases.

The present invention addresses these needs for novel therapies, new treatment methods, compounds, and pharmaceutical compositions.

Additional features of the invention will be apparent from review of the disclosure, figures and description of the invention below.

BRIEF SUMMARY OF THE INVENTION

The present invention relates to compounds according to any of Formula I, II, IVC, VIIIC, IXC, or XC as defined herein, compositions thereof and methods for the prevention and/or treatment of caspase-mediated diseases in subjects. Particular aspects of the invention relates to use of compounds according to any of Formula I, II, IVC, VIIIC, IXC, or XC as defined herein.

One aspect of the invention concerns a method for preventing and/or treating a caspase-mediated disease in a subject in need thereof, comprising administering to said subject an effective amount of a compound represented by any of Formula I, II, IVC, VIIIC, IXC, or XC as defined herein.

One aspect of the invention concerns the use of a compound represented by any of Formula I, II, IVC, VIIIC, IXC, or XC as defined herein for preventing and/or treating of caspase-mediated diseases in a subject in need thereof.

Another related aspect of the invention concerns the use of a compound represented by any of Formula I, II, IVC, VIIIC, IXC, or XC as defined herein for the manufacture of a medication for preventing and/or treating of caspase-mediated diseases in a subject in need thereof.

An additional aspect of the invention concerns a compound a compound represented by any of Formula I, II, IVC, VIIIC, IXC, or XC as defined herein for use in preventing and/or treating a caspase-mediated diseases in a subject in need thereof.

One aspect of the invention concerns a method of treating excessive apoptosis affected by caspase activity in a cell or a tissue, the method comprising: contacting the cell or tissue with an effective amount of one or more compounds represented by any of Formula I, II, IVC, VIIIC, IXC, or XC as defined herein, so as to treat the excessive apoptosis.

One particular aspect of the invention concerns the use of a compound represented by any of Formula I, II, IVC, VIIIC, IXC, or XC as defined herein for use in apoptosis-mediated diseases.

Specific examples of compounds are provided in Tables 1 and 2.

The invention also concerns methods and strategies of targeting caspases. In one embodiment the approach consists of designing a suicide substrate leading to a permanent inhibition of the caspase. Preferably, the approach consists of designing a substrate that is recognizable enough for caspases, especially one or more specific caspase(s), to fit into it, to be potentially cleaved at a specific position in a way that makes the caspase enzyme irreversibly linked to the substrate thereby leading to a permanent inhibition of the caspase. In some embodiments, the suicide substrates of this invention are vinyl electron withdrawing group (EWG).

The invention further relates to methods for synthesizing peptides comprising two, three, four or more amino acids. These methods are particularly useful for making selected compounds according to the invention.

Further aspects of the invention will be apparent to a person skilled in the art from the following description, and claims and generalizations therein.

BRIEF DESCRIPTION OF THE DRAWINGS

In order that the invention may be readily understood, embodiments of the invention are illustrated by way of example in the accompanying drawings. See figure legend at the bottom of each figure.

DETAILED DESCRIPTION OF THE INVENTION

A) General Overview of the Invention

Figure 1A:
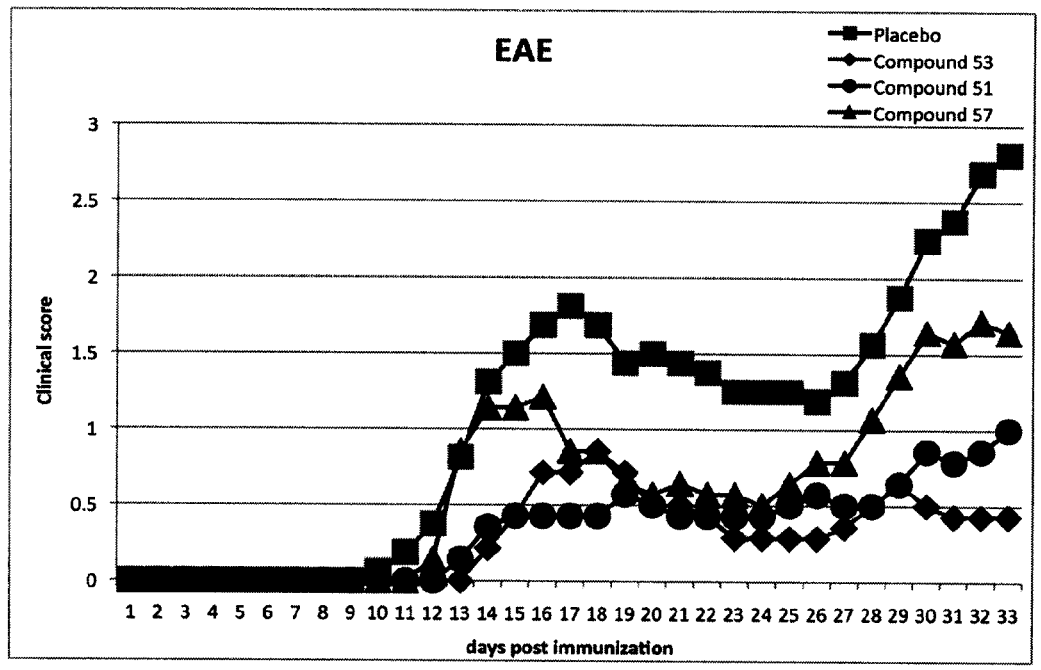
FIGS. 1A to 1D are graphs showing treatment of EAE mice with Compound 51, 53 and 57 for a period of 6 days after the onset of disease symptoms. Data represent average daily scores of the 7 mice in each group. Treatment with compound 51 and 53 i.p. from day 10 to 16 post immunization had identical ameliorating effects on clinical course of EAE. Disease onset was delayed and severity was reduced significantly. Compound 57 reduced also the clinical severity of the disease but without delaying the onset of the disease (FIG. 1A). Cumulative and maximal clinical scores were significantly lower compared to placebo in compound 51 and 53 treated mice (FIG. 1C and FIG. D). Compound 57 reduced the cumulative score without any significant effect on the maximal score compared to placebo (FIG. 1C and FIG. D). Loss of body weight in compound 51 and 53 treated groups was also less than the placebo, whereas the compound 57 did not show and difference compared to placebo (FIG. 1B).
Figure 1B:
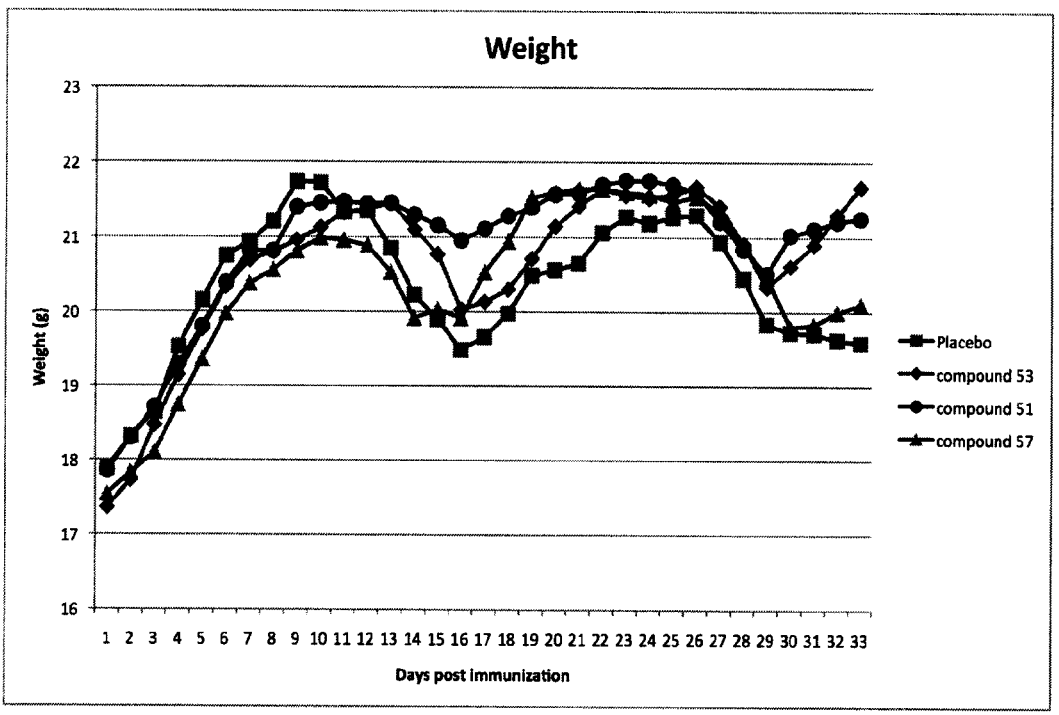
Figure 1C:
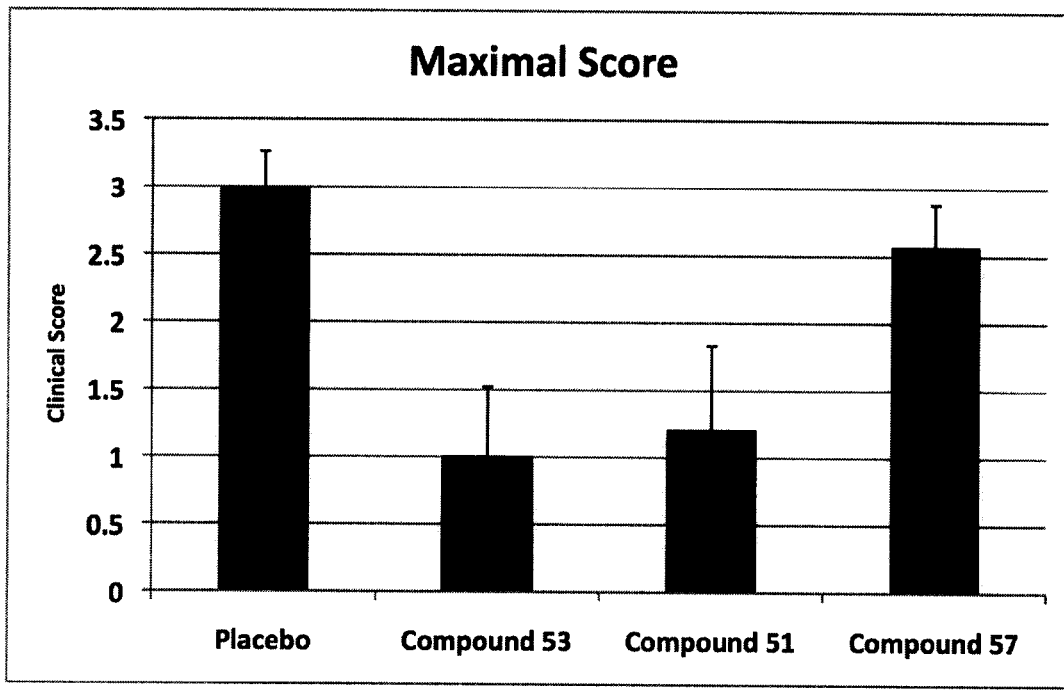
Figure 1D:
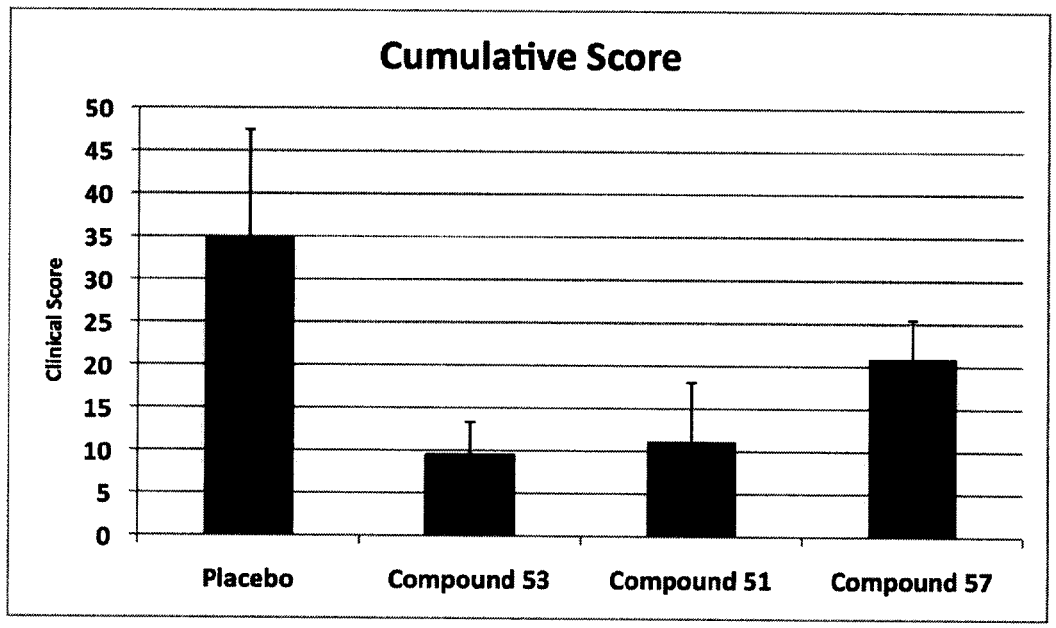
Figure 2A:
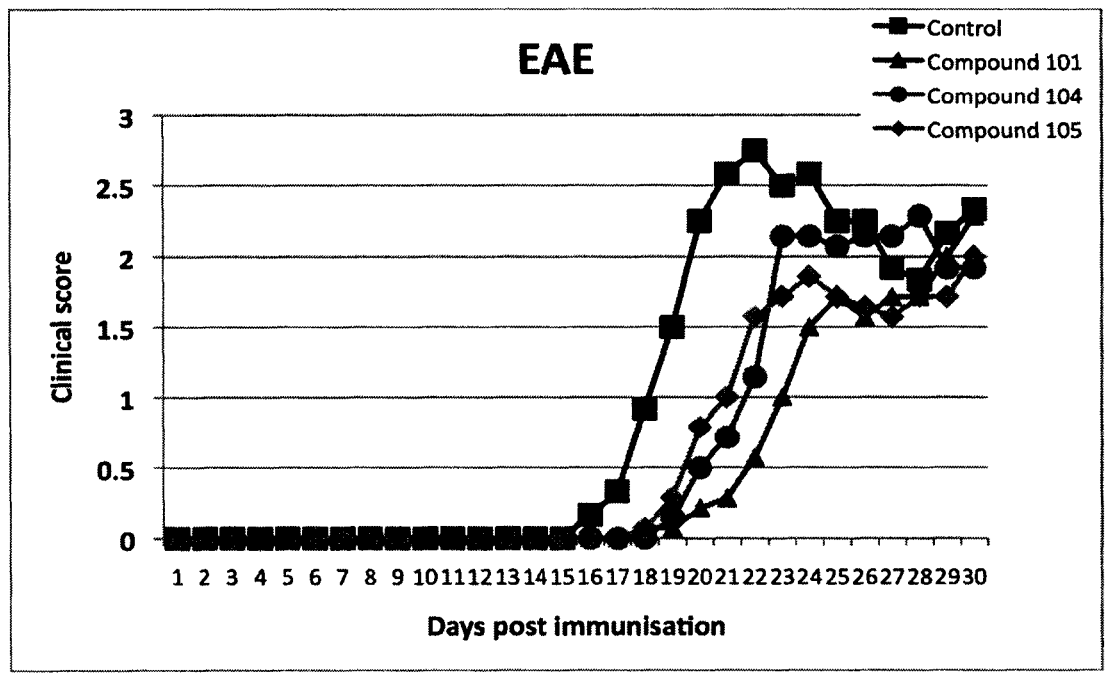
FIGS. 2A to 2D are graphs showing treatment of EAE mice with Compound 101, 104 and 105 for a period of 6 days after the onset of disease symptoms. Data represent average daily scores of the 7 mice in each group. The effectiveness of compound 101, 104 and 105 versus placebo on EAE in C57BL/6 mice was compared. Treatment with compound 101, 104 and 105 i.p. from day 10 to 16 post immunization shows identical ameliorating effects on clinical course of EAE. Disease onset was delayed and severity was reduced significantly at the early stage of the disease. At the late stage of the disease evolution the severity of the disease in all treated group was similar (FIG. 2A). Cumulative clinical scores were significantly lower compared to placebo in all compound treated mice (FIG. 2C and FIG. 2D). The treatment with the different compounds did not show any effect in the severity of the disease (maximal scores were similar after treatment with compound with placebo group) (FIG. 2C and FIG. 2D). Loss of body weight in compound 101 and 105 treated groups was also less than placebo, whereas the compound 104 did not show and significant difference compared to placebo (FIG. 2B).
Figure 2B:
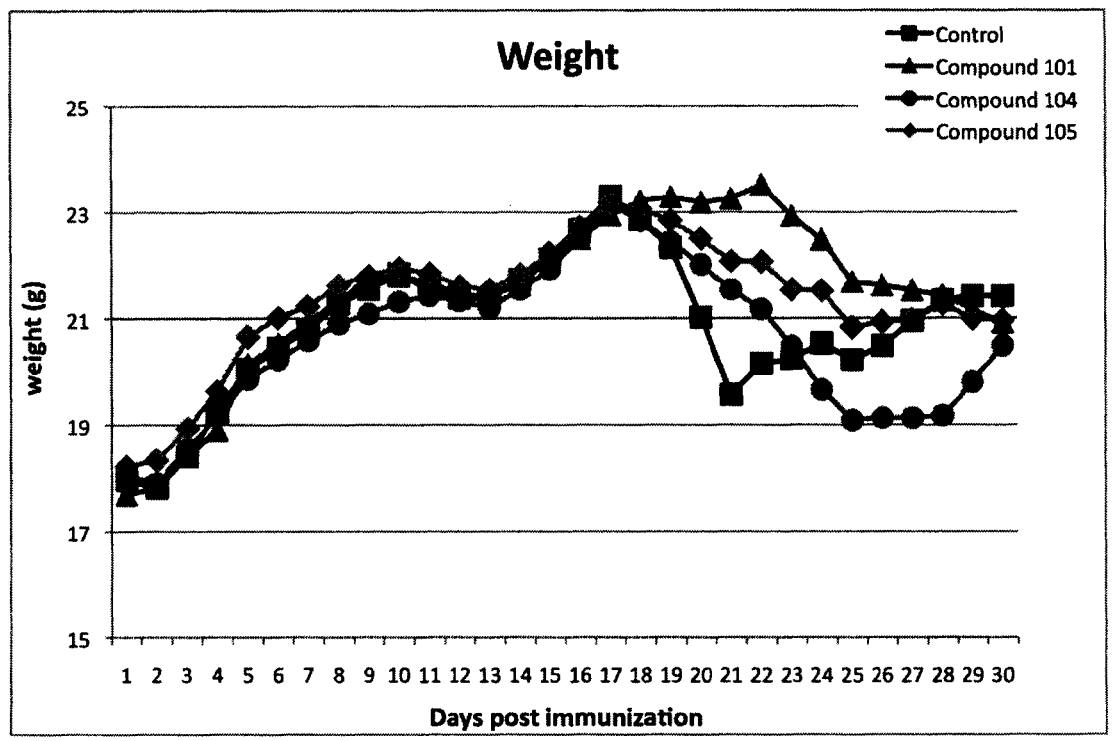
Figure 2C:
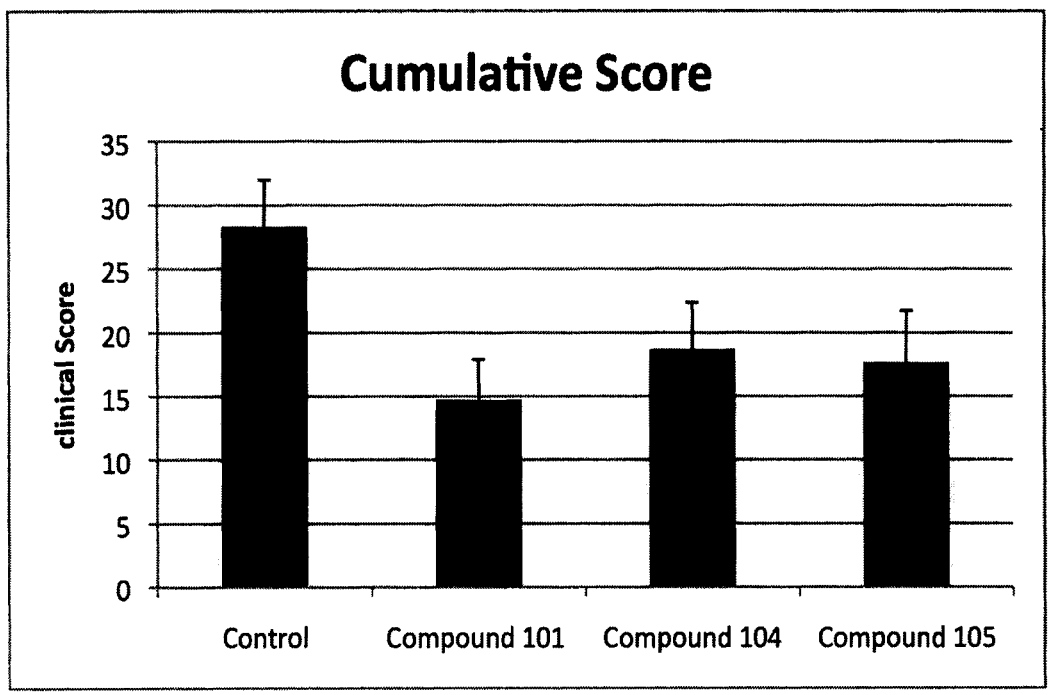
Figure 2D:
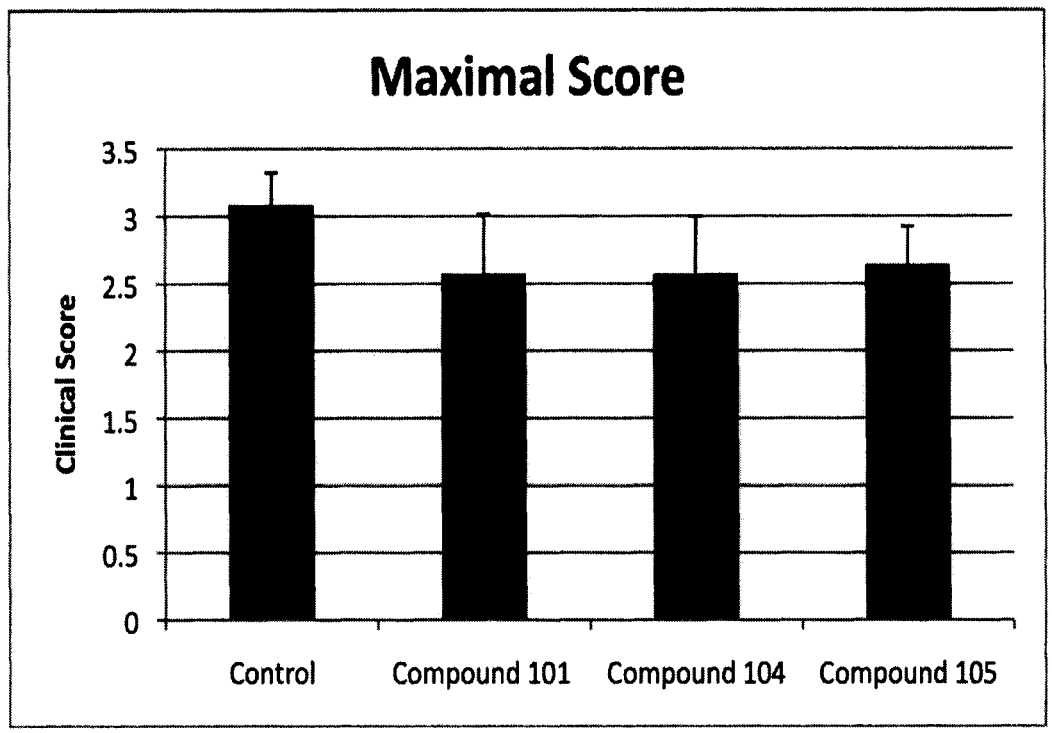
Figure 3A:
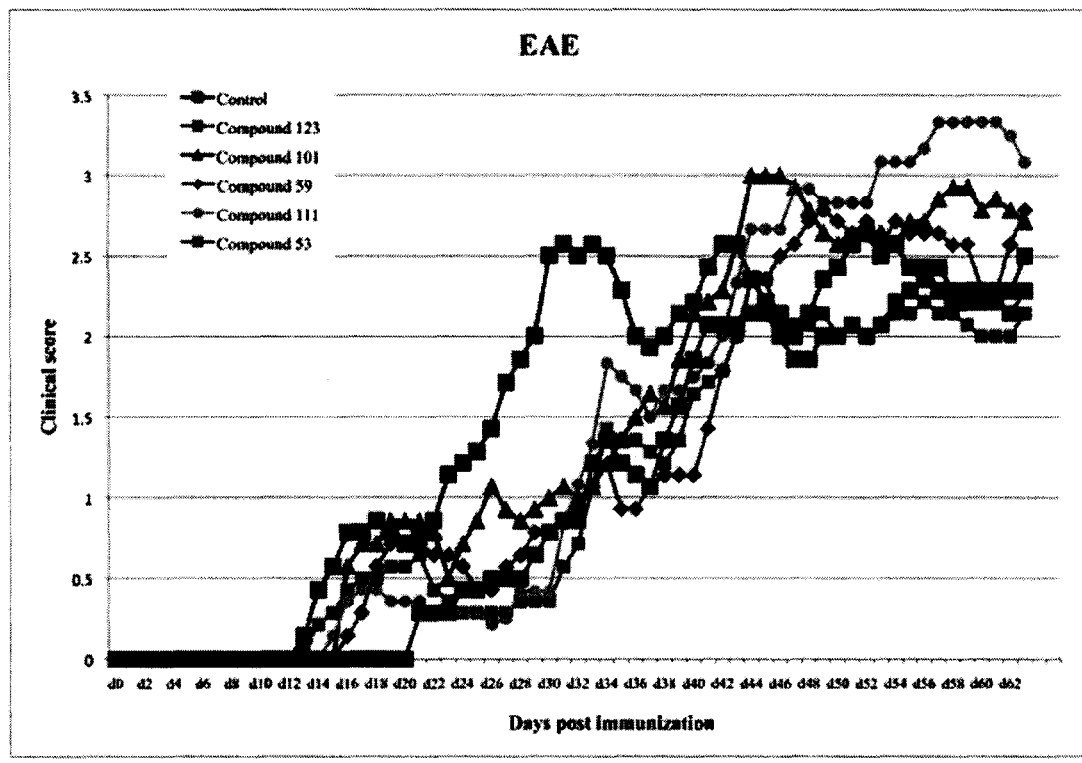
FIGS. 3A to 3D are graphs showing treatment of EAE mice with Compound 53, 59, 101, 111 and 123 for a period of 6 days after the onset of disease symptoms. Day 14 post-immunization represents the day when the mice first started showing clear symptoms of EAE, and this became the first day of compound administration. Data represent average daily scores of the 7 mice in each group for a total period of 9 weeks. The effectiveness of compound 53, 59, 101, 111 and 123 versus placebo on EAE in C57BU6 mice was compared over the standard 30-day period of the study. Treatment with compounds 53, 95, 111 and 123 i.p. from day 14 to 19 post immunization had ameliorating effects on the clinical course of EAE. Disease severity was reduced significantly in all compound-treated groups. Compound 53 delayed significantly the clinical score (symptoms of EAE) compared to placebo; in fact, this delay was for the entire period of compound administration plus one more day thereafter (it should be noted that twice the concentration of compound 53 was given than in previous studies and compared to the other compounds administered in this study). The cumulative and maximal clinical scores were analyzed for only the standard 30-day period of the study since most of the effects of the compound treatments are expected to have worn off by then, and were significantly lower (i.e. significantly improved clinical outcomes) for all compound treated mice groups compared to the placebo group (FIG. 3C and FIG. 3D). Loss of body weight in all compound treated groups was also less than in the placebo group, especially for compounds 53, 101 and 123 (FIG. 3B).
Figure 3B:
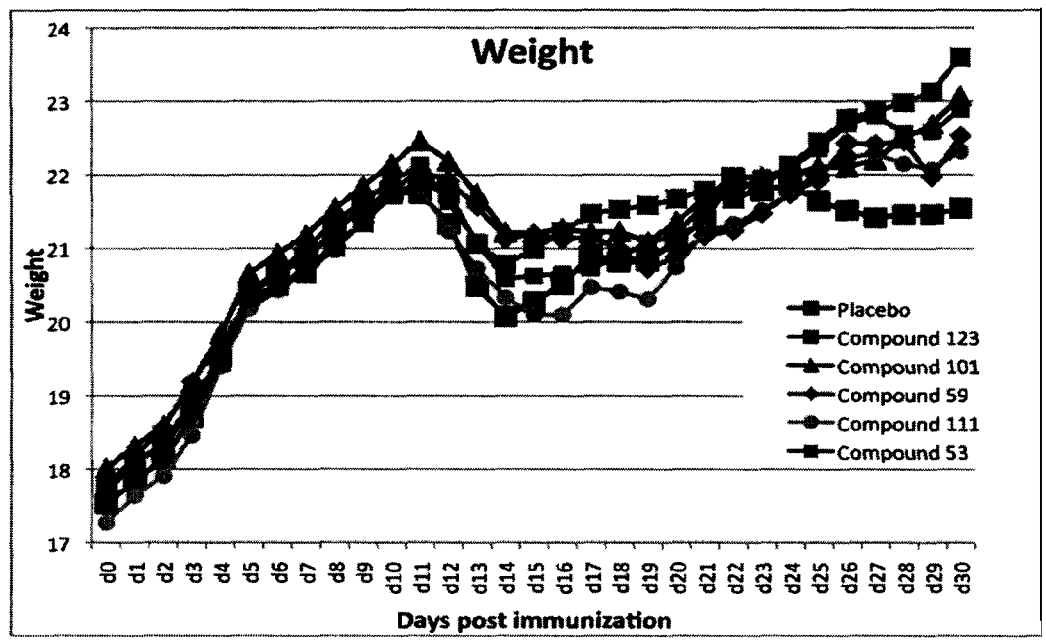
Figure 3C:
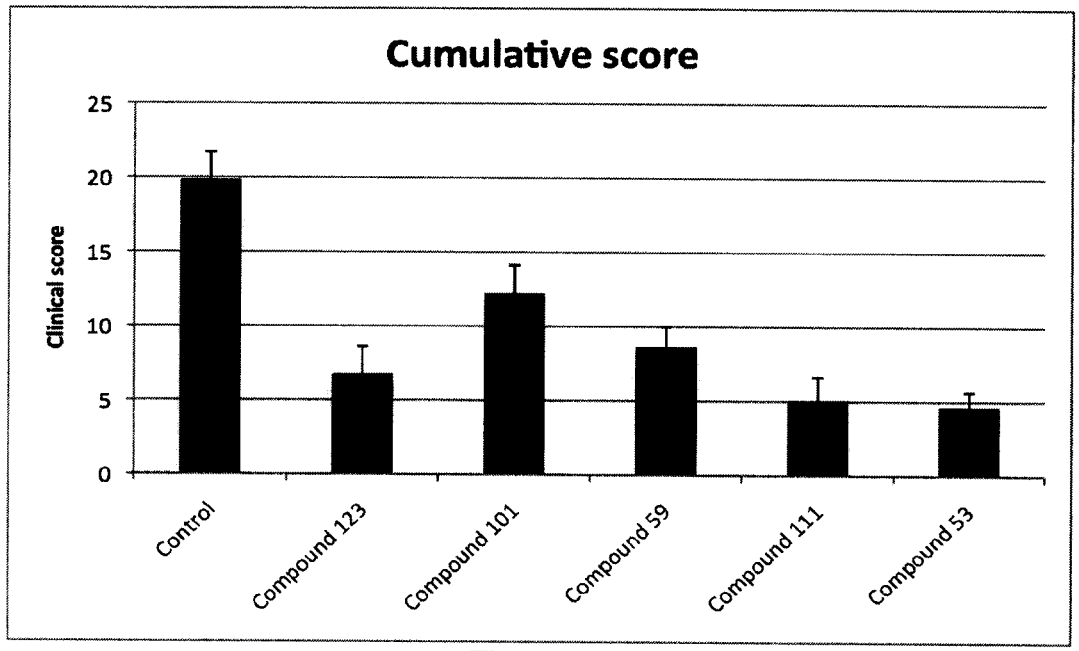
Figure 3D:
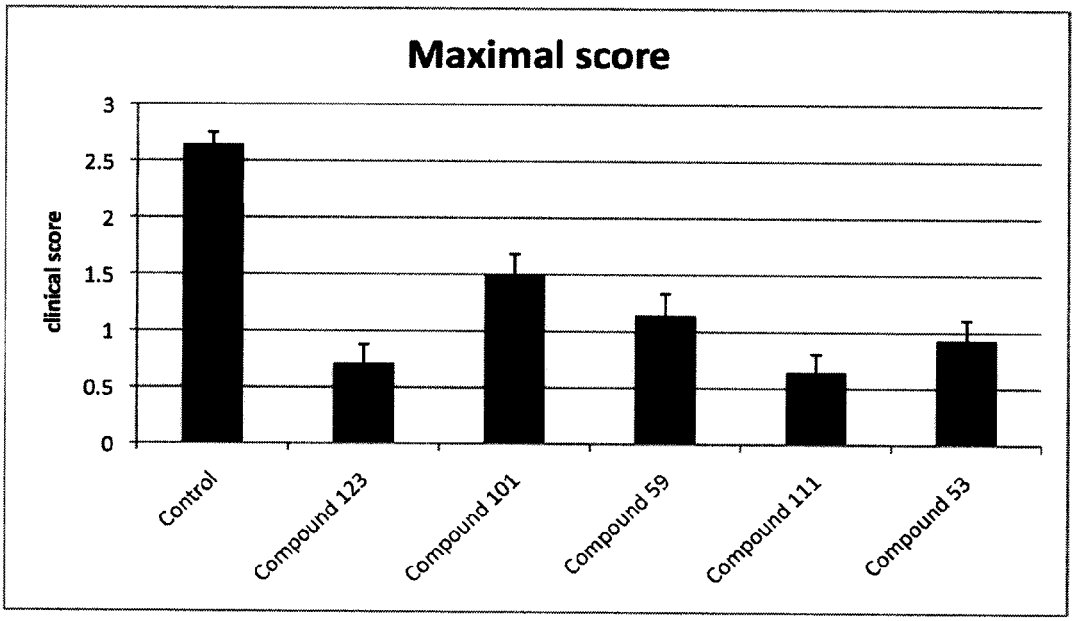
Figure 4A:
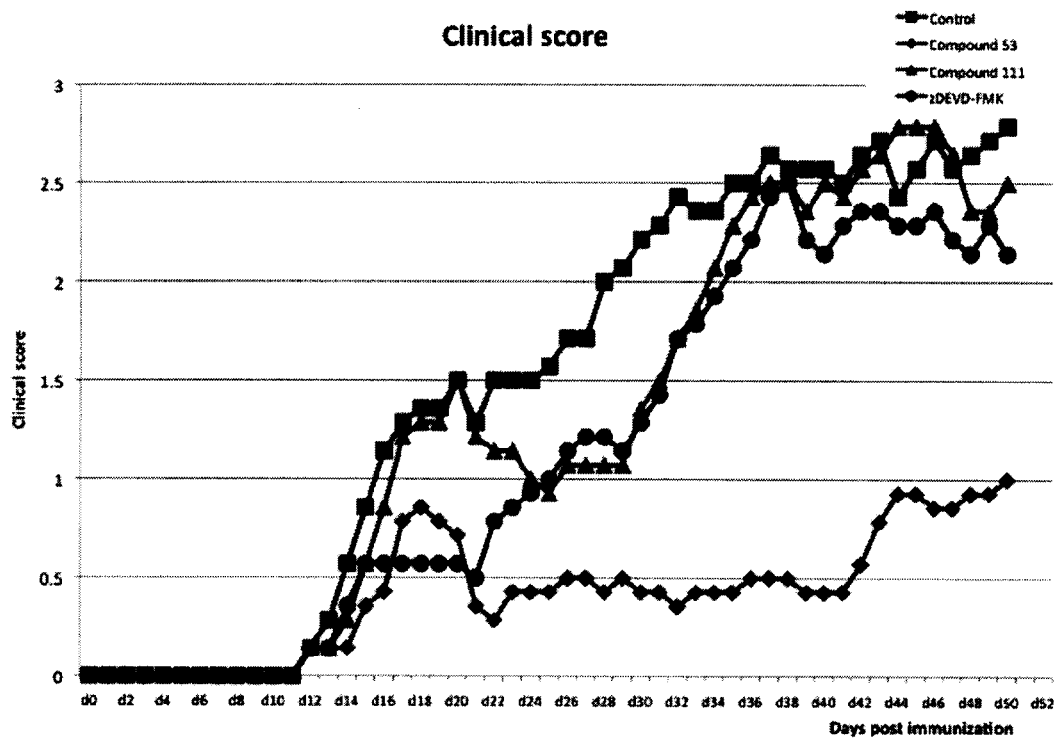
FIGS. 4A to 4D are graphs showing treatment of EAE mice with Compound 53, 111 and zDEVD-FMK (positive control, used as a prodrug: z-D(OMe)E(OMe)VD(OMe)FMK) for a period of 15 Days after the onset of disease symptoms. Day 12 post-immunization represents the day when one mouse from each group reached score one (1) of EAE symptoms, and this became the first day of compound administration. Data represent average daily scores of the 7 mice in each group. The effectiveness of compound 53; 111 and zDEVD-FMK versus placebo on EAE in C57BU6 mice was compared. Disease severity was reduced significantly in all compound-treated groups. zDEVD-FMK delayed the onset and reduced the severity of the disease, especially for the first 10 days of compound treatment after which it started to lose these effects—this seems at least partially to be due to the high inhibitory activity towards the initiator caspases (see Example 59 and FIG. 5) strongly reducing disease progression in the beginning but an inability to sustain this due to lack of inhibitory activity towards the effector caspases. Compound 53, on the other hand, did not reduce the severity of the disease as much as zDEVD-FMK in the very beginning (possibly due to lack of initiator caspase inhibitory activity, see Example 59 and FIG. 5), but then began to reverse the effects of the disease and reduced the severity of the disease continuously (even after several days after the end of compound administration) more significantly that zDEVD-FMK which appears to be due to its high inhibitory activity towards effector caspases (Caspase-3 and -7). Compound 111 with its high Caspase-3 inhibitory activity (but no initiator caspase inhibitory activity, see Example 59 and FIG. 5) also did not reduce the severity of the disease as much as zDEVD-FMK in the beginning (but also not as much as Compound 53, possibly due to either lacking strong Caspase-7 inhibitory activity like Compound 53 or lacking pro-inflammatory caspase inhibitory activity like compound 53 and zDEVD-FMK which probably slowed down the progression of the disease), but then was able to start reversing the effects of the disease and reduced the severity of the disease for the rest of the period of compound administration. Thus, at least in this model, inhibition of effector caspases, especially Caspase-3, was able to reverse the progression of the neurodegenerative disease. Loss of body weight in all compound treated groups was less than placebo, especially for compound 53, indicating lessened disease severity (see FIG. 4B).
Figure 4B:
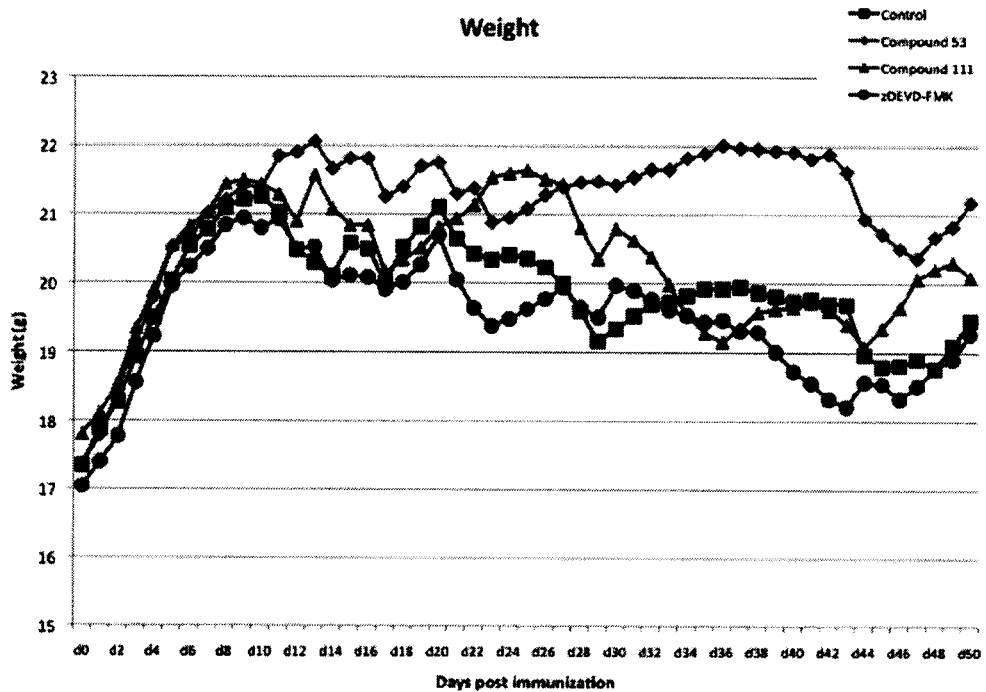
Figure 4C:
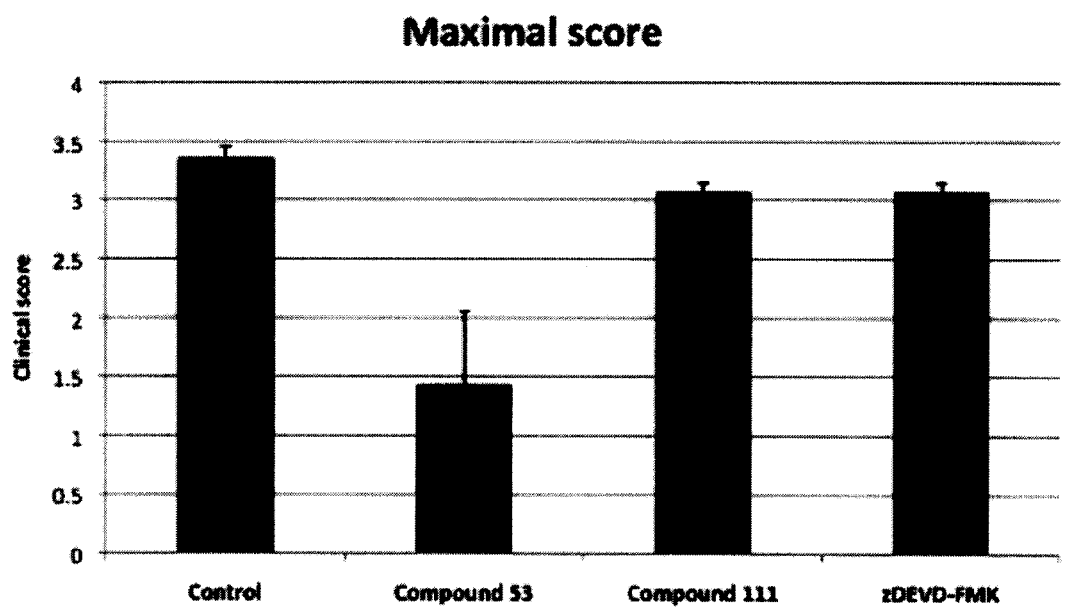
Figure 4D:
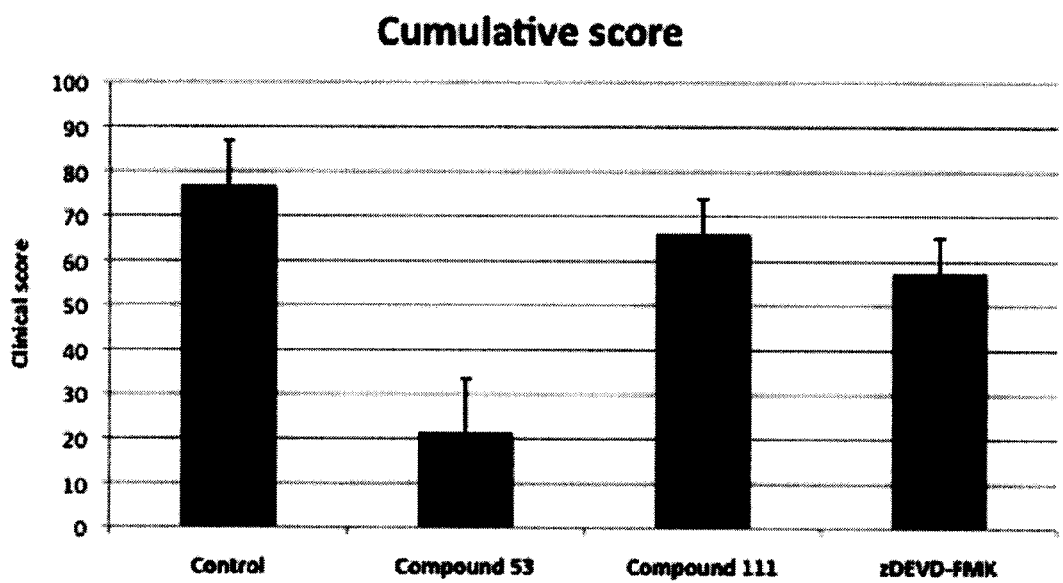
Figure 5A:
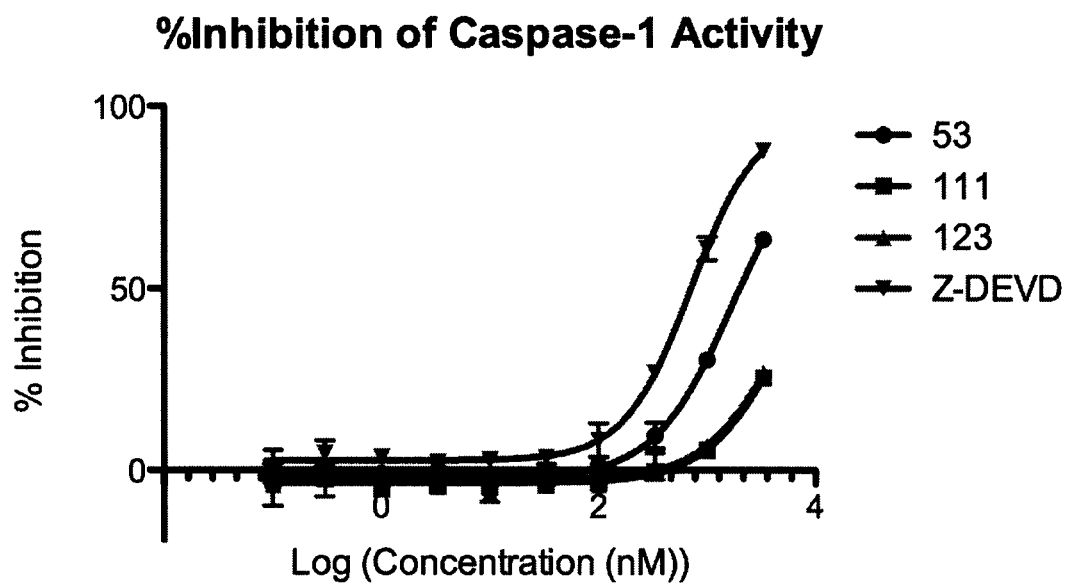
FIGS. 5A to 5J are line graphs showing inhibitory activity of Compounds 53, 111, 123, zDEVD-FMK (positive control, used as a prodrug: z-D(OMe)E(OMe)VD(OMe)FMK) against Caspases 1-10 (FIG. 5A-J). Compounds #53 and #123 exhibited high inhibitory activity towards the effector (executioner) caspases Caspase-3 and -7, but compound #53 also exhibited inhibitory activity towards the pro-inflammatory caspases Caspase-1 and -4 while compound #123 exhibited inhibitory activity towards the initiator caspases Caspase-9 and -10. Compound #111 exhibited high inhibitory activity only towards Caspase-3. Z-DEVD-FMK exhibited inhibitory activity towards the pro-inflammatory caspases Caspase-1 and -4 as well as the initiator caspases Caspase-8, -9 and -10.
Figure 5B:
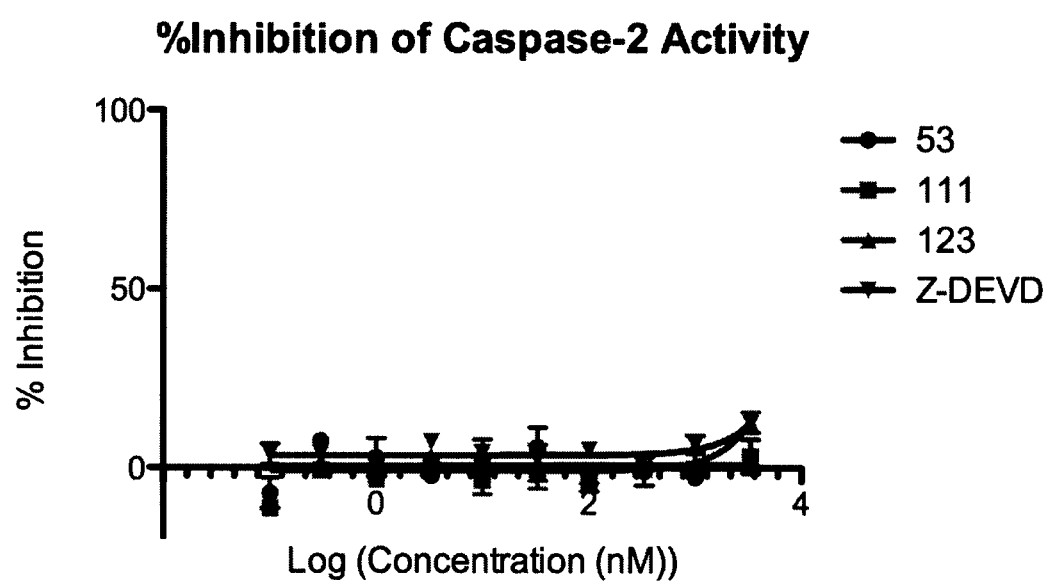
Figure 5C:
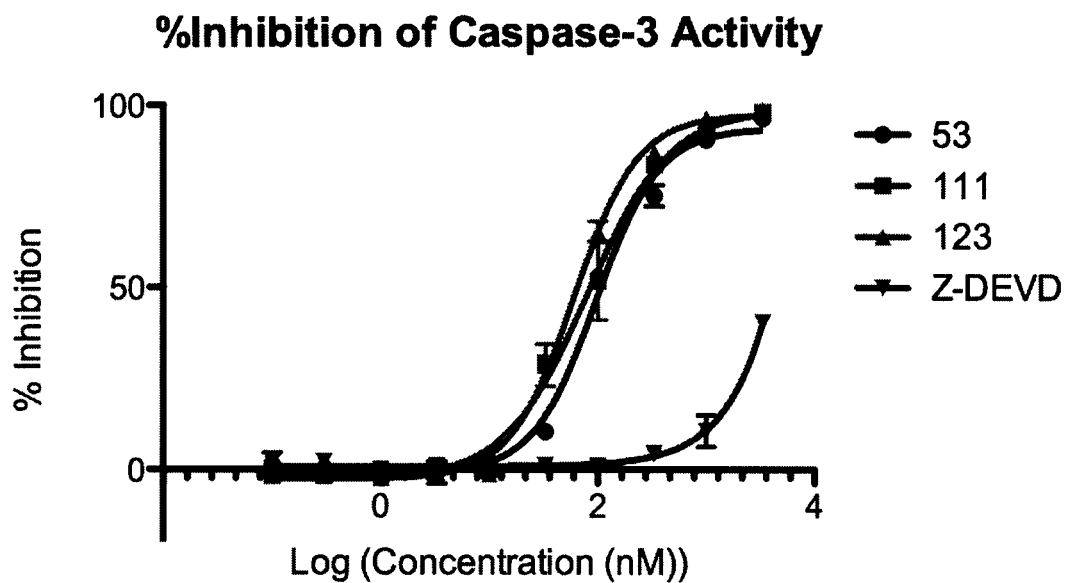
Figure 5D:
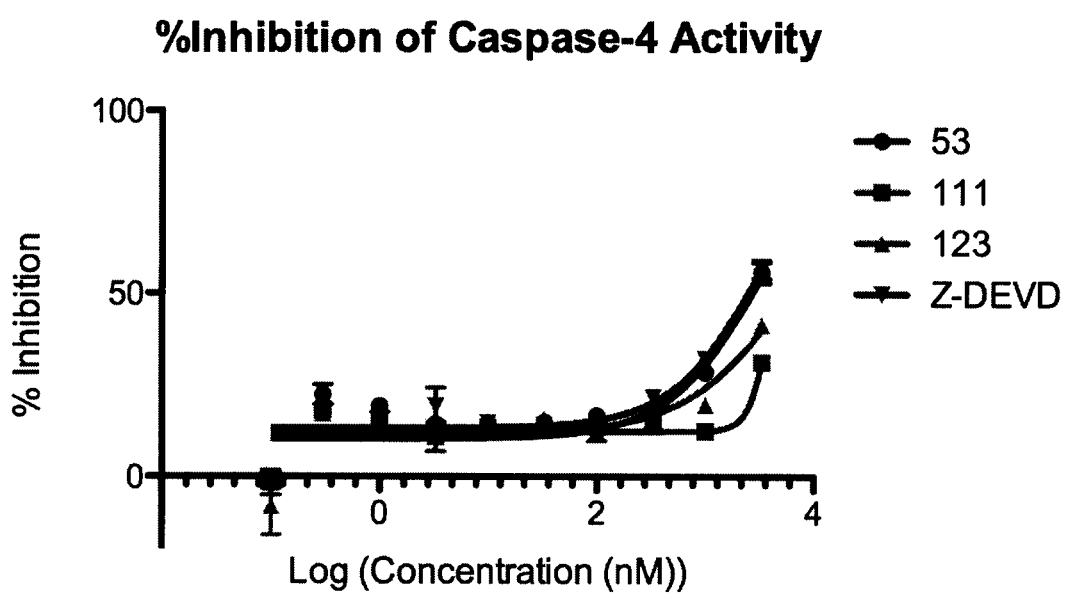
Figure 5E:
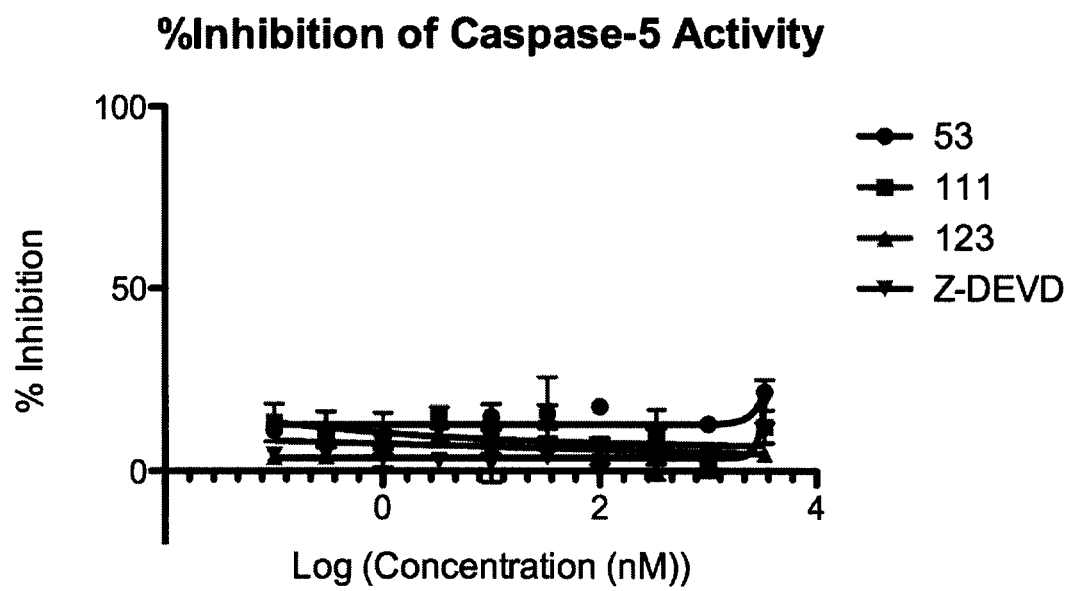
Figure 5F:
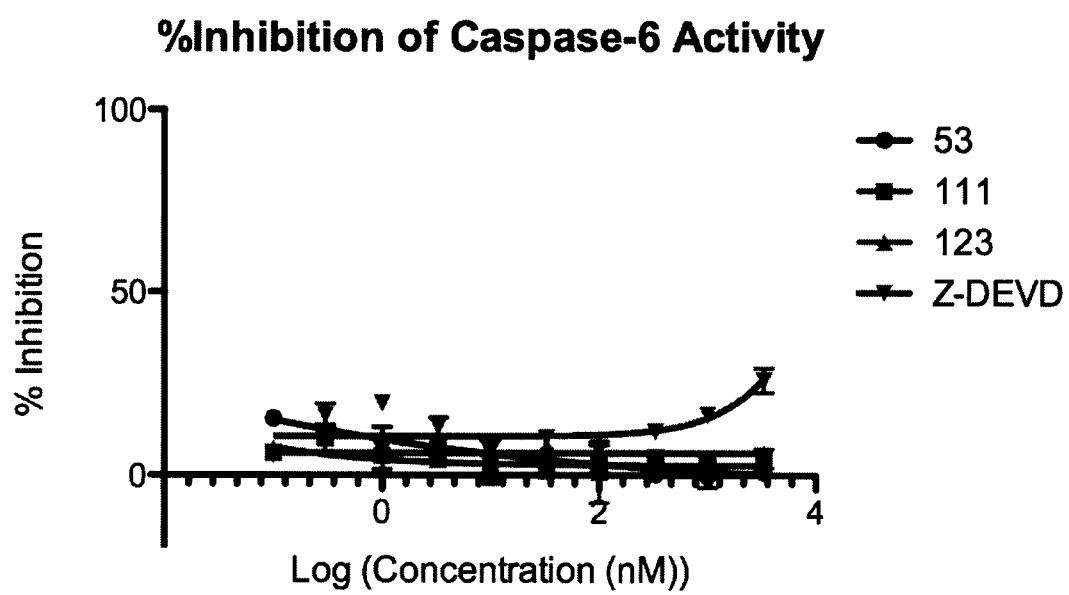
Figure 5G:
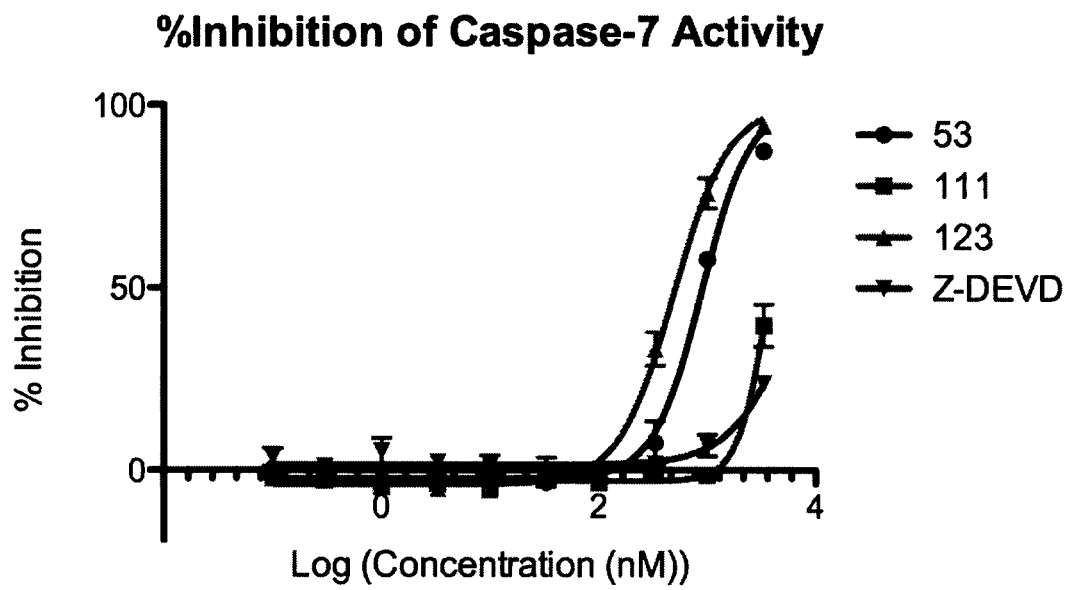
Figure 5H:
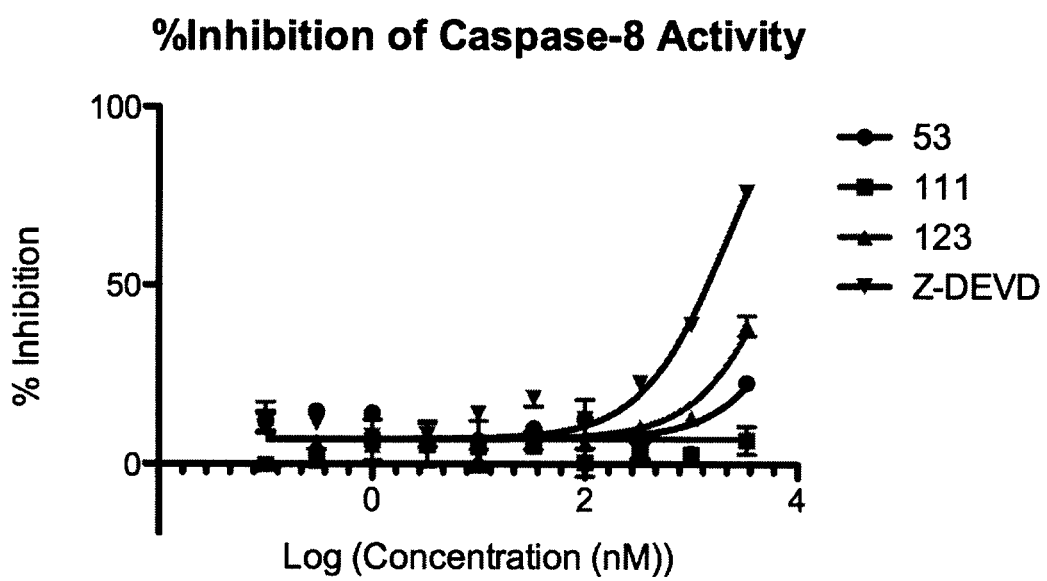
Figure 5I:
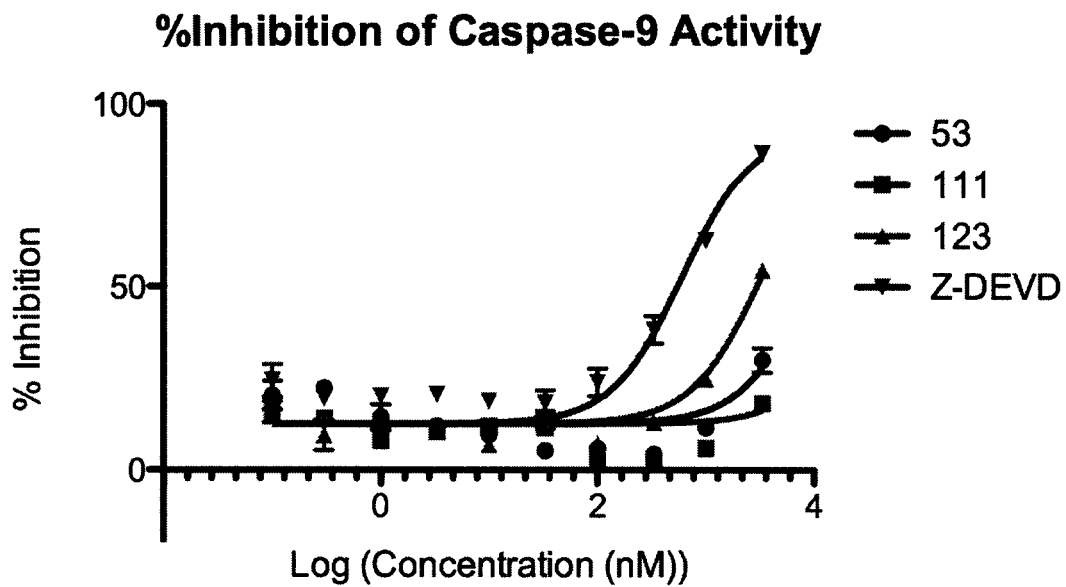
Figure 5J:
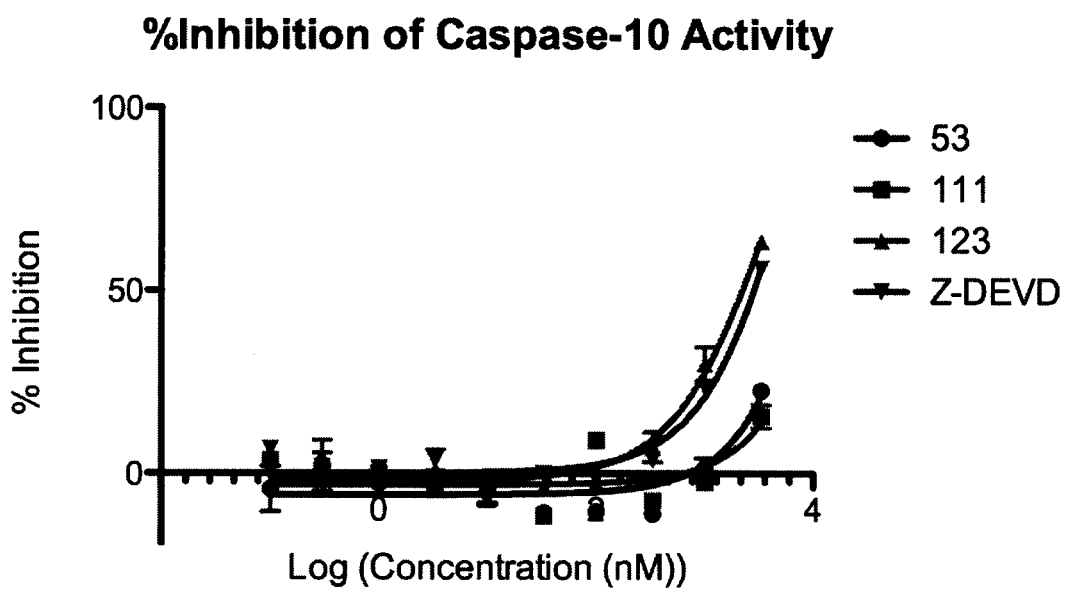

The present inventors have discovered compounds that have beneficial pharmaceutical properties and that these compounds may be effective for use in caspase-mediated diseases such as sepsis, myocardial infarction, ischemic stroke, spinal cord injury (SCI), traumatic brain injury (TBI) and neurodegenerative disease (e.g. multiple sclerosis (MS) and Alzheimer's, Parkinson's, and Huntington's diseases).

B) Compounds of the Invention

Broadly speaking, the invention concerns a compound represented by Formula I

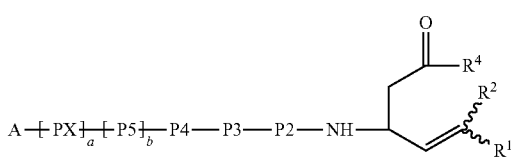

I wherein A, PX, P5, P4, P3, P2, $R^1$, $R^2$, $R^4$, a and b are as defined hereinabove and hereinbelow; or a prodrug, or a pharmaceutically acceptable salt to allow the drug to penetrate the cell membrane or the compound is labeled with a detectable label or an affinity tag thereof.

The line "-" when located between P2, P3, P4, P5 and PX represents a peptide bond or a peptidomimetic bond; The PX, P5, P4, P3, P2 amino acid residues are normally linked via a peptide bond, that is, a peptidic carbamoyl group, i.e. —CONH—. However, peptidomimetic bonds are also contemplated, such as $CH_2$—NH, CO—$CH_2$, azapeptide and retro-inverso bonds.

Residues PX, P5, P4, P3, P2 are natural and non-natural amino acid residues as defined herein.

The $R^1$ and $R^2$ that are bonded to the vinyl group can be either in the cis configuration or the trans configuration, as represented by the wavy lines. In one example, $R^1$ is configured to be trans such that the electron withdrawing capability of the $R^1$ group is stabilized.

In all embodiments described herein, the following compounds in Table 1A are explicitly excluded from the scope of the invention:

TABLE 1A

Compounds

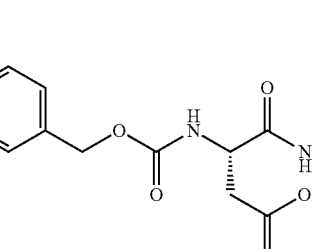

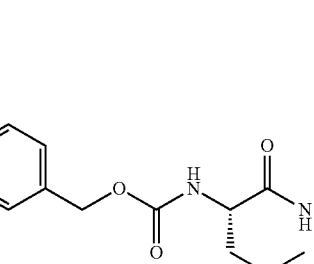

TABLE 1A-continued
Compounds
Further included within the scope of the invention are compounds of Formula IA:
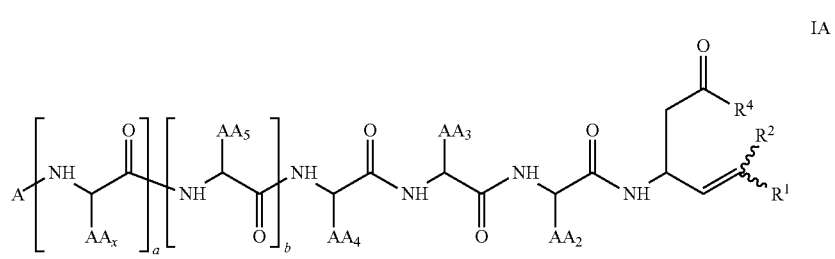

wherein A, $AA_x$, $AA_5$, $AA_4$, $AA_3$, $AA_2$, $R^1$, $R^2$, $R^4$, a and b are as defined hereinabove and hereinbelow;

or a prodrug, or a pharmaceutically acceptable salt to allow the drug to penetrate the cell membrane, or the compound is labeled with a detectable label or an affinity tag thereof.

Thus, when a and b are both 0, the present invention includes compounds of Formula II:

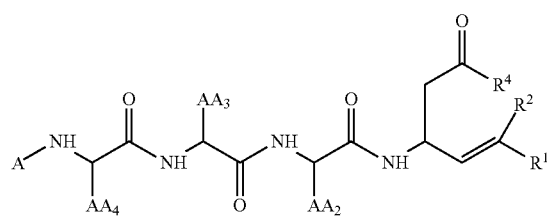

II

One subset of compounds of Formula III includes compounds of Formula IIIA:

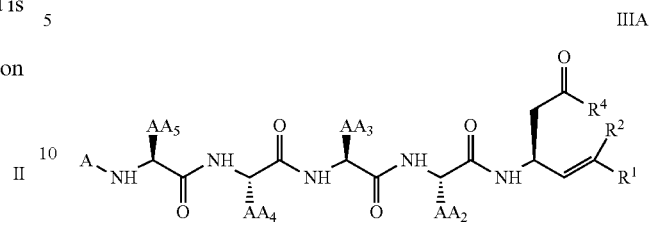

IIIA wherein A, $AA_5$, $AA_4$, $AA_3$, $AA_2$, $R^1$, $R^2$ and $R^4$ are as defined hereinabove and hereinbelow.

Further included within the scope of the invention are compounds of Formula IV:

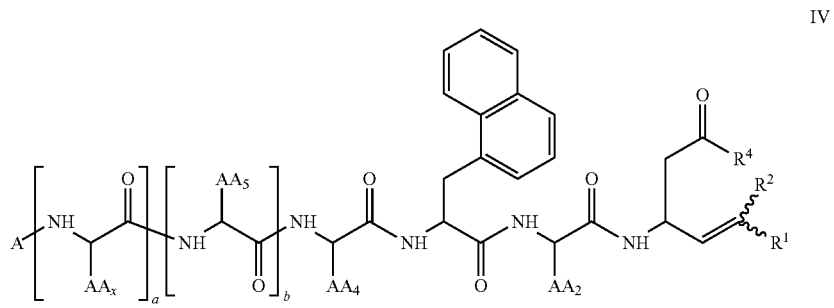

IV wherein A, $AA_4$, $AA_3$, $AA_2$, $R^1$, $R^2$ and $R^4$ are as defined hereinabove and hereinbelow. Furthermore, when a is 0 and b is 1, the present invention includes compounds of Formula III

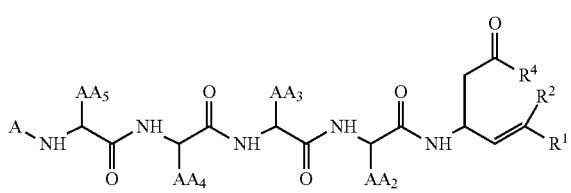

III wherein A, $AA_5$, $AA_4$, $AA_3$, $AA_2$, $R^1$, $R^2$ and $R^4$ are as defined hereinabove and hereinbelow. One subset of compounds of Formula II includes compounds of Formula IIA:

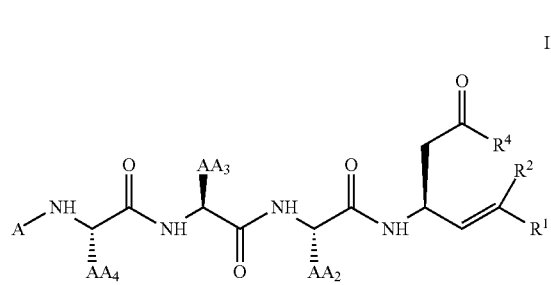

IIA wherein A, $AA_4$, $AA_3$, $AA_2$, $R^1$, $R^2$, $R^4$ are as defined hereinabove and hereinbelow.

wherein A, $AA_x$, $AA_5$, $AA_4$, $AA_2$, $R^1$, $R^2$, $R^4$, a and b are as defined hereinabove and hereinbelow; or a prodrug, or a pharmaceutically acceptable salt to allow the drug to penetrate the cell membrane, or the compound is labeled with a detectable label or an affinity tag thereof.

Thus, when a and b are both 0, the present invention includes compounds of Formula IVA:

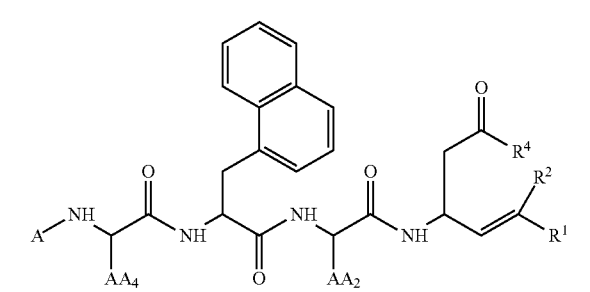

IVA wherein A, $AA_4$, $AA_2$, $R^1$, $R^2$ and $R^4$ are as defined hereinabove and hereinbelow.

Furthermore, when a is 0 and b is 1, the present invention includes compounds of Formula IVB:

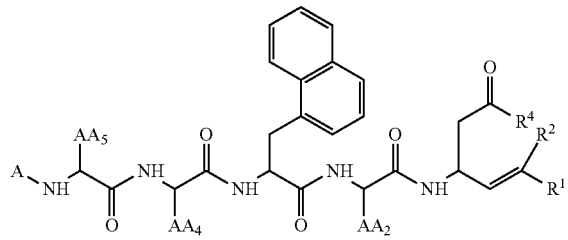
IVB wherein A, $AA_5$, $AA_4$, $AA_2$, $R^1$, $R^2$ and $R^4$ are as defined hereinabove and hereinbelow.

One subset of compounds of Formula IVA includes compounds of Formula IVC:

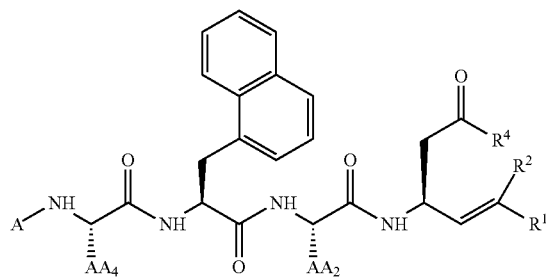
IVC wherein A, $AA_4$, $AA_2$, $R^1$, $R^2$ and $R^4$ are as defined hereinabove and hereinbelow.

One subset of compounds of Formula IVB includes compounds of Formula IVD:

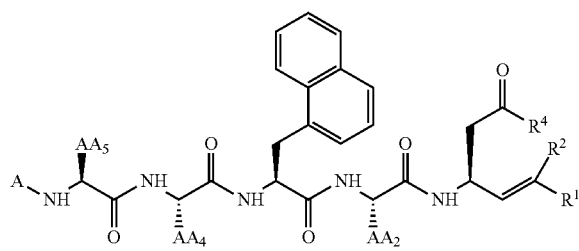
IVD wherein A, $AA_5$, $AA_4$, $AA_2$, $R^1$, $R^2$ and $R^4$ are as defined hereinabove and hereinbelow.

Further included are compounds of Formula V to VII:

V

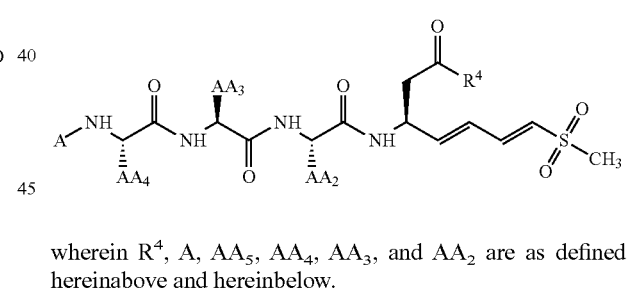

wherein $R^4$, A, $AA_5$, $AA_4$, $AA_3$, and $AA_2$ are as defined hereinabove and hereinbelow;

VI wherein $R^4$, A, $AA_5$, $AA_4$, $AA_3$, and $AA_2$ are as defined hereinabove and hereinbelow;

VII wherein $R^4$, A, $AA_5$, $AA_4$, $AA_3$, and $AA_2$ are as defined hereinabove and hereinbelow.

Further included within the scope of the invention are compounds of Formula VIII:

VIII

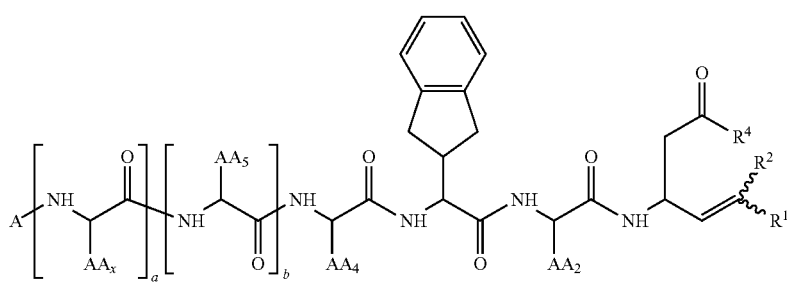

wherein A, $AA_X$, $AA_5$, $AA_4$, $AA_2$, $R^1$, $R^2$, $R^4$, a and b are as defined hereinabove and hereinbelow; or a prodrug, or a pharmaceutically acceptable salt to allow the drug to penetrate the cell membrane, or the compound is labeled with a detectable label or an affinity tag thereof.

Thus, when a and b are both 0, the present invention includes compounds of Formula VIIIA:

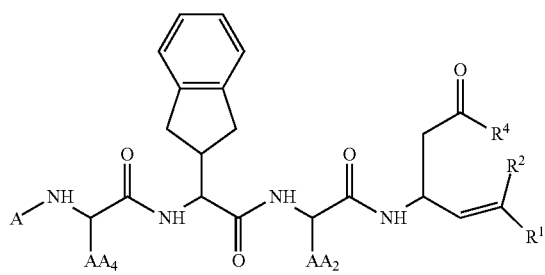

VIIIA wherein A, $AA_4$, $AA_2$, $R^1$, $R^2$ and $R^4$ are as defined hereinabove and hereinbelow.

One subset of compounds of Formula VIIIA includes compounds of Formula VIIIC:

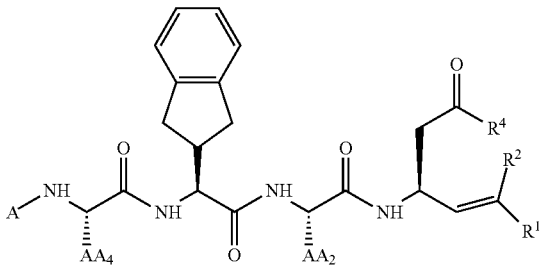

VIIIC wherein A, $AA_4$, $AA_2$, $R^1$, $R^2$ and $R^4$ are as defined hereinabove and hereinbelow.

Further included within the scope of the invention are compounds of Formula IX:

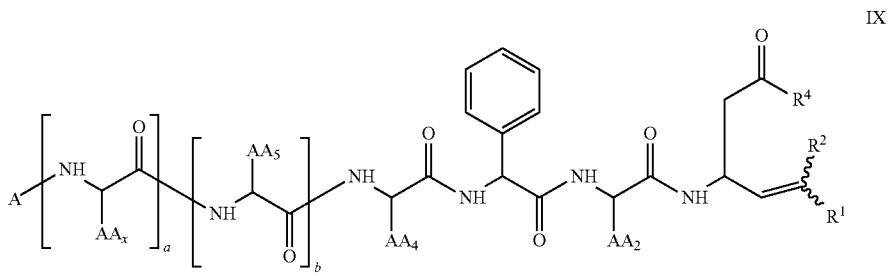

IX wherein A, $AA_X$, $AA_5$, $AA_4$, $AA_2$, $R^1$, $R^2$, $R^4$, a and b are as defined hereinabove and hereinbelow; or a prodrug, or a pharmaceutically acceptable salt to allow the drug to penetrate the cell membrane, or the compound is labeled with a detectable label or an affinity tag thereof.

Thus, when a and b are both 0, the present invention includes compounds of Formula IXA:

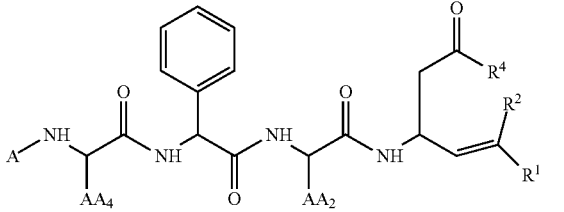

IXA wherein A, $AA_4$, $AA_2$, $R^1$, $R^2$ and $R^4$ are as defined hereinabove and hereinbelow.

Furthermore, when a is 0 and b is 1, the present invention includes compounds of Formula IXB:

Furthermore, when a is 0 and b is 1, the present invention includes compounds of Formula VIIIB:

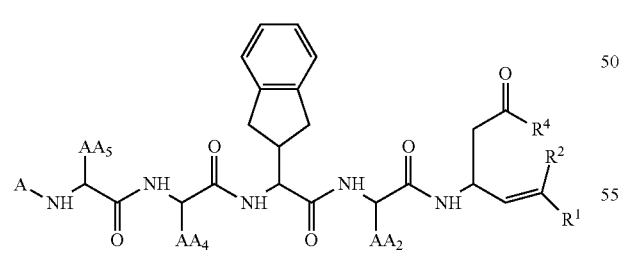

VIIIB wherein A, $AA_5$, $AA_4$, $AA_2$, $R^1$, $R^2$ and $R^4$ are as defined hereinabove and hereinbelow.

IXB

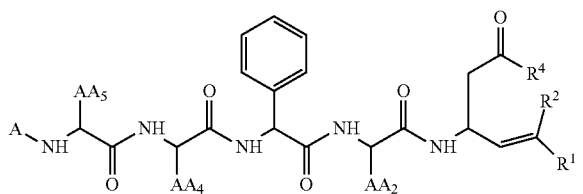

wherein A, $AA_5$, $AA_4$, $AA_2$, $R^1$, $R^2$ and $R^4$ are as defined hereinabove and hereinbelow.

One subset of compounds of Formula IXA includes compounds of Formula: IXC:

IXC

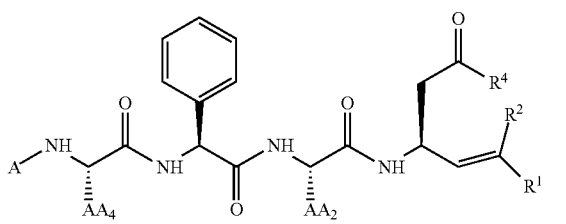

wherein A, $AA_4$, $AA_2$, $R^1$, $R^2$ and $R^4$ are as defined hereinabove and hereinbelow.

Further included within the scope of the invention are compounds of Formula X:

X

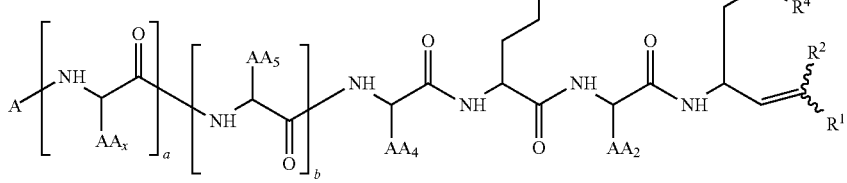

wherein A, $AA_X$, $AA_5$, $AA_4$, $AA_2$, $R^1$, $R^2$, $R^4$, $R^{40}$, a and b are as defined hereinabove and hereinbelow;
or a prodrug, or a pharmaceutically acceptable salt to allow the drug to penetrate the cell membrane, or the compound is labeled with a detectable label or an affinity tag thereof.

Thus, when a and b are both 0, the present invention includes compounds of Formula XA:

XA

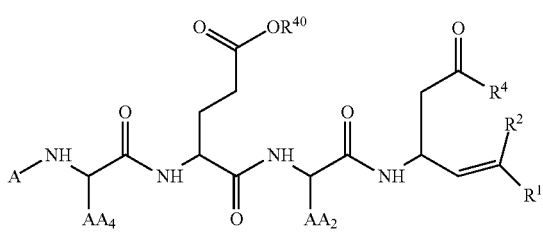

wherein A, $AA_4$, $AA_2$, $R^1$, $R^2$, $R^4$ and $R^{40}$ are as defined hereinabove and hereinbelow.

Furthermore, when a is 0 and b is 1, the present invention includes compounds of Formula XB:

XB

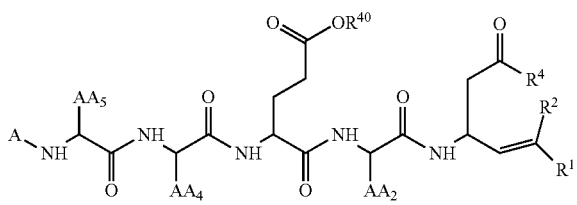

wherein A, $AA_5$, $AA_4$, $AA_2$, $R^1$, $R^2$, $R^4$ and $R^{40}$ are as defined hereinabove and hereinbelow.

One subset of compounds of Formula XA includes compounds of Formula XC:

XC

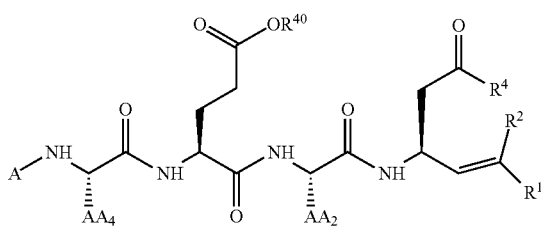

wherein A, $AA_4$, $AA_2$, $R^1$, $R^2$, $R^4$ and $R^{40}$ are as defined hereinabove and hereinbelow.

$AA_2$, $AA_3$ and $AA_4$:

In one subset, $AA_2$ is the (R) or (S) amino acid side chain of Val or Ser; or $AA_2$ is Ser (phosphate).

In one subset, $AA_3$ is the (R) or (S) amino acid side chain of Glu; or $AA_3$ is phenylglycine, indanylglycine, 3-(1-naphtyl)alanine, Glu(β-ethyl), or Glu(β-tert butyl).

In one subset, $AA_4$ is the (R) or (S) amino acid side chain of Asp, or $AA_4$ is Asp(β-methyl), Asp(β-ethyl), or Asp(β-tert butyl).

Any and each individual definition of $AA_2$, $AA_3$ and $AA_4$ as set out herein may be combined with any and each individual definition of A, a, b, $R^1$, $R^2$ and $R^4$ as set out herein.

a and b:

In one subset of compounds, a is 0 or 1; and b is 0 or 1 provided that when b is 0, a is 0.

In one example, a and b are both 0.

In another example, a is 0 and b is 1.

Any and each individual definition of a and b as set out herein may be combined with any and each individual definition of $AA_2$, $AA_3$ and $AA_4$, A, $R^1$, $R^2$ and $R^4$ as set out herein.

A:
   In one subset, A is
   1) H,
   2) $C_1$-$C_6$ alkyl,
   3) aryl,
   4) heteroaryl,
   5) heterocyclyl,
   6) $R^3$—C(O)—,
   7) $R^3$—OC(O)—,
   8) $R^3$—$CH_2$OC(O)—,
   9) $R^3$—C(O)O—, or
   10) $R^3$—S(O)$_2$—.
   In one example, A is H.
   In one example, A is $R^3$—$CH_2$OC(O)—.
   In one example, A is $PhCH_2OC(O)$—.

Any and each individual definition of A as set out herein may be combined with any and each individual definition of $AA_2$, $AA_3$ and $AA_4$, a, b, $R^1$, $R^2$ and $R^4$ as set out herein.

$R^1$:
   In one subset, $R^1$ is an electron withdrawing group (EWG) selected from:
   1) aryl,
   2) heteroaryl,
   3) heterocyclyl,
   4) $C_2$-$C_6$ alkene-$R^{20}$,
   5) $SO_2R^5$,
   6) $SO_3R^5$,
   7) $SOR^5$,
   8) $SONHR^5$,
   9) $SO_2NHR^5$,
   10) CN,
   11) $CO_2R^5$,
   12) $COR^5$,
   13) $PO_3R^5$,
   14) $PO(OR^5)_2$, or
   15) $PO(OR^5)$,
   wherein the aryl, the heteroaryl, or the heterocyclyl are optionally substituted with one or more $R^{30}$.
   In one example, $R^1$ is in the trans configuration.
   In one example, $R^1$ is $SO_2R^5$, wherein $R^5$ is $C_1$-$C_6$ alkyl.

Any and each individual definition of $R^1$ as set out herein may be combined with any and each individual definition of $AA_2$, $AA_3$ and $AA_4$, A, a, b, $R^2$ and $R^4$ as set out herein.

$R^2$:
   In one subset, $R^2$ is
   1) $R^1$; or
   2) H,
   3) halogen,
   4) haloalkyl,
   5) $C_1$-$C_6$ alkyl,
   6) $C_2$-$C_6$ alkene,
   7) $C_3$-$C_7$ cycloalkyl,
   8) $OR^9$,
   9) $SR^9$,
   10) $N^+(R^4)_3$,
   10) $OCOR^6$,
   11) $OCO_2R^6$,
   12) $NR^7R^8$,
   13) $NHSO_2R^6$,
   14) $NHCOR^6$,
   15) aryl,
   16) heteroaryl, or
   17) heterocyclyl;
   wherein $R^1$, $R^6$, $R^7$, $R^8$ and $R^9$ are as defined hereinabove and hereinbelow.

In one example, $R^2$ is H.
   In another example, $R^2$ is halogen.
   In yet another example, $R^2$ is Cl.

Any and each individual definition of $R^2$ as set out herein may be combined with any and each individual definition of $AA_2$, $AA_3$ and $AA_4$, A, a, b, $R^1$ and $R^4$ as set out herein.

$R^3$:
   In one subset, $R^3$ is
   1) $C_1$-$C_6$ alkyl,
   2) aryl-$C_1$-$C_6$ alkyl,
   3) heteroaryl, or
   4) heterocyclyl.

Any and each individual definition of $R^3$ as set out herein may be combined with any and each individual definition of $AA_2$, $AA_3$ and $AA_4$, A, a, b, $R^1$, $R^2$ and $R^4$ as set out herein.

$R^4$:
   In one subset, $R^4$ is
   1) OH,
   2) $OC_1$-$C_6$ alkyl,
   3) $NR^7R^8$, or
   4) $NHSO_2R^9$.
   In one example, $R^4$ is OH or $OC_1$-$C_6$ alkyl.
   In one example, $R^4$ is OH, $OCH_3$, $OCH_2CH_3$, $OCH_2CH_2CH_3$, or $OC(CH_3)_3$.

Any and each individual definition of $R^4$ as set out herein may be combined with any and each individual definition of $AA_2$, $AA_3$ and $AA_4$, A, a, b, $R^1$ and $R^2$ as set out herein.

$R^5$:
   In one subset, $R^5$ is
   1) H,
   2) $C_1$-$C_6$ alkyl,
   3) $C_2$-$C_6$ alkene,
   4) $C_3$-$C_7$ cycloalkyl,
   5) haloalkyl,
   6) aryl,
   7) heteroaryl,
   8) heterocyclyl,
   9) $NHCH_2C(O)OH$, or
   10) (D) or (L) natural or non-natural amino acid derivatives optionally protected with an amino acid protecting group.

Examples of amino acid protecting groups are known to those skilled in the art and include, for example, tert-butyl, benzoyl, methyl and the like.

Any and each individual definition of $R^5$ as set out herein may be combined with any and each individual definition of $AA_2$, $AA_3$ and $AA_4$, A, a, b, $R^1$, $R^2$ and $R^4$ as set out herein.

$R^6$:
   In one subset, $R^6$ is
   11) any (D) or (L) amino acid residue,
   2) $C_1$-$C_6$ alkyl,
   3) $C_3$-$C_7$ cycloalkyl,
   4) aryl,
   5) heteroaryl, or
   6) heterocyclyl,
   in which the alkyl or the cycloalkyl are optionally substituted with one or more $R^{10}$ substituents; and in which the aryl, heteroaryl or heterocyclyl are optionally substituted with one or more $R^{20}$ substituents.

Any and each individual definition of $R^6$ as set out herein may be combined with any and each individual definition of $AA_2$, $AA_3$ and $AA_4$, A, a, b, $R^1$, $R^2$ and $R^4$ as set out herein.

$R^7$ and $R^8$:
   In one subset, $R^7$ and $R^8$ are independently selected from:
   1) H,
   2) $C_1$-$C_6$ alkyl,
   3) $C_3$-$C_7$ cycloalkyl,
   4) haloalkyl,
   5) aryl, 6) heteroaryl, or
7) heterocyclyl,
wherein the alkyl and the cycloalkyl are optionally substituted with one or more $R^{19}$ substituents, and the aryl, the heteroaryl and the heterocyclyl are optionally substituted with one or more $R^{20}$ substituents.

Any and each individual definition of $R^7$ and $R^8$ as set out herein may be combined with any and each individual definition of $AA_2$, $AA_3$ and $AA_4$, A, a, b, $R^1$, $R^2$ and $R^4$ as set out herein.

$R^9$:

In one subset, $R^9$ is
1) H,
2) $C_1$-$C_6$ alkyl,
3) $C_3$-$C_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents.

Any and each individual definition of $R^9$ as set out herein may be combined with any and each individual definition of $AA_2$, $AA_3$ and $AA_4$, A, a, b, $R^1$, $R^2$ and $R^4$ as set out herein.

$R^{10}$:

In one subset, $R^{10}$ is independently selected from:
1) halogen,
2) $C_1$-$C_6$ alkyl,
3) $C_3$-$C_7$ cycloalkyl,
4) haloalkyl,
5) aryl,
6) heteroaryl,
7) heterocyclyl,
8) $OR^9$,
9) $S(O)_m R^9$,
10) $NR^7 R^8$,
11) $COR^9$,
12) $C(O)OR^9$,
13) $OC(O)R^9$,
14) $SC(O)R^9$,
15) $CONR^7 R^8$, or
16) $S(O)_2 NR^7 R^8$,
wherein m is an integer of 0, 1, or 2, wherein $R^7$, $R^8$ and $R^9$ are as defined hereinabove and hereinbelow.

Any and each individual definition of $R^{10}$ as set out herein may be combined with any and each individual definition of $AA_2$, $AA_3$ and $AA_4$, A, a, b, $R^1$, $R^2$ and $R^4$ as set out herein.

$R^{20}$:

In one subset, $R^{20}$ is independently selected from:
1) halogen,
2) $NO_2$,
3) CN,
4) $C_1$-$C_6$ alkyl,
5) haloalkyl,
6) $C_3$-$C_7$ cycloalkyl,
7) $OR^7$,
8) $NR^7 R^8$,
9) $SR^7$,
10) aryl,
11) heteroaryl,
12) heterocyclyl,
13) $SO_2 R^5$,
14) $SO_3 R^5$,
15) $SOR^5$,
16) $SONHR^5$,
17) $SO_2 NHR^5$,
18) $PO_3 R^5$,
19) $PO(OR^5)_2$,
20) $PO(OR^5)$,
21) $COR^5$,
22) $COR^7$,
23) $CO_2 R^7$,
24) $S(O)_m R^7$,
25) $CONR^7 R^8$, or
26) $S(O)_2 NR^7 R^8$,
wherein the alkyl and the cycloalkyl are optionally substituted with one or more $R^8$ substituents; and wherein the aryl, the heteroaryl, or the heterocyclyl are optionally substituted with one or more $R^{30}$; wherein m is an integer of 0, 1, or 2; wherein $R^7$, $R^8$ and m are as defined hereinabove and hereinbelow.

Any and each individual definition of $R^{20}$ as set out herein may be combined with any and each individual definition of $AA_2$, $AA_3$ and $AA_4$, A, a, b, $R^1$, $R^2$ and $R^4$ as set out herein.

$R^{30}$:

In one subset, $R^{30}$ is
1) $NO_2$,
2) $C_2$-$C_6$ alkene-$R^{20}$,
3) $SO_2 R^5$,
4) $SOR^5$,
5) $SONHR^5$,
6) $SO_2 NHR^5$,
7) CN,
8) $CO_2 R^5$,
9) $COR^5$,
10) $PO_3 R^5$,
11) $PO(OR^5)_2$, or
12) $PO(OR^5)$;
wherein $R^5$ and $R^{20}$ are as defined hereinabove and hereinbelow.

Any and each individual definition of $R^{30}$ as set out herein may be combined with any and each individual definition of $AA_2$, $AA_3$ and $AA_4$, A, a, b, $R^1$, $R^2$ and $R^4$ as set out herein.

$R^{40}$:

In one subset, $R^{40}$ is
1) H, or
2) $C_1$-$C_6$ alkyl.

Any and each individual definition of $R^{40}$ as set out herein may be combined with any and each individual definition of $AA_2$, $AA_3$ and $AA_4$, A, a, b, $R^1$, $R^2$ and $R^4$ as set out herein.

Specific Embodiments

More particularly, compounds of Formula IVC include:

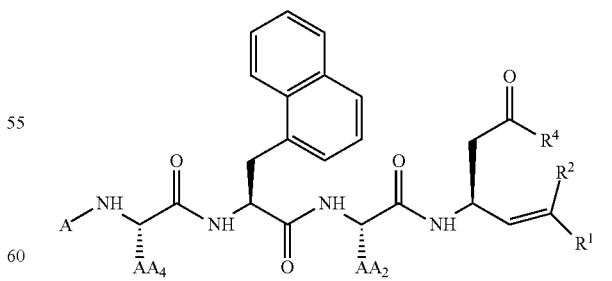

IVC wherein
A is
1) H,
2) $C_1$-$C_6$ alkyl,
3) aryl, 4) heteroaryl,
5) heterocyclyl,
6) $R^3$—C(O)—,
7) $R^3$—OC(O)—,
8) $R^3$—CH$_2$OC(O)—,
9) $R^3$—C(O)O—, or
10) $R^3$—S(O)$_2$—;
AA$_2$ is the (R) or (S) amino acid side chain of Val;
AA$_4$ is the (R) or (S) amino acid side chain of Asp, or AA$_4$ is Asp(β-methyl), Asp(β-ethyl), or Asp (β-tert butyl);
$R^1$ is
1) aryl,
2) heteroaryl,
3) heterocyclyl,
4) C$_2$-C$_6$ alkene-$R^{20}$,
5) SO$_2$R$^5$,
6) SO$_3$R$^5$,
7) SOR$^5$,
8) SONHR$^5$,
9) SO$_2$NHR$^5$,
10) CN,
11) CO$_2$R$^5$,
12) COR$^5$,
13) PO$_3$R$^5$,
14) PO(OR$^5$)$_2$, or
15) PO(OR$^5$),
wherein the aryl, the heteroaryl, or the heterocyclyl are optionally substituted with one or more $R^{30}$;
$R^2$ is
1) $R^1$; or
2) H,
3) halogen,
4) haloalkyl,
5) C$_1$-C$_6$ alkyl,
6) C$_2$-C$_6$ alkene,
7) C$_3$-C$_7$ cycloalkyl,
8) OR$^9$,
9) SR$^9$,
10) N$^+$(R$^4$)$_3$,
10) OCOR$^6$,
11) OCO$_2$R$^6$,
12) NR$^7$R$^9$,
13) NHSO$_2$R$^6$,
14) NHCOR$^6$,
15) aryl,
16) heteroaryl, or
17) heterocyclyl;
$R^3$ is
1) C$_1$-C$_6$ alkyl,
2) aryl-C$_1$-C$_6$ alkyl,
3) heteroaryl, or
4) heterocyclyl;
$R^4$ is
1) OH,
2) OC$_1$-C$_6$ alkyl,
3) NR$^7$R$^6$, or
4) NHSO$_2$R$^9$;
$R^5$ is
1) H,
2) C$_1$-C$_6$ alkyl,
3) C$_2$-C$_6$ alkene,
4) C$_3$-C$_7$ cycloalkyl,
5) haloalkyl,
6) aryl,
7) heteroaryl,
8) heterocyclyl,
9) NHCH$_2$C(O)OH, or
10) (D) or (L) natural or non-natural amino acid derivatives optionally protected with an amino acid protecting group;
$R^6$ is
1) any (D) or (L) amino acid residue,
2) C$_1$-C$_6$ alkyl,
3) C$_3$-C$_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents;
$R^7$ and $R^8$ are independently selected from:
1) H,
2) C$_1$-C$_6$ alkyl,
3) C$_3$-C$_7$ cycloalkyl,
4) haloalkyl,
5) aryl,
6) heteroaryl, or
7) heterocyclyl,
wherein the alkyl and the cycloalkyl are optionally substituted with one or more $R^{10}$ substituents, and the aryl, the heteroaryl and the heterocyclyl are optionally substituted with one or more $R^{20}$ substituents;
$R^9$ is
1) H,
2) C$_1$-C$_6$ alkyl,
3) C$_3$-C$_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents;
$R^{10}$ is independently selected from:
1) halogen,
2) C$_1$-C$_6$ alkyl,
3) C$_3$-C$_7$ cycloalkyl,
4) haloalkyl,
5) aryl,
6) heteroaryl,
7) heterocyclyl,
8) OR$^9$,
9) S(O)$_m$R$^9$,
10) NR$^7$R$^8$,
11) COR$^9$,
12) C(O)OR$^9$,
13) OC(O)R$^9$,
14) SC(O)R$^9$,
15) CONR$^7$R$^8$, or
16) S(O)$_2$NR$^7$R$^8$,
wherein m is an integer of 0, 1, or 2;
$R^{20}$ is independently selected from:
1) halogen,
2) NO$_2$,
3) CN,
4) C$_1$-C$_6$ alkyl,
5) haloalkyl,
6) C$_3$-C$_7$ cycloalkyl,
7) OR$^7$,
8) NR$^7$R$^8$,
9) SR$^7$, 10) aryl,
11) heteroaryl,
12) heterocyclyl,
13) $SO_2R^5$,
14) $SO_3R^5$,
15) $SOR^5$,
16) $SONHR^5$,
17) $SO_2NHR^5$,
18) $PO_3R^5$,
19) $PO(OR^5)_2$,
20) $PO(OR^5)$,
21) $COR^5$,
22) $COR^7$,
23) $CO_2R^7$,
24) $S(O)_mR^7$,
25) $CONR^7R^8$, or
26) $S(O)_2NR^7R^8$, wherein the alkyl and the cycloalkyl are optionally substituted with one or more $R^6$ substituents; and wherein the aryl, the heteroaryl, or the heterocyclyl are optionally substituted with one or more $R^{30}$; wherein m is an integer of 0, 1, or 2; and $R^{30}$ is
1) $NO_2$,
2) $C_2$-$C_6$ alkene-$R^{20}$,
3) $SO_2R^5$,
4) $SOR^5$,
5) $SONHR^5$,
6) $SO_2NHR^5$,
7) CN,
8) $CO_2R^5$,
9) $COR^5$,
10) $PO_3R^5$,
11) $PO(OR^5)_2$, or
12) $PO(OR^5)$;

or a prodrug, or a pharmaceutically acceptable salt, or the compound is labeled with a detectable label or an affinity tag thereof.

In one example of compounds of Formula IVC include:
A is $PhCH_2OC(O)$—;
$AA_2$ is the (R) or (S) amino acid side chain of Val;
$AA_4$ is the (R) or (S) amino acid side chain of Asp, or $AA_4$ is Asp(β-ethyl) or Asp(βtert butyl);
$R^1$ is $SO_2R^5$;
$R^2$ is H or halogen;
$R^4$ is OH or $OC_1$-$C_6$ alkyl; and
$R^5$ is $C_1$-$C_6$ alkyl;
or a pharmaceutically acceptable salt thereof.

Specifically, compounds of Formula IVC include:
A is $PhCH_2OC(O)$—;
$AA_2$ is the (R) or (S) amino acid side chain of Val;
$AA_4$ is the (R) or (S) amino acid side chain of Asp, or $AA_4$ is Asp(βethyl) or Asp(βtert butyl);
$R^1$ is $SO_2R^5$;
$R^2$ is H or Cl;
$R^4$ is OH, $OCH_2CH_3$, or $OC(CH_3)_3$; and
$R^5$ is $CH_3$;
or a pharmaceutically acceptable salt thereof.

More particularly, compounds of Formula VIIIC include:

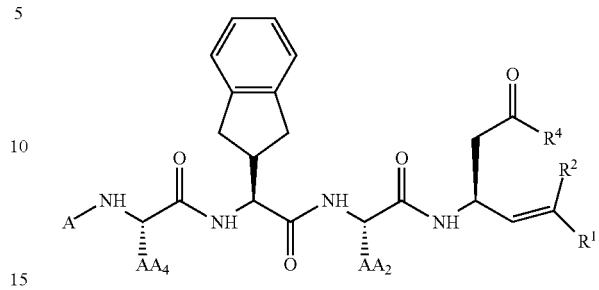

VIIIC wherein
A is
1) H,
2) $C_1$-$C_6$ alkyl,
3) aryl,
4) heteroaryl,
5) heterocyclyl,
6) $R^3$—C(O)—,
7) $R^3$—OC(O)—,
8) $R^3$—$CH_2OC(O)$—,
9) $R^3$—C(O)O—, or
10) $R^3$—$S(O)_2$—;
$AA_2$ is the (R) or (S) amino acid side chain of Val;
$AA_4$ is Asp(β-methyl) or Asp(β-ethyl);
$R^1$ is
1) aryl,
2) heteroaryl,
3) heterocyclyl,
4) $C_2$-$C_6$ alkene-$R^{20}$,
5) $SO_2R^5$,
6) $SO_3R^5$,
7) $SOR^5$,
8) $SONHR^5$,
9) $SO_2NHR^5$,
10) CN,
11) $CO_2R^5$,
12) $COR^5$,
13) $PO_3R^5$,
14) $PO(OR^5)_2$, or
15) $PO(OR^5)$,
wherein the aryl, the heteroaryl, or the heterocyclyl are optionally substituted with one or more $R^{30}$;
$R^2$ is
1) $R^1$; or
2) H,
3) halogen,
4) haloalkyl,
5) $C_1$-$C_6$ alkyl,
6) $C_2$-$C_6$ alkene,
7) $C_3$-$C_7$ cycloalkyl,
8) $OR^9$,
9) $SR^9$,
10) $N^+(R^4)_3$,
10) $OCOR^6$,
11) $OCO_2R^6$,
12) $NR^7R^8$,
13) $NHSO_2R^6$,
14) $NHCOR^6$,
15) aryl,
16) heteroaryl, or
17) heterocyclyl;

$R^3$ is
1) $C_1$-$C_6$ alkyl,
2) aryl-$C_1$-$C_6$ alkyl,
3) heteroaryl, or
4) heterocyclyl;
$R^4$ is $OCH_2CH_3$;
$R^5$ is
1) H,
2) $C_1$-$C_6$ alkyl,
3) $C_2$-$C_6$ alkene,
4) $C_3$-$C_7$ cycloalkyl,
5) haloalkyl,
6) aryl,
7) heteroaryl,
8) heterocyclyl,
9) $NHCH_2C(O)OH$, or
10) (D) or (L) natural or non-natural amino acid derivatives optionally protected with an amino acid protecting group;
$R^6$ is
1) any (D) or (L) amino acid residue,
2) $C_1$-$C_6$ alkyl,
3) $C_3$-$C_7$ cycloalkyl,
4) aryl,
5) heteroaryl, or
6) heterocyclyl,
in which the alkyl or the cycloalkyl are optionally substituted with one or more $R^{19}$ substituents; and in which the aryl, heteroaryl or heterocyclyl are optionally substituted with one or more $R^{20}$ substituents;
$R^7$ and $R^8$ are independently selected from:
1) H,
2) $C_1$-$C_6$ alkyl,
3) $C_3$-$C_7$ cycloalkyl,
4) haloalkyl,
5) aryl,
6) heteroaryl, or
7) heterocyclyl,
wherein the alkyl and the cycloalkyl are optionally substituted with one or more $R^{10}$ substituents, and the aryl, the heteroaryl and the heterocyclyl are optionally substituted with one or more $R^{20}$ substituents;
$R^9$ is
1) H,
2) $C_1$-$C_6$ alkyl,
3) $C_3$-$C_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents;
$R^{10}$ is independently selected from:
1) halogen,
2) $C_1$-$C_6$ alkyl,
3) $C_3$-$C_7$ cycloalkyl,
4) haloalkyl,
5) aryl,
6) heteroaryl,
7) heterocyclyl,
8) $OR^9$,
9) $S(O)_mR^9$,
10) $NR^7R^8$,
11) $COR^9$,
12) $C(O)OR^9$,
13) $OC(O)R^9$,
14) $SC(O)R^9$,
15) $CONR^7R^8$, or
16) $S(O)_2NR^7R^8$,
wherein m is an integer of 0, 1, or 2;
$R^{20}$ is independently selected from:
1) halogen,
2) $NO_2$,
3) CN,
4) $C_1$-$C_6$ alkyl,
5) haloalkyl,
6) $C_3$-$C_7$ cycloalkyl,
7) $OR^7$,
8) $NR^7R^8$,
9) $SR^7$,
10) aryl,
11) heteroaryl,
12) heterocyclyl,
13) $SO_2R^5$,
14) $SO_3R^5$,
15) $SOR^5$,
16) $SONHR^5$,
17) $SO_2NHR^5$,
18) $PO_3R^5$,
19) $PO(OR^5)_2$,
20) $PO(OR^5)$,
21) $COR^5$,
22) $COR^7$,
23) $CO_2R^7$,
24) $S(O)_mR^7$,
25) $CONR^7R^8$, or
26) $S(O)_2NR^7R^8$,
wherein the alkyl and the cycloalkyl are optionally substituted with one or more $R^6$ substituents; and wherein the aryl, the heteroaryl, or the heterocyclyl are optionally substituted with one or more $R^{30}$; wherein m is an integer of 0, 1, or 2; and
$R^{30}$ is
1) $NO_2$,
2) $C_2$-$C_6$ alkene-$R^{20}$,
3) $SO_2R^5$,
4) $SOR^5$,
5) $SONHR^5$,
6) $SO_2NHR^5$,
7) CN,
8) $CO_2R^5$,
9) $COR^5$,
10) $PO_3R^5$,
11) $PO(OR^5)_2$, or
12) $PO(OR^5)$;
or a prodrug, or a pharmaceutically acceptable salt, or the compound is labeled with a detectable label or an affinity tag thereof.

In one example, the compounds of Formula VIIIC include:
A is $PhCH_2OC(O)$—;
$AA_2$ is the (R) or (S) amino acid side chain of Val;
$AA_4$ is Asp(β-methyl) or Asp(β-ethyl);
$R^1$ is $SO_2R^5$;
$R^2$ is H or halogen;
$R^4$ is $OCH_2CH_3$; and
$R^5$ is $C_1$-$C_6$ alkyl;
or a pharmaceutically acceptable salt thereof.

Specifically, the compounds of Formula VIIC include:
A is $PhCH_2OC(O)$—;
$AA_2$ is the (R) or (S) amino acid side chain of Val;
$AA_4$ is Asp(β-methyl) or Asp(β-ethyl);
$R^1$ is $SO_2R^5$;
$R^2$ is H or Cl;
$R^4$ is $OCH_3$ or $OCH_2CH_3$; and
$R^5$ is $CH_3$;
or a pharmaceutically acceptable salt thereof.

More particularly, compounds of Formula IXC include:

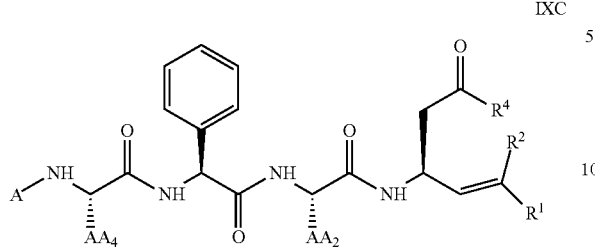

wherein
A is
1) H,
2) $C_1$-$C_6$ alkyl,
3) aryl,
4) heteroaryl,
5) heterocyclyl,
6) $R^3$—C(O)—,
7) $R^3$—OC(O)—,
8) $R^3$—$CH_2$OC(O)—,
9) $R^3$—C(O)O—, or
10) $R^3$—S(O)$_2$—;
$AA_2$ is the (R) or (S) amino acid side chain of Val;
$AA_4$ is the (R) or (S) amino acid side chain of Asp; or $AA_4$ is Asp(β-methyl), Asp(β-ethyl) or Asp(β-tert butyl);
$R^1$ is
1) aryl,
2) heteroaryl,
3) heterocyclyl,
4) $C_2$-$C_6$ alkene-$R^{20}$,
5) $SO_2R^5$,
6) $SO_3R^5$,
7) $SOR^5$,
8) $SONHR^5$,
9) $SO_2NHR^5$,
10) CN,
11) $CO_2R^5$,
12) $COR^5$,
13) $PO_3R^5$,
14) $PO(OR^5)_2$, or
15) $PO(OR^5)$,
wherein the aryl, the heteroaryl, or the heterocyclyl are optionally substituted with one or more $R^{30}$;
$R^2$ is
1) $R^1$; or
2) H,
3) halogen,
4) haloalkyl,
5) $C_1$-$C_6$ alkyl,
6) $C_2$-$C_6$ alkene,
7) $C_3$-$C_7$ cycloalkyl,
8) $OR^9$,
9) $SR^9$,
10) $N^+(R^4)_3$,
10) $OCOR^6$,
11) $OCO_2R^6$,
12) $NR^7R^8$,
13) $NHSO_2R^6$,
14) $NHCOR^6$,
15) aryl,
16) heteroaryl, or
17) heterocyclyl;

$R^3$ is
1) $C_1$-$C_6$ alkyl,
2) aryl-$C_1$-$C_6$ alkyl,
3) heteroaryl, or
4) heterocyclyl;
$R^4$ is
1) OH,
2) $OC_1$-$C_6$ alkyl,
3) $NR^7R^8$, or
4) $NHSO_2R^9$;
$R^5$ is
1) H,
2) $C_1$-$C_6$ alkyl,
3) $C_2$-$C_6$ alkene,
4) $C_3$-$C_7$ cycloalkyl,
5) haloalkyl,
6) aryl,
7) heteroaryl,
8) heterocyclyl,
9) $NHCH_2C(O)OH$, or
10) (D) or (L) natural or non-natural amino acid derivatives optionally protected with an amino acid protecting group;
$R^6$ is
1) any (D) or (L) amino acid residue,
2) $C_1$-$C_6$ alkyl,
3) $C_3$-$C_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents;
$R^7$ and $R^8$ are independently selected from:
1) H,
2) $C_1$-$C_6$ alkyl,
3) $C_3$-$C_7$ cycloalkyl,
4) haloalkyl,
5) aryl,
6) heteroaryl, or
7) heterocyclyl,
wherein the alkyl and the cycloalkyl are optionally substituted with one or more $R^{10}$ substituents, and the aryl, the heteroaryl and the heterocyclyl are optionally substituted with one or more $R^{20}$ substituents;
$R^9$ is
1) H,
2) $C_1$-$C_6$ alkyl,
3) $C_3$-$C_7$ cycloalkyl,
4) aryl,
5) heteroaryl, or
6) heterocyclyl,
in which the alkyl or the cycloalkyl are optionally substituted with one or more $R^{10}$ substituents; and in which the aryl, heteroaryl or heterocyclyl are optionally substituted with one or more $R^{20}$ substituents;
$R^{10}$ is independently selected from:
1) halogen,
2) $C_1$-$C_6$ alkyl,
3) $C_3$-$C_7$ cycloalkyl,
4) haloalkyl,
5) aryl,
6) heteroaryl,
7) heterocyclyl, 8) $OR^9$,
9) $S(O)_mR^9$,
10) $NR^7R^8$,
11) $COR^9$,
12) $C(O)OR^9$,
13) $OC(O)R^9$,
14) $SC(O)R^9$,
15) $CONR^7R^8$, or
16) $S(O)_2NR^7R^8$, wherein m is an integer of 0, 1, or 2;
$R^{20}$ is independently selected from:
1) halogen,
2) $NO_2$,
3) CN,
4) $C_1$-$C_6$ alkyl,
5) haloalkyl,
6) $C_3$-$C_7$ cycloalkyl,
7) $OR^7$,
8) $NR^7R^8$,
9) $SR^7$,
10) aryl,
11) heteroaryl,
12) heterocyclyl,
13) $SO_2R^5$,
14) $SO_3R^5$,
15) $SOR^5$,
16) $SONHR^5$,
17) $SO_2NHR^5$,
18) $PO_3R^5$,
19) $PO(OR^5)_2$,
20) $PO(OR^5)$,
21) $COR^5$,
22) $COR^7$,
23) $CO_2R^7$,
24) $S(O)_mR^7$,
25) $CONR^7R^8$, or
26) $S(O)_2NR^7R^8$, wherein the alkyl and the cycloalkyl are optionally substituted with one or more $R^6$ substituents; and wherein the aryl, the heteroaryl, or the heterocyclyl are optionally substituted with one or more $R^{30}$; wherein m is an integer of 0, 1, or 2;
$R^{30}$ is
1) $NO_2$,
2) $C_2$-$C_6$ alkene-$R^{20}$,
3) $SO_2R^5$,
4) $SOR^5$,
5) $SONHR^5$,
6) $SO_2NHR^5$,
7) CN,
8) $CO_2R^5$,
9) $COR^5$,
10) $PO_3R^5$,
11) $PO(OR^5)_2$, or
12) $PO(OR^5)$;

or a prodrug, or a pharmaceutically acceptable salt, or the compound is labeled with a detectable label or an affinity tag thereof.

In one example, the compounds of Formula IXC include:
A is $PhCH_2OC(O)$—;
$AA_2$ is the (R) or (S) amino acid side chain of Val;
$AA_4$ is the (R) or (S) amino acid side chain of Asp; or $AA_4$ is Asp(β-methyl), Asp(β-ethyl) or Asp(β-tert butyl);
$R^1$ is $SO_2R^5$;
$R^2$ is H or halogen;
$R^4$ is OH or $OC_1$-$C_6$ alkyl; and
$R^5$ is $C_1$-$C_6$ alkyl;
or a pharmaceutically acceptable salt thereof.

Specifically, the compounds of Formula IXC include:
A is $PhCH_2OC(O)$—;
$AA_2$ is the (R) or (S) amino acid side chain of Val;
$AA_4$ is the (R) or (S) amino acid side chain of Asp; or $AA_4$ is Asp(β-methyl), Asp(β-ethyl) or Asp(β-tert butyl);
$R^1$ is $SO_2R^5$;
$R^2$ is H or Cl;
$R^4$ is OH, OMe, $OCH_2CH_3$, or $OC(CH_3)_3$; and
$R^5$ is $CH_3$, $CH_2CH_3$, $CH(CH_3)_2$;
or a pharmaceutically acceptable salt thereof.

More particularly, the compounds of Formula XC include:

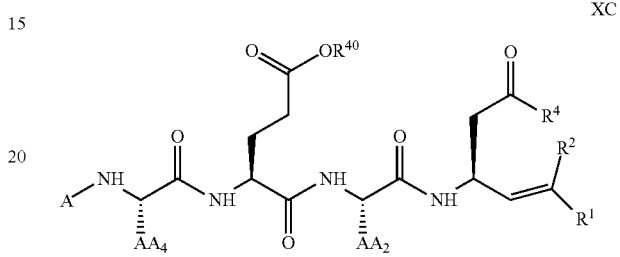

XC wherein
A is
1) H,
2) $C_1$-$C_6$ alkyl,
3) aryl,
4) heteroaryl,
5) heterocyclyl,
6) $R^3$—C(O)—,
7) $R^3$—OC(O)—,
8) $R^3$—$CH_2OC(O)$—,
9) $R^3$—C(O)O—, or
10) $R^3$—$S(O)_2$—;
$AA_2$ is the (R) or (S) amino acid side chain of Val;
$AA_4$ is Asp; or $AA_4$ is Asp(βethyl) or Asp(βtert butyl);
$R^1$ is
1) aryl,
2) heteroaryl,
3) heterocyclyl,
4) $C_2$-$C_6$ alkene-$R^{20}$,
5) $SO_2R^5$,
6) $SO_3R^5$,
7) $SOR^5$,
8) $SONHR^5$,
9) $SO_2NHR^5$,
10) CN,
11) $CO_2R^5$,
12) $COR^5$,
13) $PO_3R^5$,
14) $PO(OR^5)_2$, or
15) $PO(OR^5)$,
wherein the aryl, the heteroaryl, or the heterocyclyl are optionally substituted with one or more $R^{30}$;
$R^2$ is
1) $R^1$; or
2) H,
3) halogen,
4) haloalkyl,
5) $C_1$-$C_6$ alkyl,
6) $C_2$-$C_6$ alkene,
7) $C_3$-$C_7$ cycloalkyl,
8) $OR^9$,
9) $SR^9$, 10) N⁺(R⁴)₃,
10) OCOR⁶,
11) OCO₂R⁶,
12) NR⁷R⁸,
13) NHSO₂R⁶,
14) NHCOR⁶,
15) aryl,
16) heteroaryl, or
17) heterocyclyl;

$R^3$ is
1) $C_1$-$C_6$ alkyl,
2) aryl-$C_1$-$C_6$ alkyl,
3) heteroaryl, or
4) heterocyclyl;

$R^4$ is
1) OH, or
2) O$C_1$-$C_6$ alkyl;

$R^5$ is
1) H,
2) $C_1$-$C_6$ alkyl,
3) $C_2$-$C_6$ alkene,
4) $C_3$-$C_7$ cycloalkyl,
5) haloalkyl,
6) aryl,
7) heteroaryl,
8) heterocyclyl,
9) NHCH₂C(O)OH, or
10) (D) or (L) natural or non-natural amino acid derivatives optionally protected with an amino acid protecting group;

$R^6$ is
1) any (D) or (L) amino acid residue,
2) $C_1$-$C_6$ alkyl,
3) $C_3$-$C_7$ cycloalkyl,
4) aryl,
5) heteroaryl, or
6) heterocyclyl, in which the alkyl or the cycloalkyl are optionally substituted with one or more $R^{10}$ substituents; and in which the aryl, heteroaryl or heterocyclyl are optionally substituted with one or more $R^{20}$ substituents;

$R^7$ and $R^8$ are independently selected from:
1) H,
2) $C_1$-$C_6$ alkyl,
3) $C_3$-$C_7$ cycloalkyl,
4) haloalkyl,
5) aryl,
6) heteroaryl, or
7) heterocyclyl, wherein the alkyl and the cycloalkyl are optionally substituted with one or more $R^{10}$ substituents, and the aryl, the heteroaryl and the heterocyclyl are optionally substituted with one or more $R^{20}$ substituents;

$R^9$ is
1) H,
2) $C_1$-$C_6$ alkyl,
3) $C_3$-$C_7$ cycloalkyl,
4) aryl,
5) heteroaryl, or
6) heterocyclyl, in which the alkyl or the cycloalkyl are optionally substituted with one or more $R^{10}$ substituents; and in which the aryl, heteroaryl or heterocyclyl are optionally substituted with one or more $R^{20}$ substituents;

$R^{10}$ is independently selected from:
1) halogen,
2) $C_1$-$C_6$ alkyl,
3) $C_3$-$C_7$ cycloalkyl,
4) haloalkyl,
5) aryl,
6) heteroaryl,
7) heterocyclyl,
8) OR⁹,
9) S(O)ₘR⁹,
10) NR⁷R⁸,
11) COR⁹,
12) C(O)OR⁹,
13) OC(O)R⁹,
14) SC(O)R⁹,
15) CONR⁷R⁸, or
16) S(O)₂NR⁷R⁸, wherein m is an integer of 0, 1, or 2;

$R^{20}$ is independently selected from:
1) halogen,
2) NO₂,
3) CN,
4) $C_1$-$C_6$ alkyl,
5) haloalkyl,
6) $C_3$-$C_7$ cycloalkyl,
7) OR⁷,
8) NR⁷R⁸,
9) SR⁷,
10) aryl,
11) heteroaryl,
12) heterocyclyl,
13) SO₂R⁵,
14) SO₃R⁵,
15) SOR⁵,
16) SONHR⁵,
17) SO₂NHR⁵,
18) PO₃R⁵,
19) PO(OR⁵)₂,
20) PO(OR⁵),
21) COR⁵,
22) COR⁷,
23) CO₂R⁷,
24) S(O)ₘR⁷,
25) CONR⁷R⁸, or
26) S(O)₂NR⁷R⁸, wherein the alkyl and the cycloalkyl are optionally substituted with one or more $R^6$ substituents; and wherein the aryl, the heteroaryl, or the heterocyclyl are optionally substituted with one or more $R^{30}$; wherein m is an integer of 0, 1, or 2;

$R^{30}$ is
1) NO₂,
2) $C_2$-$C_6$ alkene-$R^{20}$,
3) SO₂R⁵,
4) SOR⁵,
5) SONHR⁵,
6) SO₂NHR⁵,
7) CN,
8) CO₂R⁵,
9) COR⁵,
10) PO₃R⁵,
11) PO(OR⁵)₂, or
12) PO(OR⁵); and $R^{40}$ is
1) H, or
2) $C_1$-$C_6$ alkyl;

or a prodrug, or a pharmaceutically acceptable salt, or the compound is labeled with a detectable label or an affinity tag thereof.

In on example, the compounds of Formula XC include
A is PhCH$_2$OC(O)—;
AA$_2$ is the (R) or (S) amino acid side chain of Val;
AA$_4$ is Asp; or AA$_4$ is Asp(βethyl) or Asp(βtert butyl);
R$^1$ is SO$_2$R$^5$;
R$^2$ is H or halogen;
R$^4$ is OH or OC$_1$-C$_6$ alkyl;
R$^5$ is C$_1$-C$_6$ alkyl; and
R$^{40}$ is H, or C$_1$-C$_6$ alkyl;
or a pharmaceutically acceptable salt thereof.

Specifically, the compounds of Formula XC include:
A is PhCH$_2$OC(O)—;
AA$_2$ is the (R) or (S) amino acid side chain of Val;
AA$_4$ is Asp; or AA$_4$ is Asp(β-ethyl) or Asp(β-tert butyl);
R$^1$ is SO$_2$R$^5$;
R$^2$ is H or Cl;
R$^4$ is OH, OCH$_2$CH$_3$, or OC(CH$_3$)$_3$;
R$^5$ is CH$_3$; and
R$^{40}$ is H, CH$_2$CH$_3$, or C(CH$_3$)$_3$;
or a pharmaceutically acceptable salt thereof.

Caspase 3 Inhibitors

The present invention includes compounds of Formula IIA:

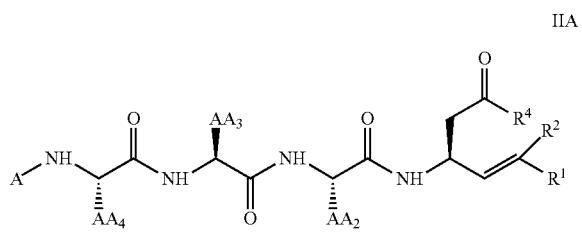

wherein
AA$_2$ is the amino acid side chain of Val, Leu, Pro, Met, Ala, Thr, His, Ser (O-phosphate), Thr (O-phosphate) (wherein the oxygen of the phosphate is free or protected).
AA$_3$ is the amino acid side chain of Trp, Tyr, Ala, Asp, Glu, Gln, Phe, Ser, Thr, Val, Tyr, Gly, Leu; or AA$_3$ is the amino acid side chain of 3-(1-naphtyl)-alanine, phenylglycine, indanylglycine, Ala-(2'-quinolyl), 2-pyridylAla or 4-methyl phenylalanine;
AA$_4$ is the amino acid side chain of Asp;
and wherein A, R$^1$, R$^2$ and R$^4$ are as defined hereinabove and hereinbelow.

Caspase 8/Caspase 9 Inhibitors

The present invention includes compounds of Formula IIA:

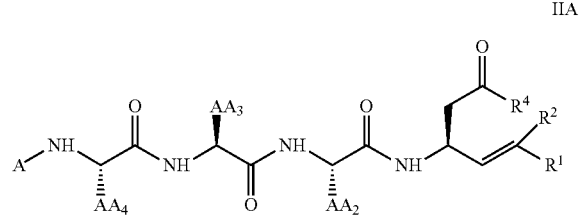

wherein
AA$_2$ is the amino acid side chain of Val, Ala, Thr, or His;
AA$_3$ is the amino acid side chain of Glu, Gln, Asp, Ala, Gly, Thr, Val, Trp; or AA$_3$ is phenylglycine or indanylglycine;
AA$_4$ is the amino acid side chain of Tyr, Trp, Phe, or Asp;
and wherein A, R$^1$, R$^2$ and R$^4$ are as defined hereinabove and hereinbelow.

wherein
AA$_2$ is the amino acid side chain of Tyr, Thr, His, Val, Trp, Ile, or Ala
AA$_3$ is the amino acid side chain of Glu or AA$_3$ is Ala-(2'-quinolyl);
AA$_4$ is the amino acid side chain of Ile, Leu, Glu, Asp, Ala, Pro, Val or 4-methyl phenylalanine;
and wherein A, R$^1$, R$^2$ and R$^4$ are as defined hereinabove and hereinbelow.

Caspase 2 Inhibitors

The present invention includes compounds of Formula IIIA

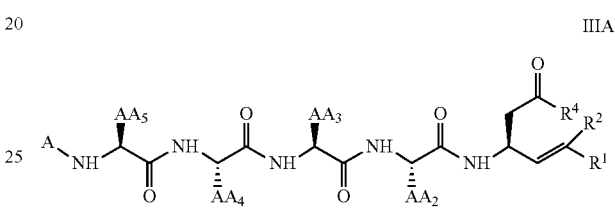

wherein
AA$_2$ is the amino acid side chain of Ala, Ser, Lys or Val;
AA$_3$ is the amino acid side chain of Val, Glu, Thr, or Gln;
AA$_4$ is the amino acid side chain of Asp, or Leu;
AA$_5$ is the amino acid side chain of Val or Leu;
and wherein A, R$^1$, R$^2$ and R$^4$ are as defined hereinabove and hereinbelow.

Caspase 1 Inhibitors

The present invention includes compounds of Formula IIA (caspase 1 inhibitors)

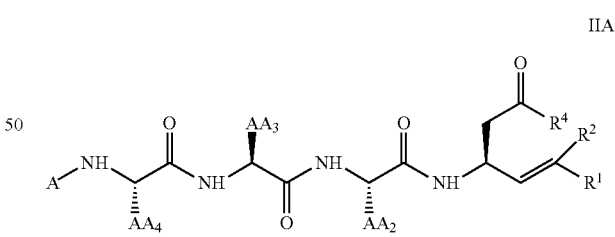

Compounds and intermediate compounds synthesized include those in Table 1 and Table 2:

TABLE 1

| CPD N° | CPD NAME | STRUCTURE |
| --- | --- | --- |
| 1 | Fmoc-Ala(2'-quinolyl)-Val-OAllyl | 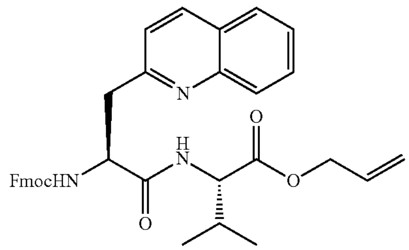 |
| 2 | Ala(2'-quinolyl)-Val-OAllyl | 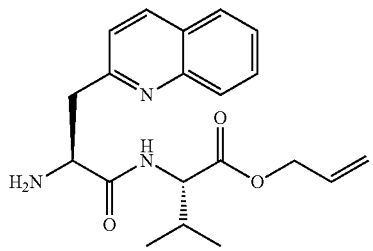 [SMILES: C=CCOC(=O)[C@@H](NC(=O)[C@@H](N)Cc1ccc2ccccc2n1)C(C)C] |
| 3 | Cbz-Asp(O-tBu)-Ala(2'-quinolyl)-Val-OAllyl | 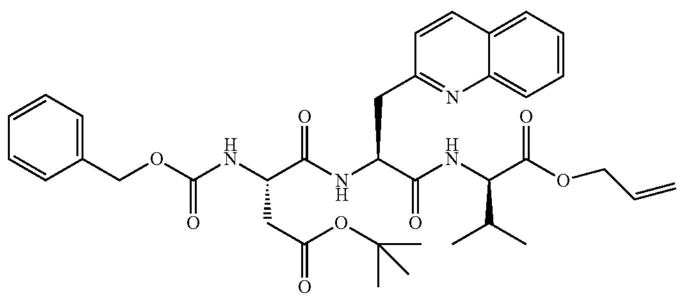 [SMILES: C=CCOC(=O)[C@H](NC(=O)[C@H](Cc1ccc2ccccc2n1)NC(=O)[C@H](CC(=O)OC(C)(C)C)NC(=O)OCc1ccccc1)C(C)C] |
| 4 | Cbz-Asp(O-tBu)-Ala(2'-quinolyl)-ValOH | 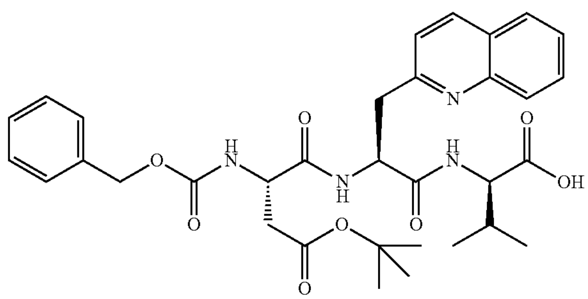 [SMILES: CC(C)[C@@H](NC(=O)[C@H](Cc1ccc2ccccc2n1)NC(=O)[C@H](CC(=O)OC(C)(C)C)NC(=O)OCc1ccccc1)C(=O)O] |
| 5 | Ts-Ala(2'-quinolyl)-Val-OH | 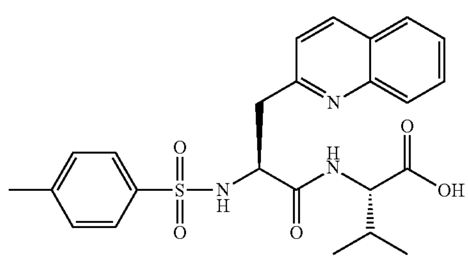 [SMILES: Cc1ccc(S(=O)(=O)N[C@@H](Cc2ccc3ccccc3n2)C(=O)N[C@H](C(=O)O)C(C)C)cc1] |

TABLE 1-continued

| CPD N° | CPD NAME | STRUCTURE |
|---|---|---|
| 6 | Ts-Ala(2'-quinolyl)-OH | 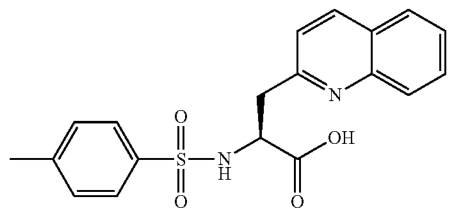 [SMILES: Cc1ccc(S(=O)(=O)N[C@@H](Cc2ccc3ccccc3n2)C(=O)O)cc1] |
| 7 | Ts-Ala(2'-quinolyl)-Val-OAllyl | 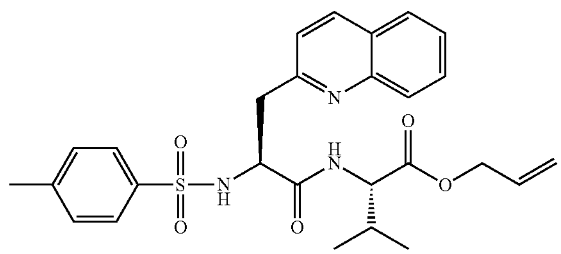 [SMILES: C=CCOC(=O)[C@@H](NC(=O)[C@H](Cc1ccc2ccccc2n1)NS(=O)(=O)c1ccc(C)cc1)C(C)C] |
| 8 | Z-Asp(OtBu)-Tyr(OtBu)-Val-Asp(OtBu)methyl vinyl sulfone | 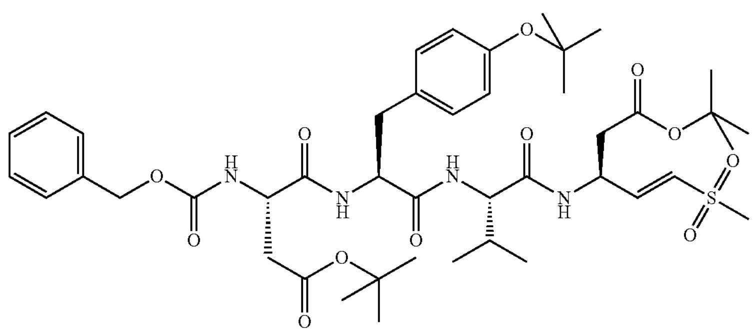 [SMILES: CC(C)[C@H](NC(=O)[C@H](Cc1ccc(OC(C)(C)C)cc1)NC(=O)[C@H](CC(=O)OC(C)(C)C)NC(=O)OCc1ccccc1)C(=O)N[C@H](/C=C/S(C)(=O)=O)CC(=O)OC(C)(C)C] |
| 9 | Fmoc-Indanyl-glycine-Val-OAllyl | 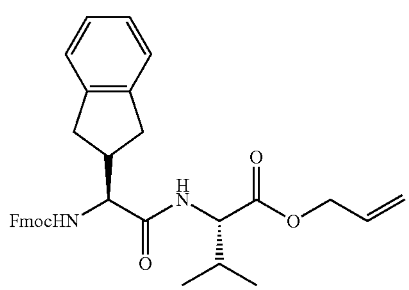 |
| 10 | Indanyl-glycine-Val-OAllyl | 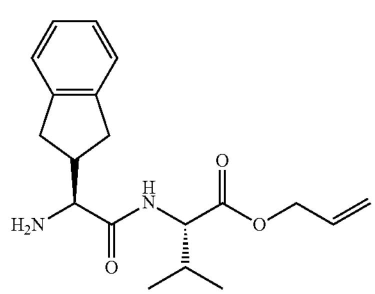 [SMILES: C=CCOC(=O)[C@@H](NC(=O)[C@@H](N)C1Cc2ccccc2C1)C(C)C] |

TABLE 1-continued

| CPD N° | CPD NAME | STRUCTURE |
|---|---|---|
| 11 | Cbz-Asp(O-tBu)-Indanyl-glycine-Val-OAllyl | 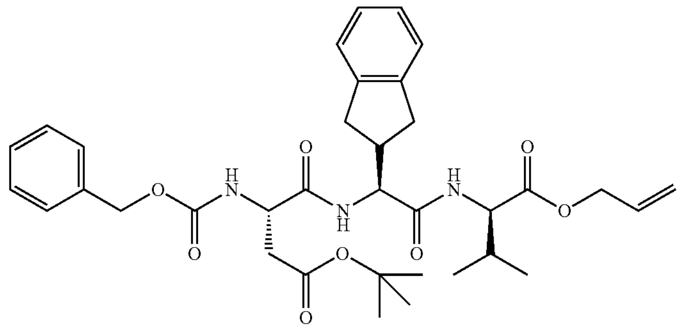 [SMILES: C=CCOC(=O)[C@H](NC(=O)[C@@H](NC(=O)[C@H](CC(=O)OC(C)(C)C)NC(=O)OCc1ccccc1)C1Cc2ccccc2C1)C(C)C] |
| 12 | Cbz-Asp(O-tBu)-Indanyl-glycine-Val-OH | 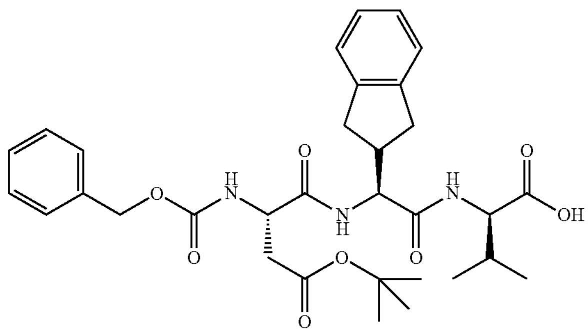 [SMILES: CC(C)[C@@H](NC(=O)[C@@H](NC(=O)[C@H](CC(=O)OC(C)(C)C)NC(=O)OCc1ccccc1)C1Cc2ccccc2C1)C(=O)O] |
| 13 | Fmoc-Phg-Val-OAllyl | 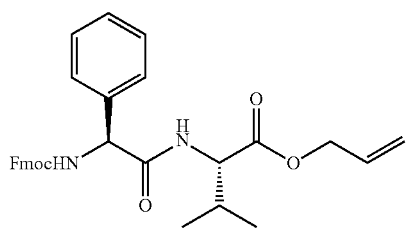 |
| 14 | Phg-Val-OAllyl | 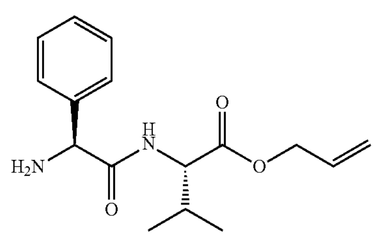 [SMILES: C=CCOC(=O)[C@@H](NC(=O)[C@@H](N)c1ccccc1)C(C)C] |
| 15 | Z-Asp(β-tert-Butyl)-Phg-Val-OAllyl. | 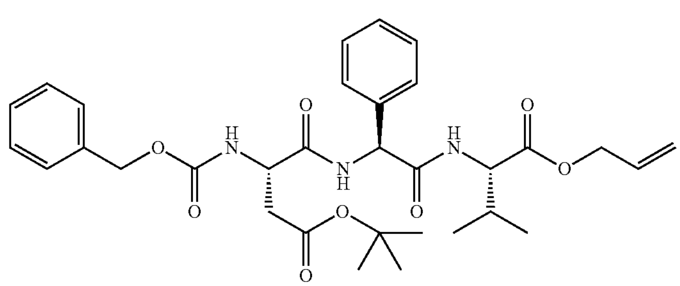 [SMILES: C=CCOC(=O)[C@@H](NC(=O)[C@@H](NC(=O)[C@H](CC(=O)OC(C)(C)C)NC(=O)OCc1ccccc1)c1ccccc1)C(C)C] |

TABLE 1-continued
| CPD N° | CPD NAME | STRUCTURE |
|---|---|---|
| 16 | Z-Asp(β-tert-Butyl)-Phg-Val-OH. | 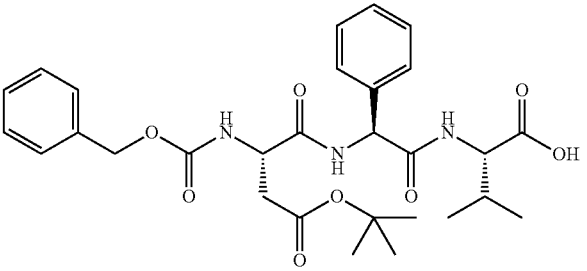 [SMILES: CC(C)[C@H](NC(=O)[C@@H](NC(=O)[C@H](CC(=O)OC(C)(C)C)NC(=O)OCc1ccccc1)c1ccccc1)C(=O)O] |
| 17 | Fmoc-Glu(O-tBu)-Val-OAllyl | 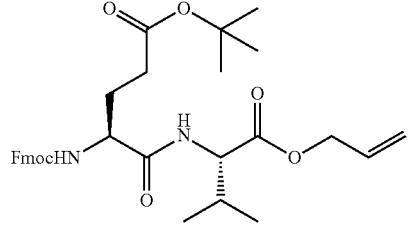 |
| 18 | Glu(O-tBu)-Val-OAllyl | 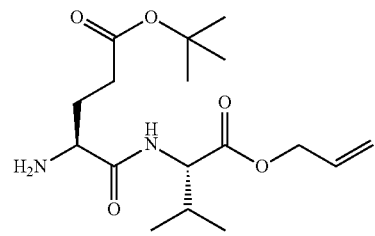 |
| 19 | Cbz-Asp(O-tBu)-Glu(O-tBu)-Val-OAllyl | 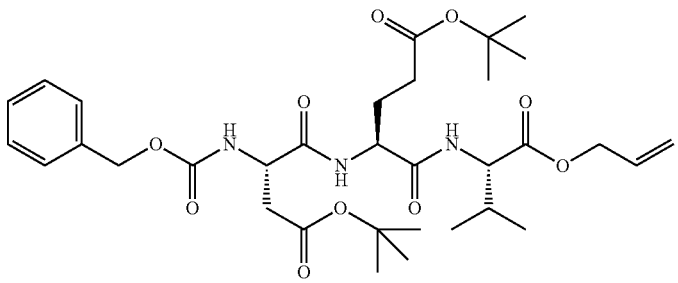 [SMILES: C=CCOC(=O)[C@@H](NC(=O)[C@H](CCC(=O)OC(C)(C)C)NC(=O)[C@H](CC(=O)OC(C)(C)C)NC(=O)OCc1ccccc1)C(C)C] |
| 20 | Cbz-Asp(O-tBu)-Glu(O-tBu)-Val-OH | 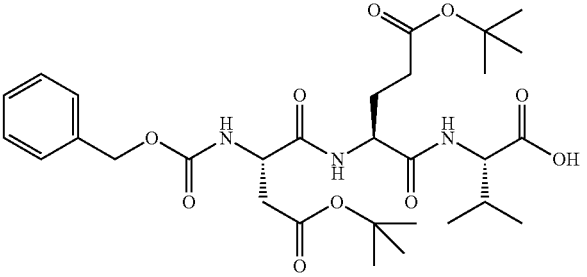 [SMILES: CC(C)[C@H](NC(=O)[C@H](CCC(=O)OC(C)(C)C)NC(=O)[C@H](CC(=O)OC(C)(C)C)NC(=O)OCc1ccccc1)C(=O)O] |
| 21 | Diethyl chloro (methyl-sulfone) methylphosphonate | 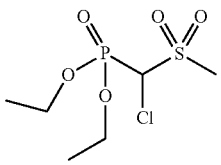 |

TABLE 1-continued

| CPD N° | CPD NAME | STRUCTURE |
|---|---|---|
| 22 | Boc-Asp (β-tert-butyl) αchlorovinyl methylsulfone | 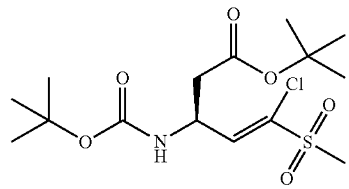 [SMILES: CC(C)(C)OC(=O)C[C@@H](/C=C(\Cl)S(C)(=O)=O)NC(=O)OC(C)(C)C] |
| 23 | Asp(β-tert-butyl)αchlorovinlyl methylsulfone tosyl salt | 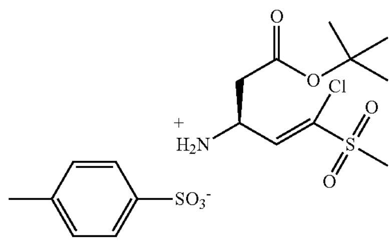 |
| 24 | Diethyl chloro (phenylsulfone) methyl phosphonate | 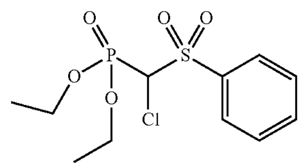 [SMILES: CCOP(=O)(OCC)C(Cl)S(=O)(=O)c1ccccc1] |
| 25 | Boc-Asp(β-tert-butyl) αchlorovinyl phenylsulfone | 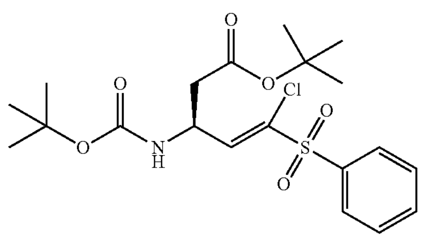 [SMILES: CC(C)(C)OC(=O)C[C@@H](/C=C(\Cl)S(=O)(=O)c1ccccc1)NC(=O)OC(C)(C)C] |
| 26 | Asp(β-tert-butyl)αchlorovinlyl phenylsulfone tosyl salt | 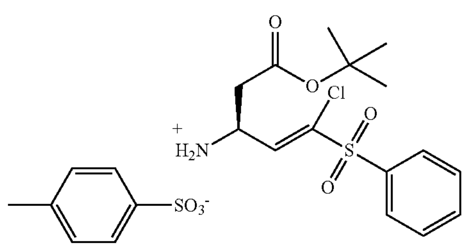 |
| 27 | Boc-Aspartimol (β-Methyl) | 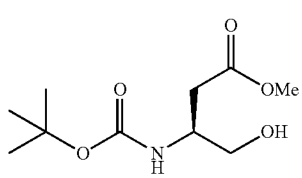 [SMILES: COC(=O)C[C@@H](CO)NC(=O)OC(C)(C)C] |
| 28 | Boc-Asp(β-Methyl)-H | 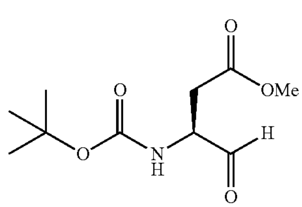 [SMILES: COC(=O)C[C@@H](C=O)NC(=O)OC(C)(C)C] |

TABLE 1-continued

| CPD N° | CPD NAME | STRUCTURE |
|---|---|---|
| 29 | Boc-Asp(β-Methyl) methyl vinyl sulfone | 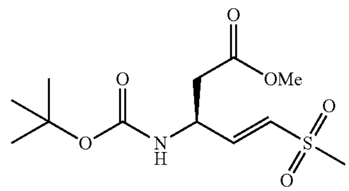 [SMILES: COC(=O)C[C@@H](/C=C/S(C)(=O)=O)NC(=O)OC(C)(C)C] |
| 30 | Boc-Asp(β-Methyl) methyl vinyl sulfone tosyl salt | 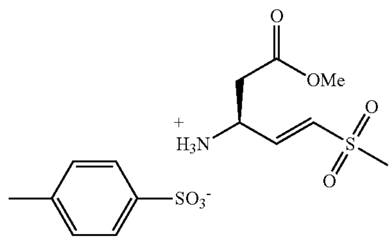 |
| 31 | Diethyl (methylsulfone) methylphosphonate | 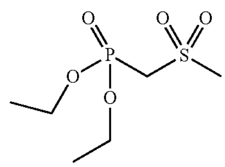 |
| 32 | Boc-Asp(β-tert-butyl) methyl vinyl sulfone | 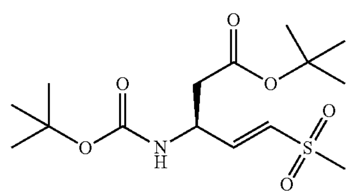 [SMILES: CC(C)(C)OC(=O)C[C@@H](/C=C/S(C)(=O)=O)NC(=O)OC(C)(C)C] |
| 33 | Asp(β-tert-butyl)methyl vinyl sulfone tosyl salt | 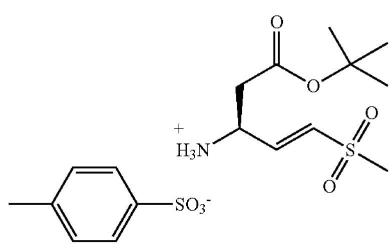 |
| 34 | Diethyl phenylsulfonylmethylphosphonate | 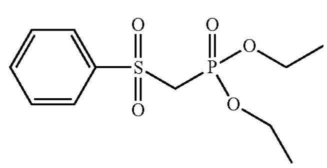 [SMILES: CCOP(=O)(CS(=O)(=O)c1ccccc1)OCC] |
| 35 | Boc-Asp(β-tert-Butyl)-H | 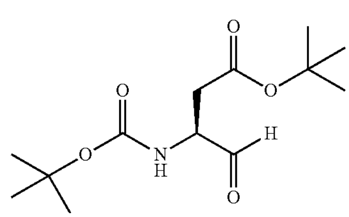 [SMILES: CC(C)(C)OC(=O)C[C@@H](C=O)NC(=O)OC(C)(C)C] |

TABLE 1-continued
| CPD N° | CPD NAME | STRUCTURE |
|---|---|---|
| 36 | Boc-Asp-vinyl phenyl sulfone | 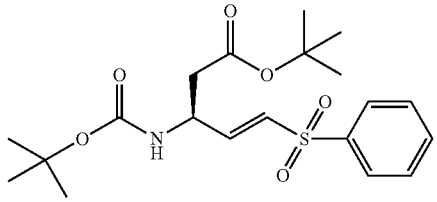 [SMILES: CC(C)(C)OC(=O)C[C@@H](/C=C/S(=O)(=O)c1ccccc1)NC(=O)OC(C)(C)C] |
| 37 | AspVinyl phenyl sulfone tosyl salt | 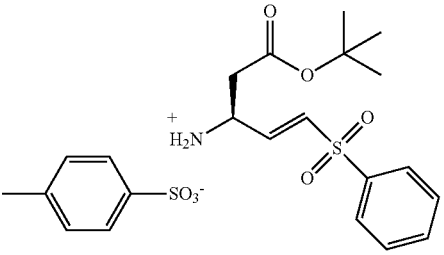 |
| 38 | Diethyl (phenoxy-sulfone) methylphosphonate | 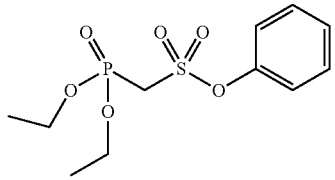 [SMILES: CCOP(=O)(CS(=O)(=O)Oc1ccccc1)OCC] |
| 39 | Asp(β-tert-butyl) phenoxy vinyl sulfone | 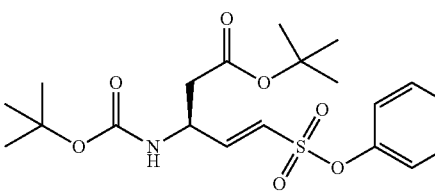 |
| 40 | Asp(β-tert-butyl) phenoxy vinyl sulfone tosyl salt | 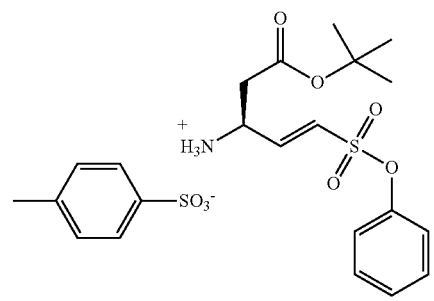 |
| 41 | Diethyl (isopropyl-sulfone) methylphosphonate | 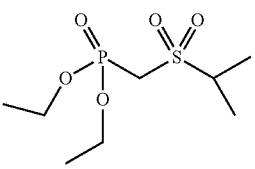 |
| 42 | BocAsp(β-tert-butyl) isopropyl vinyl sulfone | 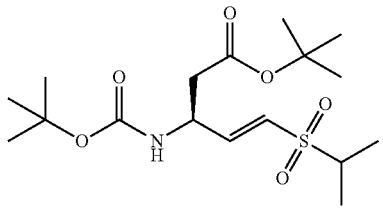 [SMILES: CC(C)S(=O)(=O)/C=C/[C@H](CC(=O)OC(C)(C)C)NC(=O)OC(C)(C)C] |

TABLE 1-continued

| CPD N° | CPD NAME | STRUCTURE |
|---|---|---|
| 43 | Asp(β-tert-butyl) isopropyl vinyl sulfone tosyl salt | 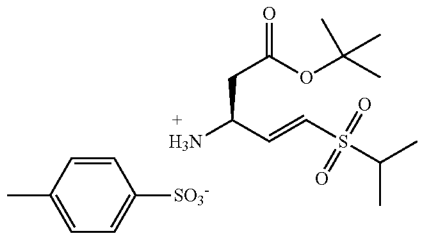 |
| 44 | Diethyl (morpholine-sulfone) methylphosphonate | 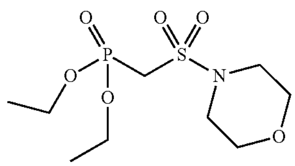 [SMILES: CCOP(=O)(CS(=O)(=O)N1CCOCC1)OCC] |
| 45 | Boc-Asp(β-tert-butyl) morpholine vinyl sulfone | 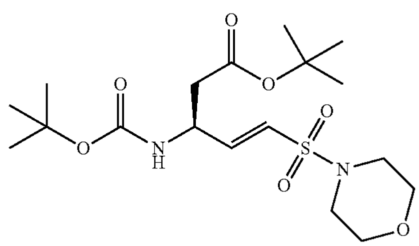 [SMILES: CC(C)(C)OC(=O)C[C@@H](/C=C/S(=O)(=O)N1CCOCC1)NC(=O)OC(C)(C)C] |
| 46 | Asp(β-tert-butyl) morpholine vinyl sulfone tosyl salt | 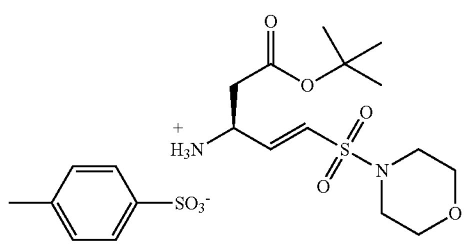 |
| 47 | Z-Asp(β-tert-Butyl)-Ala(2'-quinolyl)-Val-Asp(β-tert-Butyl)αchlorovinyl methylsulfone | 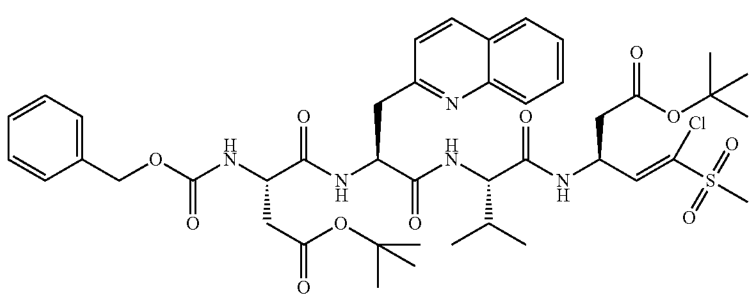 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C(\Cl)S(C)(=O)=O)CC(=O)OC(C)(C)C] |
| 48 | Z-Asp-Ala(2'-quinolyl)-Val-Asp-αchlorovinyl methylsulfone | 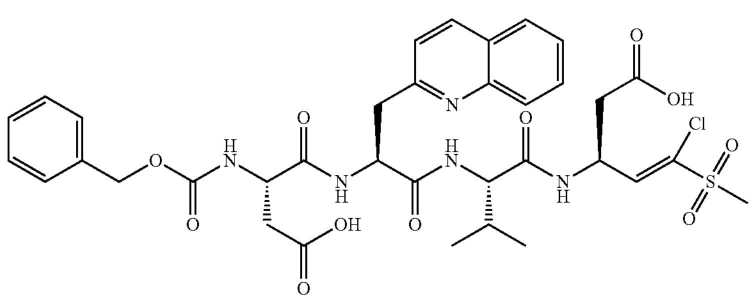 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C(\Cl)S(C)(=O)=O)CC(=O)O] |

TABLE 1-continued

| CPD N° | CPD NAME | STRUCTURE |
|---|---|---|
| 49 | Ts-Ala(2'-quinolyl)-Val-Asp(β-tert-Butyl)αchlorovinyl methylsulfone | 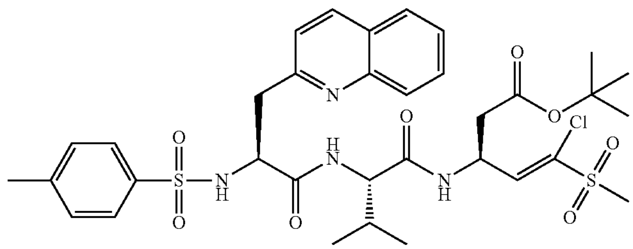 [SMILES: Cc1ccc(S(=O)(=O)N[C@@H](Cc2ccc3ccccc3n2)C(=O)N[C@H](C(=O)N[C@H](/C=C(\Cl)S(C)(=O)=O)CC(=O)OC(C)(C)C)C(C)C)cc1] |
| 50 | Ts-Ala(2'-quinolyl)-Val-Asp-αchlorovinyl methylsulfone | 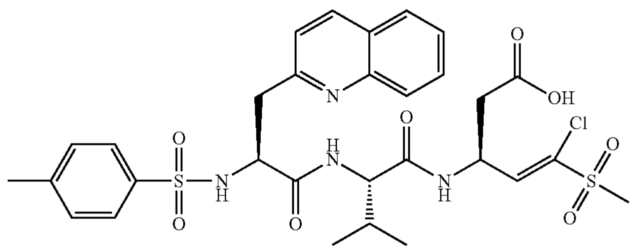 |
| 51 | Z-Asp(β-methyl)-Indanylglycine-Val-Asp(β-methyl) methyl vinyl sulfone | 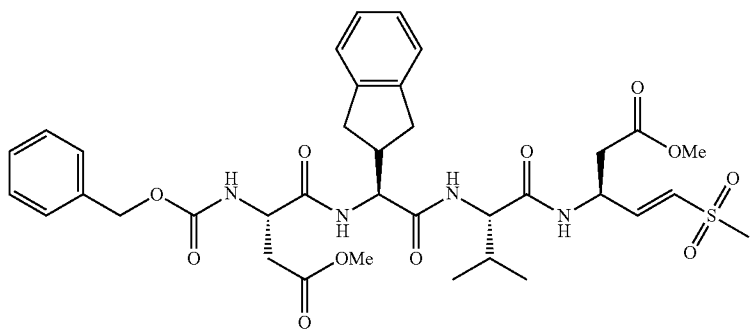 [SMILES: COC(=O)C[C@@H](/C=C/S(C)(=O)=O)NC(=O)[C@@H](NC(=O)[C@@H](NC(=O)[C@H](CC(=O)OC)NC(=O)OCc1ccccc1)C1Cc2ccccc2C1)C(C)C] |
| 52 | Z-Asp(β-tert-Butyl)-Phg-Val-Asp (β-tert-Butyl)methyl vinyl sulfone | 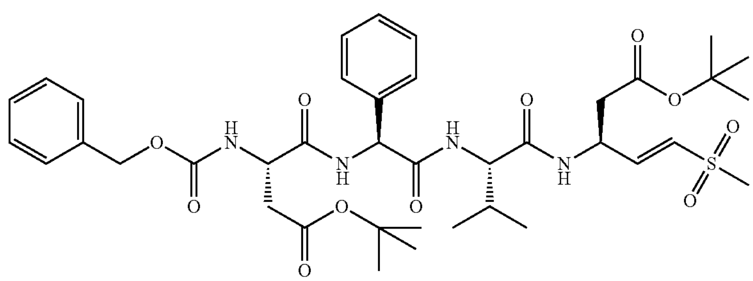 [SMILES: CC(C)[C@H](NC(=O)[C@@H](NC(=O)[C@H](CC(=O)OC(C)(C)C)NC(=O)OCc1ccccc1)c1ccccc1)C(=O)N[C@H](/C=C/S(C)(=O)=O)CC(=O)OC(C)(C)C] |
| 53 | Z-Asp-Phg-Val-Asp methyl vinyl sulfone | 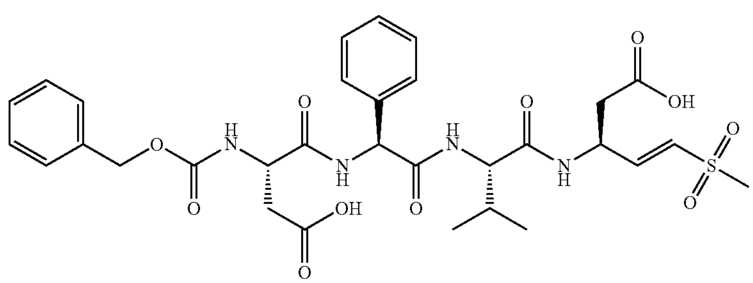 [SMILES: CC(C)[C@H](NC(=O)[C@@H](NC(=O)[C@H](CC(=O)O)NC(=O)OCc1ccccc1)c1ccccc1)C(=O)N[C@H](/C=C/S(C)(=O)=O)CC(=O)O] |

TABLE 1-continued
| CPD N° | CPD NAME | STRUCTURE |
|---|---|---|
| 54 | Z-Asp(β-tert-Butyl)-Al(2'-quinolyl)-Val-Asp(β-tert-Butyl)methyl vinyl sulfone | 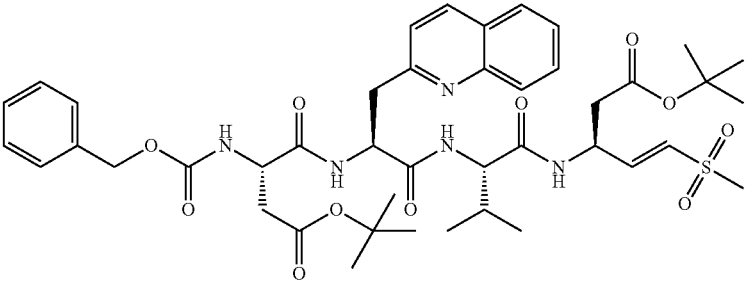 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(C)(=O)=O)CC(=O)OC(C)(C)C] |
| 55 | Z-Asp-Ala(2'-quinolyl)-Val-Aspmethyl-vinyl sulfone | 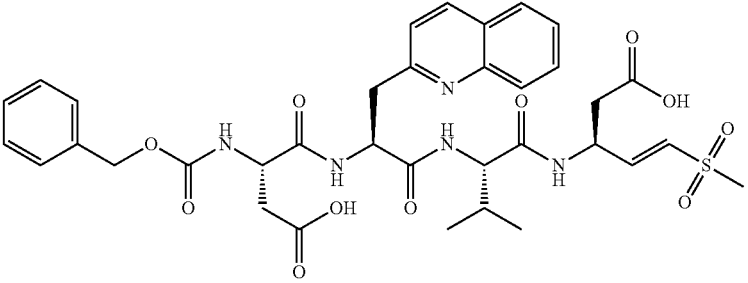 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(C)(=O)=O)CC(=O)O] |
| 56 | Z-Asp(β-tert-Butyl)-Indanyl-glycine-Val-Asp(β-tert-Butyl)methyl vinyl sulfone | 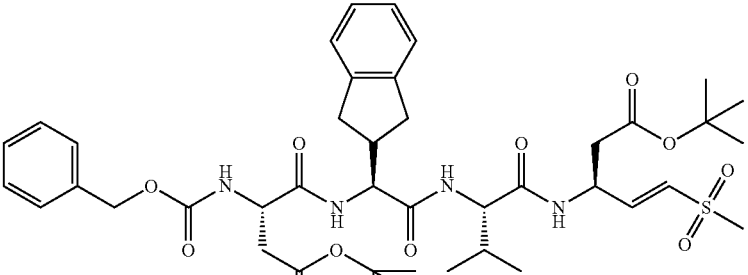 |
| 57 | Z-Asp-Indanyl-glycine-Val-Aspmethyl vinyl sulfone | 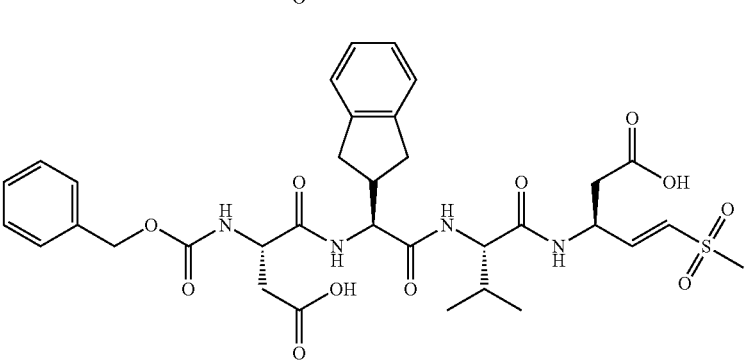 |
| 58 | Z-Asp(β-tert-Butyl)-Glu(β-tert-Butyl)-Val-Asp(β-tert-Butyl)methyl vinyl sulfone | 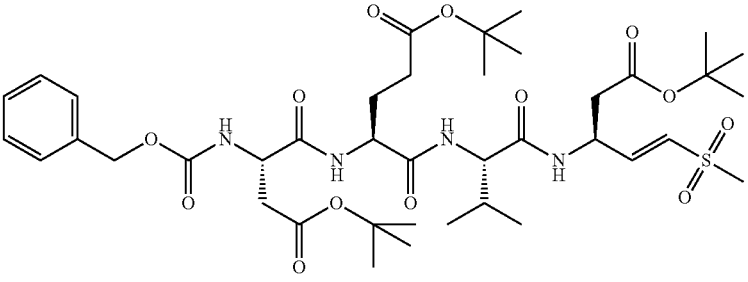 [SMILES: CC(C)[C@H](NC(=O)[C@H](CCC(=O)OC(C)(C)C)NC(=O)[C@H](CC(=O)OC(C)(C)C)NC(=O)OCc1ccccc1)C(=O)N[C@H](/C=C/S(C)(=O)=O)CC(=O)OC(C)(C)C] |

TABLE 1-continued

| CPD N° | CPD NAME | STRUCTURE |
|---|---|---|
| 59 | Z-Asp-Glu-Val-Aspmethyl vinyl sulfone | 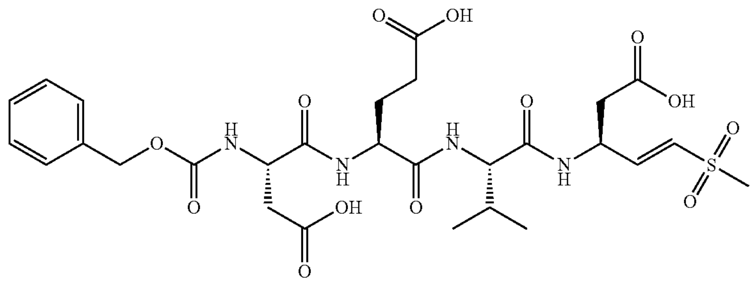 [SMILES: CC(C)[C@H](NC(=O)[C@H](CCC(=O)O)NC(=O)[C@H](CC(=O)O)NC(=O)OCc1ccccc1)C(=O)N[C@H](/C=C/S(C)(=O)=O)CC(=O)O] |
| 60 | Z-Val-Asp(β-tert-Butyl) methyl vinyl sulfone | 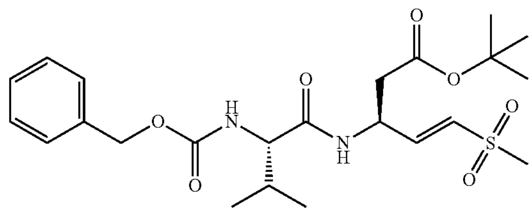 [SMILES: CC(C)[C@H](NC(=O)OCc1ccccc1)C(=O)N[C@H](/C=C/S(C)(=O)=O)CC(=O)OC(C)(C)C] |
| 61 | Z-Val-Aspmethyl vinyl sulfone | 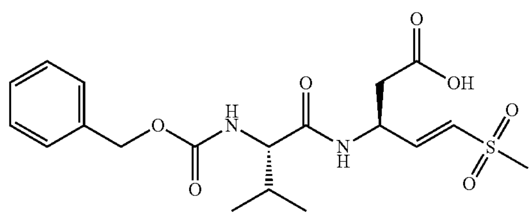 [SMILES: CC(C)[C@H](NC(=O)OCc1ccccc1)C(=O)N[C@H](/C=C/S(C)(=O)=O)CC(=O)O] |
| 62 | Z-Asp(β-tert-Butyl)-Ala(2'-quinolyl)-Val-Asp(β-tert-Butyl)phenyl vinyl sulfone | 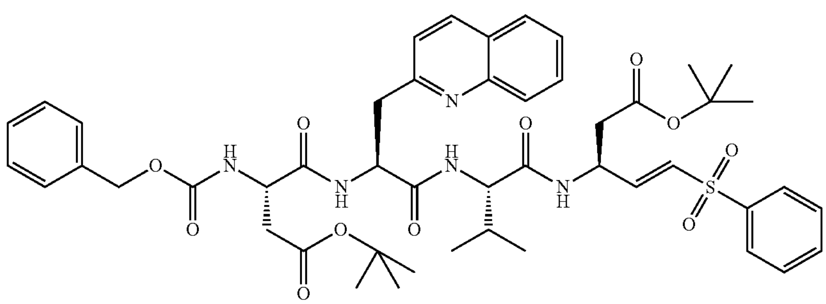 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(=O)(=O)c1ccccc1)CC(=O)OC(C)(C)C] |
| 63 | Z-Asp-Ala(2'-quinolyl)-Val-Aspphenyl vinyl sulfone | 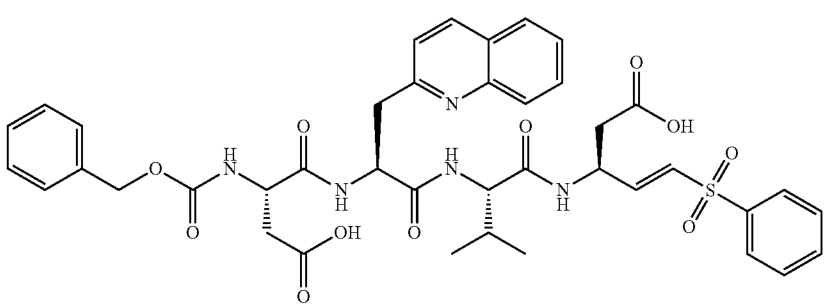 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(=O)(=O)c1ccccc1)CC(=O)O] |

TABLE 1-continued

| CPD N° | CPD NAME | STRUCTURE |
|---|---|---|
| 64 | Z-Asp(β-tert-Butyl)-Ala(2'-quinolyl)-Val-Asp(β-tert-Butyl)phenoxy vinyl sulfone | 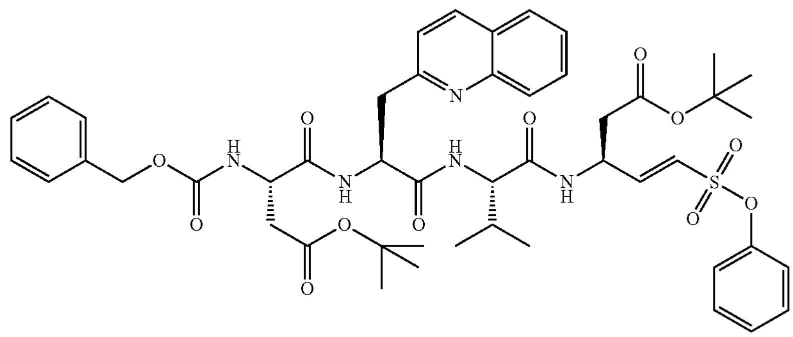 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(=O)(=O)Oc1ccccc1)CC(=O)OC(C)(C)C] |
| 65 | Z-Asp-Ala(2'-quinolyl)-Val-Aspphenoxy vinyl sulfone | 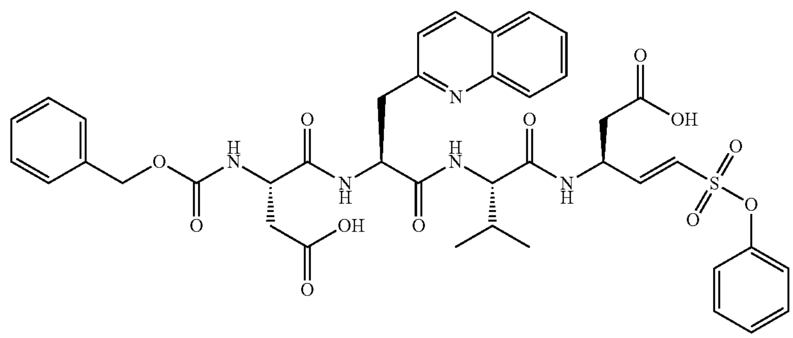 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(=O)(=O)Oc1ccccc1)CC(=O)O] |
| 66 | Z-Asp(β-tert-Butyl)-Ala(2'-quinolyl)-Val-Asp(β-tert-Butyl) morpholine vinyl sulfone | 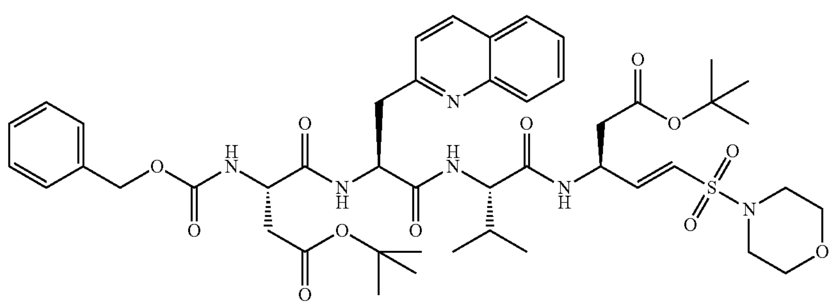 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(=O)(=O)N1CCOCC1)CC(=O)OC(C)(C)C] |
| 67 | Z-Asp-Ala(2'-quinolyl)-Val-Aspmorpholine vinyl sulfone | 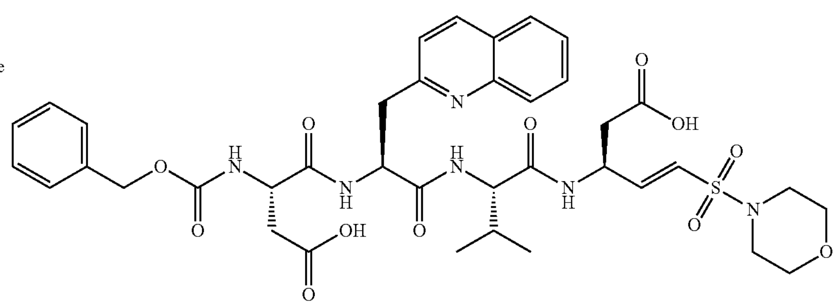 |
| 68 | Z-Asp-Indanyl-glycine-Val-Aspisopropyl vinyl sulfone | 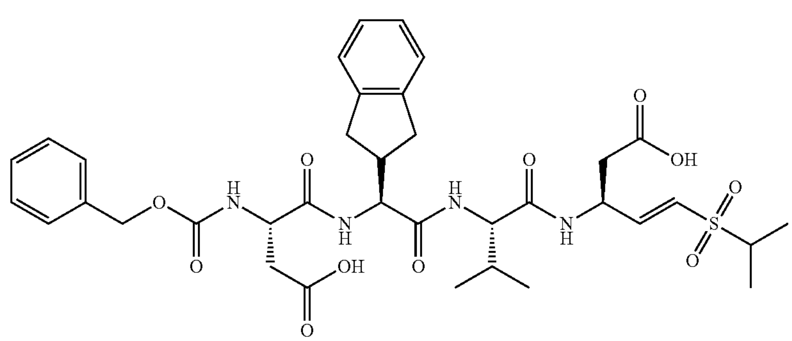 [SMILES: CC(C)[C@H](NC(=O)[C@@H](NC(=O)[C@H](CC(=O)O)NC(=O)OCc1ccccc1)C1Cc2ccccc2C1)C(=O)N[C@H](/C=C/S(=O)(=O)C(C)C)CC(=O)O] |

TABLE 1-continued

| CPD N° | CPD NAME | STRUCTURE |
|---|---|---|
| 69 | Z-Asp-Phg-Val-Asp-phenyl vinylsulfone | 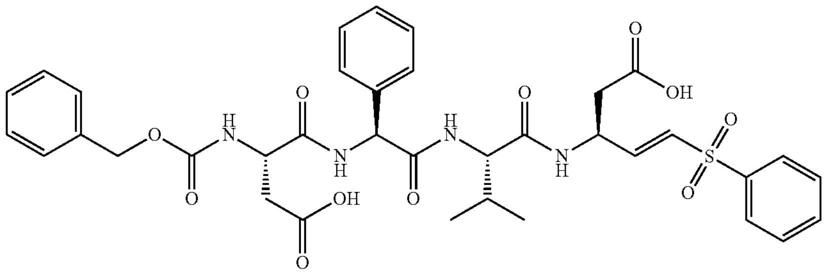 [SMILES: CC(C)[C@H](NC(=O)[C@@H](NC(=O)[C@H](CC(=O)O)NC(=O)OCc1ccccc1)c1ccccc1)C(=O)N[C@H](/C=C/S(=O)(=O)c1ccccc1)CC(=O)O] |
| 70 | Z-Asp-(D,L Ala(2'-quinolyl))-Val-Aspphenyl vinylsulfone | 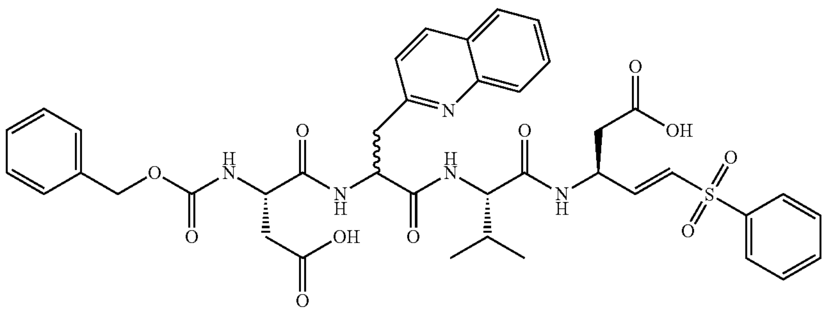 [SMILES: CC(C)[C@H](NC(=O)C(Cc1ccc2ccccc2n1)NC(=O)[C@H](CC(=O)O)NC(=O)OCc1ccccc1)C(=O)N[C@H](/C=C/S(=O)(=O)c1ccccc1)CC(=O)O] |
| 71 | Z-Asp-(D,L Ala(2'-quinolyl))-Val-Aspmethyl vinylsulfone | 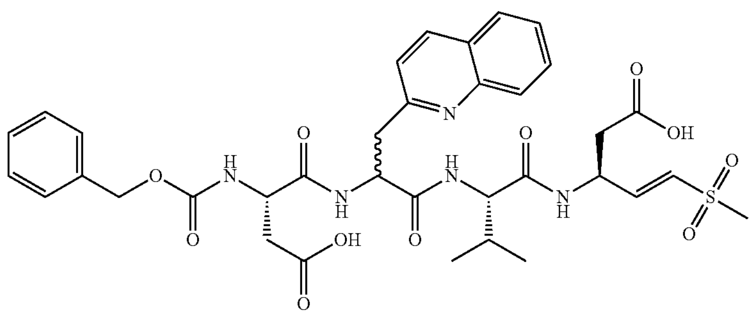 [SMILES: CC(C)[C@H](NC(=O)C(Cc1ccc2ccccc2n1)NC(=O)[C@H](CC(=O)O)NC(=O)OCc1ccccc1)C(=O)N[C@H](/C=C/S(C)(=O)=O)CC(=O)O] |
| 72 | Fmoc-Tyr(O-tBu)-Val-Oallyl | 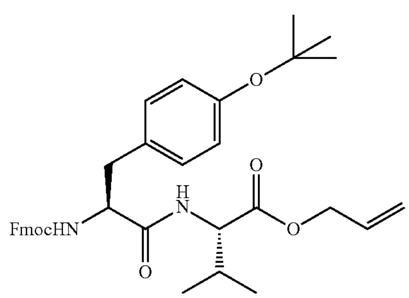 |
| 73 | Tyr(O-tBu)-Val-Oallyl | 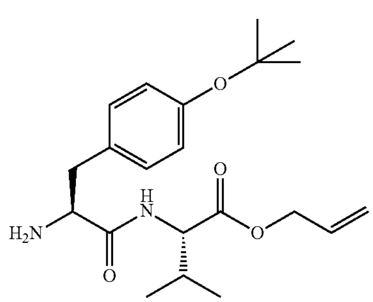 [SMILES: C=CCOC(=O)[C@@H](NC(=O)[C@@H](N)Cc1ccc(OC(C)(C)C)cc1)C(C)C] |

TABLE 1-continued

| CPD N° | CPD NAME | STRUCTURE |
| --- | --- | --- |
| 74 | Z-Asp(O-tBu)-Tyr(O-tBu)-Val-Oallyl | 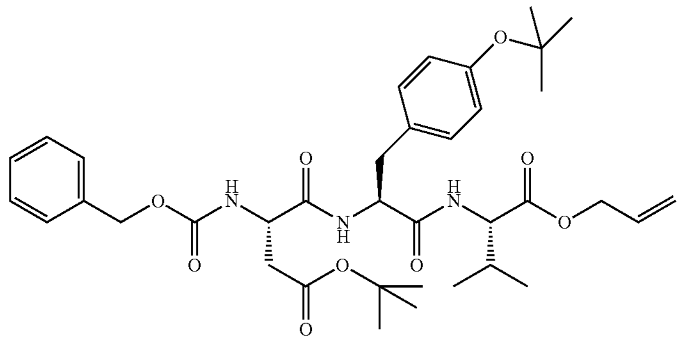 [SMILES: C=CCOC(=O)[C@@H](NC(=O)[C@H](Cc1ccc(OC(C)(C)C)cc1)NC(=O)[C@H](CC(=O)OC(C)(C)C)NC(=O)OCc1ccccc1)C(C)C] |
| 75 | Z-Asp(O-tBu)-Tyr(O-tBu)-Val-OH | 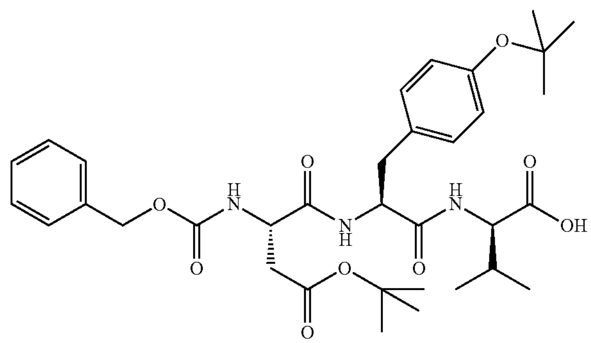 [SMILES: CC(C)[C@@H](NC(=O)[C@H](Cc1ccc(OC(C)(C)C)cc1)NC(=O)[C@H](CC(=O)OC(C)(C)C)NC(=O)OCc1ccccc1)C(=O)O] |
| 76 | Z-Asp-Tyr-Val-Aspmethyl vinyl sulfone | 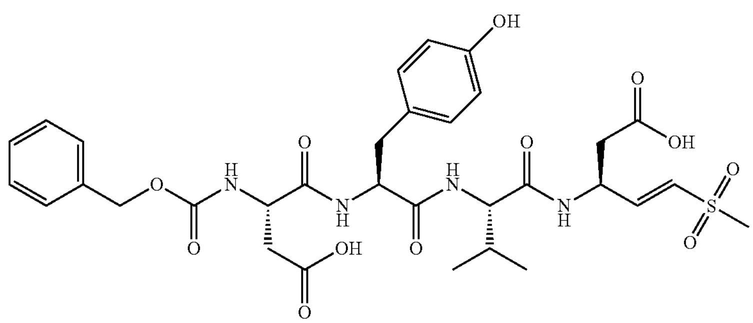 [SMILES: CC(C)[C@H](NC(=O)[C@H](Cc1ccc(O)cc1)NC(=O)[C@H](CC(=O)O)NC(=O)OCc1ccccc1)C(=O)N[C@H](/C=C/S(C)(=O)=O)CC(=O)O] |
| 77 | Fmoc-Glu(O-tBu)-Val-Oallyl | 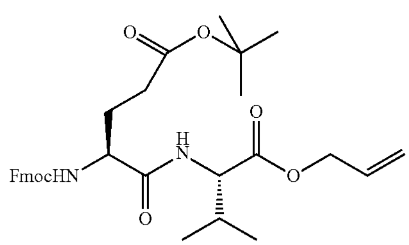 |
| 78 | Glu(O-tBu)-Val-Oallyl | 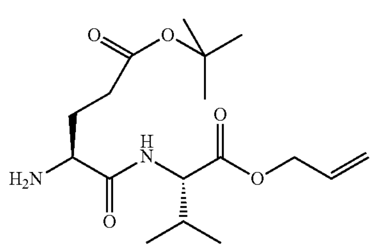 [SMILES: C=CCOC(=O)[C@@H](NC(=O)[C@@H](N)CCC(=O)OC(C)(C)C)C(C)C] |

TABLE 1-continued

| CPD N° | CPD NAME | STRUCTURE |
|---|---|---|
| 79 | Z-Tyr(O-tBu)-Glu(O-tBu)-Val-Oallyl | 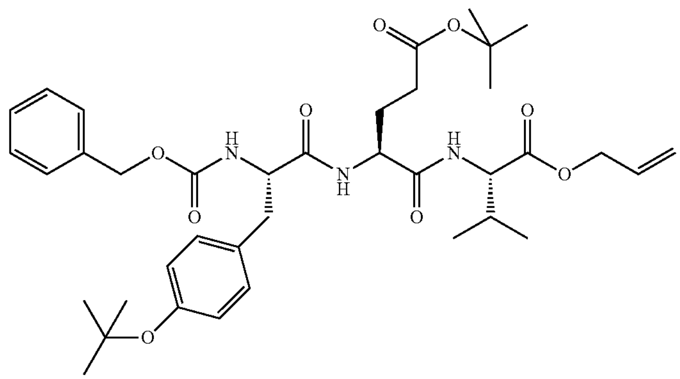 [SMILES: C=CCOC(=O)[C@@H](NC(=O)[C@H](CCC(=O)OC(C)(C)C)NC(=O)[C@H](Cc1ccc(OC(C)(C)C)cc1)NC(=O)OCc1ccccc1)C(C)C] |
| 80 | Z-Tyr(O-tBu)-Glu(O-tBu)-Val-OH | 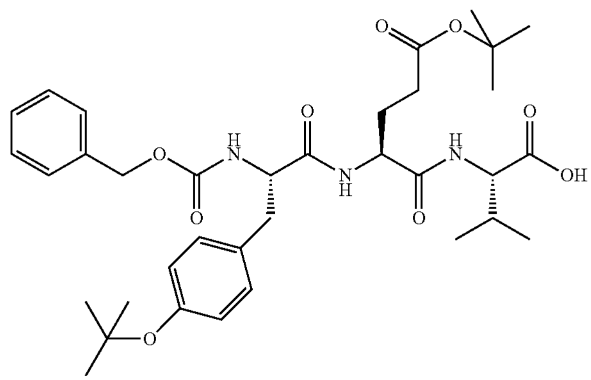 [SMILES: CC(C)[C@H](NC(=O)[C@H](CCC(=O)OC(C)(C)C)NC(=O)[C@H](Cc1ccc(OC(C)(C)C)cc1)NC(=O)OCc1ccccc1)C(=O)O] |
| 81 | Z-Tyr(O-tBu)-Glu(O-tBu)-Val-Asp(OtBu) methyl vinyl sulfone | 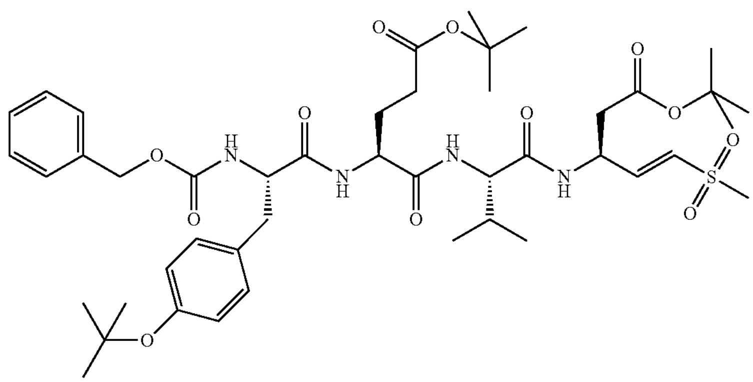 [SMILES: CC(C)[C@H](NC(=O)[C@H](CCC(=O)OC(C)(C)C)NC(=O)[C@H](Cc1ccc(OC(C)(C)C)cc1)NC(=O)OCc1ccccc1)C(=O)N[C@H](/C=C/S(C)(=O)=O)CC(=O)OC(C)(C)C] |
| 82 | Z-Tyr-Glu-Val-Aspmethyl vinyl sulfone | 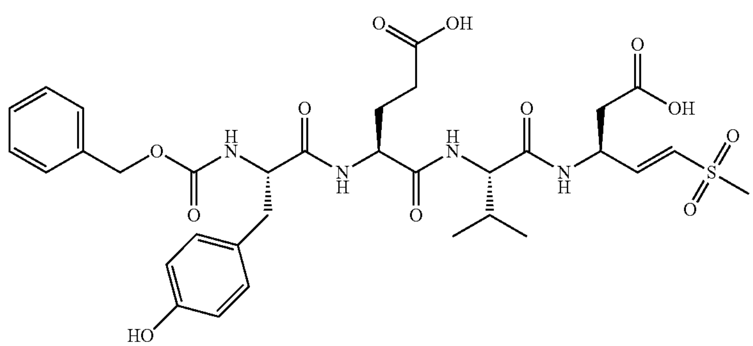 [SMILES: CC(C)[C@H](NC(=O)[C@H](CCC(=O)O)NC(=O)[C@H](Cc1ccc(O)cc1)NC(=O)OCc1ccccc1)C(=O)N[C@H](/C=C/S(C)(=O)=O)CC(=O)O] |

TABLE 1-continued

| CPD N° | CPD NAME | STRUCTURE |
|---|---|---|
| 83 | Z-Asp(O-tBu)-Ala-(2'-pyridine)-Val-OH | 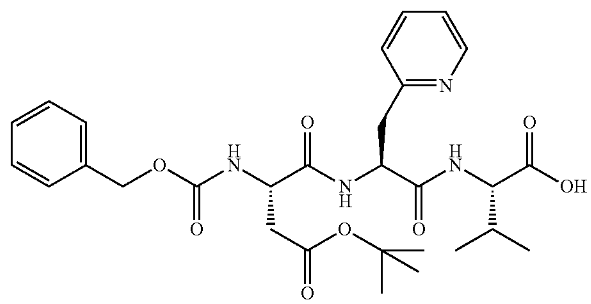 [SMILES: CC(C)[C@H](NC(=O)[C@H](Cc1ccccn1)NC(=O)[C@H](CC(=O)OC(C)(C)C)NC(=O)OCc1ccccc1)C(=O)O] |
| 84 | Z-Asp(O-tBu)-Ala-(2'-pyridine)-Val-Asp(O-tBu) phenyl vinyl sulfone | 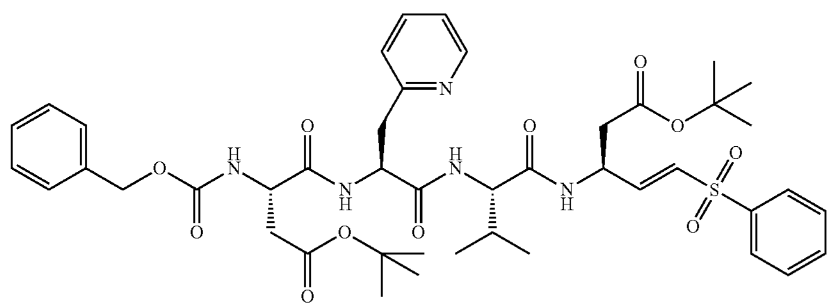 [SMILES: CC(C)[C@H](NC(=O)[C@H](Cc1ccccn1)NC(=O)[C@H](CC(=O)OC(C)(C)C)NC(=O)OCc1ccccc1)C(=O)N[C@H](/C=C/S(=O)(=O)c1ccccc1)CC(=O)OC(C)(C)C] |
| 85 | Z-Asp-Ala(2'-pyridyl)-Val-Aspphenyl vinylsulfone | 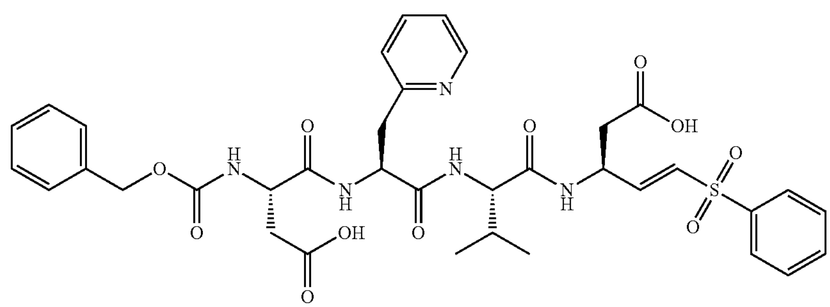 [SMILES: CC(C)[C@H](NC(=O)[C@H](Cc1ccccn1)NC(=O)[C@H](CC(=O)O)NC(=O)OCc1ccccc1)C(=O)N[C@H](/C=C/S(=O)(=O)c1ccccc1)CC(=O)O] |
| 86 | Z-Asp(O-tBu)-Trp-Val-OH | 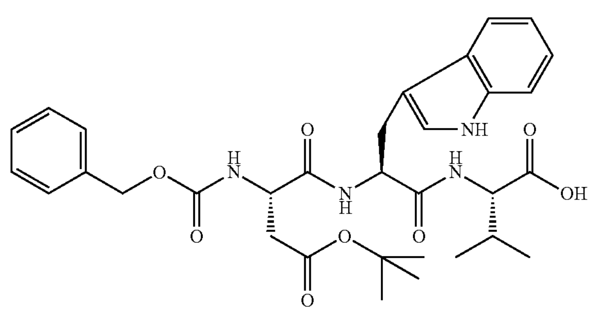 [SMILES: CC(C)[C@H](NC(=O)[C@H](Cc1c[nH]c2ccccc12)NC(=O)[C@H](CC(=O)OC(C)(C)C)NC(=O)OCc1ccccc1)C(=O)O] |
| 87 | Z-Asp(O-tBu)-Trp-Val-Asp(OtBu)methyl vinyl sulfone | 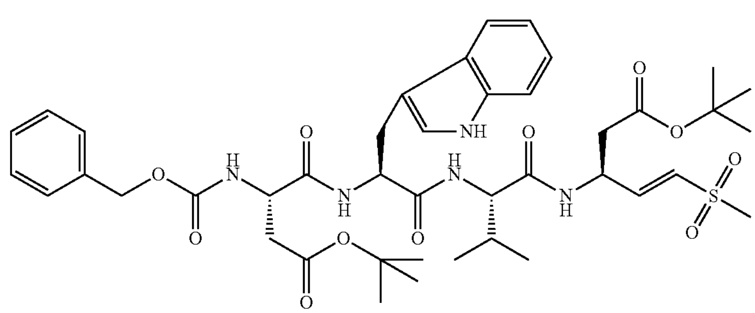 [SMILES: CC(C)[C@H](NC(=O)[C@H](Cc1c[nH]c2ccccc12)NC(=O)[C@H](CC(=O)OC(C)(C)C)NC(=O)OCc1ccccc1)C(=O)N[C@H](/C=C/S(C)(=O)=O)CC(=O)OC(C)(C)C] |

TABLE 1-continued

| CPD N° | CPD NAME | STRUCTURE |
|---|---|---|
| 88 | Z-Asp-Trp-Val-Aspmethyl vinyl sulfone | 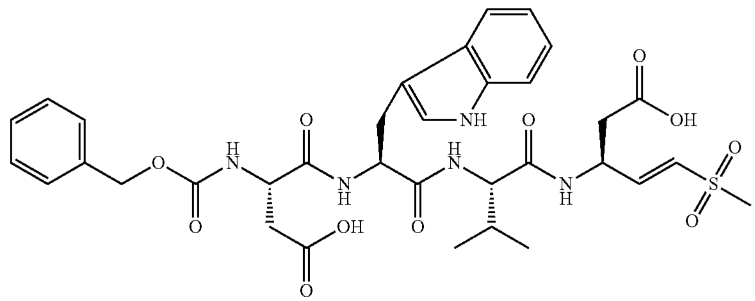 [SMILES: CC(C)[C@H](NC(=O)[C@H](Cc1c[nH]c2ccccc12)NC(=O)[C@H](CC(=O)O)NC(=O)OCc1ccccc1)C(=O)N[C@H](/C=C/S(C)(=O)=O)CC(=O)O] |
| 89 | Boc-Asp(β-methyll) αchlorovinyl methylsulfone | 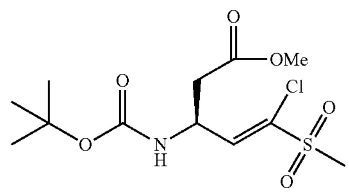 [SMILES: COC(=O)C[C@@H](/C=C(\Cl)S(C)(=O)=O)NC(=O)OC(C)(C)C] |
| 90 | Asp(β-methyll) αchlorovinyl methylsulfone tosyl salt | 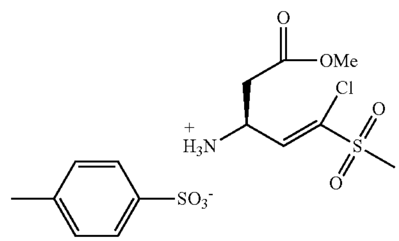 |
| 91 | Boc-Asp(β-methyll) αmethoxyvinyl methylsulfone | 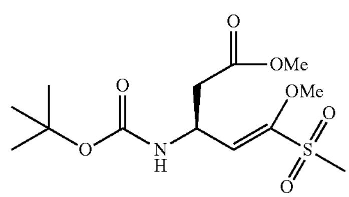 [SMILES: COC(=O)C[C@@H](/C=C(\OC)S(C)(=O)=O)NC(=O)OC(C)(C)C] |
| 92 | Asp(β-methyll) αmethoxyvinyl methylsulfone tosyl salt | 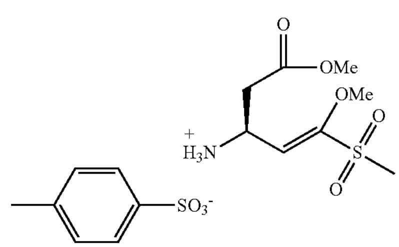 |
| 93 | Aspmethyl vinyl sulfone tosyl salt | 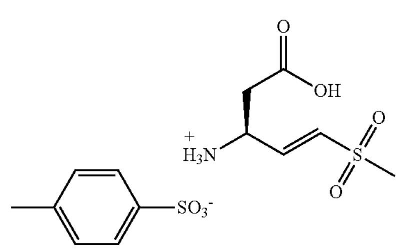 |

TABLE 1-continued

| CPD N° | CPD NAME | STRUCTURE |
|---|---|---|
| 94 | Z-Tyr(OtBu)-Val-Ala-OH | 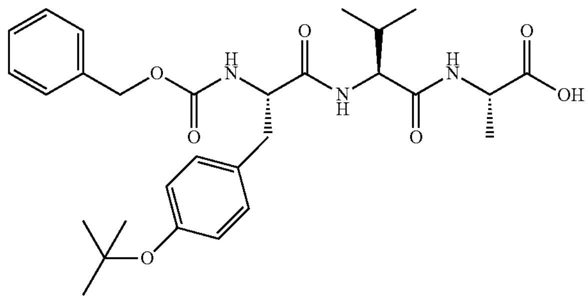 [SMILES: CC(C)[C@H](NC(=O)[C@H](Cc1ccc(OC(C)(C)C)cc1)NC(=O)OCc1ccccc1)C(=O)N[C@@H](C)C(=O)O] |
| 95 | Z-Tyr(OtBu)-Val-Ala-Asp(OtBu) phenyl vinyl sulfone | 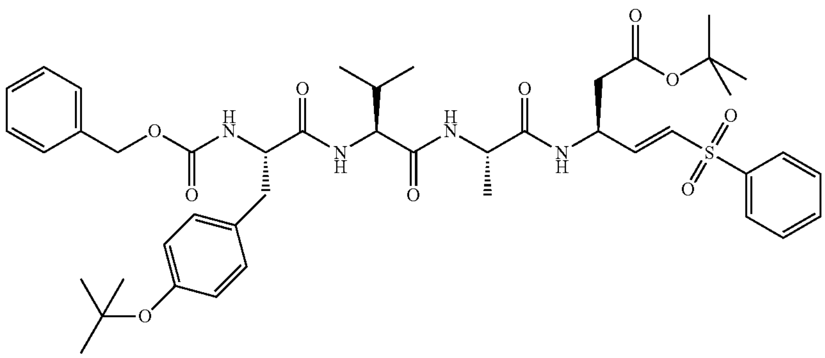 [SMILES: CC(C)[C@H](NC(=O)[C@H](Cc1ccc(OC(C)(C)C)cc1)NC(=O)OCc1ccccc1)C(=O)N[C@@H](C)C(=O)N[C@H](/C=C/S(=O)(=O)c1ccccc1)CC(=O)OC(C)(C)C] |
| 96 | Z-Tyr-Val-Ala-Asp phenyl vinyl sulfone | 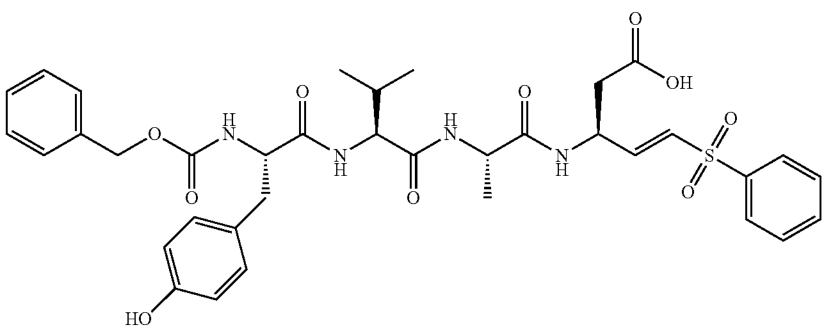 [SMILES: CC(C)[C@H](NC(=O)[C@H](Cc1ccc(O)cc1)NC(=O)OCc1ccccc1)C(=O)N[C@@H](C)C(=O)N[C@H](/C=C/S(=O)(=O)c1ccccc1)CC(=O)O] |
| 97 | 2-Quinaldic acid-Asp(β-tert-Butyl)-methyl vinyl sulfone | 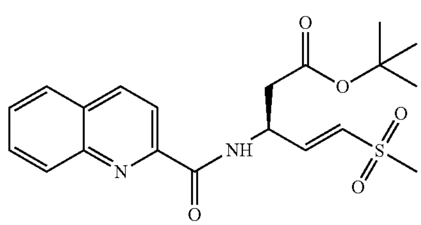 [SMILES: CC(C)(C)OC(=O)C[C@@H](/C=C/S(C)(=O)=O)NC(=O)c1ccc2ccccc2n1] |
| 98 | 2-Quinaldic acid-Asp-methyl vinyl sulfone | 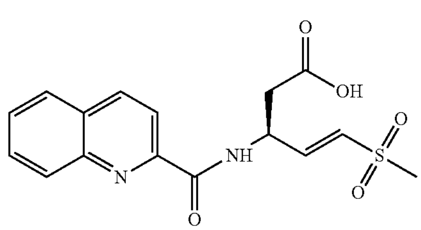 [SMILES: CS(=O)(=O)/C=C/[C@H](CC(=O)O)NC(=O)c1ccc2ccccc2n1] |

TABLE 1-continued

| CPD N° | CPD NAME | STRUCTURE |
|---|---|---|
| 99 | Cbz-Asp(β-methyl)-phenylglycine-Val-Oallyl | 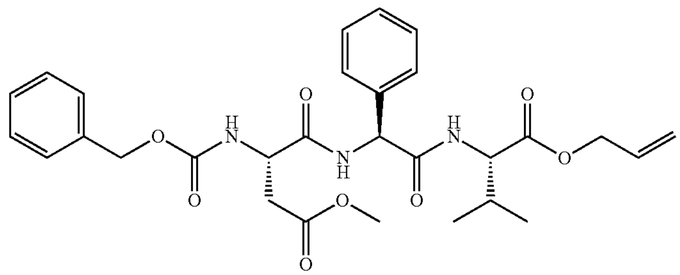 [SMILES: C=CCOC(=O)[C@@H](NC(=O)[C@@H](NC(=O)[C@H](CC(=O)OC)NC(=O)OCc1ccccc1)c1ccccc1)C(C)C] |
| 100 | Cbz-Asp(βmethyl)Phenylglycine-Val-OH | 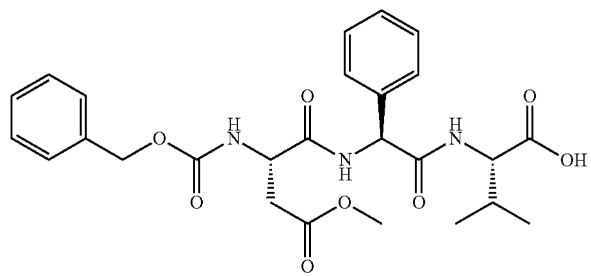 [SMILES: COC(=O)C[C@H](NC(=O)OCc1ccccc1)C(=O)N[C@H](C(=O)N[C@H](C(=O)O)C(C)C)c1ccccc1] |
| 101 | Z-Asp(β-methyl)-phenylglycine-Val-Asp(β-methyl)methyl vinyl sulfone | 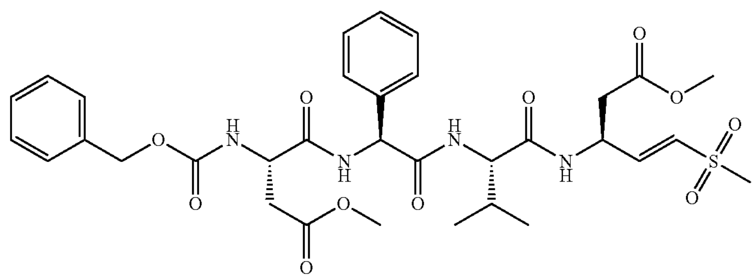 [SMILES: COC(=O)C[C@@H](/C=C/S(C)(=O)=O)NC(=O)[C@@H](NC(=O)[C@@H](NC(=O)[C@H](CC(=O)OC)NC(=O)OCc1ccccc1)c1ccccc1)C(C)C] |
| 102 | Cbz-Asp(β-methyl)-Indanylglycine-Val-OAllyl | 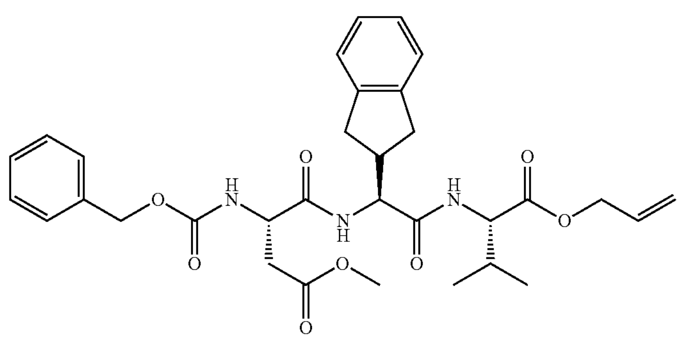 [SMILES: C=CCOC(=O)[C@@H](NC(=O)[C@@H](NC(=O)[C@H](CC(=O)OC)NC(=O)OCc1ccccc1)C1Cc2ccccc2C1)C(C)C] |
| 103 | Cbz-Asp(β-methyl)-Indanylglycine-Val-OH | 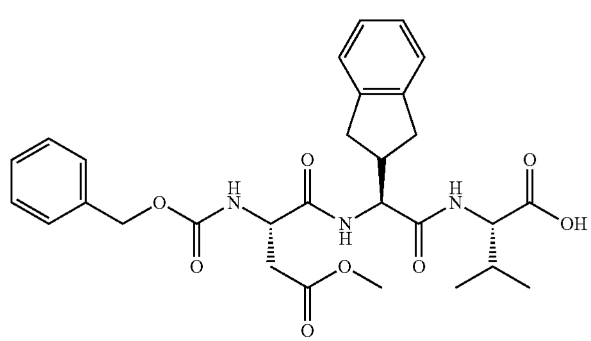 [SMILES: COC(=O)C[C@H](NC(=O)OCc1ccccc1)C(=O)N[C@H](C(=O)N[C@H](C(=O)O)C(C)C)C1Cc2ccccc2C1] |

TABLE 1-continued

| CPD N° | CPD NAME | STRUCTURE |
|---|---|---|
| 104 | Z-Asp(β-methyl)-phenylglycine-Val-Asp(β-methyl) αchlorovinyl methylsulfone | 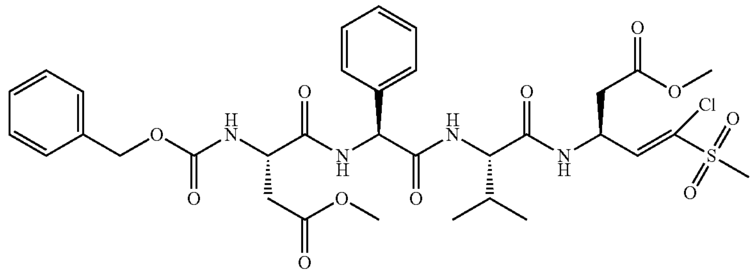 [SMILES: COC(=O)C[C@@H](/C=C(\Cl)S(C)(=O)=O)NC(=O)[C@@H](NC(=O)[C@@H](NC(=O)[C@H](CC(=O)OC)NC(=O)OCc1ccccc1)c1ccccc1)C(C)C] |
| 105 | Z-Asp(β-methyl)-indanylglycine-Val-Asp(β-methyl) αchlorovinyl methylsulfone | 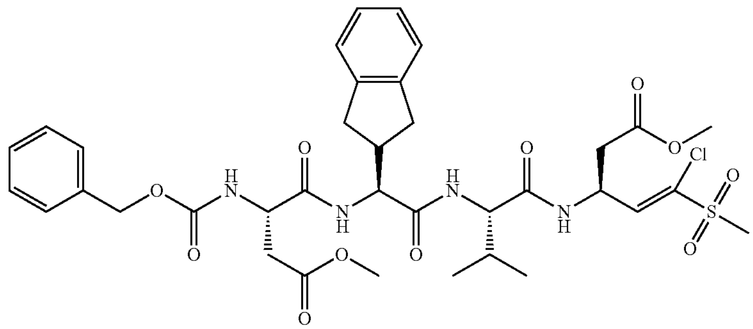 [SMILES: COC(=O)C[C@@H](/C=C(\Cl)S(C)(=O)=O)NC(=O)[C@@H](NC(=O)[C@@H](NC(=O)[C@H](CC(=O)OC)NC(=O)OCc1ccccc1)C1Cc2ccccc2C1)C(C)C] |
| 106 | Fmoc-3-(1-naphtyl)-L-alanine-Val-O-allyl | 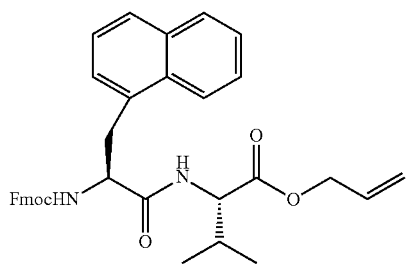 |
| 107 | 3-(1-naphtyl)-L-alanine-Val-O-allyl | 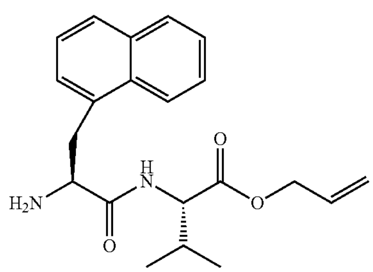 [SMILES: C=CCOC(=O)[C@@H](NC(=O)[C@@H](N)Cc1cccc2ccccc12)C(C)C] |
| 108 | Cbz-Asp(O-tBu)-3-(1-naphtyl)-L-alanine-Val-O-allyl | 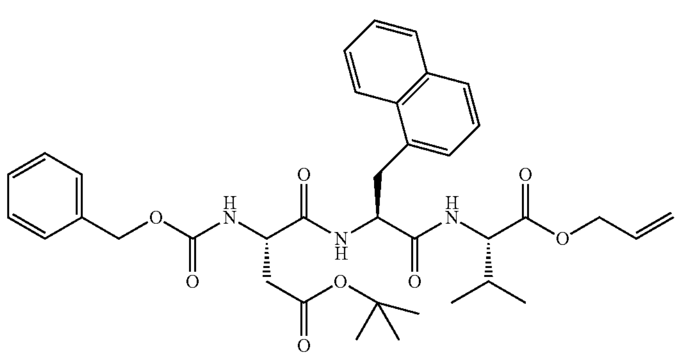 [SMILES: C=CCOC(=O)[C@@H](NC(=O)[C@H](Cc1cccc2ccccc12)NC(=O)[C@H](CC(=O)OC(C)(C)C)NC(=O)OCc1ccccc1)C(C)C] |

TABLE 1-continued

| CPD N° | CPD NAME | STRUCTURE |
|---|---|---|
| 109 | Cbz-Asp(O-tBu)-3-(1-naphtyl)-L-alanine-Val-OH | 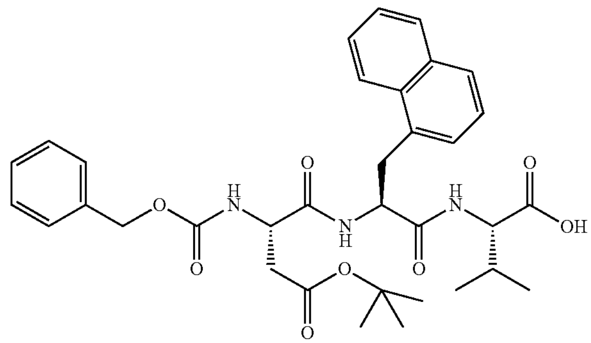 [SMILES: CC(C)[C@H](NC(=O)[C@H](Cc1cccc2ccccc12)NC(=O)[C@H](CC(=O)OC(C)(C)C)NC(=O)OCc1ccccc1)C(=O)O] |
| 110 | Z-Asp(β-tert-Butyl)-3-(1-naphtyl)-L-alanine-Val-Asp(β-tert-Butyl)methyl vinyl sulfone | 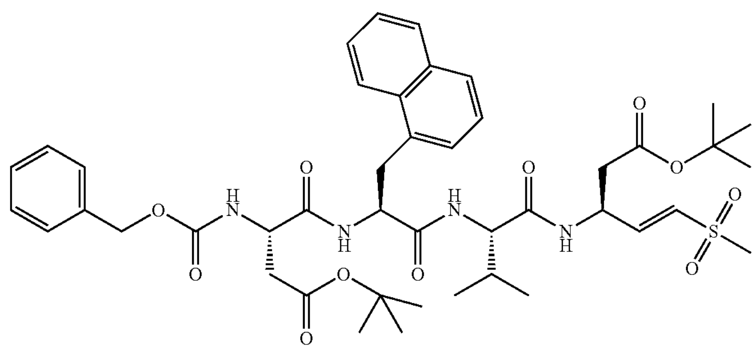 [SMILES: CC(C)[C@H](NC(=O)[C@H](Cc1cccc2ccccc12)NC(=O)[C@H](CC(=O)OC(C)(C)C)NC(=O)OCc1ccccc1)C(=O)N[C@H](/C=C/S(C)(=O)=O)CC(=O)OC(C)(C)C] |
| 111 | Z-Asp-3-(1-naphtyl)-L-alanine-Val-Asp methyl vinyl sulfone | 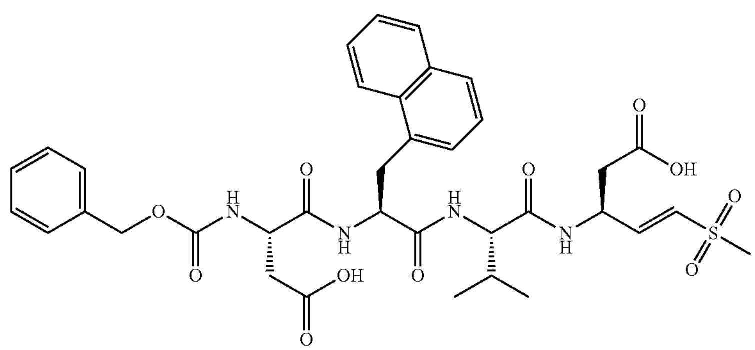 [SMILES: CC(C)[C@H](NC(=O)[C@H](Cc1cccc2ccccc12)NC(=O)[C@H](CC(=O)O)NC(=O)OCc1ccccc1)C(=O)N[C@H](/C=C/S(C)(=O)=O)CC(=O)O] |
| 112 | Z-Asp(β-tert-Butyl)-3-(1-naphtyl)-L-alanine-Val-Asp(β-tert-Butyl) αchlorovinyl methylsulfone | 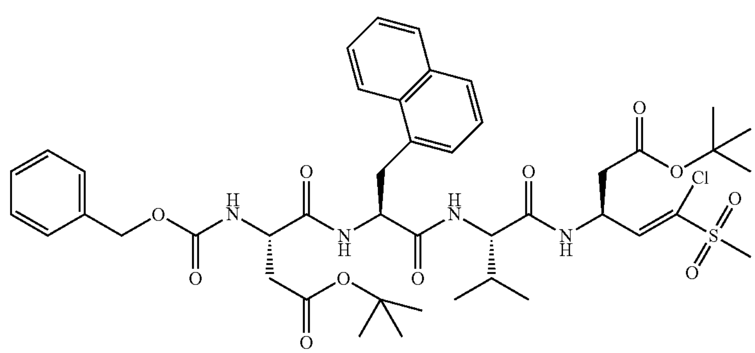 [SMILES: CC(C)[C@H](NC(=O)[C@H](Cc1cccc2ccccc12)NC(=O)[C@H](CC(=O)OC(C)(C)C)NC(=O)OCc1ccccc1)C(=O)N[C@H](/C=C(\Cl)S(C)(=O)=O)CC(=O)OC(C)(C)C] |

TABLE 1-continued
| CPD N° | CPD NAME | STRUCTURE |
|---|---|---|
| 113 | Z-Asp-3-(1-naphtyl)-L-alanine-Val-Asp αchlorovinyl methylsulfone | 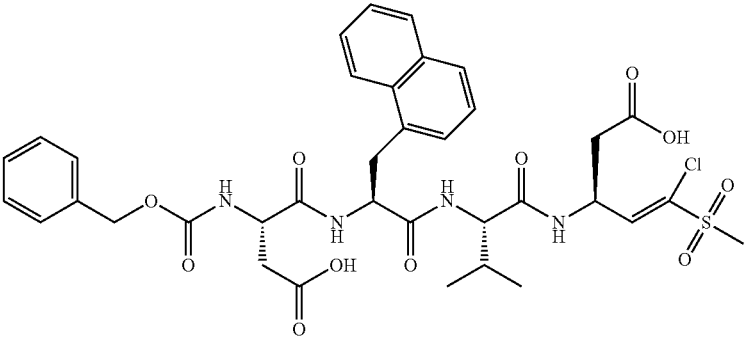 [SMILES: CC(C)[C@H](NC(=O)[C@H](Cc1cccc2ccccc12)NC(=O)[C@H](CC(=O)O)NC(=O)OCc1ccccc1)C(=O)N[C@H](/C=C(\Cl)S(C)(=O)=O)CC(=O)O] |
| 118 | Z-Asp(β-tert-Butyl)-Val-O-Allyl | 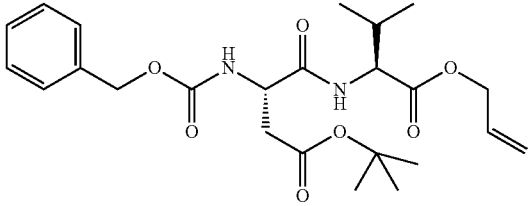 [SMILES: C=CCOC(=O)[C@@H](NC(=O)[C@H](CC(=O)OC(C)(C)C)NC(=O)OCc1ccccc1)C(C)C] |
| 119 | Z-Asp(β-tert-Butyl)-Val-OH | 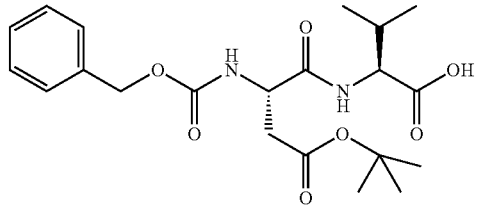 [SMILES: CC(C)[C@H](NC(=O)[C@H](CC(=O)OC(C)(C)C)NC(=O)OCc1ccccc1)C(=O)O] |
| 120 | Z-Asp(β-tert-Butyl)-Val-Asp(β-tert-Butyl) methyl vinyl sulfone | 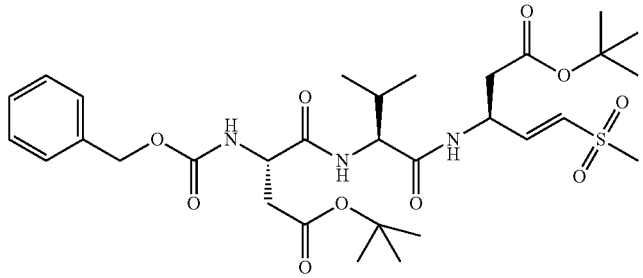 [SMILES: CC(C)[C@H](NC(=O)[C@H](CC(=O)OC(C)(C)C)NC(=O)OCc1ccccc1)C(=O)N[C@H](/C=C/S(C)(=O)=O)CC(=O)OC(C)(C)C] |
| 121 | Z-Asp-Val-Asp-methyl vinyl sulfone | 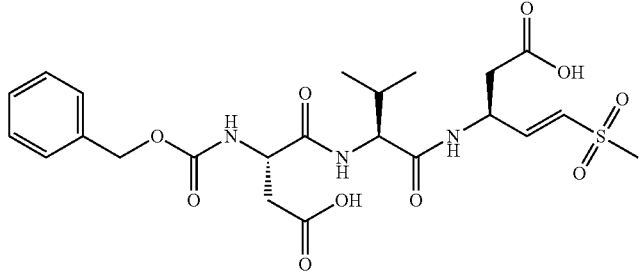 [SMILES: CC(C)[C@H](NC(=O)[C@H](CC(=O)O)NC(=O)OCc1ccccc1)C(=O)N[C@H](/C=C/S(C)(=O)=O)CC(=O)O] |

TABLE 1-continued
| CPD N° | CPD NAME | STRUCTURE |
|---|---|---|
| 122 | Z-Asp(β-tert-Butyl)-phenylglycine-Val-Asp(β-tert-Butyl)-αchlorovinyl methylsulfone | 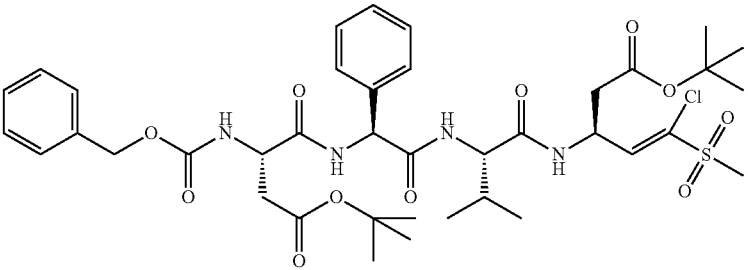 [SMILES: CC(C)[C@H](NC(=O)[C@@H](NC(=O)[C@H](CC(=O)OC(C)(C)C)NC(=O)OCc1ccccc1)c1ccccc1)C(=O)N[C@H](/C=C(\Cl)S(C)(=O)=O)CC(=O)OC(C)(C)C] |
| 123 | Z-Asp-phenylglycine-Val-Asp-αchlorovinyl methylsulfone | 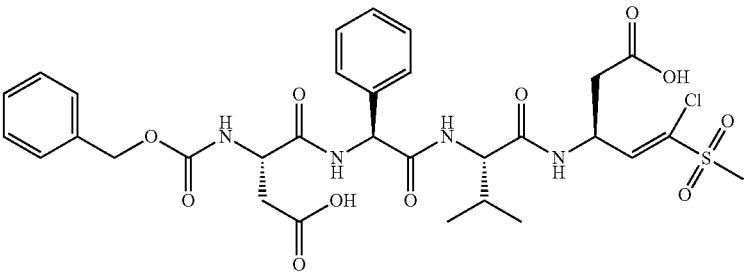 [SMILES: CC(C)[C@H](NC(=O)[C@@H](NC(=O)[C@H](CC(=O)O)NC(=O)OCc1ccccc1)c1ccccc1)C(=O)N[C@H](/C=C(\Cl)S(C)(=O)=O)CC(=O)O] |
| 124 | Boc-3-(1-naphtyl)-L-alanine-Val-O-allyl | 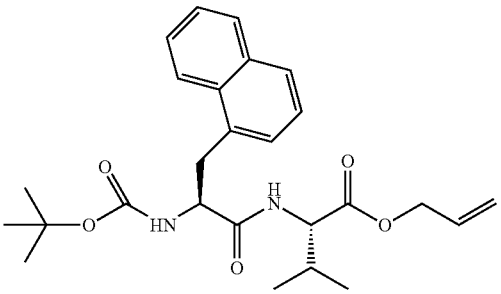 [SMILES: C=CCOC(=O)[C@@H](NC(=O)[C@H](Cc1cccc2ccccc12)NC(=O)OC(C)(C)C)C(C)C] |
| 125 | 3-(1-naphtyl)-L-alanine-Val-O-allyl TFA salt | 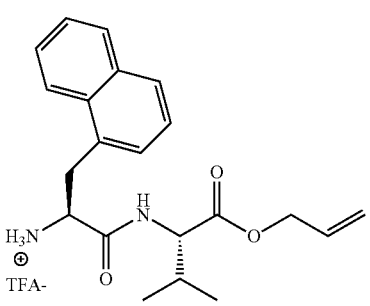 [SMILES: C=CCOC(=O)[C@@H](NC(=O)[C@@H]([NH3+])Cc1cccc2ccccc12)C(C)C] |
| 126 | Boc-Phg-Val-OAllyl | 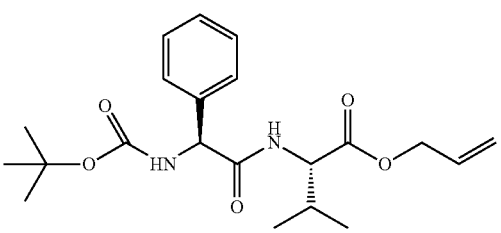 [SMILES: C=CCOC(=O)[C@@H](NC(=O)[C@@H](NC(=O)OC(C)(C)C)c1ccccc1)C(C)C] |

TABLE 1-continued

| CPD N° | CPD NAME | STRUCTURE |
|---|---|---|
| 127 | Phg-Val-OAllyl TFA salt | 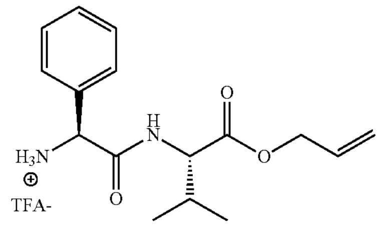 [SMILES: C=CCOC(=O)[C@@H](NC(=O)[C@@H]([NH3+])c1ccccc1)C(C)C] |
| 128 | Boc-Asp (β-Ethyl) methylsulfone | 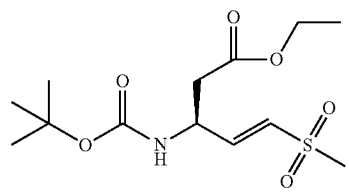 [SMILES: CCOC(=O)C[C@@H](/C=C/S(C)(=O)=O)NC(=O)OC(C)(C)C] |
| 129 | Asp (β-Ethyl) methylsulfone Tosyl salt | 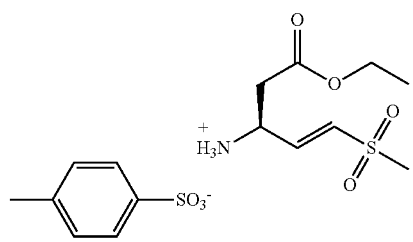 |
| 130 | Boc-Asp (β-Ethyl) αchlorovinyl methylsulfone | 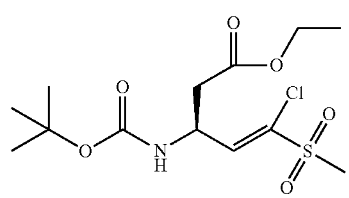 [SMILES: CCOC(=O)C[C@@H](/C=C(\Cl)S(C)(=O)=O)NC(=O)OC(C)(C)C] |
| 131 | Asp (β-Ethyl) αchlorovinyl methylsulfone Tosyl salt | 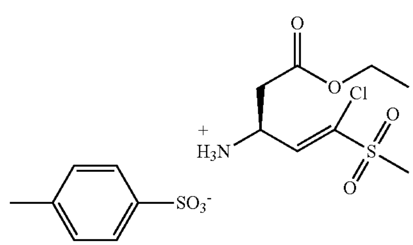 |
| 132 | Cbz-Asp(O-Ethyl)-Glu(O-Ethyl)-Val-OAllyl | 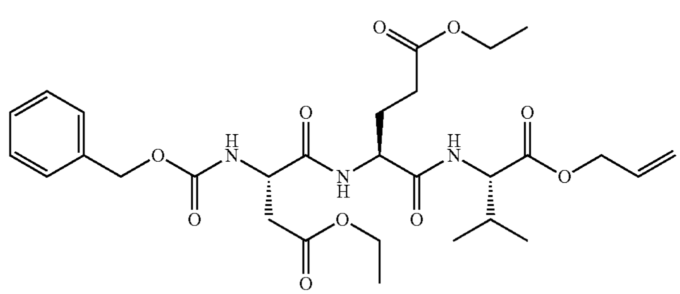 [SMILES: C=CCOC(=O)[C@@H](NC(=O)[C@H](CCC(=O)OCC)NC(=O)[C@H](CC(=O)OCC)NC(=O)OCc1ccccc1)C(C)C] |

TABLE 1-continued

| CPD N° | CPD NAME | STRUCTURE |
|---|---|---|
| 133 | Cbz-Asp(O-Ethyl)-Glu(O-Ethyl)-Val-OH | 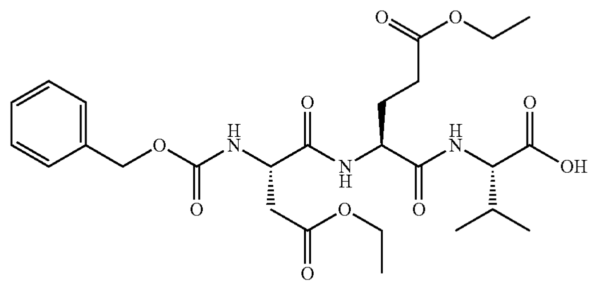 [SMILES: CCOC(=O)CC[C@H](NC(=O)[C@H](CC(=O)OCC)NC(=O)OCc1ccccc1)C(=O)N[C@H](C(=O)O)C(C)C] |
| 134 | Z-Asp(β-Ethyl)-Phg-Val-OAllyl | 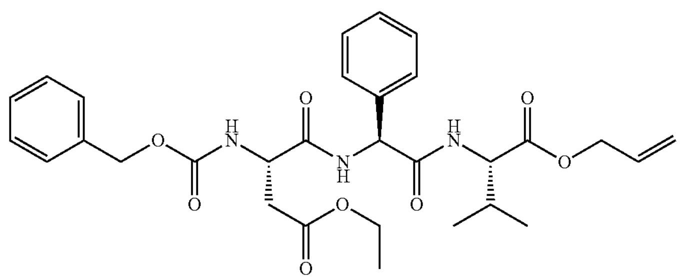 [SMILES: C=CCOC(=O)[C@@H](NC(=O)[C@@H](NC(=O)[C@H](CC(=O)OCC)NC(=O)OCc1ccccc1)c1ccccc1)C(C)C] |
| 135 | Z-Asp(β-Ethyl)-Phg-Val-OH | 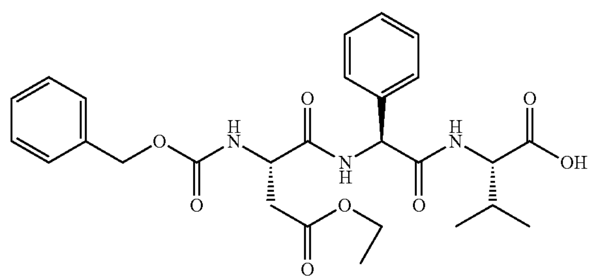 [SMILES: CCOC(=O)C[C@H](NC(=O)OCc1ccccc1)C(=O)N[C@H](C(=O)N[C@H](C(=O)O)C(C)C)c1ccccc1] |
| 136 | Cbz-Asp(O-Ethyl)-3-(1-naphtyl)-L-alanine-Val-O-allyl | 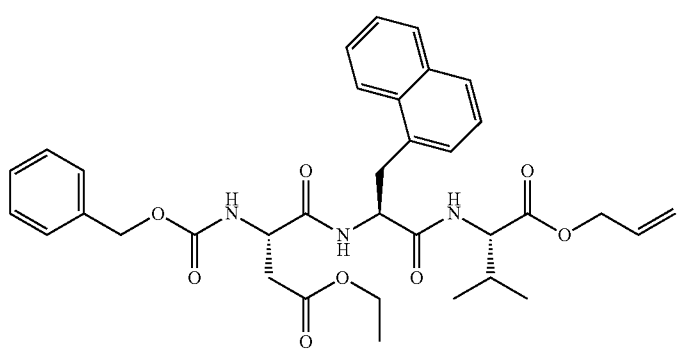 [SMILES: C=CCOC(=O)[C@@H](NC(=O)[C@H](Cc1cccc2ccccc12)NC(=O)[C@H](CC(=O)OCC)NC(=O)OCc1ccccc1)C(C)C] |
| 137 | Cbz-Asp(O-Ethyl)-3-(1-naphtyl)-L-alanine-Val-OH | 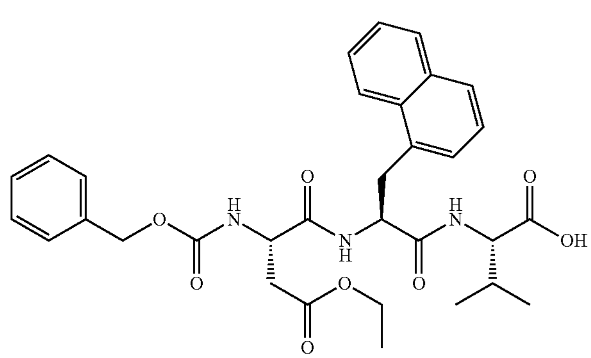 [SMILES: CCOC(=O)C[C@H](NC(=O)OCc1ccccc1)C(=O)N[C@@H](Cc1cccc2ccccc12)C(=O)N[C@H](C(=O)O)C(C)C] |

TABLE 1-continued
| CPD N° | CPD NAME | STRUCTURE |
|---|---|---|
| 138 | Cbz-Asp(O-Ethyl)-Indanylglycine-Val-OAllyl | 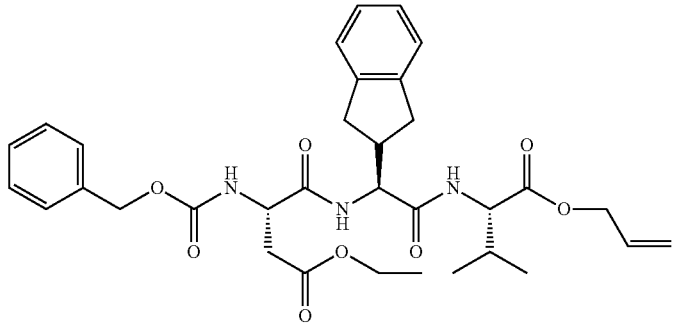 [SMILES: C=CCOC(=O)[C@@H](NC(=O)[C@@H](NC(=O)[C@H](CC(=O)OCC)NC(=O)OCc1ccccc1)C1Cc2ccccc2C1)C(C)C] |
| 139 | Cbz-Asp(O-Ethyl)-Indanylglycine-Val-OH | 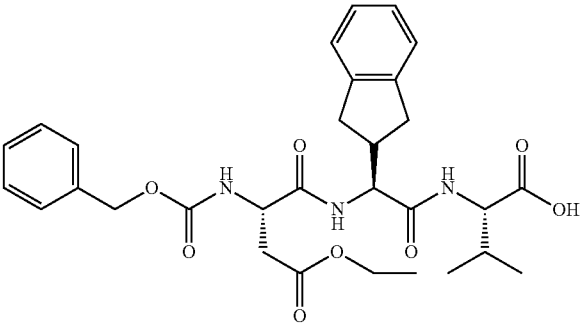 |
| 140 | Z-Asp(β-Ethyl)-Glu(β-Ethyl)-Val-Asp(β-Ethyl)-αchlorovinyl methylsulfone | 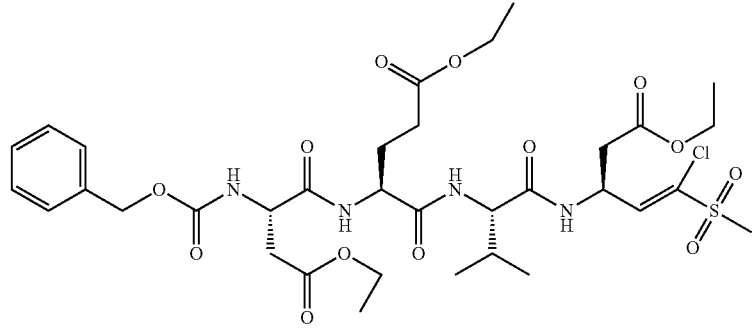 [SMILES: CCOC(=O)CC[C@H](NC(=O)[C@H](CC(=O)OCC)NC(=O)OCc1ccccc1)C(=O)N[C@H](C(=O)N[C@H](/C=C(\Cl)S(C)(=O)=O)CC(=O)OCC)C(C)C] |
| 141 | Z-Asp(β-Ethyl)-Glu(β-Ethyl)-Val-Asp(β-Ethyl)-methylsulfone | 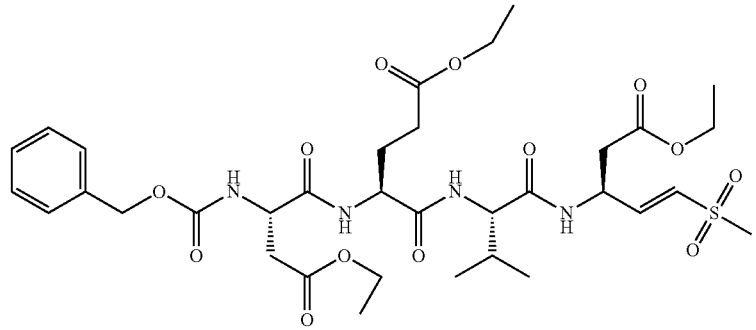 [SMILES: CCOC(=O)CC[C@H](NC(=O)[C@H](CC(=O)OCC)NC(=O)OCc1ccccc1)C(=O)N[C@H](C(=O)N[C@H](/C=C/S(C)(=O)=O)CC(=O)OCC)C(C)C] |

TABLE 1-continued

| CPD N° | CPD NAME | STRUCTURE |
|---|---|---|
| 142 | Z-Asp(β-Ethyl)-Indanylglycine-Val-Asp(β-Ethyl) methyl vinyl sulfone | 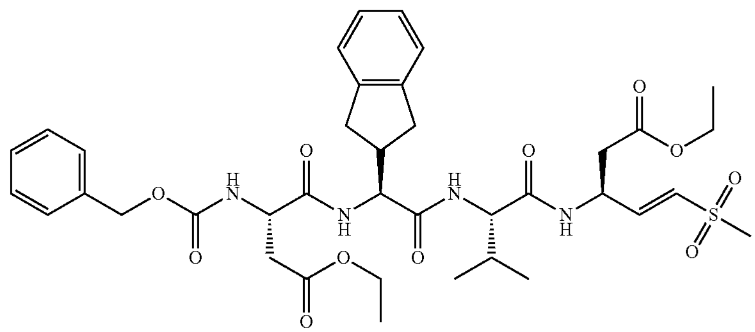 [SMILES: CCOC(=O)C[C@@H](/C=C/S(C)(=O)=O)NC(=O)[C@@H](NC(=O)[C@@H](NC(=O)[C@H](CC(=O)OCC)NC(=O)OCc1ccccc1)C1Cc2ccccc2C1)C(C)C] |
| 143 | Z-Asp(β-Ethyl)-Indanylglycine-Val-Asp(β-Ethyl) αchloromethyl methyl vinyl sulfone | 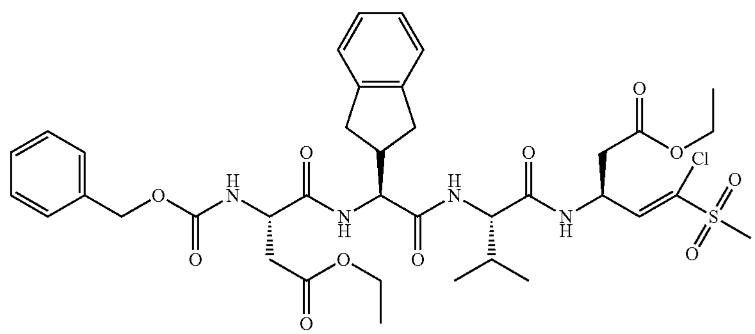 [SMILES: CCOC(=O)C[C@@H](/C=C(\Cl)S(C)(=O)=O)NC(=O)[C@@H](NC(=O)[C@@H](NC(=O)[C@H](CC(=O)OCC)NC(=O)OCc1ccccc1)C1Cc2ccccc2C1)C(C)C] |
| 144 | Z-Asp(β-Ethyl)-phenylglycine-Val-Asp(β-Ethyl)methyl vinyl sulfone | 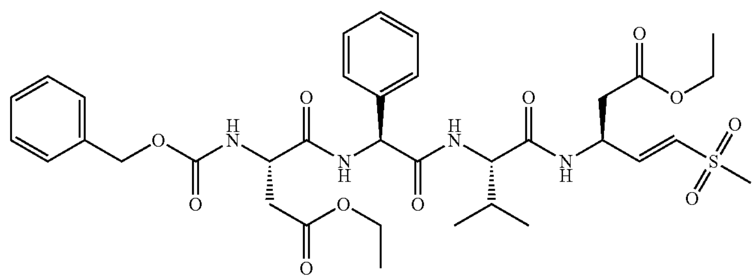 [SMILES: CCOC(=O)C[C@@H](/C=C/S(C)(=O)=O)NC(=O)[C@@H](NC(=O)[C@@H](NC(=O)[C@H](CC(=O)OCC)NC(=O)OCc1ccccc1)c1ccccc1)C(C)C] |
| 145 | Z-Asp(β-Ethyl)-phenylglycine-Val-Asp(β-Ethyl) αchloromethyl methyl vinyl sulfone | 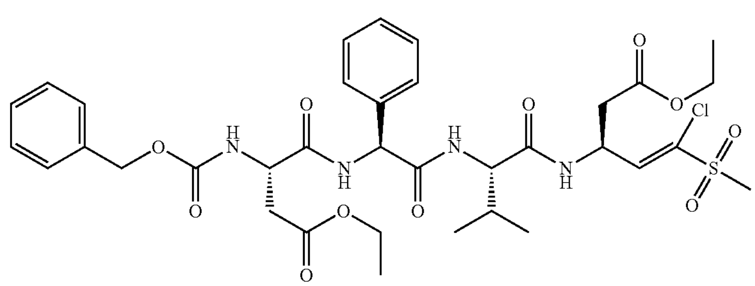 [SMILES: CCOC(=O)C[C@@H](/C=C(\Cl)S(C)(=O)=O)NC(=O)[C@@H](NC(=O)[C@@H](NC(=O)[C@H](CC(=O)OCC)NC(=O)OCc1ccccc1)c1ccccc1)C(C)C] |
| 146 | Z-Asp(β-Ethyl)-phenylglycine-Val-Asp methyl vinyl sulfone | 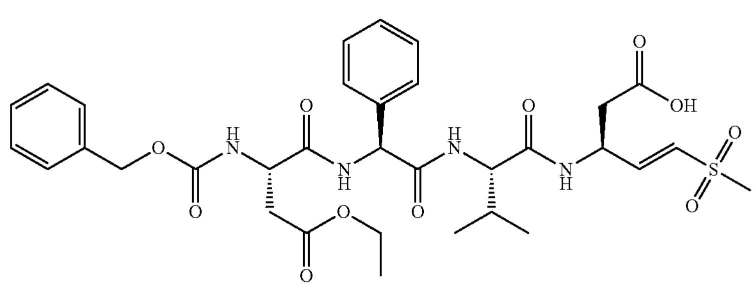 [SMILES: CCOC(=O)C[C@H](NC(=O)OCc1ccccc1)C(=O)N[C@H](C(=O)N[C@H](C(=O)N[C@H](/C=C/S(C)(=O)=O)CC(=O)O)C(C)C)c1ccccc1] |

TABLE 1-continued

| CPD N° | CPD NAME | STRUCTURE |
|---|---|---|
| 147 | Z-Asp-phenylglycine-Val-Asp(β-Ethyl)methyl vinyl sulfone | 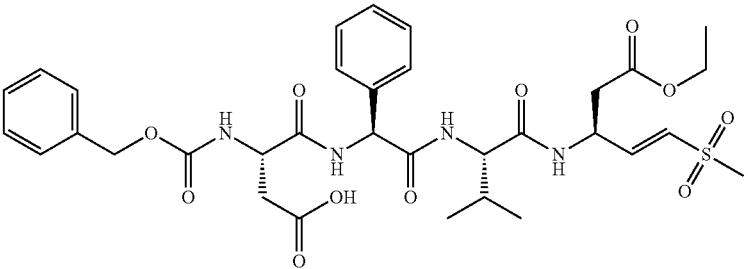 [SMILES: CCOC(=O)C[C@@H](/C=C/S(C)(=O)=O)NC(=O)[C@@H](NC(=O)[C@@H](NC(=O)[C@H](CC(=O)O)NC(=O)OCc1ccccc1)c1ccccc1)C(C)C] |
| 148 | Z-Asp-(β-Ethyl)phenylglycine-Val-Asp αchloro methyl vinyl sulfone | 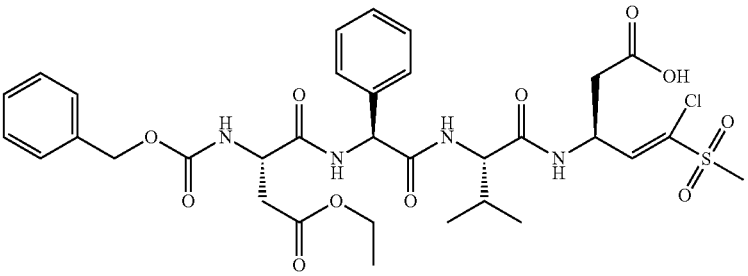 [SMILES: CCOC(=O)C[C@H](NC(=O)OCc1ccccc1)C(=O)N[C@H](C(=O)N[C@H](C(=O)N[C@H](/C=C(\Cl)S(C)(=O)=O)CC(=O)O)C(C)C)c1ccccc1] |
| 149 | Z-Asp-phenylglycine-Val-Asp(β-Ethyl) αchloro vinyl methyl sulfone | 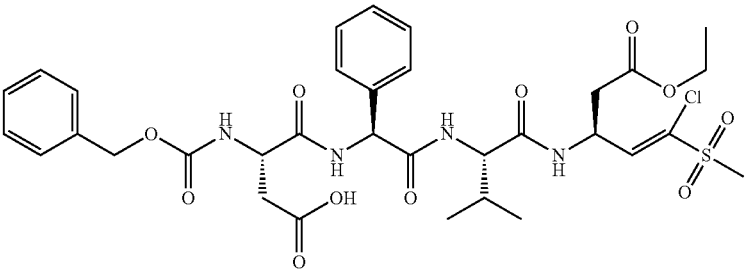 [SMILES: CCOC(=O)C[C@@H](/C=C(\Cl)S(C)(=O)=O)NC(=O)[C@@H](NC(=O)[C@@H](NC(=O)[C@H](CC(=O)O)NC(=O)OCc1ccccc1)c1ccccc1)C(C)C] |
| 150 | Z-Asp(β-Ethyl)-phenylglycine-Val-Asp(β-Ethyl) isopropyl vinyl sulfone | 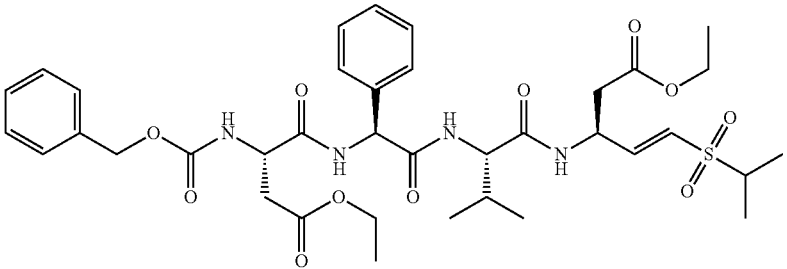 [SMILES: CCOC(=O)C[C@@H](/C=C/S(=O)(=O)C(C)C)NC(=O)[C@@H](NC(=O)[C@@H](NC(=O)[C@H](CC(=O)OCC)NC(=O)OCc1ccccc1)c1ccccc1)C(C)C] |
| 151 | Z-Asp(β-Ethyl)-phenylglycine-Val-Asp(β-Ethyl) αchloro isopropyl vinyl sulfone | 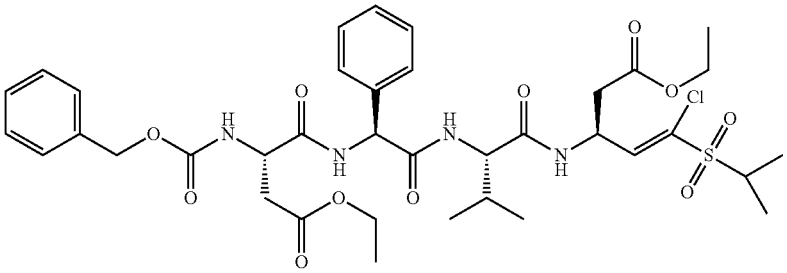 [SMILES: CCOC(=O)C[C@@H](/C=C(\Cl)S(=O)(=O)C(C)C)NC(=O)[C@@H](NC(=O)[C@@H](NC(=O)[C@H](CC(=O)OCC)NC(=O)OCc1ccccc1)c1ccccc1)C(C)C] |

TABLE 1-continued
| CPD N° | CPD NAME | STRUCTURE |
|---|---|---|
| 152 | Z-Asp(β-Ethyl)-phenylglycine-Val-Asp(β-Ethyl) ethyl vinyl sulfone | 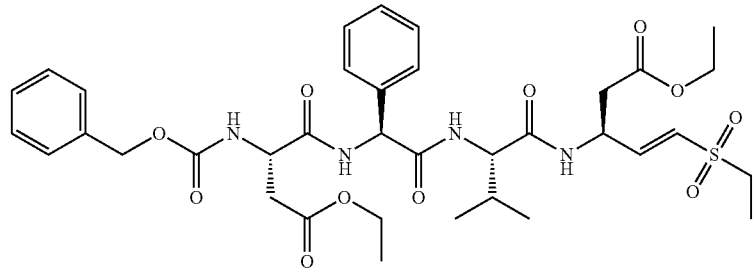 [SMILES: CCOC(=O)C[C@@H](/C=C/S(=O)(=O)CC)NC(=O)[C@@H](NC(=O)[C@@H](NC(=O)[C@H](CC(=O)OCC)NC(=O)OCc1ccccc1)c1ccccc1)C(C)C] |
| 153 | Z-Asp(β-Ethyl)-phenylglycine-Val-Asp(β-Ethyl) αchloro ethyl vinyl sulfone | 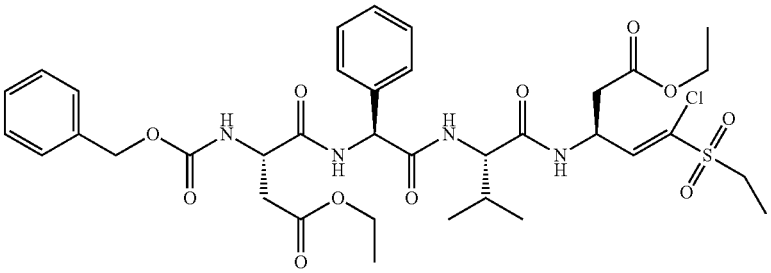 [SMILES: CCOC(=O)C[C@@H](/C=C(\Cl)S(=O)(=O)CC)NC(=O)[C@@H](NC(=O)[C@@H](NC(=O)[C@H](CC(=O)OCC)NC(=O)OCc1ccccc1)c1ccccc1)C(C)C] |
| 154 | Z-Asp-phenylglycine-Val-Asp ethyl vinyl sulfone | 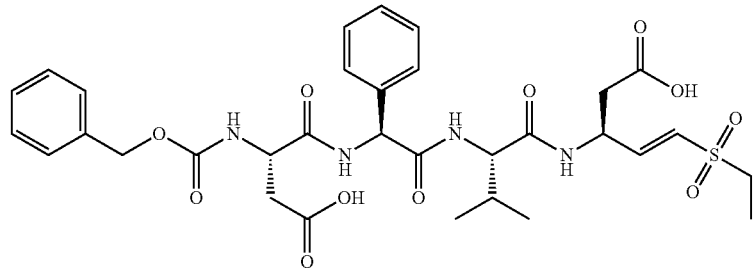 [SMILES: CCS(=O)(=O)/C=C/[C@H](CC(=O)O)NC(=O)[C@@H](NC(=O)[C@@H](NC(=O)[C@H](CC(=O)O)NC(=O)OCc1ccccc1)c1ccccc1)C(C)C] |
| 155 | Z-Asp-phenylglycine-Val-Asp αchloro ethyl vinyl sulfone | 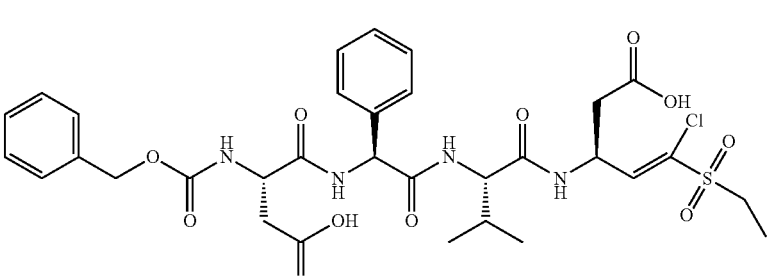 |
| 156 | Z-Asp-phenylglycine-Val-Asp isopropyl vinyl sulfone | 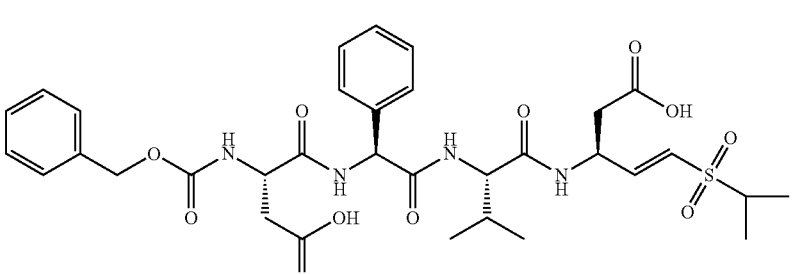 |

TABLE 1-continued

| CPD N° | CPD NAME | STRUCTURE |
|---|---|---|
| 157 | Z-Asp-phenylglycine-Val-Asp αchloro isopropyl vinyl sulfone | 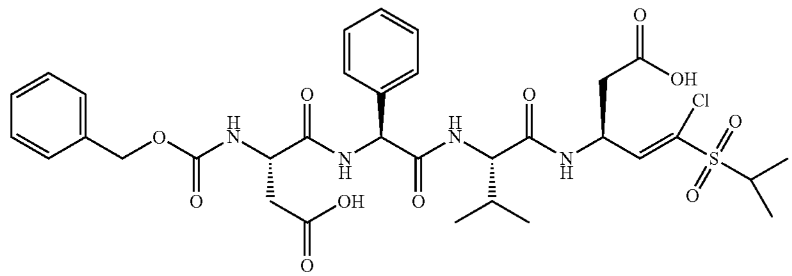 [SMILES: CC(C)[C@H](NC(=O)[C@@H](NC(=O)[C@H](CC(=O)O)NC(=O)OCc1ccccc1)c1ccccc1)C(=O)N[C@H](/C=C(\Cl)S(=O)(=O)C(C)C)CC(=O)O] |
| 158 | Z-Asp(β-Ethyl)-3-(1-naphtyl)-L-alanine-Val-Asp(β-Ethyl)methyl vinyl sulfone | 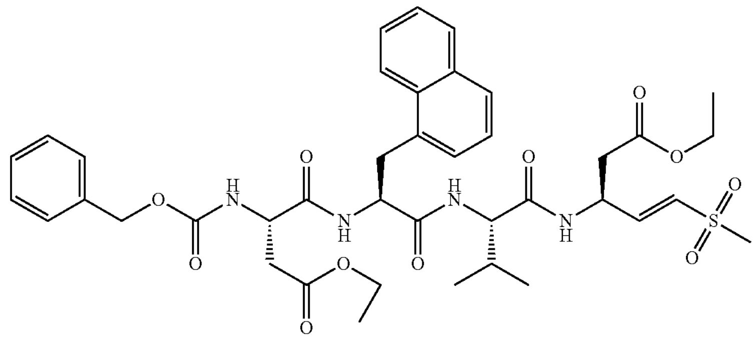 [SMILES: CCOC(=O)C[C@@H](/C=C/S(C)(=O)=O)NC(=O)[C@@H](NC(=O)[C@H](Cc1cccc2ccccc12)NC(=O)[C@H](CC(=O)OCC)NC(=O)OCc1ccccc1)C(C)C] |
| 159 | Z-Asp(β-Ethyl)-3-(1-naphtyl)-L-alanine-Val-Asp(β-Ethyl) αchloro methyl vinyl sulfone | 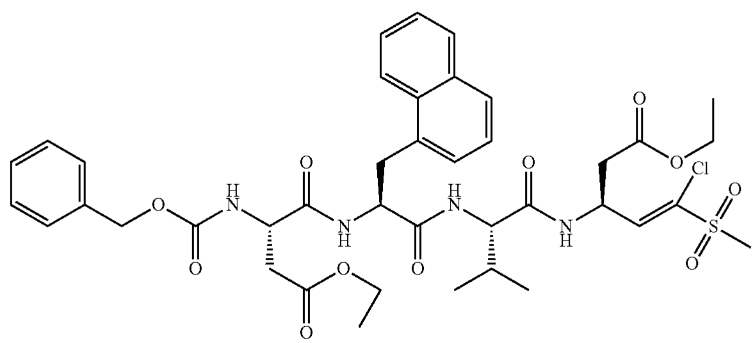 [SMILES: CCOC(=O)C[C@@H](/C=C(\Cl)S(C)(=O)=O)NC(=O)[C@@H](NC(=O)[C@H](Cc1cccc2ccccc12)NC(=O)[C@H](CC(=O)OCC)NC(=O)OCc1ccccc1)C(C)C] |
| 160 | Boc-Asp (β-Ethyl) αchloro ethyl sulfone | 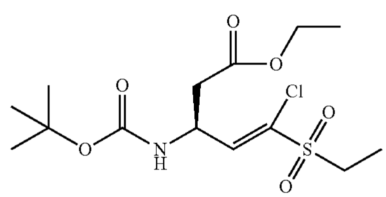 [SMILES: CCOC(=O)C[C@@H](/C=C(\Cl)S(=O)(=O)CC)NC(=O)OC(C)(C)C] |
| 161 | Asp (β-Ethyl) αchloro ethyl sulfone Tosyl salt | 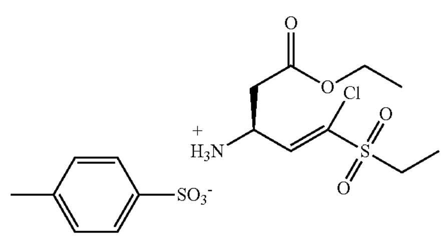 |
| 162 | Boc-Asp (β-Ethyl) αchlorovinyl isopropyl sulfone | 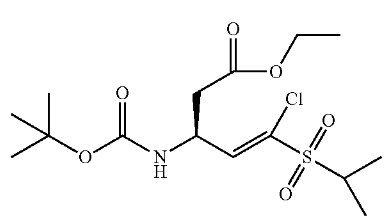 [SMILES: CCOC(=O)C[C@@H](/C=C(\Cl)S(=O)(=O)C(C)C)NC(=O)OC(C)(C)C] |

TABLE 1-continued

| CPD N° | CPD NAME | STRUCTURE |
|---|---|---|
| 163 | Asp (β-Ethyl) αchlorovinyl isopropyl sulfone Tosyl salt | 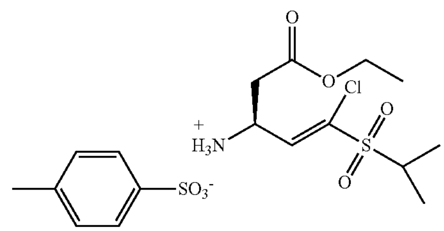 |
| 164 | Z-Asp(β-tert-Butyl)-phenylglycine-Val-Asp(β-tert-Butyl)-isopropyl sulfone | 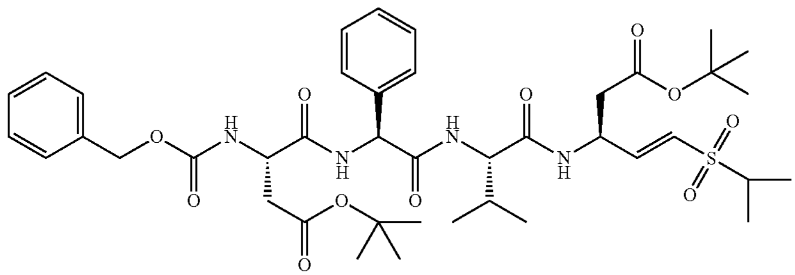 [SMILES: CC(C)[C@H](NC(=O)[C@@H](NC(=O)[C@H](CC(=O)OC(C)(C)C)NC(=O)OCc1ccccc1)c1ccccc1)C(=O)N[C@H](/C=C/S(=O)(=O)C(C)C)CC(=O)OC(C)(C)C] |
| 165 | Z-Asp(β-tert-Butyl)-phenylglycine-Val-Asp(β-tert-Butyl)-αchlorovinyl isopropyl sulfone | 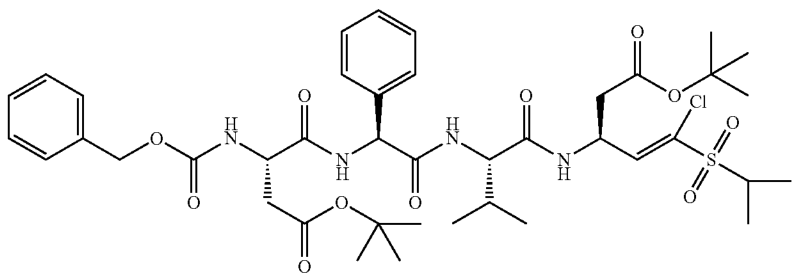 [SMILES: CC(C)[C@H](NC(=O)[C@@H](NC(=O)[C@H](CC(=O)OC(C)(C)C)NC(=O)OCc1ccccc1)c1ccccc1)C(=O)N[C@H](/C=C(\Cl)S(=O)(=O)C(C)C)CC(=O)OC(C)(C)C] |
| 166 | Z-Asp(β-tert-Butyl)-phenylglycine-Val-Asp(β-tert-Butyl)-ethyl sulfone | 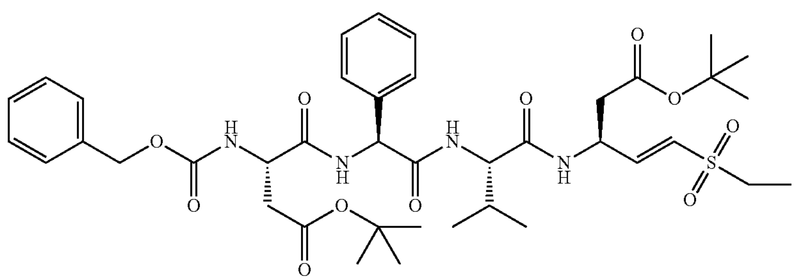 [SMILES: CCS(=O)(=O)/C=C/[C@H](CC(=O)OC(C)(C)C)NC(=O)[C@@H](NC(=O)[C@@H](NC(=O)[C@H](CC(=O)OC(C)(C)C)NC(=O)OCc1ccccc1)c1ccccc1)C(C)C] |
| 167 | Z-Asp(β-tert-Butyl)-phenylglycine-Val-Asp(β-tert-Butyl)-αchlorovinyl ethyl sulfone | 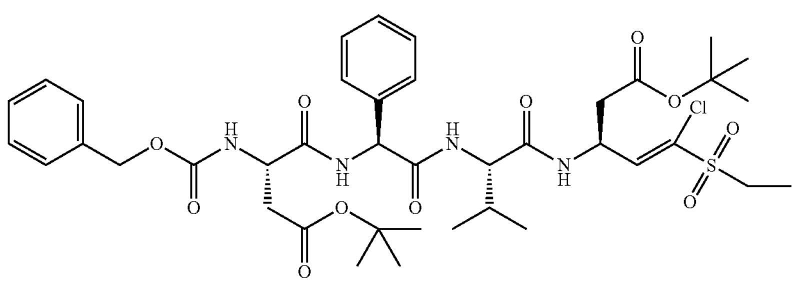 [SMILES: CCS(=O)(=O)/C(Cl)=C/[C@H](CC(=O)OC(C)(C)C)NC(=O)[C@@H](NC(=O)[C@@H](NC(=O)[C@H](CC(=O)OC(C)(C)C)NC(=O)OCc1ccccc1)c1ccccc1)C(C)C] |
| 168 | Boc-Asp (β-tert-Butyl) αchlorovinyl ethyl sulfone | 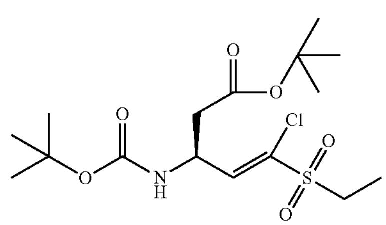 [SMILES: CCS(=O)(=O)/C(Cl)=C/[C@H](CC(=O)OC(C)(C)C)NC(=O)OC(C)(C)C] |

TABLE 1-continued

| CPD N° | CPD NAME | STRUCTURE |
|---|---|---|
| 169 | Asp (β-tert-Butyl) αchlorovinyl ethyl sulfone Tosyl salt | 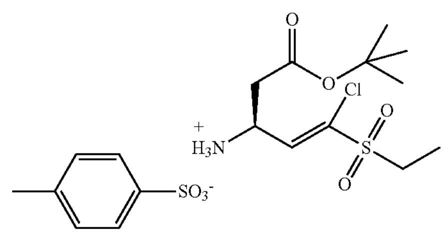 |
| 170 | Boc-Asp (β-tert-Butyl) vinyl ethyl sulfone | 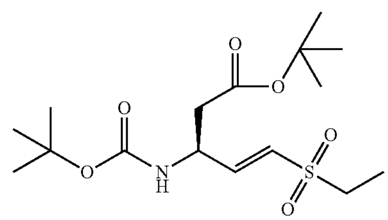 [SMILES: CCS(=O)(=O)/C=C/[C@H](CC(=O)OC(C)(C)C)NC(=O)OC(C)(C)C] |
| 171 | Asp (β-tert-Butyl) vinyl ethyl sulfone Tosyl salt | 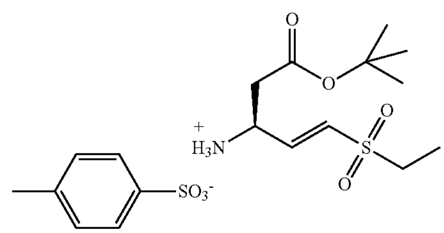 |
| 172 | Diethyl chloro (isopropyl sulfone)methyl-phosphonate | 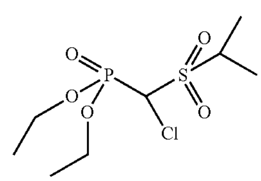 [SMILES: CCOP(=O)(OCC)C(Cl)S(=O)(=O)C(C)C] |
| 173 | Boc-Asp (β-tert-Butyl) αchlorovinyl isopropyl sulfone | 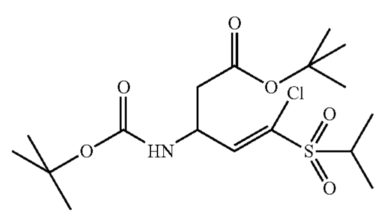 [SMILES: CC(C)S(=O)(=O)/C(Cl)=C/C(CC(=O)OC(C)(C)C)NC(=O)OC(C)(C)C] |
| 174 | Asp (β-tert-Butyl) αchlorovinyl isopropyl sulfone | 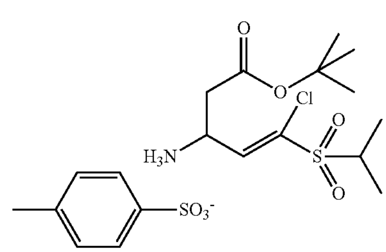 |
| 175 | Diethyl (ethyl sulfone)methyl-phosphonate | 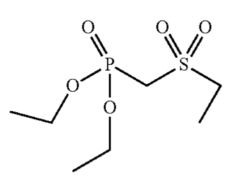 |

TABLE 1-continued

| CPD N° | CPD NAME | STRUCTURE |
|---|---|---|
| 176 | Z-Asp(β-tert-Butyl)-Glu-(β-tert-Butyl)-Val-Asp(β-tert-Butyl)-αchlorovinyl methylsulfone | 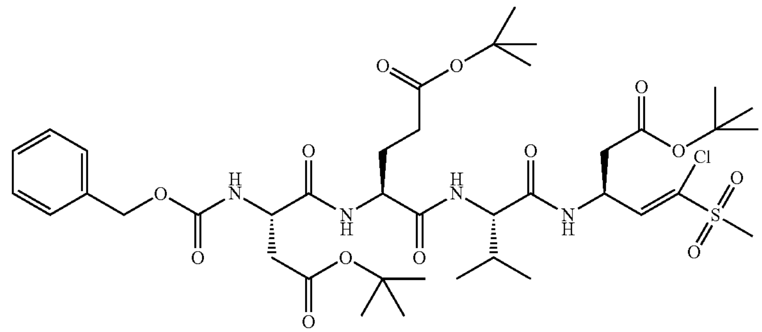 [SMILES: CC(C)[C@H](NC(=O)[C@H](CCC(=O)OC(C)(C)C)NC(=O)[C@H](CC(=O)OC(C)(C)C)NC(=O)OCc1ccccc1)C(=O)N[C@H](/C=C(\Cl)S(C)(=O)=O)CC(=O)OC(C)(C)C] |
| 177 | Z-Asp-Glu-Val-Asp-αchlorovinyl methylsulfone | 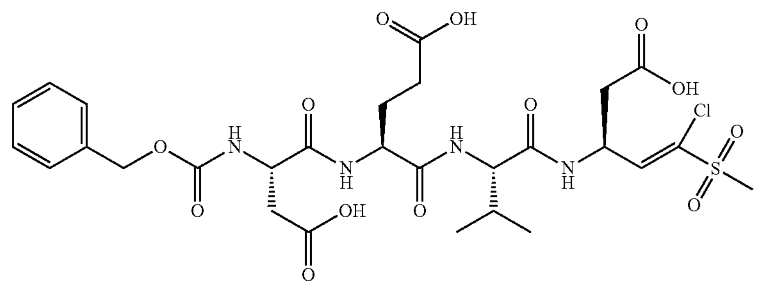 [SMILES: CC(C)[C@H](NC(=O)[C@H](CCC(=O)O)NC(=O)[C@H](CC(=O)O)NC(=O)OCc1ccccc1)C(=O)N[C@H](/C=C(\Cl)S(C)(=O)=O)CC(=O)O] |
| 178 | Boc-Asp (β-Ethyl) ethyl sulfone | 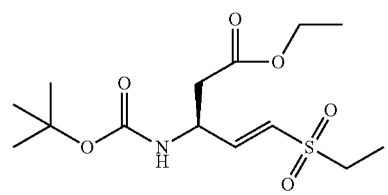 [SMILES: CCOC(=O)C[C@@H](/C=C/S(=O)(=O)CC)NC(=O)OC(C)(C)C] |
| 179 | Asp (β-Ethyl) ethyl sulfone Tosyl salt | 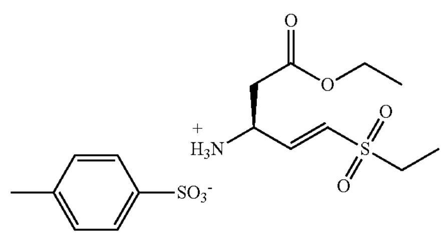 |
| 180 | Boc-Asp (β-Ethyl) isopropyl sulfone | 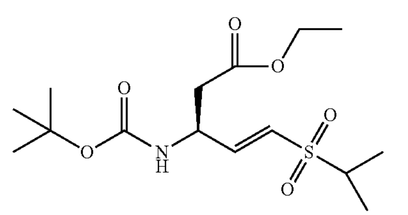 [SMILES: CCOC(=O)C[C@@H](/C=C/S(=O)(=O)C(C)C)NC(=O)OC(C)(C)C] |
| 181 | Asp (β-Ethyl) isopropyl sulfone Tosyl salt | 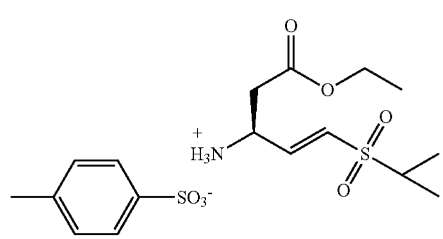 |

TABLE 2
Additional examples of compounds that may be synthesised using the methods described herein
| CPD NAME | STRUCTURE |
|---|---|
| Z-Asp-phenylglycine-Val-Asp-vinyl phosphonate | 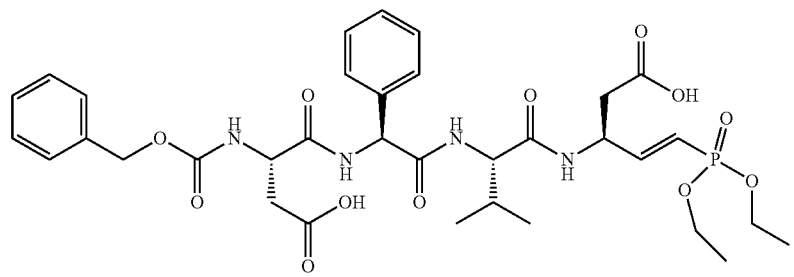 [SMILES: CCOP(=O)(/C=C/[C@H](CC(=O)O)NC(=O)[C@@H](NC(=O)[C@@H](NC(=O)[C@H](CC(=O)O)NC(=O)OCc1ccccc1)c1ccccc1)C(C)C)OCC] |
| Z-Asp-lndanylglycine-Val-Asp-vinyl phosphonate | 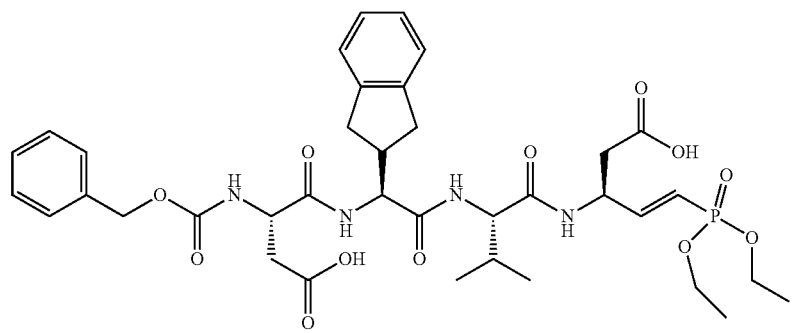 [SMILES: CCOP(=O)(/C=C/[C@H](CC(=O)O)NC(=O)[C@@H](NC(=O)[C@@H](NC(=O)[C@H](CC(=O)O)NC(=O)OCc1ccccc1)C1Cc2ccccc2C1)C(C)C)OCC] |
| Z-Asp-phenylglycine-Val-Asp-vinyl nitrite | 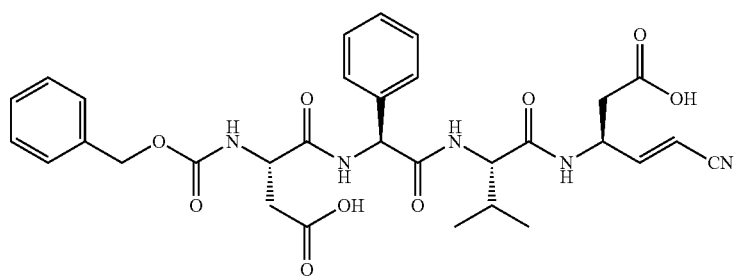 [SMILES: CC(C)[C@H](NC(=O)[C@@H](NC(=O)[C@H](CC(=O)O)NC(=O)OCc1ccccc1)c1ccccc1)C(=O)N[C@H](/C=C/C#N)CC(=O)O] |
| Z-Asp-indanylglycine-Val-Asp-vinyl nitrite | 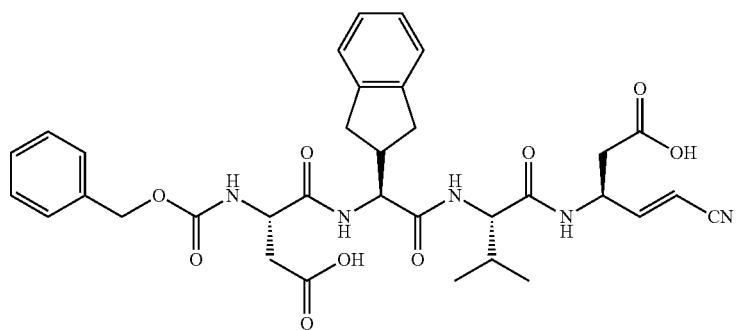 [SMILES: CC(C)[C@H](NC(=O)[C@@H](NC(=O)[C@H](CC(=O)O)NC(=O)OCc1ccccc1)C1Cc2ccccc2C1)C(=O)N[C@H](/C=C/C#N)CC(=O)O] |
| Z-Asp-phenylglycine-Val-Asp-methyl dienne sulfone | 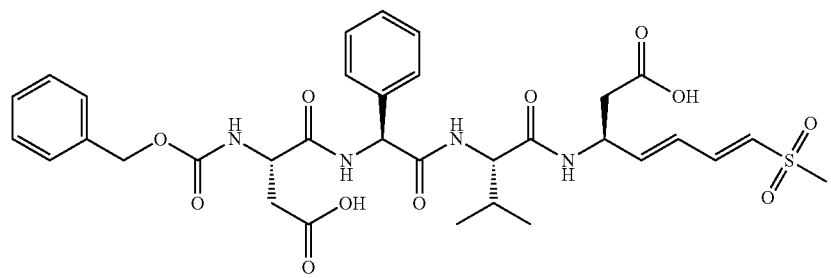 [SMILES: CC(C)[C@H](NC(=O)[C@@H](NC(=O)[C@H](CC(=O)O)NC(=O)OCc1ccccc1)c1ccccc1)C(=O)N[C@H](/C=C/C=C/S(C)(=O)=O)CC(=O)O] |

TABLE 2-continued

Additional examples of compounds that may be synthesised using the methods described herein

| CPD NAME | STRUCTURE |
| --- | --- |
| Z-Asp-indanylglycine-Val-Asp-methyl dienne sulfone | 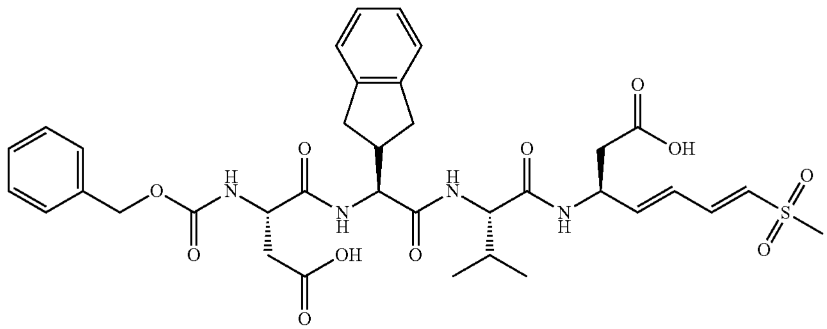 [SMILES: CC(C)[C@H](NC(=O)[C@@H](NC(=O)[C@H](CC(=O)O)NC(=O)OCc1ccccc1)C1Cc2ccccc2C1)C(=O)N[C@H](/C=C/C=C/S(C)(=O)=O)CC(=O)O] |
| Z-Asp-phenylglycine-Val-Asp-vinyl amide glycine | 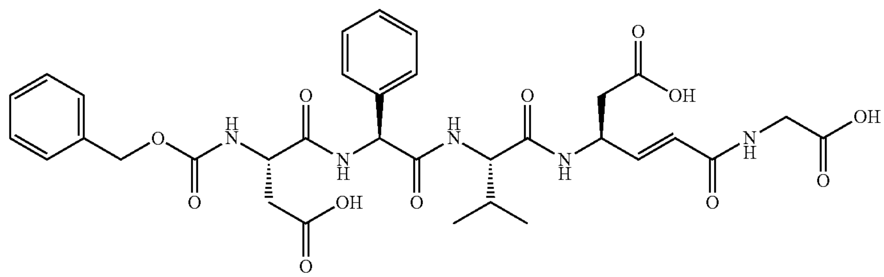 [SMILES: CC(C)[C@H](NC(=O)[C@@H](NC(=O)[C@H](CC(=O)O)NC(=O)OCc1ccccc1)c1ccccc1)C(=O)N[C@H](/C=C/C(=O)NCC(=O)O)CC(=O)O] |
| Z-Asp-indanylglycine-Val-Asp-vinyl amide glycine | 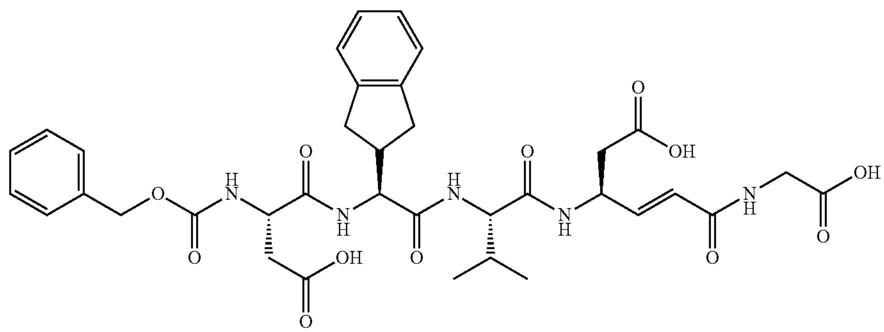 [SMILES: CC(C)[C@H](NC(=O)[C@@H](NC(=O)[C@H](CC(=O)O)NC(=O)OCc1ccccc1)C1Cc2ccccc2C1)C(=O)N[C@H](/C=C/C(=O)NCC(=O)O)CC(=O)O] |

Definitions

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein, the term "alkyl" is intended to include both branched and straight chain saturated aliphatic hydrocarbon groups having the specified number of carbon atoms, for example, $C_1$-$C_6$ as in $C_1$-$C_6$-alkyl is defined as including groups having 1, 2, 3, 4, 5 or 6 carbons in a linear or branched arrangement. Examples of $C_1$-$C_6$-alkyl and $C_1$-$C_4$ alkyl as defined above include, but are not limited to, methyl, ethyl, n-propyl, i-propyl, n-butyl, t-butyl, i-butyl, pentyl and hexyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regiochemistry and combinations thereof. For example, $C_2$-$C_6$ as in $C_2$-$C_6$ alkenyl is defined as including groups having 1, 2, 3, 4, 5, or 6 carbons in a linear or branched arrangement, at least two of the carbon atoms being bonded together by a double bond. Examples of $C_2$-$C_6$ alkenyl include ethenyl(vinyl), 1-propenyl, 2-propenyl, 1-butenyl and the like.

As used herein, the term "cycloalkyl" is intended to mean a monocyclic saturated aliphatic hydrocarbon group having the specified number of carbon atoms therein, for example, $C_3$-$C_7$ as in $C_3$-$C_7$ cycloalkyl is defined as including groups having 3, 4, 5, 6, or 7 carbons in a monocyclic arrangement. Examples of $C_3$-$C_7$ cycloalkyl as defined above include, but are not limited to, cyclopropyl, cyclobutyl, cyclopentyl, cyclohexyl and cycloheptyl.

As used herein, the term "halo" or "halogen" is intended to mean fluorine, chlorine, bromine and iodine.

As used herein, the term "haloalkyl" is intended to mean an alkyl as defined above, in which each hydrogen atom may be successively replaced by a halogen atom. Examples of haloalkyls include, but are not limited to, $CH_2F$, $CHF_2$ and $CF_3$.

As used herein, the term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The aryls may be connected to another group either at a suitable position on the cycloalkyl ring or the aromatic ring.

As used herein, the term "heteroaryl" is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, and fluoroscein derivatives.

As used herein, the term "heterocycle", "heterocyclic" or "heterocyclyl" is intended to mean a 5, 6, or 7 membered non-aromatic ring system containing from 1 to 4 heteroatoms selected from the group consisting of O, N and S. Examples of heterocycles include, but are not limited to pyrrolidinyl, tetrahydrofuranyl, piperidyl, pyrrolinyl, piperazinyl, imidazolidinyl, morpholinyl, imidazolinyl, pyrazolidinyl, and pyrazolinyl.

As used herein, the term "electron withdrawing group (EWG)" is intended to mean a functional group that allows nucleophilic attack by the thiol-group of a caspase at the alkene bond of the inhibitor as a result of the electron withdrawing properties of the EWG. The EWG is conjugated with the alkene bond, such that the electron withdrawing properties of the EWG allow nucleophilic attack by a caspase at the alkene bond, i.e. the alkene bond and the EWG are electronically conjugated. Thus, the covalent bond between the alkene bond and the EWG is a direct one, without intervening moieties that would prevent the electron withdrawing properties of the EWG from being exerted on the alkene bond.

As used herein, the term "detectable label" is intended to mean a group that may be linked to a compound of the present invention to produce a probe or to a caspase, such that when the probe is associated with the caspase, the label allows either direct or indirect recognition of the probe so that it may be detected, measured and quantified.

As used herein, the term "affinity tag" is intended to mean a ligand or group, which is linked to either a compound of the present invention or to a caspase to allow another compound to be extracted from a solution to which the ligand or group is attached.

As used herein, the term "probe" is intended to mean a compound of Formula I, IA, II, IIA, III, or IIIA, which is labeled with either a detectable label or an affinity tag, and which is capable of binding, either covalently or non-covalently, to a caspase. When, for example, the probe is non-covalently bound, it may be displaced by a test compound. When, for example, the probe is bound covalently, it may be used to form cross-linked adducts, which may be quantified and inhibited by a test compound.

As used herein, the term "optionally substituted with one or more substituents" or its equivalent term "optionally substituted with at least one substituent" is intended to mean that the subsequently described event of circumstances may or may not occur, and that the description includes instances where the event or circumstance occurs and instances in which it does not. The definition is intended to mean from zero to five substituents.

If the substituents themselves are incompatible with the synthetic methods of the present invention, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Examples of protecting groups used throughout include, but are not limited to Fmoc, Bn, Boc, CBz and $COCF_3$. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

Three and single letter abbreviations for natural α-amino acids used throughout are as follows:

| Amino acid | Abbreviation | Abbreviation |
| --- | --- | --- |
| α-Amino butyric acid | Abu | — |
| Alanine | Ala | A |
| Arginine | Arg | R |
| Aspartic acid | Asp | D |
| Asparagine | Asn | N |
| Cysteine | Cys | C |
| Glutamic acid | Glu | E |
| Glutamine | Gln | Q |
| Glycine | Gly | G |
| Isoleucine | Ile | I |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A series of non natural amino acids which may be used in place of natural amino acids include, but are not limited to, 3-amino 2-hydroxy pyridine; (2-furyl)alanine; 1-amino-1-cyclohexane carboxylic acid; (2-thienyl)alanine; 2-aminobenzoic acid (2-Abz); 2-pyridylalanine; 1-amino-1-cyclopentanecarboxilic acid; 2-aminobutyric acid (2-Abu); 3-amino-3-phenylpropionic acid; aminocyclopentane carboxylic acid (ACPC); 4-aminomethylbenzoic acid (Amb); aminoisobutiric acid (Aib); p-benzoyl-1-phenylalanine (Bpa); allylglycine; 4-aminomethyl cyclohexane carboxylic acid (Amc); cyclohexyl-alanine (Cha); delta-valine; deltaleucine; cyanobbutylalanine (Cba); indanylglycine (Igl); 3-(1-naphtyl)-alanine; 3-(2-naphthyl)alanine (1-Nal); biphenylalanine (Bip); hydroxyproline (Hyp); isonipecotic acid (Inp); norvaline (Nva); 4-iodophenylalanine (Phe(pI)); 4-nitrophenylalanine; 4-methylphenylalanine; homophenylalanine (hPhe); 4-aminophenylalanine (Phe4NH(Boc); phenyl glycine; alanine(2'-quinolyl); alanine (2' pyridine); tryptophan; pipecolic acid (Pip); propargylglycine; thioproline (Thz); butylglycine (Tle); 3-nitrotyrosine; 3-aminobenzoic acid (β-Abz); 3-amino-3-phenyl propionic acid; (1-indanylglycine); (2-indanylglycine); allyl glycine; 3-nitrotyrosine; 1,2,3,4-tetrahydroisoquinoline-3-carboxylic acid; beta amino acids; gamma amino acids; Asp(tert-butyl)-OH, 3,3-diphenyl-alanine; 3,3,3 dimethylphenyl-alanine; Asp(β ethyl); Glu(β-ethyl), Asp(β-methyl), Asp(β-tert butyl), Glu (β-tert butyl), Leu(O-phosphate), Serine(O-phosphate), Serine(phosphate), leucine phosphate derivatives. The side chains illustrated as $AA_X$, $AA_5$, $AA_4$, $AA_3$, $AA_2$ in the Formulae described above are the side chains of the aforesaid natural and non-natural amino acids.

As used herein, the term "residue" when referring to α-amino acids is intended to mean a radical derived from the corresponding α-amino acid by eliminating the hydroxyl of the carboxy group and one hydrogen of the α-amino group. For example, the terms Gln, Ala, Gly, Ile, Arg, Asp, Phe, Ser, Leu, Cys, Asn, and Tyr represent the residues of L-glutamine, L-alanine, glycine, L-isoleucine, L-arginine, L-aspartic acid, L-phenylalanine, L-serine, L-leucine, L-cysteine, L-asparagine, and L-tyrosine, respectively.

As used herein the term "amino acid side chain" is intended to mean the part of an amino acid's chemistry that differentiates it from other amino acids. Amino acid structure includes a carboxyl group, an amine group plus the individual side chain. Each amino acid has a unique side chain. This is applied to unnatural amino acids as well. This side chain may exist in protected form or not.

As used herein, the term "prodrug" is intended to mean a compound that may be converted under physiological conditions or by solvolysis to a biologically active compound of the present invention. Thus, the term "prodrug" refers to a precursor of a compound of the invention that is pharmaceutically acceptable. A prodrug may be inactive or display limited activity when administered to a subject in need thereof, but is converted in vivo to an active compound of the present invention. Typically, prodrugs are transformed in vivo to yield the compound of the invention, for example, by hydrolysis in blood or other organs by enzymatic processing. The prodrug compound often offers advantages of solubility, tissue compatibility or delayed release in the subject (see, Bundgard, H., Design of Prodrugs (1985), pp. 7-9, 21-24 (Elsevier, Amsterdam). The definition of prodrug includes any covalently bonded carriers which release the active compound of the invention in vivo when such prodrug is administered to a subject. Prodrugs of a compound of the present invention may be prepared by modifying functional groups present in the compound of the invention in such a way that the modifications are cleaved, either in routine manipulation or in vivo, to a parent compound of the invention.

As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, the term "pharmaceutically acceptable base addition salt" is intended to mean those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

The compounds of the present invention, or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present invention is intended to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds of the present invention may exist as a mix of epimers. Epimers means diastereoisomers that have the opposite configuration at only one of two or more stereogenic centres present in the respective compound.

Certain compounds of the present invention may exist in Zwitterionic form and the present invention includes Zwitterionic forms of these compounds and mixtures thereof.

In addition, the compounds of the invention also may exist in hydrated and anhydrous forms. Hydrates of the compound of any of the formulas described herein are included as compounds of the invention. In a further embodiment, the compound according to any of the formulas described herein is a monohydrate. In one embodiment, the compound of the invention comprises about 10% or less, about 9% or less, about 8% or less, about 7% or less, about 6% or less, about 5% or less, about 4% or less, about 3% or less, about 2% or less, about 1% or less, about 0.5% or less, about 0.1% or less by weight of water. In another embodiment, the compounds of the invention comprise, about 0.1% or more, about 0.5% or more, about 1% or more, about 2% or more, about 3% or more, about 4% or more, about 5% or more, or about 6% or more by weight of water.

C) Methods of Preparation

General and particular methods for the synthesis of the compounds of the present invention are shown below and are disclosed merely for the purpose of illustration and are not meant to be interpreted as limiting the processes to make the compounds by any other methods. Those skilled in the art will readily appreciate that a number of methods are available for the preparation of the compounds of the present invention.

An additional aspect of the invention relates to methods for synthesizing peptides comprising two, three, four or more amino acids as described hereinafter. In one embodiment the method is for synthesizing tripeptide A and comprises:

a) preparing intermediate A by coupling XX—NHCH(AA$_3$)C(O)OH with Salt NH$_3$CH(AA$_2$)C(O)O—ZZ;

b) deprotecting the protecting group (XX) followed with coupling intermediate A with a protected amino acid A-NHCHAA$_4$-OH to produce allyl derivatives intermediate B; and c) removing the ZZ protecting group from intermediate B to produce tripeptide A, according to the scheme:

ZZ is a C-terminal protecting group, including but not limited to: 3-methylbut-2-enyl(prenyl); methallyl; allyl; 2-methylbut-3-en-2-yl; cinnamyl; alpha-methyl cinnamyl.

Various deprotections methods are suitable, including but not limited to, hydrolysis under basic or acidic conditions and π-allyl derivative deprotection. In one particular embodiment, the deprotection comprises using (i) a base selected from the group consisting of morpholine, N-diisopropyl ethylamine, N-methyl morpholine; and (ii) a catalyst selected from the group consisting of tetrakis, palladium II catalysts.

Similarly, various coupling methods are suitable, including but not limited to, coupling using EDC (coupling agent) and HOBT (catalyst). Depending of the compounds and reaction conditions, the deprotection may require activation of the amino acid using a base such as N-diisopropyl ethylamine.

The synthesis method of the invention provides quantitative yield without requiring purification of the intermediates. In particular embodiments, the method for synthesizing tripeptide A is according to Procedure A or is according to Procedure B, as defined hereinafter. Procedure A is more advantageous and generally preferred because the tripeptides are obtained with minor or no isomerisation at all.

Those skilled in the art will appreciate that the synthesis method of the invention is flexible enough to make a peptide of two amino acids. For instance, this can be achieved by coupling A-NHCH(AA$_3$)C(O)OH with Salt NH$_3$CH(AA$_2$)C(O)O—ZZ followed with allyl derivatives deprotection, according to the scheme:

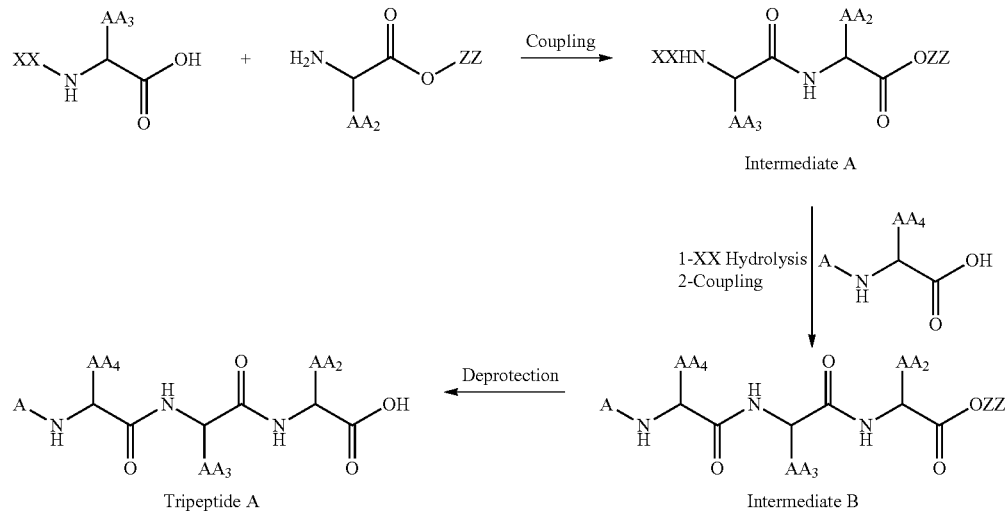

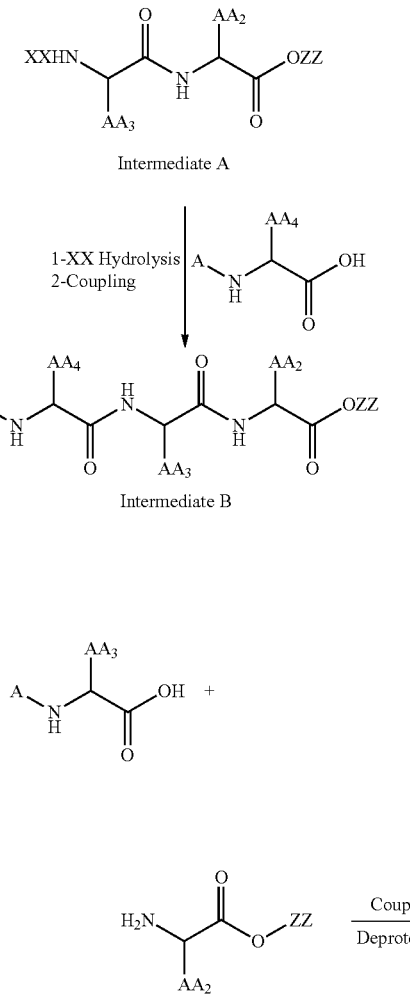

wherein

AA$_2$, AA$_3$ and AA$_4$ are any (D) or (L) amino acid residue side chains;

XX is a N-amino acid protecting group, including but not limited to Boc, Fmoc;

A is 1) H,
2) C$_1$-C$_6$ alkyl,
3) aryl,
4) heteroaryl,
5) heterocyclyl,
6) R$^3$—C(O)—,
7) R$^3$—OC(O)—,
8) R$^3$—CH$_2$OC(O)—,
9) R$^3$—C(O)O—, or
10) R$^3$—S(O)$_2$—;

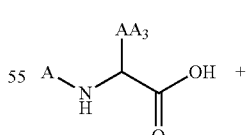

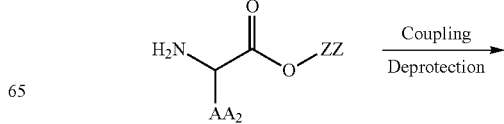

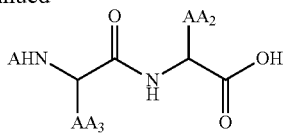

The synthesis method of the invention can also afford to make peptides having four amino acids or more. For instance, this can be achieved according to the following steps: Intermediate A undergoes XX hydrolysis to liberate the N-terminal side followed with coupling with XX—NHCH(AA$_4$)C(O)OH. The obtained peptide undergoes XX deprotection and coupling with A-NHCHAA$_5$-OH to afford after allyl derivatives deprotection a peptide of 4 amino acids, according to the scheme:

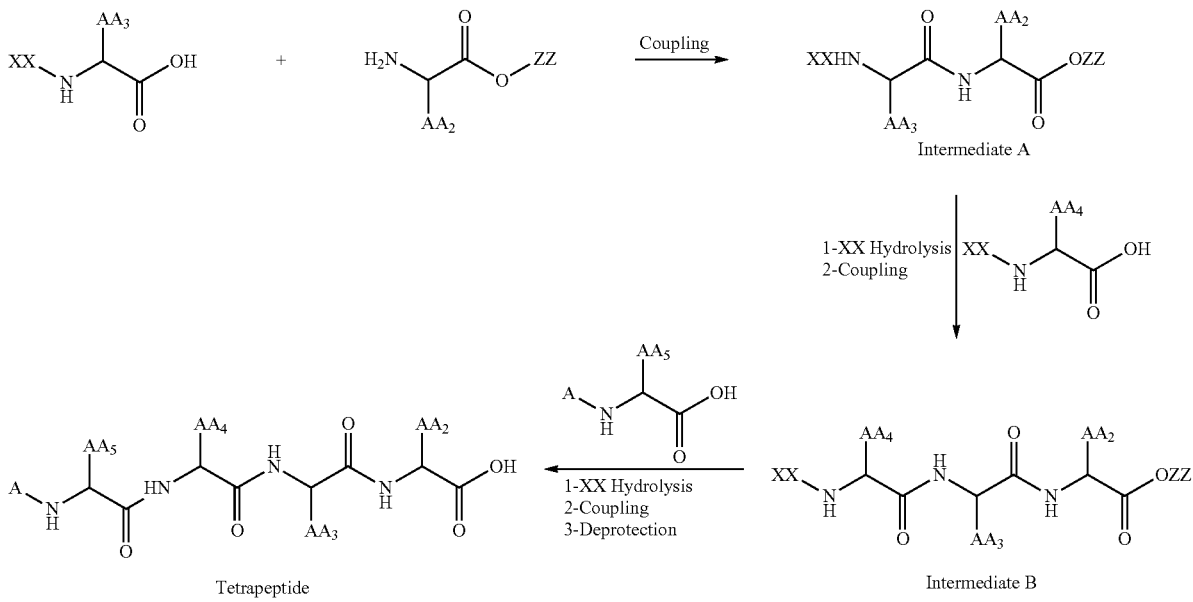

mix formation (isobutyl chloroformate, −12/−20° C.) to avoid any racemisation of amino acids.

Is some embodiments, removal of the amino protecting group is carried out but by piperidine in dichloromethane (Fmoc protecting group). The removal of β-tert-butyl carboxylic acid is carried out by TFA. Selective removal of N-Boc from B-tert butyl aspartic acid is carried out by PTSA or TFA at 0° C.

Vinyl sulfone function is elucidated as an example only in the following examples, but is not limited to it. It will be recognized by a skilled person in the art, that other vinyl electron-withdrawing group (EWG) may be used in this invention. Benzyloxycarbonyl (Z) is elucidated as an example of linkers that may facilitate the penetration of the drug into cells. It is recognized that other X—R3 may be used as well. The allyl group was introduced directly by the use of commercially available AA$_2$-OAllyl protected form or synthesized from the corresponding amino acid AA$_2$-OH.

This is a convergent synthesis, which consists of synthesizing two different fragments (suicide inhibitor linker and the peptide or peptidomimetic fragment) prior to the 'coupling step'.

1. A Compound of Formula 1a can be Prepared by the Procedure Described Below

In general, the starting materials and reagents used in preparing the compounds of the invention are either available from commercial suppliers such as Sigma-Aldrich Chemicals, Anaspec or chemipex.

The starting materials and the intermediates of the reaction may be isolated and purified if desired using conventional techniques such chromatography (Biotage flash chromatography), filtration, distillation, etc. Such materials can be characterized using conventional analytical methods such as NMR and LCMS.

As exemplified hereinafter, the coupling step is typically carried out in the presence of a coupling agent. Suitable coupling agents include, but are not limited to, diisopropyl carbodiimide (DPC), anhydride mixte (isobutylchloroformate), O-benzotriazole-1-yloxytrispyrrolidinophosphonium hexafluorophosphate (PyBOP), O-benzotriazol-1-yl-N,N,N,N tetramethyluroniumhexafluoro-phosphate (HBTU), O-(7-azabenzotriazol-1-yl)-1,1,3,3-tetramethyluronium hexafluoro-phosphate (HATU), 1-hydroxybenzotriazole (HOBT) in the presence of 1-(3-dimethylaminopropyl)-3-ethylcarbodiimide hydrochloride (EDC). A base such as N,N-diisopropylethylamine, triethyl amine, or N-methylmorpholine. The reaction is carried out at 20° C. except for anhydride Formula 1a

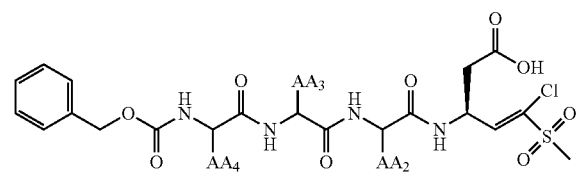

i) Left Arm Synthesis

The allyl group was introduced directly by the use of commercially available AA$_2$-OAllyl protected form or synthesized from the protected amino acid Boc-AA$_2$-OH or fmoc-AA$_2$-OH and allyl alcohol (EDC, DMAPcat, NMM, CH$_2$Cl$_2$/

DMF (5/1)) followed with Boc deprotection (TFA, CH₂Cl₂) or fmoc deprotection (piperidine, CH₂Cl₂).

Procedure A (recommended, see scale-up section): The AA₂-OAllyl is coupled to Boc-AA₃-OH with the coupling reagent EDC and HOBT, and used for the next reaction as a crude, Subsequent Boc deprotection with TFA gives after crystallization AA₃-AA₂-Oallyl (intermediate A) ready for coupling with (Z) AA₄-OH to give (Z) AA₄-AA₃-AA₂-Oallyl (intermediate B) which upon removal of allyl group (tetrakis) liberate the C-terminal carboxylic acid of the tripeptide A as described in the following scheme. Procedure B: The AA₂-OAllyl is coupled to Fmoc-AA₃-OH with the coupling reagent EDC and subsequent purification and fmoc deprotection with piperidine gives AA₃-AA₂-Oallyl (intermediate A) which is purified prior coupling with (Z) AA₄-OH to get after purification (Z) AA₄-AA₃-AA₂-Oallyl (intermediate B) which upon removal of allyl group (tetrakis) liberate the C-terminal carboxylic acid of the tripeptide A as described in the following scheme:

Procedure A

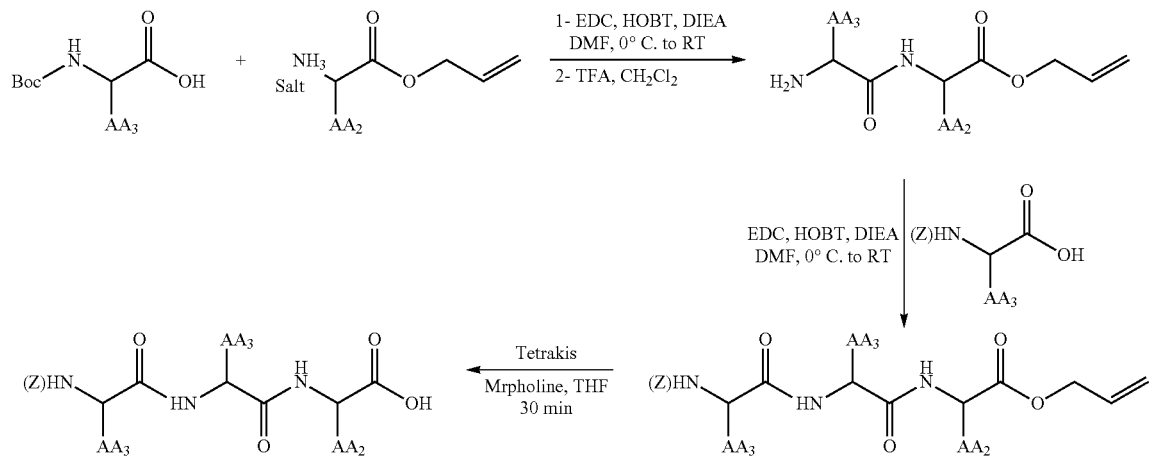

Procedure B

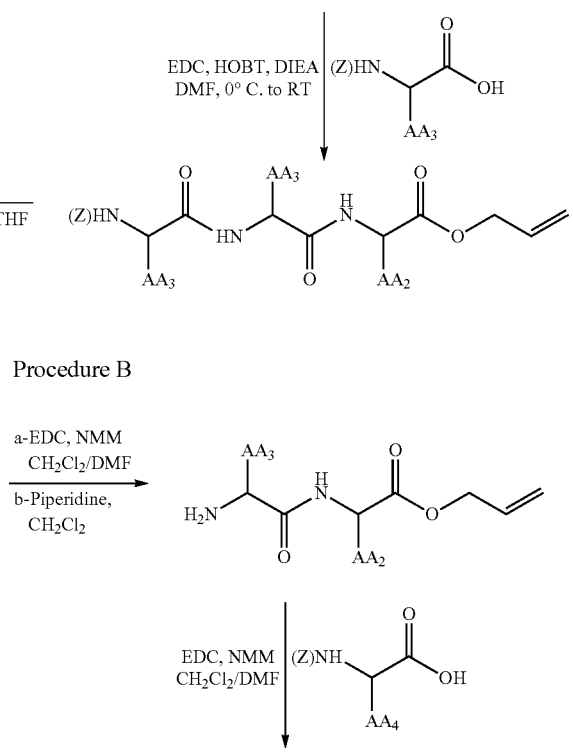

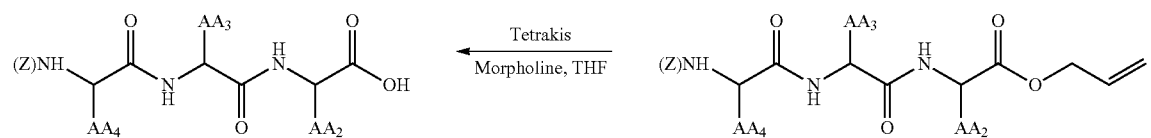

ii) Right Arm Synthesis

The suicide substrate proposed in the following scheme is Asp α-chlorovinyl methylsulfone.

The common intermediate Boc-Asp(B-tert-butyl)-H is synthesized from Boc-Asp(B-tert-butyl)-N-hydroxysuccinimide ester as reported by (Mancuso A et al., 1981, William R. Ewing et al., 1999 and Won Bum Jang. 2004).

Treatment of the aldehyde with sodium anion of Diethyl chloro(methylsulfone)methylphosphonate results in the corresponding Boc-Asp(β-tert-butyl)α-chlorovinyl-methylsulfone in the manner of Wadsworth and Emmons.

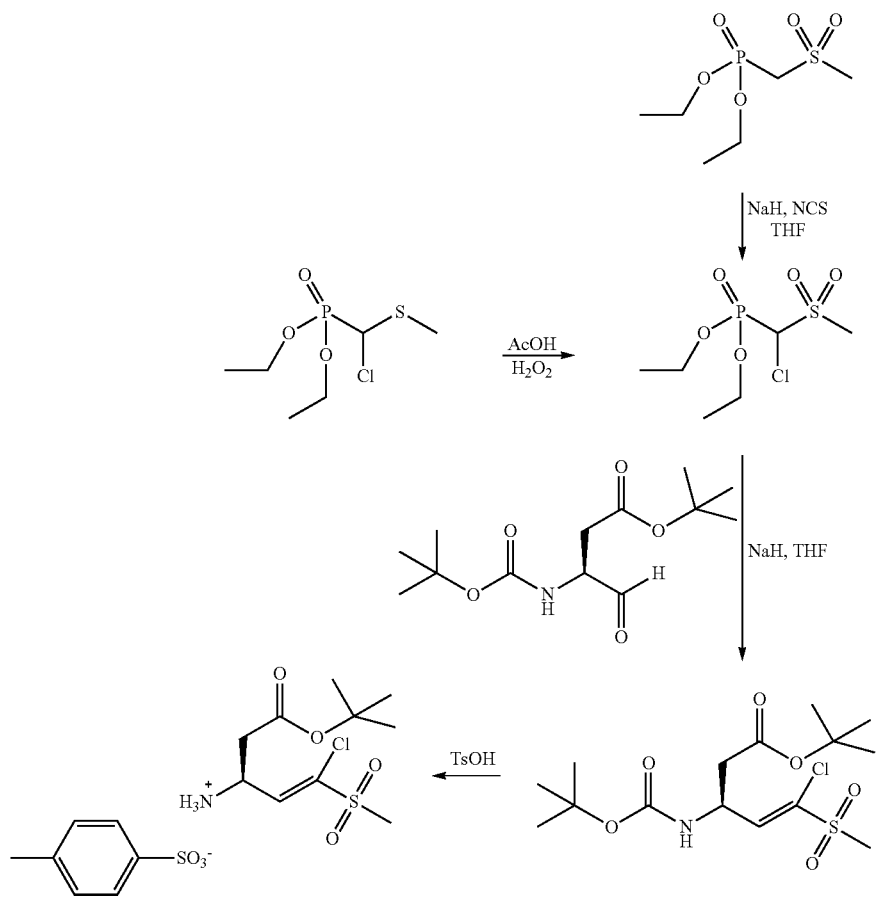
iii) Coupling Step Synthesis
The coupling step between Asp α chlorovinyl methylsulfone salt and the peptide in the presence of coupling reagents such (isobutyl chloroformate, NMM) or (HOBT, NMM, EDC; Dragovich P., S., 1999) results in Asp α-chlorovinyl methylsulfone peptide derivative.
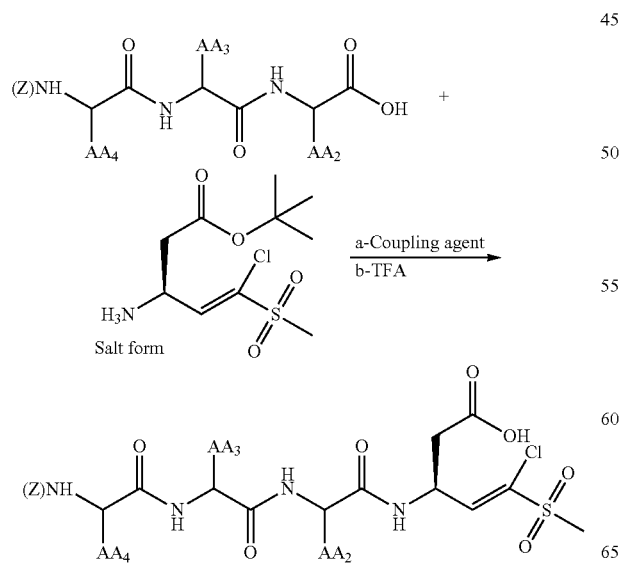

2. A Compound of Formula 1b can be Prepared by the Procedure Described Below

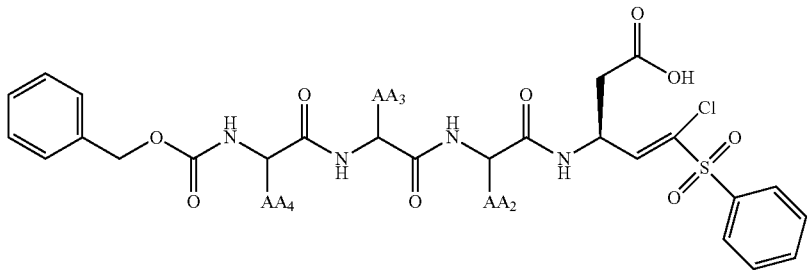

Formula 1b i) Right Arm Synthesis

The suicide substrate proposed in the following scheme is Asp α-chlorovinyl phenylsulfone.

Treatment of the aldehyde with sodium anion of Diethyl chloro(methylsulfone)phenyl phosphonate results in the corresponding Boc-Asp(β-tert-butyl)α-chlorovinyl phenylsulfone in the manner of Wadsworth and Emmons.

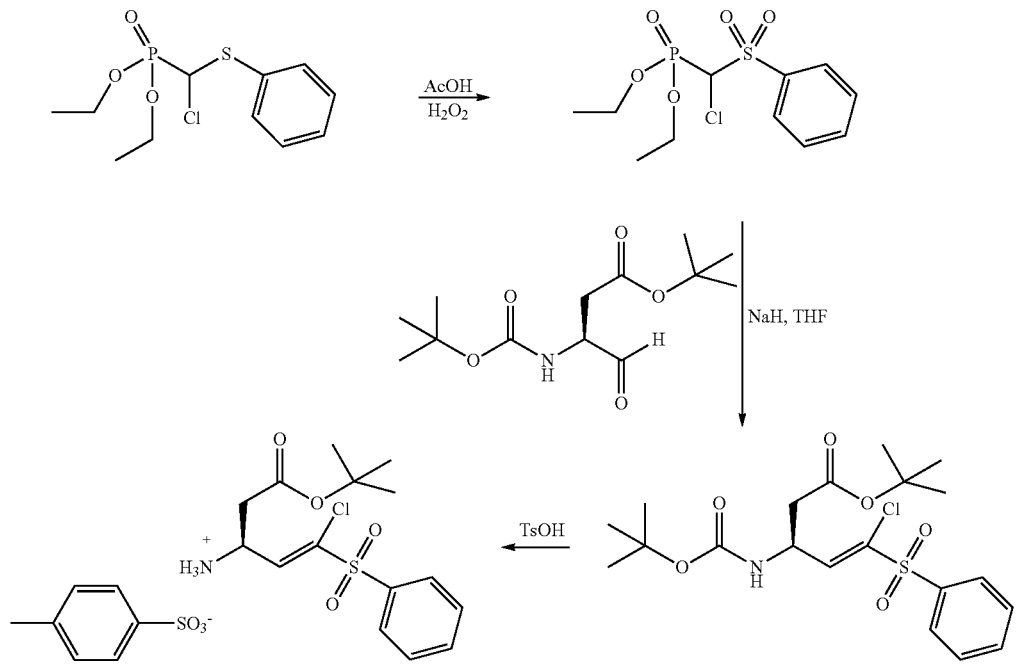

ii) Coupling Step Synthesis

The coupling step between Asp α-chlorovinyl phenylsulfone salt and the peptide in the presence of coupling reagents such (isobutyl chloroformate, NMM) or (HOBT, NMM, EDC) results in Asp α-chlorovinyl phenylsulfone peptide derivative.

3. A Compound of Formula 1c can be Prepared by the Procedure Described Below

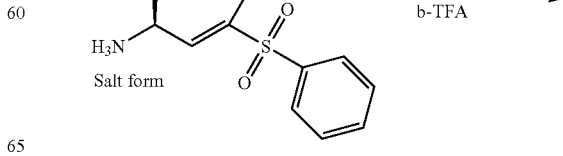

-continued

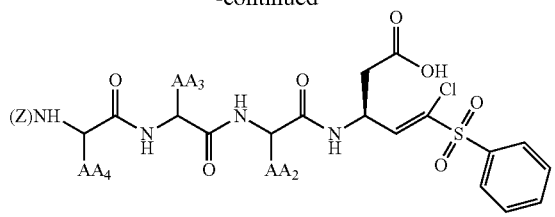

Formula 1c

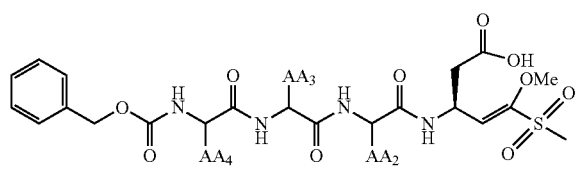

i) Right Arm Synthesis

The suicide substrate proposed in the following scheme is Asp α-methoxyvinyl methylsulfone.

Oxydation of diethyl methylthiomethylphosphonate include anodic oxidation in NaOMe/MeOH (saturated with CO2) to give the O, S-acetal of diethoxyphosphinylformaldehyde, which upon oxidation may give the corresponding sulfone as Diethyl methoxy(methylsulfone)phenyl phosphonate (Shankaran, K et al. 2001).

Treatment of the aldehyde with sodium anion of Diethyl methoxy(methylsulfone)phenyl phosphonate should result in the corresponding Boc-Asp(β-tert-butyl)α-methoxyvinyl methylsulfone in the manner of Wadsworth and Emmons.

ii) Coupling Step Synthesis

The coupling step between Asp α-methoxyvinyl methylsulfone salt and the peptide in the presence of coupling reagents such (isobutyl chloroformate, NMM) or (HOBT, NMM, EDC) results in Asp α-methoxyvinyl methylsulfone peptide derivative.

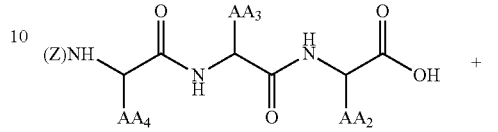

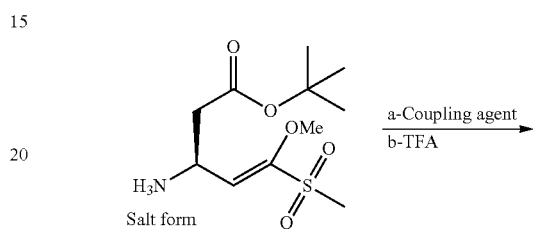

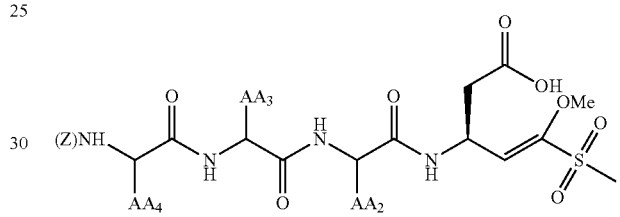

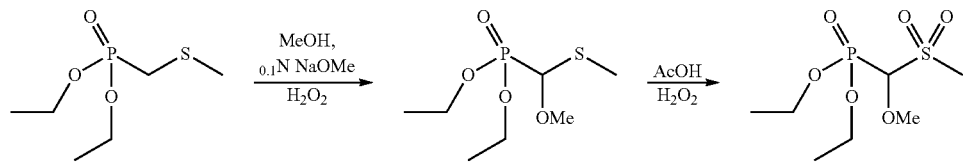

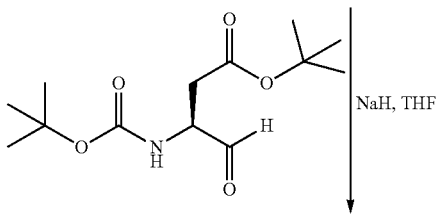

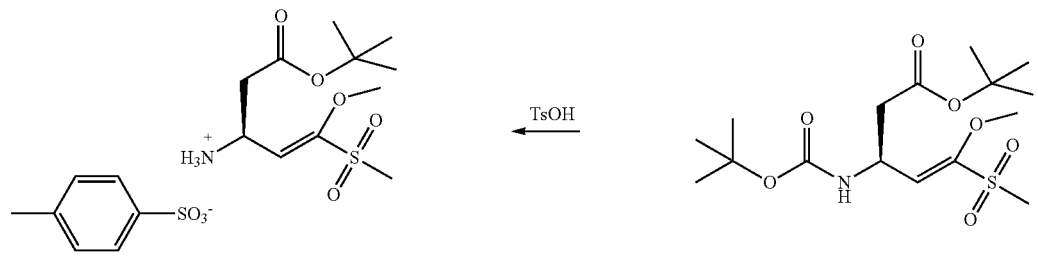

4. A Compound of Formula 1d can be Prepared by the Procedure Described Below

Formula 1d

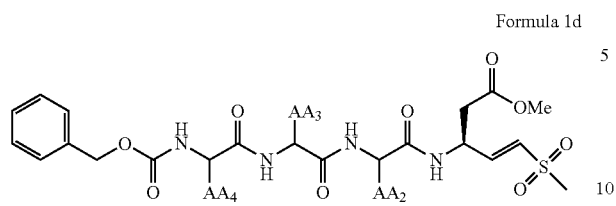

i) Right Arm Synthesis

The suicide substrate proposed in the following scheme is Asp(B-Methyl)methyl vinylsulfone.

Boc-Asp(B-Methyl)-N-hydroxysuccinimide ester was reduced to the corresponding alcohol (NaBH$_4$, THF), a subsequent oxidation (oxalyl chloride, DMSO) gave the aldehyde: Boc-Asp(B-Methyl)-H.

Treatment of Boc-Asp(B-Methyl)-H with sodium anion of Diethyl(methylsulfone)methyl phosphonate results in the corresponding Boc-Asp(β-Methyl)methyl vinylsulfone in the manner of Wadsworth and Emmons.

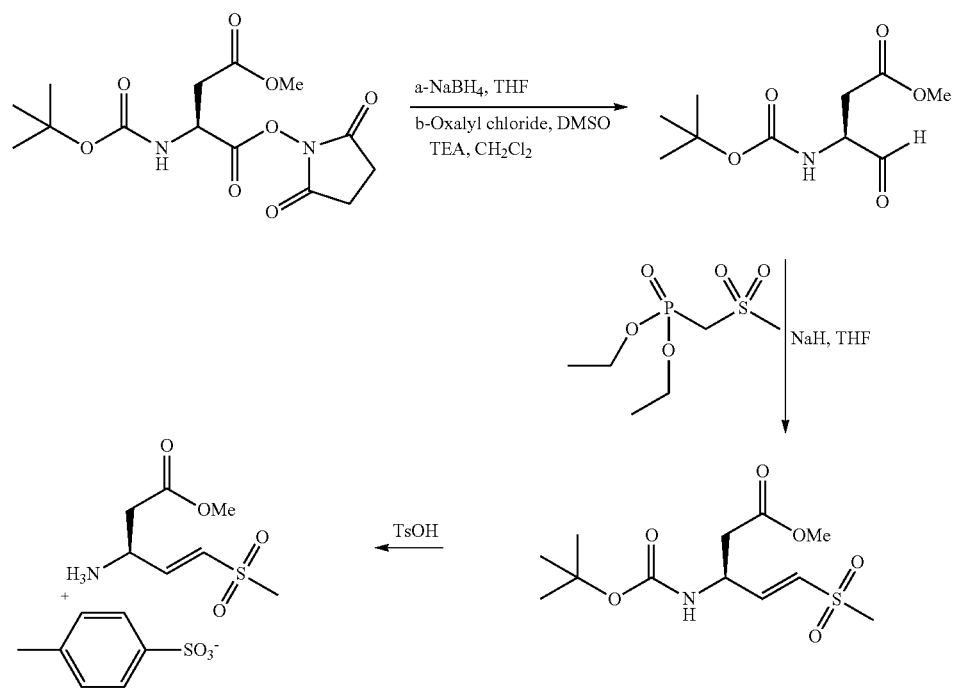

ii) Coupling Step Synthesis

The coupling step between Asp(β-Methyl)methyl vinylsulfone salt and the peptide in the presence of coupling reagents such (isobutyl chloroformate, NMM) or (HOBT, NMM, EDC) results in Asp(β-Methyl)methyl vinylsulfone peptide derivative.

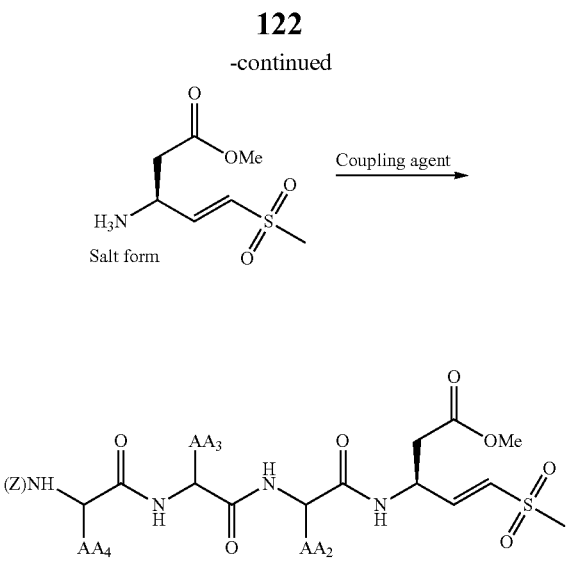

5. A Compound of Formula 1e can be Prepared by the Procedure Described Below

Formula 1e

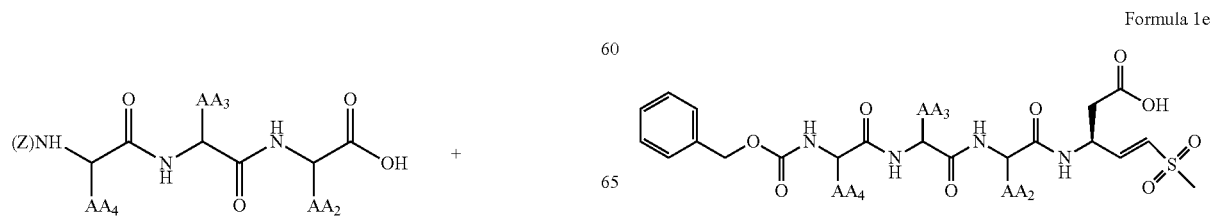

i) Right Arm Synthesis

The suicide substrate proposed in the following scheme is Asp methyl vinyllsulfone.

The common intermediate Boc-Asp(B-tert-butyl)-H is synthesized from Boc-Asp(B-tert-butyl)-N-hydroxysuccinimide ester as reported by (Mancuso A et al., 1981, William R. Ewing et al., 1999 and Won Bum Jang. 2004).

Treatment of the aldehyde with sodium anion of Diethyl (methylsulfone)methyl phosphonate results in the corresponding Boc-Asp(β-tert-butyl)methylvinylsulfone in the manner of Wadsworth and Emmons, 1961 and Palmer et al. 1995.

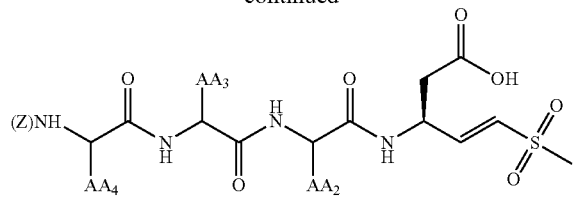

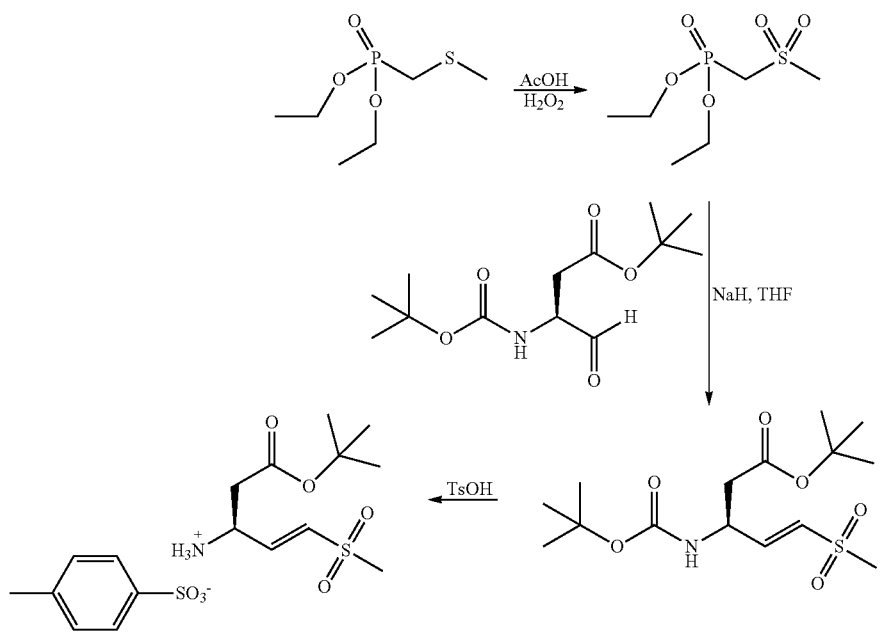

ii) Coupling Step Synthesis

The coupling step between Asp methyl vinylsulfone salt and the peptide in the presence of coupling reagents such (isobutyl chloroformate, NMM) or (HOBT, NMM, EDC) results in Asp methyl vinylsulfone peptide derivative.

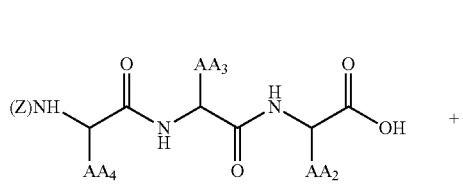

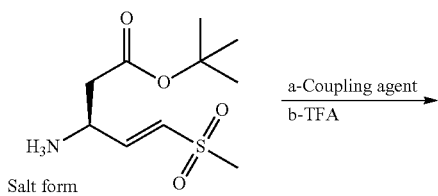

6. A Compound of Formula 1f can be Prepared by the Procedure Described Below

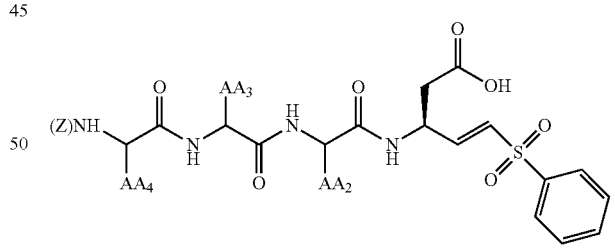

Formula 1f i) Right Arm Synthesis

The suicide substrate proposed in the following scheme is Asp phenyl vinyllsulfone.

Diethyl phenylsulfonylmethylphosphonate was obtained in one step from benzenesulfonyl fluoride and triethyl phosphorane in the presence of lithium hexamethyldisilazide (Won Bum Jang et al., 1998).

Treatment of the aldehyde with sodium anion of Diethyl (phenyl sulfone)methylphosphonate results in the corresponding Boc-Asp(β-tert-butyl)phenyl vinylsulfone in the manner of Wadsworth and Emmons, 1961 and Palmer et al. 1995.

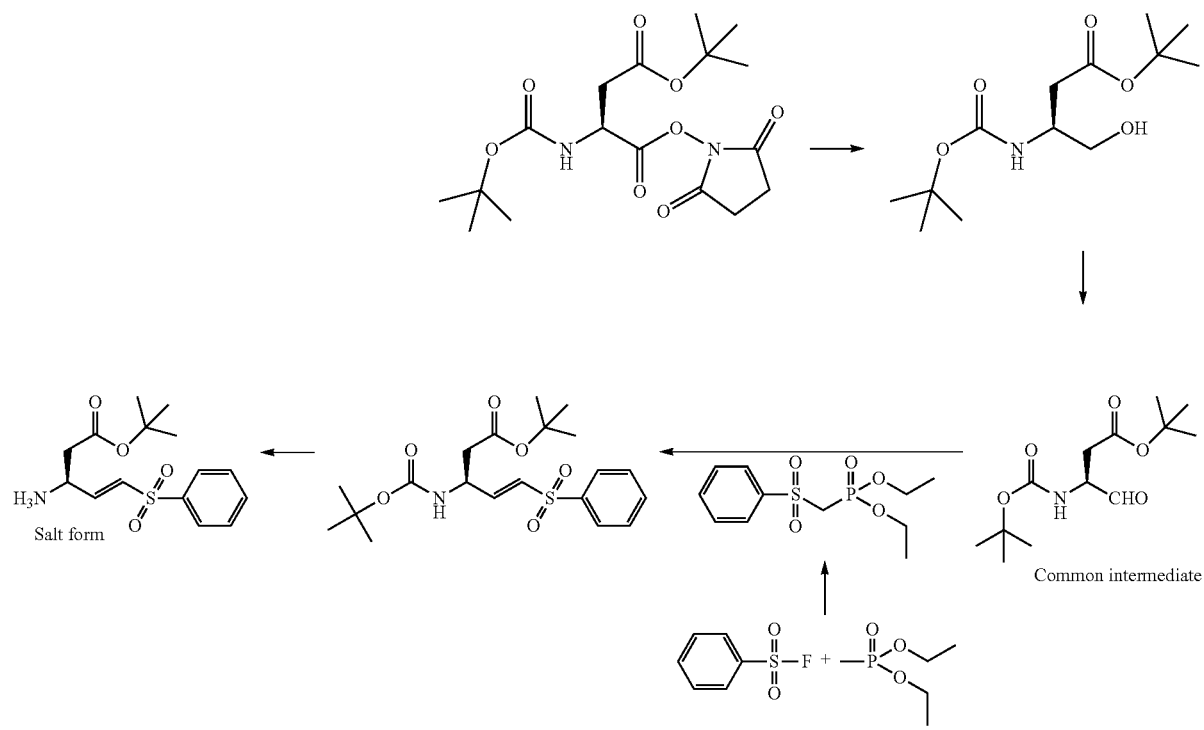
ii) Coupling Step Synthesis
The coupling step between Asp phenyl vinylsulfone salt and the peptide in the presence of coupling reagents such as (isobutyl chloroformate, NMM) or (HOBT, NMM, EDC) results in Asp phenyl vinylsulfone peptide derivative.
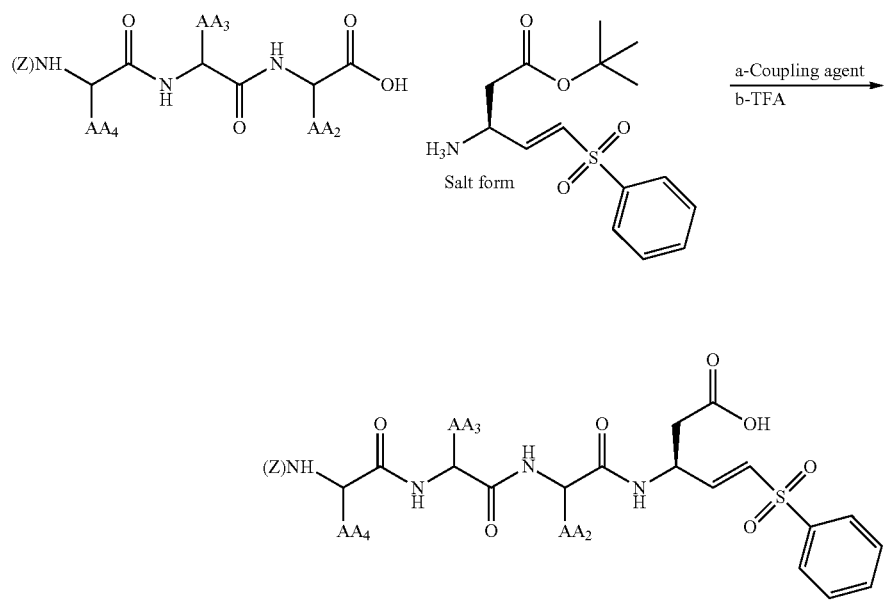

7. A Compound of Formula 1g can be Prepared by the Procedure Described Below

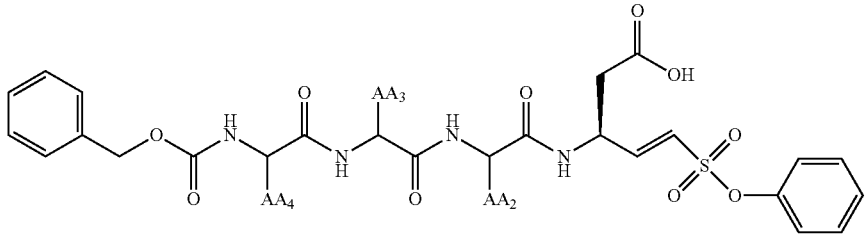

Formula 1g i) Right Arm Synthesis

The suicide substrate proposed in the following scheme is Asp phenoxy vinyllsulfone.

Diethyl(phenoxysulfone)methylphosphonate was obtained from methanesulfonyl phenoxy and diethyl chlorophosphonate in the presence of potassium bis(trimethylsilyl) amide. A subsequent oxidation (AcOH, $H_2O_2$) gave the corresponding sulfone.

Treatment of the aldehyde with sodium anion of Diethyl (phenoxy sulfone)methylphosphonate results in the corresponding Boc-Asp(β-tert-butyl)phenoxy vinylsulfone in the manner of Wadsworth and Emmons.

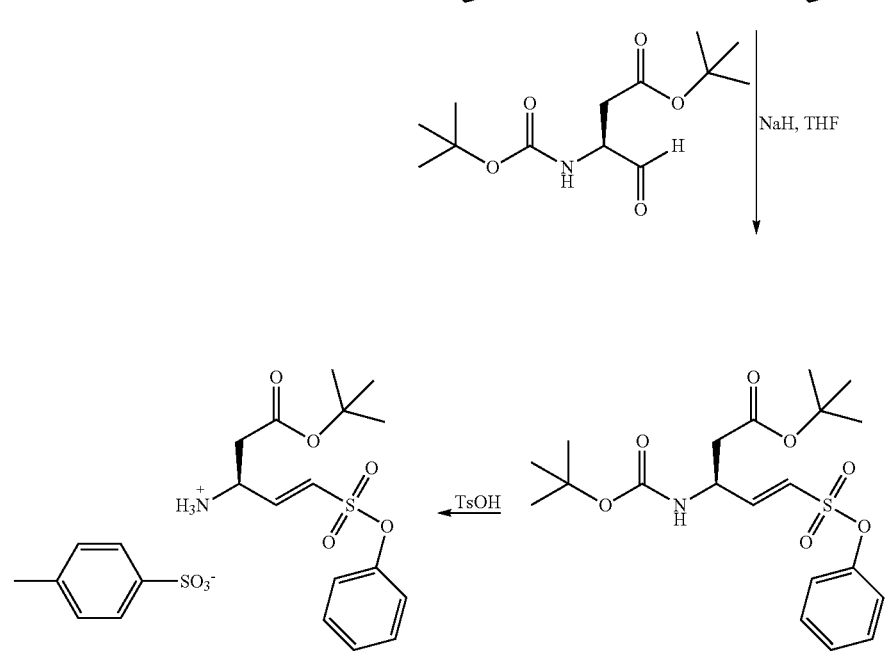

ii) Coupling Step Synthesis

The coupling step between Asp phenoxy vinylsulfone salt and the peptide in the presence of coupling reagents such (isobutyl chloroformate, NMM) or (HOBT, NMM, EDC) results in Asp phenoxy vinylsulfone peptide derivative.

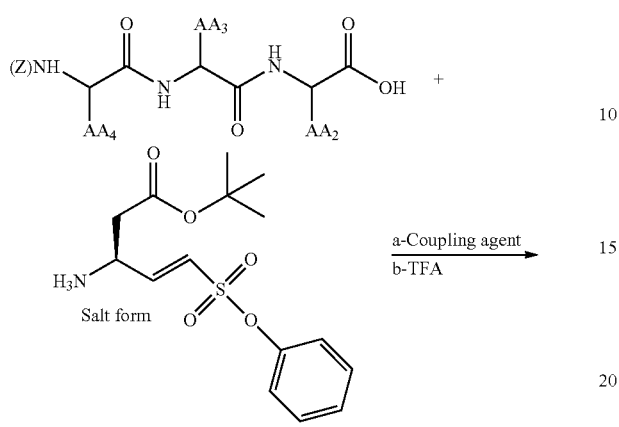

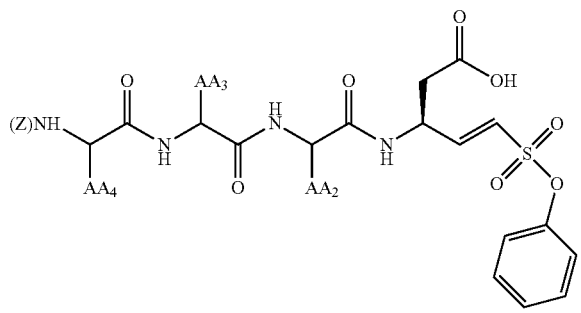

8. A Compound of Formula 1h can be Prepared by the Procedure Described Below

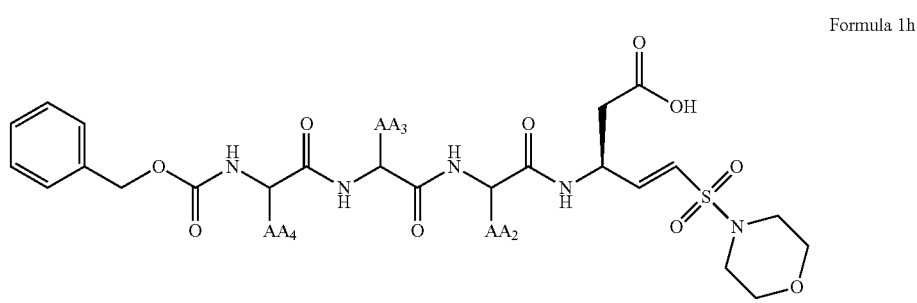

Formula 1h i) Right Arm Synthesis

The suicide substrate proposed in the following scheme is Asp morpholine vinyllsulfone.

Diethyl(morpholinesulfone)methylphosphonate was prepared from methane sulfonyl morpholine and chloromethylphosphonate in the presence of potassium bis(trimethylsilyl)amide.

Treatment of the aldehyde with sodium anion of Diethyl (morpholinesulfone)methylphosphonate results in the corresponding Boc-Asp(β-tert-butyl)morpholino vinylsulfone in the manner of Wadsworth and Emmons.

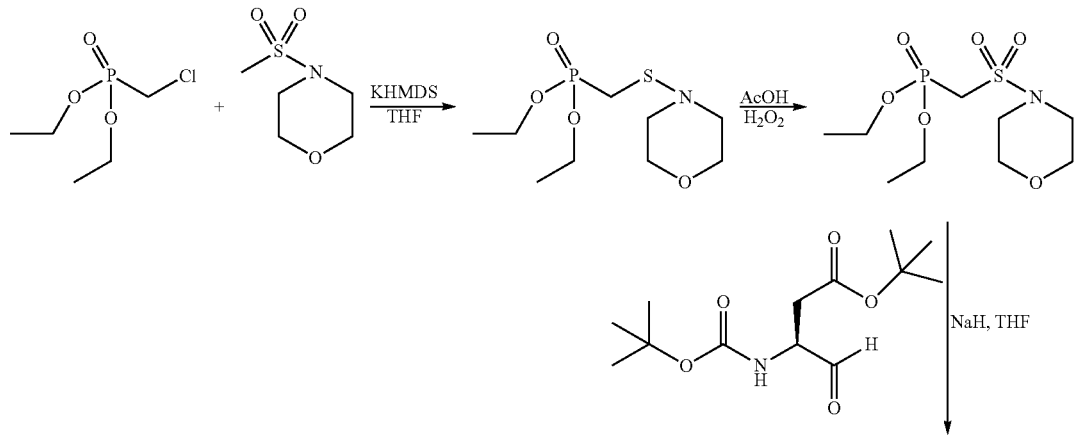

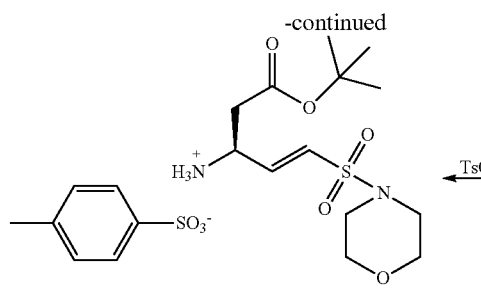
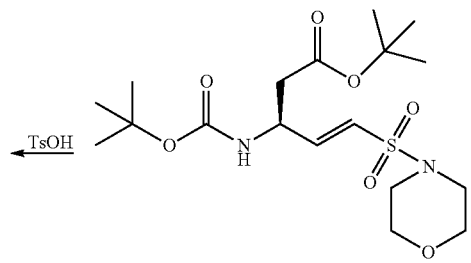

ii) Coupling Step Synthesis

The coupling step between Asp morpholine vinylsulfone salt and the peptide in the presence of coupling reagents such (isobutyl chloroformate, NMM) or (HOBT, NMM, EDC) results in Asp morpholine vinylsulfone peptide derivative 9. A Compound of Formula 1i can be Prepared by the Procedure Below

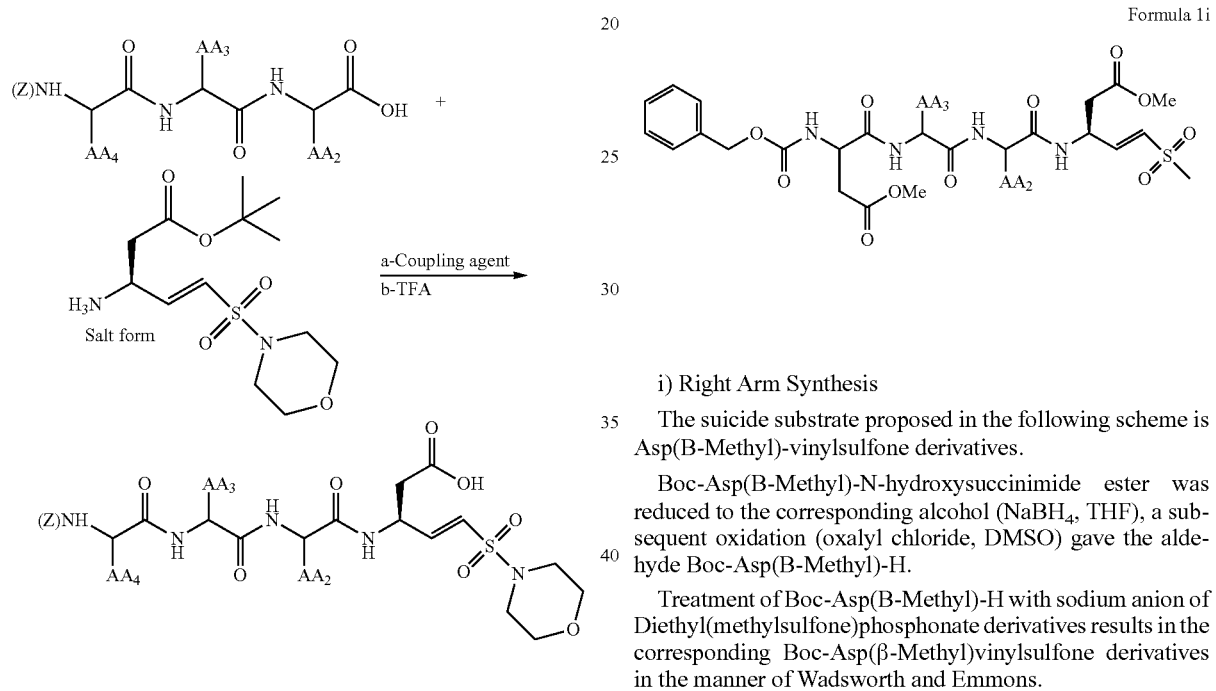

Formula 1i i) Right Arm Synthesis

The suicide substrate proposed in the following scheme is Asp(B-Methyl)-vinylsulfone derivatives.

Boc-Asp(B-Methyl)-N-hydroxysuccinimide ester was reduced to the corresponding alcohol ($NaBH_4$, THF), a subsequent oxidation (oxalyl chloride, DMSO) gave the aldehyde Boc-Asp(B-Methyl)-H.

Treatment of Boc-Asp(B-Methyl)-H with sodium anion of Diethyl(methylsulfone)phosphonate derivatives results in the corresponding Boc-Asp(β-Methyl)vinylsulfone derivatives in the manner of Wadsworth and Emmons.

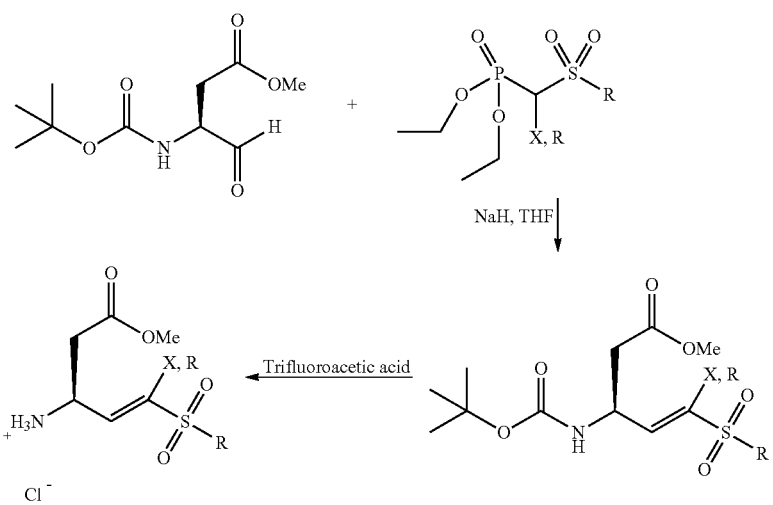

ii) Coupling Step Synthesis

The coupling step between Asp(β-Methyl)vinylsulfone derivatives salt and the caspase-3 designed peptide in the presence of coupling reagents such (isobutyl chloroformate, NMM) or (HOBT, NMM, EDC) results in Z-Asp(β-Methyl)-AA₃-AA₂-Asp(β-Methyl)vinylsulfone peptide derivatives.

This approach will allow the synthesis of a variety of prodrug vinylsulfone derivatives that could be easily obtained by choosing the appropriate combination (X, R) and applying the appropriate method mentioned above. Such combination may enhance cell permeability, selectivity and potency. Methyl ester prodrug is mentioned as an example only; other prodrugs could be used as well.

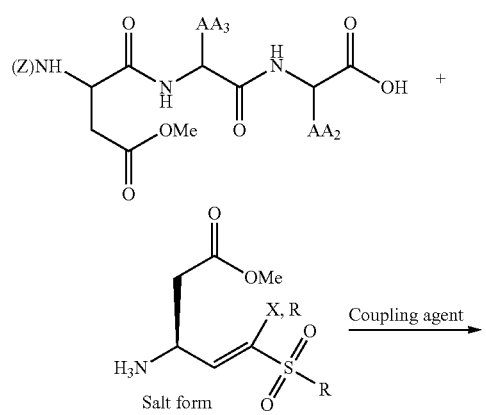

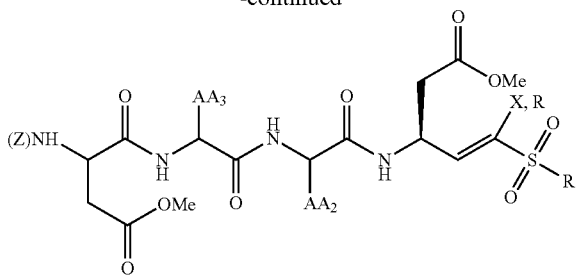

All acid, salt and other ionic and non-ionic forms of the compounds described are included as compounds of the invention. For example, if a compound is shown as an acid herein, the salt forms of the compound are also included. Likewise, if a compound is shown as a salt and the acid forms are also included.

General Method to Generate Other Peptide Asp-Vinyl Electrowithrawing Groups.

1—Vinyl Phosphonates:

Treatment of Boc-Asp(β-tert-butyl)-H with sodium anion of tetraethyl methylene diphosphonate derivatives could result in the corresponding Boc-Asp(β-tert-butyl)vinyl phosphonate derivatives in the manner of Wadsworth and Emmons.

The vinyl phosphonate derivatives could be deprotected with Tosyl acid to form the corresponding salt and coupled with the appropriate peptide to form the corresponding peptide Asp vinyl phosphonate derivatives.

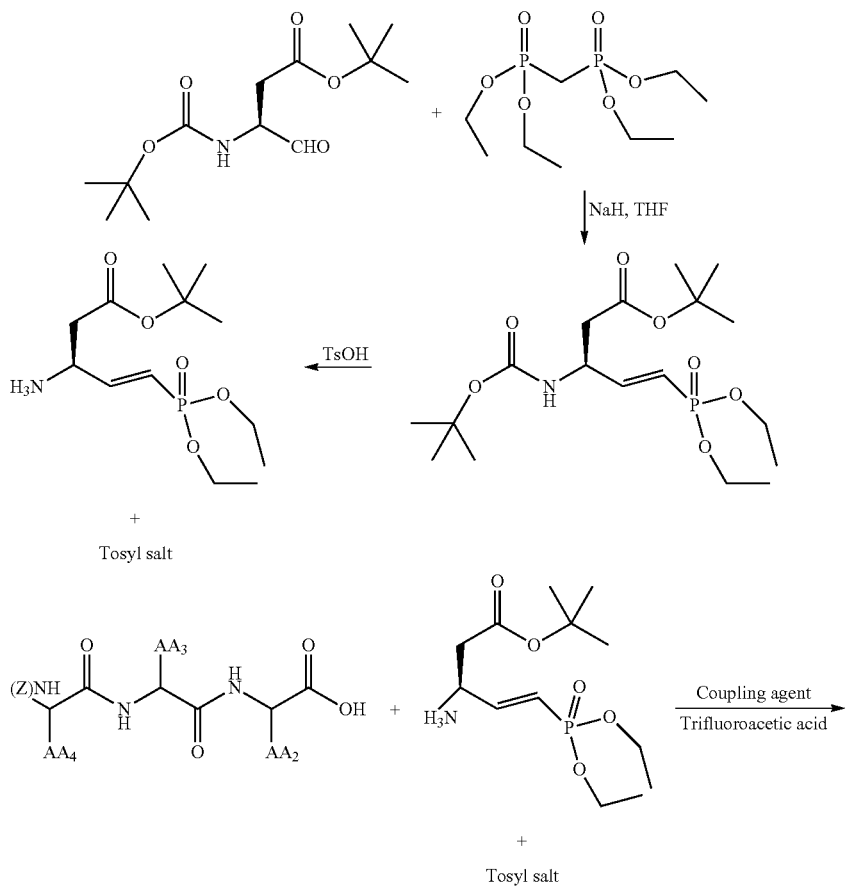

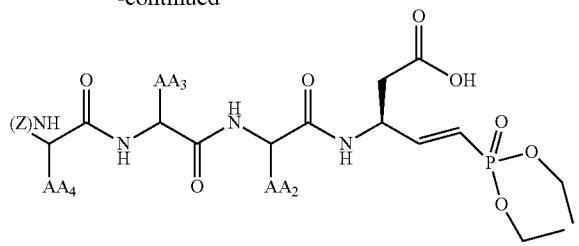

2—Vinyl Nitrites:

Treatment of Boc-Asp(β-tert-butyl)-H with sodium anion of diethyl cyanomethylphosphonate derivatives could result in the corresponding Boc-Asp(β-tert-butyl)vinyl nitrites derivatives in the manner of Wadsworth and Emmons.

The vinyl nitrites derivatives could be deprotected with Tosyl acid to form the corresponding salt and coupled with the appropriate peptide to form the corresponding peptide Asp vinyl nitrites derivatives.

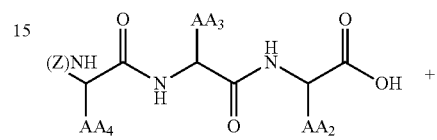

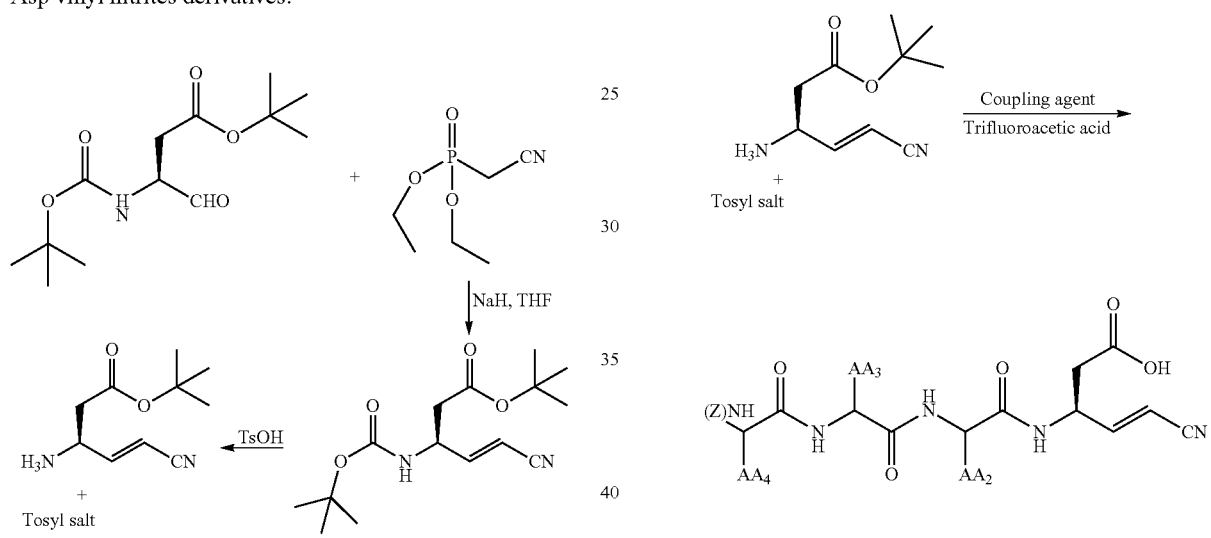

3—Diene Sulfone:

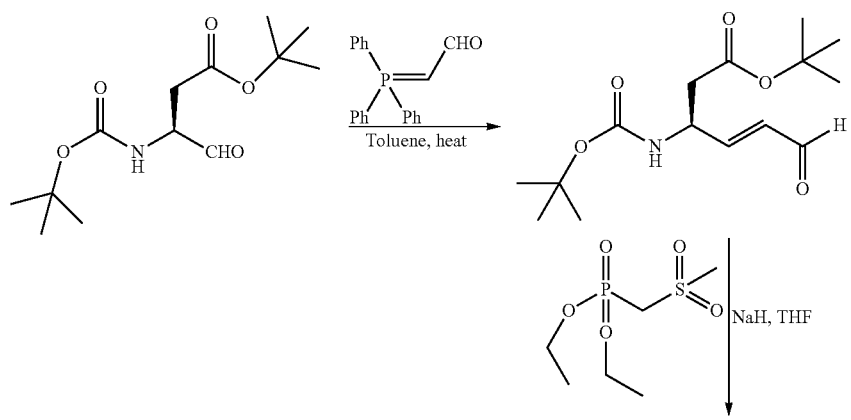

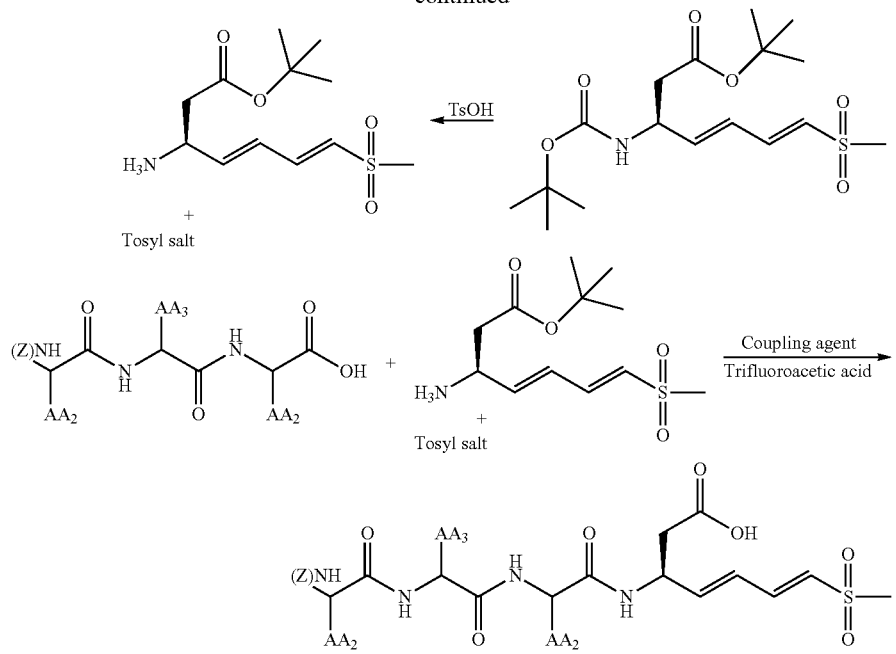

Treatment of Boc-Asp(R-tert-butyl)-H with (triphenylphosphoranylidene)acetaldehyde in toluene result in the corresponding Boc-Asp(β-tert-butyl)vinyl acetaldehyde derivatives in the manner of Wadsworth and Emmons. The sodium anion of Diethyl(methylsulfone)phosphonate derivatives could react with Boc-Asp(β-tert-butyl)vinylacetaldehyde derivatives in the manner of Wadsworth and Emmons to form the corresponding cis and trans diene sulfone derivative.

The diene sulfone derivatives could be deprotected with Tosyl acid to form the corresponding salt and coupled with the appropriate peptide to form the corresponding peptide Asp diene sulfone derivatives.

4—Vinyl Amide

Vinyl amide could be obtained by coupling diethyl phosphonoacetic acid with natural and unnatural amino acids (Ex: Glycine methyl ester or tert butyl) to form the diethyl phosphonoacetyl glycine methyl ester which upon treatment with NaH reacts with Boc-Asp(β-tert-butyl)-H to form the corresponding Boc-Asp(β-tert-butyl)vinyl amide. N-deprotection of Boc-Asp(β-tert-butyl)vinyl amide followed with coupling reaction with the appropriate peptide could afford the corresponding peptide Asp vinyl amide derivatives.

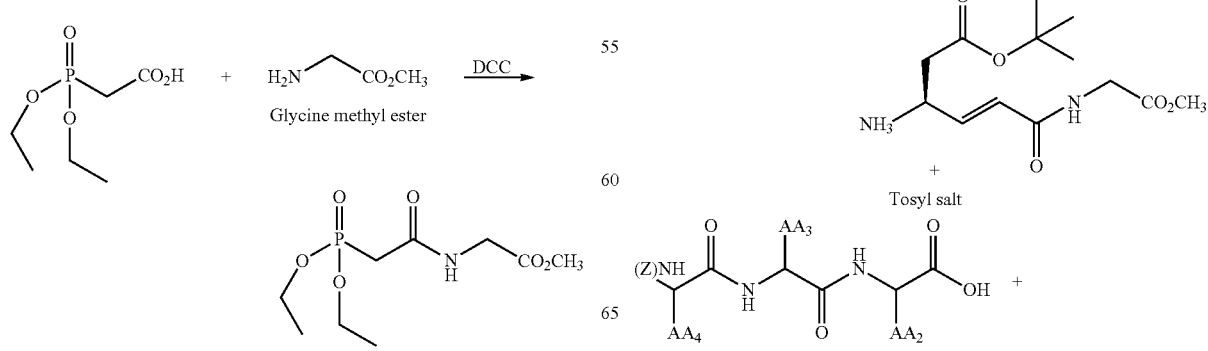

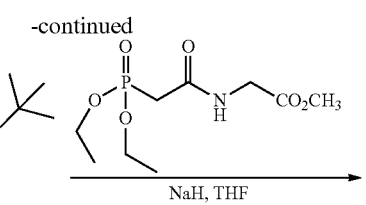

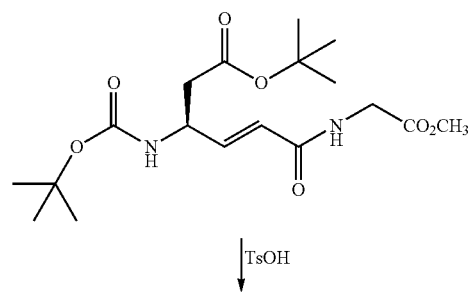

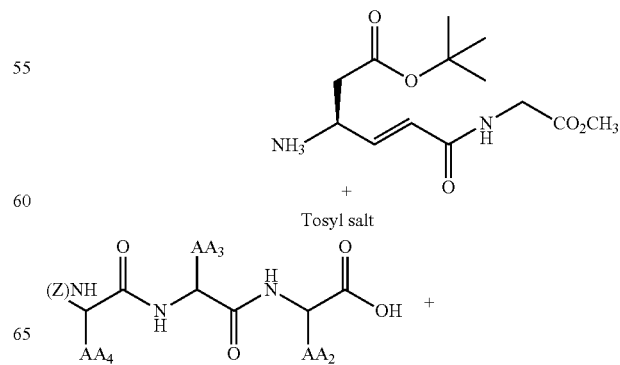

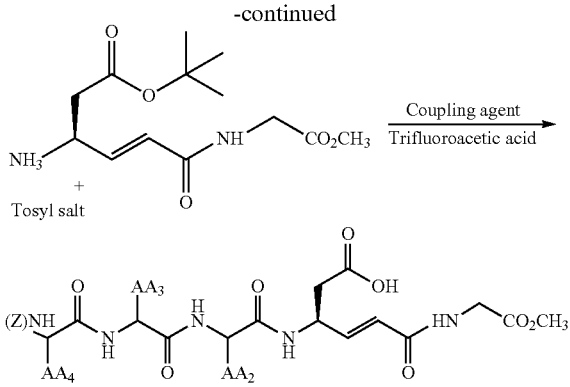

D) Development of Specific Caspase Inhibitors

An additional aspect of the invention relates to a method for designing caspase inhibitors. Following the same approach as outlined hereinafter, those skilled in the art will appreciate that it is conceivable to further improve the potency of the compounds of Formula II, e.g. Z-Asp-Phg-Val-AspVSmethyl (Compound 53), against caspase-3 and inhibit selectively additional caspases such as caspase-2, caspase-8, caspase-9 and caspase-1.

Figure 6:
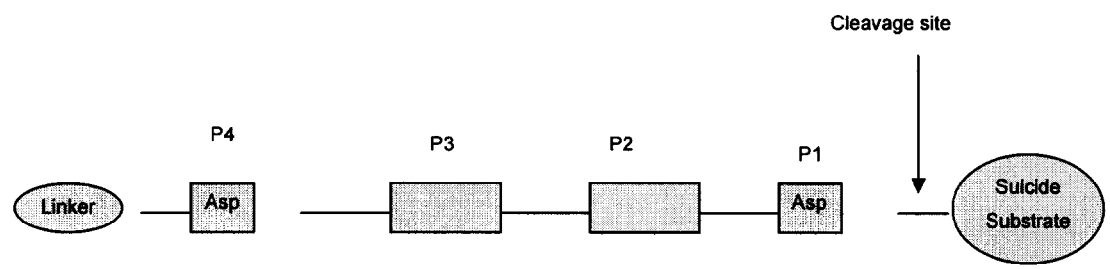
FIG. 6 is a diagram showing that, contrary to typical caspases which are known to cleave substrates to the right of the aspartic acid amino acid in position P1, caspase-3 requires an additional Asp at position P4, which confers caspase-3 its specificity.

As is known, all caspases cleave substrates to the right of the aspartic acid amino acid in position P1. However, caspase-3 requires an additional Asp at position P4, which confers caspase-3 its specificity (see FIG. 6):

As shown in Table 3 hereinafter, suicide substrates such as AspVSmethyl (Compound 93) and Asp(Otbu)VSmethyl (Compound 33) are devoid of any activity against caspase-3. The substrate z-Asp(Otbu)-Phg-val-OH (Compound 16) is also devoid of any activity against caspase-3. However the fusion product of peptide and suicide substrate, z-Asp-Phg-Val-AspVSmethyl (Compound 53), proved to be a very potent inhibitor of caspase-3 with an IC50 30-90 nM. Inhibition is selective since even though caspase-7 belongs to the same group than caspase-3, the IC50 value for this caspase was about 12 fold higher. Replacement of Phg at position P3 with Ala(2'-quinolyl) enhanced the selectivity further (about 56 fold difference, see Compound 55).

As observed with z-Val-AspVSmethyl (Compound 61), the deletion of both Aspartic acid and Ala(2'-quinolyl) at P4 and P3 positions abolished completely the activity against caspase-3. The same result was observed after the deletion of Aspartic acid only in the example of z-Ala(2'-quinolyl)-Val-Asp alpha chlorovinyl methyl sulfone (Compound 50) compared with z-Asp-Ala(2'-quinolyl)-Val-Asp alpha chlorovinyl methyl sulfone (Compound 48).

Changes at Position P3 and P2

The amino acids at both position P3 and P2 can serve to selectively target caspase-3 as observed but also to selectively target other caspases. The following examples highlight this possibility: (1) The replacement of Ala(2'-quinolyl) (Compound 55) with indalylglycine at P3 position lead to z-Asp-indalylglycine-Val-AspVSmethyl (Compound 57). This substitution enhanced the inhibitory effect against the group III of caspases (caspase-3 (30-90 nM) and 7 (0.18-0.30 uM) and, with about 29 fold less efficiency, against group 1 (caspase-1 (0.6-1.2 uM)). (2) The presence of Trp at P3 position (z-Asp-Trp-Val-AspVSmethyl; Compound 88) retained the selectivity against caspase-3 (30-90 nM) and produced an additional activity against caspase-1 (0.6-1.2 uM). This molecule possesses therefore the capability to inhibit selectively two caspases belonging to two different groups, namely the proinflammatory and the proapoptotic group. (3) The presence of Glutamic acid at P-3 position (z-Asp-Glu-Val-AspVSmethyl; Compound 59) retained the selectivity against caspase-3 (IC50 20 nM) and produced an additional activity against caspase-7 (IC50 42 nM) and caspase-9 (509 nM). This molecule therefore possesses the capability to inhibit selectively two caspases belonging to two different groups, namely initiator and executioner caspases.

Changes in Position P4

Changes in position P4 can also affect the selectivity of a given inhibitor. The amino acid that has been showed to fit well into the corresponding caspase-1 pockets at position P4 is Tyrosine. Therefore, z-Tyr-Val-Ala-AspVS phenyl (Compound 96) was tested against different caspases, and it proved to be selective against caspase-1 (IC50 1.2-1.5 µM). The amino acid that has been showed to fit well into the corresponding caspase-1 pockets at position P3 is glutamic acid. Therefore, z-Tyr-Glu-Ala-AspVS methyl (Compound 82) was tested against different caspases and the inhibition of caspase-1 was enhanced to 0.5 µM.

These specific examples demonstrate that it is possible to make selective caspase-3 inhibitors based on sequences recognized by group III caspases. Following the same approach as outlined hereinafter, it is conceivable to inhibit selectively additional caspases and to further improve the potency against selected caspases.

Design for Selective Caspase-3 Inhibitors

In one embodiment, the method comprises synthesizing compounds having the following general Formula D1:

$$D_a\text{-(P3)-(P2)-}D_b\text{-suicide substrate} \qquad (D1)$$

wherein

P2 is selected from the following amino acids: V, L, P, M, A, T, and H;

P3 is selected from the following amino acids: Phg, E, Indanylglycine, W, Y, A, D, Ala-(2'-quinolyl), 3-(1-naphtyl)-alanine, Ala-(2'-pyridine), Q, F, S, T, V, Y, G, L;

$D_a$ is (D) or (L) aspartic acid.

$D_b$ is the side chain of (D) or (L) aspartic acid.

The following compound (DEVD—vinyl phenyl sulfone) is an example a compounds having a sequence (i.e. $D_a$ is Cbz-aspartic acid; P3 is Glu; P2 is Val; $D_b$ is Asp; and the suicide substrate is vinyl phenyl sulfone) designed to selectively inhibit caspase-3:

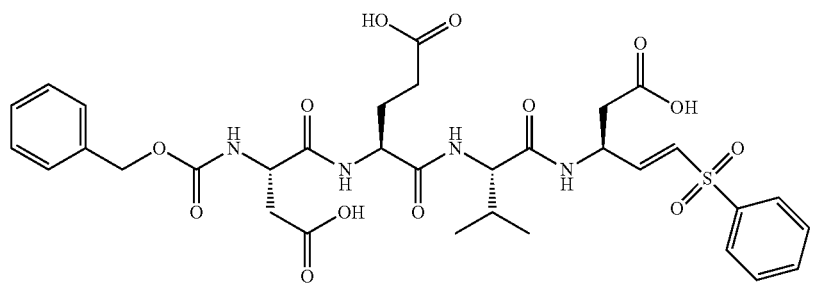 [SMILES: CC(C)[C@H](NC(=O)[C@H](CCC(=O)O)NC(=O)[C@H](CC(=O)O)NC(=O)OCc1ccccc1)C(=O)N[C@H](/C=C/S(=O)(=O)c1ccccc1)CC(=O)O]

Design for Selective Caspase-8/Caspase-9 Inhibitors

In one embodiment, the method comprises synthesizing compounds having the following general Formula D2:

(P4)-(P3)-(P2)-D-suicide substrate     (D2)

where

P2 is selected from the following amino acids: T, H, V, W, I, and A;

P3 is selected from the following amino acids: E, Ala(2'-quinolyl);

P4 is selected from the following amino acids: I, L, E, D, A, P, and V;

D is the side chain of (D) or (L) aspartic acid and the suicide substrate is vinyl phenyl sulfone.

The following is an example of a compound having a sequence (i.e. P4 is Cbz-L; P3 is Glu; P2 is His; D is Asp and the suicide substrate is vinyl phenyl sulfone) designed to selectively inhibit caspase-8:

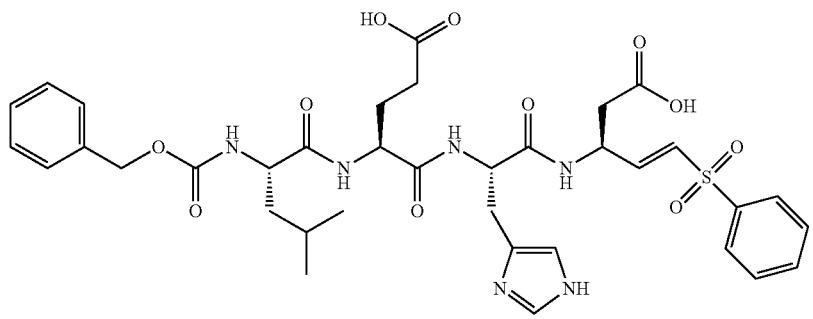 [SMILES: CC(C)C[C@H](NC(=O)OCc1ccccc1)C(=O)N[C@@H](CCC(=O)O)C(=O)N[C@@H](Cc1c[nH]cn1)C(=O)N[C@H](/C=C/S(=O)(=O)c1ccccc1)CC(=O)O]

Design for Selective Caspase-2 Inhibitors

In one embodiment, the method comprises synthesizing compounds having the following general Formula D3:

(P5)-(P4)-(P3)-(P2)-D-suicide substrate     (D3)

where

P2 is selected from the following amino acids: A, S, K and V;

P3 is selected from the following amino acids: V, E, T and Q;

P4 is selected from the following amino acids: D and L;

P5 is selected from the following amino acids: V and L;

D is the side chain of (D) or (L) aspartic acid; and the suicide substrate is selected from the group consisting of vinyl phenyl sulfone.

The following is an example of a compound (VDEHD—vinylphenyl sulfone) having a sequence (i.e. P5 is CbzVal; P4 is Asp; P3 is Glu; P2 is His and D is Asp. The suicide substrate is vinyl phenyl sulfone), which is designed to selectively inhibit caspase-2:

Design for Selective Caspase-1 Inhibitors

In one embodiment, the method comprises synthesizing compounds having the following general Formula D4:

(P4)-(P3)-(P2)-D-suicide substrate     (D4)

where

P2 is selected from the following amino acids: V, A, T, and H.

P3 is selected from the following amino acids: E, Q, D, A, G, T, V, Ala(2'-quinolyl), indanylglycine, and W;

P4 is selected from the following amino acids: Y, W, F, and D;

D is the side chain of (D) or (L) aspartic acid; and the suicide substrate is selected from the group consisting of vinyl phenyl sulfone.

The following is an example of a compound (YEHD—vinylphenyl sulfone) having a sequence (i.e. P4 is Cbz Tyr; P3 is Glu; P2 is His; D is Asp and the suicide substrate is vinyl phenyl sulfone, which is designed to selectively inhibit caspase-1:

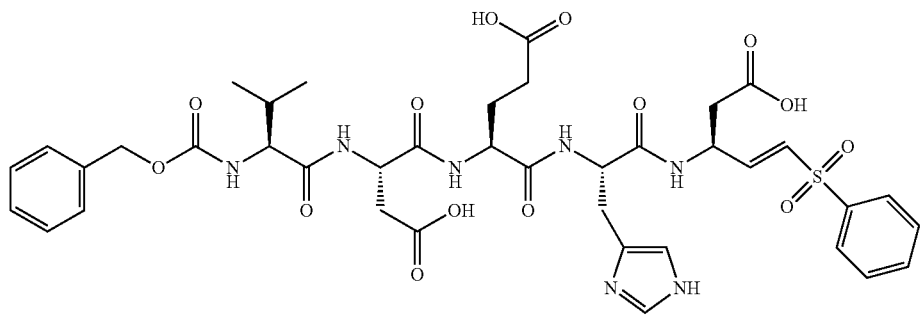 [SMILES: CC(C)[C@H](NC(=O)OCc1ccccc1)C(=O)N[C@@H](CC(=O)O)C(=O)N[C@@H](CCC(=O)O)C(=O)N[C@@H](Cc1c[nH]cn1)C(=O)N[C@H](/C=C/S(=O)(=O)c1ccccc1)CC(=O)O]

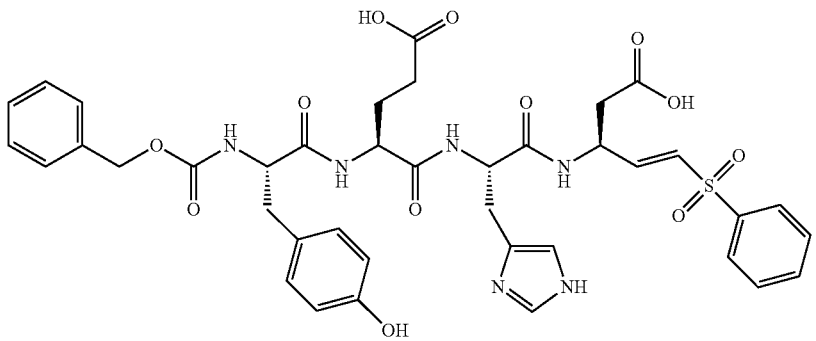 [SMILES: O=C(O)CC[C@H](NC(=O)[C@H](Cc1ccc(O)cc1)NC(=O)OCc1ccccc1)C(=O)N[C@@H](Cc1c[nH]cn1)C(=O)N[C@H](/C=C/S(=O)(=O)c1ccccc1)CC(=O)O]

D) Pharmaceutical Applications

As indicated hereinbefore and exemplified hereinafter, the compounds of the invention have beneficial pharmaceutical properties and these compounds may have pharmaceutical applications in the prevention and/or treatment of various diseases and conditions in a subject. Medical and pharmaceutical applications contemplated by the inventors include, but are not limited to, caspase-mediated diseases. In addition, the compounds of the present invention may have useful benefits on cells in vitro such as promoting cell survival or the health of the cells.

The term "subject" includes living organisms in a caspase-mediated disease can occur, or which are susceptible to such conditions. The term "subject" includes animals (e.g., mammals (e.g., cats, dogs, horses, pigs, cows, goats, sheep, rodents (e.g., mice or rats), rabbits, squirrels, bears, primates (e.g., chimpanzees, monkeys, gorillas, and humans)), as well as avians (e.g. chickens, ducks, Peking ducks, geese), and transgenic species thereof. Preferably, the subject is a mammal. More preferably, the subject is a human. Even more preferably, the subject is a human patient in need of treatment.

The term "caspase-mediated disease" includes all diseases, disorder and/or conditions in which any one or more of caspase-1, -2, -3, -4, -5, -6, -7, -8, -9, -10, -11, -12, plays a significant role. In some embodiments, the caspase-mediated disease mainly involves executioner caspases (caspase-3, 6, 7). In another embodiment, the caspase-mediated disease mainly involves initiators (caspase-2, 8, 9, 10). In some embodiments, a compound of the invention shows a high specificity towards one particular caspase. In another embodiment, a compound of the invention is able to inhibit two groups of caspases. Yet, in another embodiment, a compound of the invention even is able to inhibit two specific caspases belonging to two different groups of caspases.

Examples of caspase-mediated disease according to the invention includes, but are not limited to, apoptosis-mediated diseases, IL-1 mediated diseases, inflammatory diseases, autoimmune diseases, autoinflammatory diseases, proliferative diseases, infectious diseases, degenerative diseases, retinal disorders, inflammatory peritonitis, osteoarthritis, pancreatitis, asthma, respiratory distress syndrome, rheumatoid arthritis, systemic lupus erythematous, scleroderma, Grave's disease, autoimmune gastritis, diabetes, autoimmune hemolytic anemia, autoimmune neutropenia, thrombocytopenia, hepatitis, inflammatory bowel disease, crohn's disease, psoriasis, dermatitis, Graft vs host disease, organ transplant rejection, osteoporosis, leukemias and related disorders, multiple myeloma-related diseases, metastatic melanomas, Kaposi's sarcoma, sepsis, septic shock, Alzheimer's disease, Parkinson's disease, Huntington's disease, cerebral ischemia, epilepsy, myocardial ischemia, acute and chronic heart disease, myocardial infarction, congestive heart failure, atherosclerosis, spinal muscular atrophy, amyotrophic lateral sclerosis, multiple sclerosis, HIV-related encephalitis, aging, neurological damage due to stroke, ulcerative colitis, traumatic brain injury, spinal cord injury, hepatitis-B, hepatitis-C, hepatitis-G, liver-related diseases, renal disease, and HIV infection.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

The terms "treatment" or "treating" of a subject includes the application or administration of a compound of the invention to a subject (or application or administration of a compound of the invention to a cell or tissue from a subject) with the purpose of stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being. In some embodiments, the term "treating" can include increasing a subject's life expectancy and/or delay before additional treatments are required.

Addressing caspase-mediated diseases is among the medical and pharmaceutical applications contemplated by present invention. Therefore, in one of its aspects the present invention relates to methods, compounds and compositions for prevention and/or treatment of a caspase-mediated disease in a subject, preferably a human patient in need thereof.

Another aspect of the invention relates to the use of the compounds described herein for inhibiting a caspase or a caspase-like protein in a cell, comprising contacting the caspase or caspase-like protein with an effective amount of a caspase inhibitor according to the invention.

In some embodiments, the subject may be suffering from a viral infection. Therefore, the invention also relates to a method for the prophylaxis or therapy of a viral infection, comprising administering to a subject in need thereof an effective dose of a caspase inhibitor according to the invention (or a pharmaceutical composition comprising the same). This may be helpful for inhibiting a cellular caspase thereby inhibiting virus multiplication.

Also of particular interest is a method for the treatment of excessive apoptosis affected by caspase activity in a cell or a tissue, comprising contacting the cell or the tissue with an effective amount of one or more caspase inhibitor according to the invention (or a pharmaceutical composition comprising the same).

Also of particular interest is a method for effecting or stimulating stem cell survival and proliferation by preventing some of the stem cells from entering a partial or complete apoptosis cycle. The method for culturing a large quantity of stem cells may involves an effective amount of one or more caspase inhibitor according to the invention (or a pharmaceutical composition comprising the same) and a medium for culturing stem cells.

Also of particular interest is using compounds of the present invention for effecting or stimulating stem cell survival and proliferation in vivo by preventing some of the stem cells from entering a partial or complete apoptosis cycle. This treatment modality involves administering to the patient an effective amount of one or more caspase inhibitor according to the invention (or a pharmaceutical composition comprising the same) for effecting or stimulating stem cell survival and proliferation in the patient.

Although focusing on caspases, the present is not so limited. For instance, it is conceivable that the compounds of the invention be also effective in inhibiting additional families of proteases, including but not limited to, serine peptidases, cysteine peptidases, aspartic peptidases, metallo-peptidases, and other peptidases of unknown catalytic type. For a more elaborate listing of proteases that may be inhibited by the compounds defined herein, see ZBIGNIEW GRZONKA. Cysteine protease. Industrial Enzymes, 181-195, Chapter 11, 2007 Springer.

In order to evaluate, assess, and/or confirm the efficacy of the method, compounds and/or compositions of the invention, serial measurements can be determined. Quantitative assessment of caspase functions and parameters of caspase dysfunction are well known in the art. Examples of assays for the determination of caspases activity are provided in the Exemplification section.

The compounds according to the invention can be further analyzed, tested or validated for their ability to cross the Blood Brain Barrier BBB is so desired. Many in-vitro, in-vivo and in-silico methods may be employed during drug development to mimic the BBB (Lohmann et al. (2002) Predicting blood-brain barrier permeability of drugs: evaluation of different in vitro assays. *J Drug Target* 10:263-276; Nicolazzo et al. (2006) Methods to assess drug permeability across the blood-brain barrier. *J Pharm Pharmacol* 58:281-293). In-vitro models include primary endothelial cell culture and immortalized cell lines such as Caco-2, BMEC, MDCK. These cells are useful as a screening method and can appropriately rank compounds in order of BBB permeability. In vivo models such as the internal carotid artery single injection or perfusion, intravenous bolus injection, brain efflux index and intracerebral microdialysis provide more accurate information regarding brain uptake, and these can be complemented with novel imaging techniques (such as magnetic resonance imaging and positron emission tomography), although such methods are not suited to high-throughput permeability assessment.

In certain embodiments, at least some of the prodrugs administered generates the corresponding pharmaceutical compound only after absorption by the gastrointestinal tract and/or only once it has reached the brain, i.e. after it has passed the blood brain barrier (BBB).

E) Pharmaceutical Compositions and Formulations

A related aspect of the invention concerns pharmaceutical compositions comprising one or more of the compounds of the invention described herein. As indicated hereinbefore, the compounds of the invention may be useful in preventing and/or treating caspase-mediated disease, and more particularly sepsis, myocardial infarction, ischemic stroke, spinal cord injury (SCI), traumatic brain injury (TBI) and neurodegenerative disease (e.g. multiple sclerosis (MS) and Alzheimer's, Parkinson's, and Huntington's diseases.

As used herein, the term "therapeutically effective amount" means the amount of compound that, when administered to a subject for treating or preventing a particular disorder, disease or condition, is sufficient to effect such treatment or prevention of that disorder, disease or condition. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject and the properties of the compounds (e.g. bioavailability, stability, potency, toxicity, etc), and the particular disorder(s) the subject is suffering from. In addition, the therapeutically effective amount may depend on the subject's blood parameters (e.g. lipid profile, insulin levels, glycemia), the severity of the disease state, organ function, or underlying disease or complications. Such appropriate doses may be determined using any available assays including the assays described herein. When one or more of the compounds of the invention is to be administered to humans, a physician may for example, prescribe a relatively low dose at first, subsequently increasing the dose until an appropriate response is obtained.

As used herein, the term "pharmaceutical composition" refers to the presence of at least one compound of the invention according to any one of Formula I, II, IVC, VIIIC, IXC, or XC as defined herein and at least one pharmaceutically acceptable vehicle. Examples of representative compounds of the invention include the compounds in Table 1 and Table 2, and pharmaceutically acceptable salts thereof.

"Pharmaceutically acceptable vehicle" refers to a diluent, adjuvant, excipient, or carrier with which a compound is administered. The term "pharmaceutically acceptable" refers to drugs, medicaments, inert ingredients etc., which are suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or state government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (for example, glycerol, propylene glycol, and liquid polyethylene glycol, and the like), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin. Nanoparticles, liposomes, and antibodies conjugated to nanoparticles or combinations thereof, are also contemplated as pharmaceutically acceptable vehicles.

In some embodiments, the compositions of the invention comprise an effective amount of a compound of the Formula I, II, IVC, VIIIC, IXC, or XC as described hereinbefore, preferably compound Z-Asp(β-tert-Butyl)-Phg-Val-Asp(β-tert-Butyl)methyl vinyl sulfone (52); Z-Asp(β-tert-Butyl)-Al(2'-quinolyl)-Val-Asp(β-tert-Butyl)methyl vinyl sulfone (54); Z-Asp(β-tert-Butyl)-Indanylglycine-Val-Asp(β-tert-Butyl)methyl vinyl sulfone (56); Z-Asp-Indanylglycine-Val-Aspmethyl vinyl sulfone (57); Z-Asp(β-tert-Butyl)-Glu(β-tert-Butyl)-Val-Asp(β-tert-Butyl)methyl vinyl sulfone (58); Z-Asp-Glu-Val-Aspmethyl vinyl sulfone (59) Z-Asp-Ala(2'-quinolyl)-Val-Aspmethyl vinyl sulfone (55); Z-Asp-Phg-Val-Aspmethyl vinyl sulfone (53); Z-Asp-Ala(2'-quinolyl)-Val-Asp-achlorovinyl methylsulfone (48); Z-Asp(β-methyl)-Indanylglycine-Val-Asp(β-methyl)methyl vinyl sulfone (51) Z-Asp-Tyr-Val-Aspmethyl vinyl sulfone (76) Z-Asp-Trp-Val-Aspmethyl vinyl sulfone (88); Z-Asp-Ala(2'-quinolyl)-Val-Aspphenyl vinyl sulfone (63); Z-Asp-Ala(2'-quinolyl)-Val-Aspphenoxy vinyl sulfone (65); Z-Asp(β-methyl)-phenylglycine-Val-Asp(β-methyl)methyl vinyl sulfone (101); Z-Asp(β-tert-Butyl)-3-(1-naphtyl)-L-alanine-Val-Asp(β-tert-Butyl)methyl vinyl sulfone (110); Z-Asp-3-(1-naphtyl)-L-alanine-Val-Aspmethyl vinyl sulfone (111); Z-Asp(β-tert-Butyl)-3-(1-naphtyl)-L-alanine-Val-Asp(β-tert-Butyl) achlorovinyl methylsulfone (112), Z-Asp-3-(1-naphtyl)-L-alanine-Val-Asp achlorovinyl methylsulfone (113), Z-Asp(β-tert-Butyl)-phenylglycine-Val-Asp(β-tert-Butyl)-achlorovinyl methylsulfone (122); Z-Asp-phenylglycine-Val-Asp-achlorovinyl methylsulfone (123); Z-Asp(β-Ethyl)-phenylglycine-Val-Asp(β-Ethyl)methyl vinyl sulfone (144); Z-Asp(β-Ethyl)-phenylglycine-Val-Asp(β-Ethyl) achloromethyl methyl vinyl sulfone (145); Z-Asp(β-Ethyl)-phenylglycine-Val-Asp methyl vinyl sulfone (146); Z-Asp(β-Ethyl)-phenylglycine-Val-Asp achloro methyl vinyl sulfone (148); Z-Asp(β-Ethyl)-phenylglycine-Val-Asp(β-Ethyl)isopropyl vinyl sulfone (150); Z-Asp-phenylglycine-Val-Asp ethyl vinyl sulfone (154); Z-Asp-phenylglycine-Val-Asp isopropyl vinyl sulfone(156); Z-Asp-phenylglycine-Val-Asp achloro ethyl vinyl sulfone (155); Z-Asp-phenylglycine-Val-Asp achloro isopropyl vinyl sulfone(157); Z-Asp(β-Ethyl)-3-(1-naphtyl)-L-alanine-Val-Asp(β-Ethyl)methyl vinyl sulfone (158); Z-Asp(β-Ethyl)-3-(1-naphtyl)-L-alanine-Val-Asp(β-Ethyl)achloro methyl vinyl sulfone (159); Z-Asp(β-tert-Butyl)-Glu(β-tert-Butyl)-Val-Asp(β-tert-Butyl)-achlorovinyl methylsulfone (176); Z-Asp-Glu-Val-Asp-achlorovinyl methylsulfone (177); or a pharmaceutically acceptable salt, or prodrug, thereof.

In some embodiments the invention pertains to pharmaceutical compositions for preventing and/or treating diseases or other medical conditions in which at least one caspase is significantly involved that include one or more compounds of Formula I, II, IVC, VIIIC, IXC, or XC as defined herein.

In some embodiments the invention pertains to pharmaceutical compositions for preventing and/or treating diseases or other medical conditions in which at least one caspase is significantly involved, the composition comprising one or more compounds of Formula I, II, IVC, VIIIC, IXC, or XC as defined herein.

The compounds of the invention may be formulated prior to administration into pharmaceutical compositions using available techniques and procedures. For instance, the pharmaceutical compositions may be formulated into suitable administration (orally, parenterally, (intravascular (IV), intraarterial (IA), intramuscular (IM), depo-IM, subcutaneous (SC), and depo SC), sublingually, intranasally (inhalation), intrathecally, topically, or rectally.

Preferably, the compound(s) of the invention can be orally administered. The formulations may conveniently be presented in unit dosage form and may be prepared by any methods well known in the art of pharmacy. Methods of preparing these formulations or compositions include the step of bringing into association a compound of the present invention with a pharmaceutically acceptable vehicle (e.g. an inert diluent or an assimilable edible carrier) and, optionally, one or more accessory ingredients. In general, the formulations are prepared by uniformly and intimately bringing into association a compound of the present invention with liquid carriers, or finely divided solid carriers, or both, and then, if necessary, shaping the product. The amount of the therapeutic agent in such therapeutically useful compositions is such that a suitable dosage will be obtained.

Formulations of the invention suitable for oral administration may be in the form of capsules (e.g. hard or soft shell gelatin capsule), cachets, pills, tablets, lozenges, powders, granules, pellets, dragees, e.g., coated (e.g., enteric coated) or uncoated, or as a solution or a suspension in an aqueous or non-aqueous liquid, or as an oil-in-water or water-in-oil liquid emulsion, or as an elixir or syrup, or as pastilles or as mouth washes and the like, each containing a predetermined amount of a compound of the present invention as an active ingredient. A compound of the present invention may also be administered as a bolus, electuary or paste, or incorporated directly into the subject's diet. Moreover, in certain embodiments these pellets can be formulated to (a) provide for instant or rapid drug release (i.e., have no coating on them); (b) be coated, e.g., to provide for sustained drug release over time; or (c) be coated with an enteric coating for better gastrointestinal tolerability. Coating may be achieved by conventional methods, typically with pH or time-dependent coatings, such that the compound(s) of the invention is released in the vicinity of the desired location, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

In solid dosage forms for oral administration a compound of the present invention may be mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Peroral compositions typically include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions suitable for injectable use may include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

Pharmaceutical formulations are also provided which are suitable for administration as an aerosol, by inhalation. These formulations comprise a solution or suspension of the desired compound of any Formula herein or a plurality of solid particles of such compound(s). The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of any Formula described herein, or a salt thereof, in any appropriate manner known in the art, such as by micronization. The size of the solid particles or droplets will be, for example, from about 1 to about 2 microns. In this respect, commercial nebulizers are available to achieve this purpose. A pharmaceutical formulation suitable for administration as an aerosol may be in the form of a liquid, the formulation will comprise a water-soluble agent of any Formula described herein, or a salt thereof, in a carrier which comprises water. A surfactant may be present which lowers the surface tension of the formulation sufficiently to result in the formation of droplets within the desired size range when subjected to nebulization.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of a compound of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Other compositions useful for attaining systemic delivery of the subject agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compound(s) of the invention may also be administered parenterally, intraperitoneally, intravenously, intraspinally, intrathecally or intracerebrally. For such compositions, the compound(s) of the invention can be prepared in glycerol, liquid polyethylene glycols, and mixtures thereof and in oils. Under ordinary conditions of storage and use, these preparations may contain a preservative to prevent the growth of microorganisms.

In addition to the traditional drug delivery systems (oral, subcutaneous, intravenous (IV), intraperitoneal (IP)) intranasal drug delivery may constitutes a suitable alternative to deliver the compound(s) of the invention directly to CNS (critical reviews in therapeutic Drug Carrier Systems 23(4): 319-347, 2006).

Intranasal drug delivery allows certain drugs to be delivered in low doses, avoiding hepatic first pass metabolism with minimal side effects, improving cost effectiveness and better patient compliance. Intranasal delivery allows the drug that do not cross the BBB to be delivered to the central nervous system within minutes. It also directly delivers drugs that do cross the BBB to the brain. This is due to the unique connection that the olfactory and trigeminal nerves provide between the brain and external environment (Recent Patents on drug Delivery & Formulation 2008, 2, 25-40).

Formulation of the invention suitable for intranasal administration may involve gelling agent or gel-forming carriers such as hydroxypropylcellulose, methylcellulose, poly(vinyl pyrrlidone); poly(ethylene oxide); crosslinked poly(acrylic acid), and chitosan. Such agents can increase the residence time and uptake of the compound(s) of the invention in the nasal cavity, Cosolvents such as glycols ethyl alcohol, diethylene glycol monoethyl ether, medium chain glycerides, and labrasol are examples of agents that can be used to enhance solubility. The use of surfactans or cyclodextrins such as hydroxypropyl-B-cyclodextrine in combination with lipophilic absorption enhancers can be considered as well. Other Intranasal formulation involves cationic liposomes, microspheres, nanoparticles. Regardless to the method of the formulation used, buffering agents and protease inhibitors may be added as well.

The method of treatment of the present invention may also include co-administration of the at least one compound according to the invention, or a pharmaceutically acceptable salt thereof together with the administration of another therapeutically effective agent. Therefore, an additional aspect of the invention relates to methods of concomitant therapeutic treatment of a subject, comprising administering to a subject in need thereof an effective amount of a first agent and a second agent, wherein the first agent is as defined in I, II, IVC, VIIIC, IXC, or XC and the second agent is for the prevention or treatment of any one of disorder or disease indicated hereinbefore. As used herein, the term "concomitant" or "concomitantly" as in the phrases "concomitant therapeutic treatment" or "concomitantly with" includes administering a first agent in the present of a second agent. A concomitant therapeutic treatment method includes methods in which the first, second, third or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g. a human).

Accordingly, the invention also relates to a method for preventing, reducing or eliminating a symptom or complication of any one of the above mentioned disease or condition. The method comprises administering, to a subject in need thereof, a first pharmaceutical composition comprising at least one compound of the invention and a second pharmaceutical composition comprising one or more additional active ingredients, wherein all active ingredients are administered in an amount sufficient to inhibit, reduce, or eliminate one or more symptoms or complications of the disease or condition to be treated. In one aspect, the administration of the first and second pharmaceutical composition is temporally spaced apart by at least about two minutes. Preferably the first agent is a compound of Formula I, II, IVC, VIIIC, IXC, or XC as defined herein, or a pharmaceutically acceptable salt thereof.

F) Screening Assays

The compounds of the present invention may also be used in screening methods. For instance, these compounds may be used in methods for tracking activity of caspases in vitro and/or in vivo. The compounds of the present invention may also be helpful for identifying other compounds that bind to a caspase active side. In some embodiments, the compounds of the invention are labeled or tagged (e.g. fluorescently or radioactively labeled, affinity tag). Fluorescent or radiolabeled compounds may also be useful in diagnostic assays.

There are a number of ways in which to determine the binding of a compound of the present invention to the caspase. In one embodiment the caspase is bound to a support, and a labeled compound of the invention is added to the assay. Alternatively, the compound of the invention may be bound to the support and the caspase is added.

The compounds of the invention may also be used as competitors to screen for additional drug candidates or test compounds. As used herein, the terms "drug candidate" or "test compounds" are used interchangeably and describe any molecule, for example, protein, oligopeptide, small organic molecule, polysaccharide, polynucleotide, and the like, to be tested for bioactivity.

Typically, the signals that are detected in the assay (e.g. in vitro, in vivo and/or diagnostic) may include fluorescence, resonance energy transfer, time resolved fluorescence, radioactivity, fluorescence polarization, plasma resonance, or chemiluminescence and the like, depending on the nature of the label. Detectable labels useful in performing screening assays in this invention include a fluorescent label such as Fluorescein, Oregon green, dansyl, rhodamine, tetramethyl rhodamine, texas red, $Eu^{3+}$; a chemiluminescent label such as luciferase; colorimetric labels; enzymatic markers; or radioisotopes such as tritium, $I^{125}$ and the like. Affinity tags, which may be useful in performing the screening assays of the present invention include be biotin, polyhistidine and the like.

F) Kits

The compound(s) of the invention may be packaged as part of a kit, optionally including a container (e.g. packaging, a box, a vial, etc). The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The compound(s) of the invention may or may not be administered to a patient at the same time or by the same route of administration. Therefore, the methods of the invention encompass kits which, when used by the medical practitioner, can simplify the administration of appropriate amounts of two or more active ingredients to a patient.

A typical kit of the invention comprises a unit dosage form of a at least one compound according to the invention, e.g., a compound of Formula I, II, IVC, VIIIC, IXC, or XC as defined herein or a pharmaceutically acceptable salt thereof, and a unit dosage form of at least one additional active ingredient. Examples of additional active ingredients that may be used in conjunction with the compounds according to the invention, include, but are not limited to any of the compounds that could be used in combination with the compound(s) of the invention as indicated herein before.

Kits of the invention can further comprise devices that are used to administer the active ingredients. Examples of such devices include, but are not limited to, syringes, drip bags, patches, inhalers, enemas, and dispensers for the administration of suppository formulations.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles are provided hereinbefore.

EXAMPLES

The Examples set forth herein below provide exemplary methods for the preparation of certain representative compounds encompassed by general Formula I, II, IVC, VIIIC, IXC, or XC. Some Examples provide exemplary uses of certain representative compounds of the invention. Also provided are exemplary methods for assaying the compounds of the invention for in vitro and in vivo efficacy.

Example 1

Synthesis of Compound 4 (Cbz-Asp(O-tBu)-Ala(2'quinolyl)-ValOH)

a) Fmoc-Ala(2'-quinolyl)-Val-OAllyl

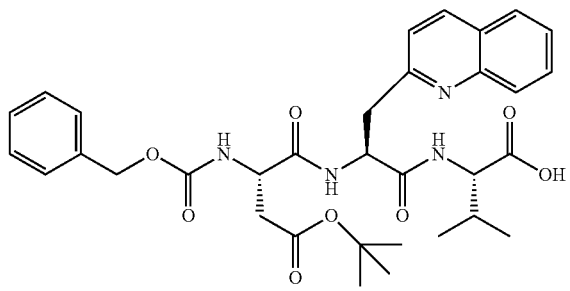 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)O]

Fmoc-Ala(2'-quinolyl)-OH (0.152 g, 0.347 mmol) was solvated in DMF (1 mL) and CH$_2$Cl$_2$ (0.9 mL). L-Val allylester toluene-4-sulfonate (0.115 g, 1.01 eq) in 0.3 mL of CH$_2$Cl$_2$ was added, followed with 4-methylmorpholine (0.04 mL, 1.05 eq) and EDC (0.0681 g, 1.02 eq). The mixture was stirred for 3 hours, and then it was extracted using CH$_2$Cl$_2$/brine. The organic layer was dried over MgSO$_4$, filtered off and concentrated to dryness.

b) Ala(2'quinolyl)-Val-OAllyl

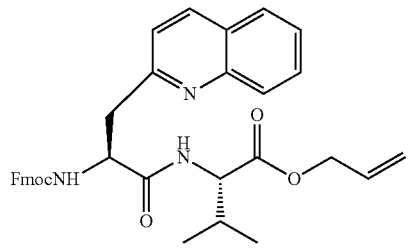

The Fmoc-Ala(2'-quinolyl)-Val(O-Allyl) (0.425 g, 0.737 mmol) was solvated in CH$_2$Cl$_2$ (40 mL) followed by dropwise addition of piperidine (0.6 mL, 8.24 eq). After 40 min the mixture was evaporated to dryness under vacuum. The product was then purified on silica using a gradient of MeOH/CH$_2$Cl$_2$ (0 to 10%) to get 0.188 g of desired compound.

NMR $^1$H (CDCl$_3$, 400 MHz) δ: 8.18 (s, 1H, NH); 8.08 (d, 1H, J=8.4 Hz); 8.03 (d, 1H, J=8.47 Hz); 7.79 (d, 1H, J=7.91 Hz); 7.71-7.68 (m, 1H); 7.52-7.49 (m, 1H); 7.35 (d, 1H, J=8.42 Hz); 5.92-5.85 (m, 2H); 5.34-5.22 (m, 2H); 4.63-4.58 (m, 2H); 4.55-4.52 (m, 1H); 3.95-3.93 (m, 1H); 3.52 (dd, 1H, J=3.95 Hz); 3.25-3.20 (m, 1H); 2.20-2.13 (m, 1H); 2.01 (m, 2H, NH$_2$); 0.85 (m, 6H).

c) Cbz-Asp(O-tBu)-Ala(2'-quinolyl)-Val-OAllyl

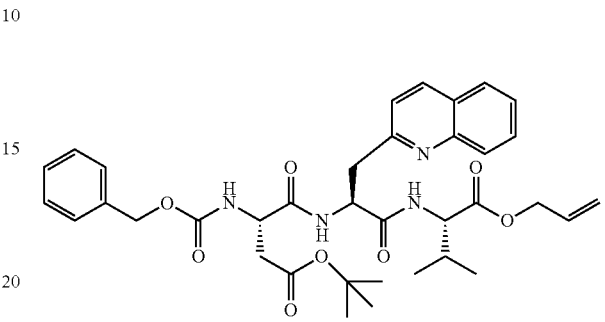

Ala(2'-quinolyl)-Val(O-Allyl) (0.054 g, 0.1519 mmol) was solvated in CH$_2$Cl$_2$ (0.7 mL) followed by addition of L-Asp (O-tBu)-OH (0.053 g, 1.08 eq) and 4-methylmorpholine (0.018 mL, 1.08 eq) and finally DPC (0.025 mL, 1.06 eq). The mixture was stirred for 1 hour. It was then subjected to a liquid extraction dichloromethane/brine. The organic layer was dried over MgSO$_4$, concentred to vacuum and purified on silica using a gradient of MeOH/CH$_2$Cl$_2$ (0 to 10%) to get 0.084 g of the desired compound.

d) Cbz-Asp(O-tBu)-Ala(2'-quinolyl)-Val-OH

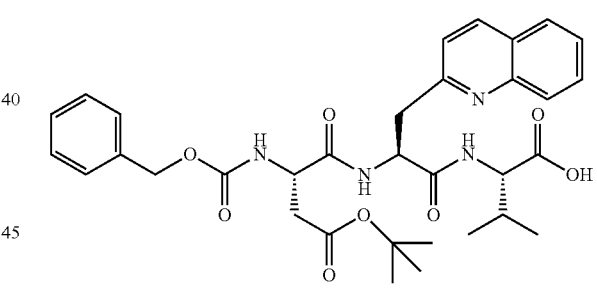

Cbz-Asp(OtBu)-Ala(2'-quinolyl)-Val (OAllyl) (0.082 g, 0.1241 mmol) was dissolved in THF (3.5 mL) and rotary evaporated to dryness, the sample was then redissolved in THF (3.5 mL) and vacuum aspirated (3*1 min of aspiration), followed by replacement of the atmosphere with Argon. Morpholine (0.04 mL, 3.7 eq) was added, followed by Pd(PPh$_3$)$_4$ (0.0171 g, 0.12 eq). The sample flask was then covered with a tin foil and kept under stirring for 3 days under Argon. The compound was evaporated to dryness and the obtained residue was subjected to purification on C$_{18}$ using a gradient MeOH/solution of H$_2$O at pH=3.5 (0 to 100%) to get 0.065 g of the desired compound.

NMR $^1$H (CD$_3$OD, 400 MHz) δ: 8.18 (d, 1H, J=8.4 Hz); 8.02 (d, 1H, J=8.49 Hz); 7.84 (d, 1H, J=8.08 Hz); 7.63 (t, 1H, J=7.51 Hz); 7.52 (t, 1H, J=7.39 Hz); 7.41 (d, 1H, J=8.3 Hz); 7.40-7.30 (m, 5H); 5.03-4.93 (m, 3H); 4.50-4.48 (m, 1H); 4.26 (d, 1H, J=4.9 Hz); 3.48-3.34 (m, 2H); 2.73-2.68 (m, 1H); 2.54-2.49 (m, 1H); 2.15-2.11 (m, 1H); 1.36 (m, 9H); 0.87-0.84 (m, 6H).

Example 2

Synthesis of Compound 5
(Ts-Ala(2'-quinolyl)-Val-OH)

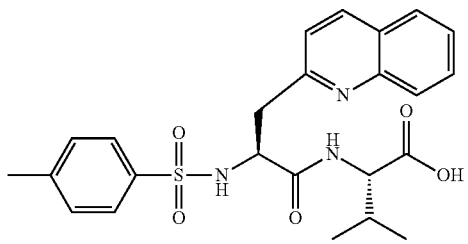 [SMILES: Cc1ccc(S(=O)(=O)N[C@@H](Cc2ccc3ccccc3n2)C(=O)N[C@H](C(=O)O)C(C)C)cc1]

a) Ts-Ala(2'-quinolyl)-OH

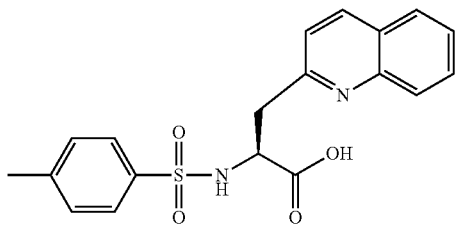 [SMILES: Cc1ccc(S(=O)(=O)N[C@@H](Cc2ccc3ccccc3n2)C(=O)O)cc1]

To L-Ala(2'-quinolyl)-OH (0.060 g, 0.277 mmol) was added H₂O (0.4 mL) and THF (0.15 mL). The mixture was stirred for 2 min before adding TEA (0.074 ml, 1.93 eq). The mixture was allowed to reach 0° C., before adding Tosyl chloride (0.052 g, 1 eq) in THF (0.4 mL) in a dropwise manner. The mixture was then allowed to warm to room temperature and stirred for 16 hours. The mixture was diluted with EtOAc (8 mL) and H₂O (2 mL), then it was acidified with HCl 1N (dropwise addition) to reach pH 3/4. The mixture was extracted with EtOAc, dried over MgSO₄ and evaporated to dryness, to get upon addition of MeOH (0.5 mL) 30 mg of precipitate; an other portion could be obtained from the solution.

NMR $^1$H (DMSO, 400 MHz) δ: 8.30-8.23 (m, 1H, NH); 8.14 (d, 1H, J=8.37 Hz); 7.89 (d, 1H, J=8.0 Hz); 7.78 (d, 1H, J=8.39 Hz); 7.70 (t, 1H, J=7.2 Hz); 7.55 (t, 1H, J=7.33 Hz); 7.32-7.27 (m, 3H); 6.88 (d, 2H, J=8.05 Hz); 4.28 (s, 1H); 3.4-3.03 (m, 2H); 2.13 (s, 3H).

b) Ts-Ala(2'-quinolyl)-Val-OAllyl

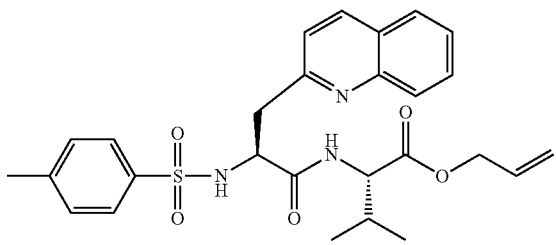 [SMILES: C=CCOC(=O)[C@@H](NC(=O)[C@H](Cc1ccc2ccccc2n1)NS(=O)(=O)c1ccc(C)cc1)C(C)C]

Ts-Ala(2'-quinolyl)-OH (0.027 g, 0.076 mmol) was solvated in CH₂Cl₂ followed by addition of L-Val-OAllyl ester toluene-4-sulfonate (0.025 g, 1.02 eq), 4-methylmorpholine (0.017 mL, 1.91 eq), DMAP (0.0012 g, 0.13 eq) and finally EDC (0.015 g, 1.04 eq). The progress of the reaction was followed by TLC. The mixture was extracted with CH₂Cl₂/brine. The organic layer was dried over MgSO₄, filtered off and concentrated to dryness. The obtained residue was purified on silica using a gradient EtOAc/Hexane (5 to 60%) to get 10 mg of the desired compound.

NMR $^1$H (CDCl₃, 400 MHz) δ: 7.99 (m, 2H); 7.89 (d, 1H, J=8.93 Hz); 7.76 (d, 1H, J=8.06 Hz); 7.72 (t, 1H, J=8.16 Hz); 7.64 (m, 2H); 7.53 (t, 1H, J=7.61 Hz); 7.45 (d, 1H, J=6.86 Hz); 7.16 (d, 1H, J=8.34 Hz); 7.08 (m, 2H); 5.86-5.79 (m, 1H); 5.27 (dd, 1H, J=17.25 Hz, J=1.36 Hz); 5.20 (dd, 1H, J=10.4 Hz, J=1.0 Hz); 4.58-4.5 (m, 2H); 4.38 (dd, 1H, J=8.78 Hz, J=5.02 Hz); 4.22 (q, 1H, J=5.58 Hz); 3.41 (dd, 1H, J=15.50 Hz, J=5.23 Hz); 3.14 (dd, 1H, J=15.53 Hz, J=5.64 Hz); 2.33 (s, 3H); 2.16-2.00 (m, 1H); 0.72 (d, 3H, J=6.8 Hz); 0.65 (d, 3H, J=6.85 Hz).

c) Ts-Ala(2'quinolyl)-Val-OH

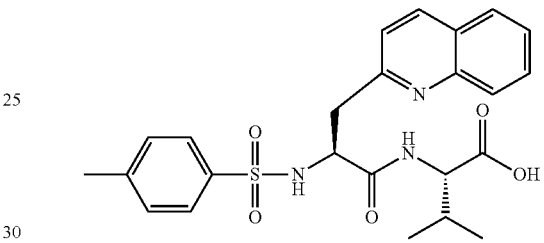

The Ts-Ala(2'-quinolyl)-OAllyl (0.010 g, 0.02 mmol) was dissolved in THF (3.5 mL) and rotary evaporated to dryness, the sample was then redissolved in THF (3.5 mL) and vacuum aspirated (3*1 min of aspiration), followed by replacement of the atmosphere with Argon. Pd(PPh₃)₄ (0.0036 g, 0.16 eq) was added under Argon, followed by Morpholine (0.007 mL, 4.1 eq). The sample flask was then covered with a tin foil and kept under stirring for 3 days under Argon. The compound was evaporated to dryness and the obtained residue was subjected to purification on C₁₈ using a gradient: MeOH/H₂O (15 to 100%) to get 0.006 g of the desired compound.

NMR $^1$H (CD₃OD, 400 MHz) δ: 8.05 (d, 1H, J=8.44 Hz); 7.88-7.84 (m, 2H); 7.76-7.72 (m, 1H); 7.58-7.55 (m, 1H); 7.33-7.29 (m, 3H); 6.78-6.76 (m, 2H); 4.35 (dd, 1H, J=10.43 Hz, J=3.38 Hz); 4.19 (d, 1H, J=4.6 Hz); 3.44-3.03 (m, 2H); 2.20-2.12 (m, 1H); 2.12 (s, 3H); 0.93-0.89 (m, 6H).

Example 3

Synthesis of Compound 12
(Cbz-Asp(O-tBu)-Indanylglycine-Val-OH)

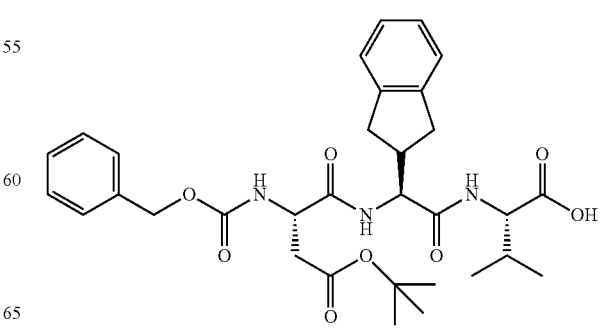

a) Fmoc-Indanylglycine-Val-OAllyl

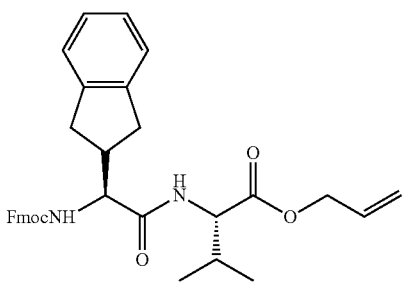

Fmoc Indanylglycine (0.54 g, 1.315 mmol) was solvated in $CH_2Cl_2$ (5 mL) and DMF (1.8 mL) followed with the addition of L-Val allylester (0.437 g, 1 eq), 4-methylmorpholine (0.15 ml, 1.04 eq) and 4 min latter DMAP (14.5 mg, 0.09 eq) then EDC (0.265 g, 1.05 eq). The mixture was stirred for 1 hour 45 min. Then it was extracted using EtOAc/brine. The organic layer was dried over $MgSO_4$, filtered off and concentrated to dryness.

b) Indanylglycine-Val-OAllyl

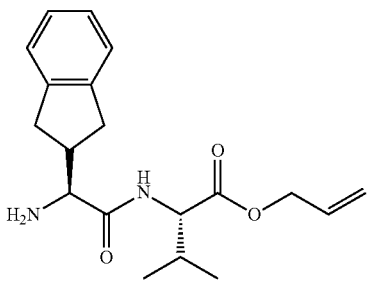 [SMILES: C=CCOC(=O)[C@@H](NC(=O)[C@@H](N)C1Cc2ccccc2C1)C(C)C]

Fmoc-Indanylglycine-Val-OAllyl (0.758 g, 1.31 mmol) was solvated in $CH_2Cl_2$ (5 mL) and DMF (1.8 mL) followed by dropwise addition of piperidine (1.05 mL, 8.1 eq) over 30 seconds. After 45 min, the mixture was subjected to extraction $CH_2Cl_2$/brine (30/15 mL) and saturated $NH_4Cl$ (5 mL). The organic layer was dried over $MgSO_4$, concentrates and purified by silica using a gradient of MeOH/$CH_2Cl_2$ (0 to 5%) to get 0.45 g of the desired compound.

NMR $^1H$ ($CDCl_3$, 400 MHz) δ: 7.80 (d, 1H, NH); 7.20-7.17 (m, 2H); 7.15-7.11 (m, 2H); 5.96-5.88 (m, 1H); 5.37-5.25 (m, 2H); 4.68-4.58 (m, 3H); 3.53 (d, 1H, J=5.05 Hz); 3.12-2.8 (m, 5H); 2.27-2.20 (m, 1H); 0.98 (d, 3H, J=6.85 Hz); 0.94 (d, 3H, J=6.88 Hz).

c) Cbz-Asp(O-tBu)-Indanylglycine-Val-OAllyl

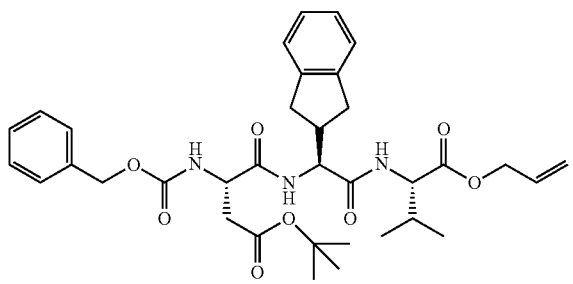 [SMILES: C=CCOC(=O)[C@@H](NC(=O)[C@@H](NC(=O)[C@H](CC(=O)OC(C)(C)C)NC(=O)OCc1ccccc1)C1Cc2ccccc2C1)C(C)C]

Indanylglycine-Val-OAllyl (0.46 g, 1.3 mmol) and Z-L-Asp(OtBu)-OH (0.425 g, 1.3 mmol) were solvated in $CH_2Cl_2$ (4.5 mL) followed by addition of 4-methylmorpholine (1.45 mL, 1.01 eq), DMAP (14 mg, 0.09 eq) then EDC (0.251 g, 1.01 eq). The mixture was stirred for 1 hour 40 min. Then it was extracted using $CH_2Cl_2$/brine. The organic layer was dried over $MgSO_4$, concentrates and purified by silica using a gradient of EtOAc/Hexane (10 to 80%) to get 0.578 g of the desired compound.

NMR $^1H$ ($CD_3OD$, 400 MHz) δ: 7.35-7.25 (m, 5H); 7.15-7.07 (m, 4H); 6.0-5.92 (m, 1H); 5.36 (dd, 1H, J=17.17 Hz, J=1.429 Hz); 5.24 (dd, 1H, J=10.45 Hz, J=1.251 Hz); 5.09-5.036 (m, 2H); 4.77-4.61 (m, 2H); 4.54-4.50 (m, 2H); 4.33 (d, 1H, J=6.04 Hz); 2.97-2.52 (m, 7H); 2.20-2.011 (m, 1H); 1.41 (s, 9H); 0.97 (d, 3H, J=1.78 Hz); 0.96 (d, 3H, J=1.78 Hz).

d) Cbz-Asp(O-tBu)Indanylglycine-Val-OH

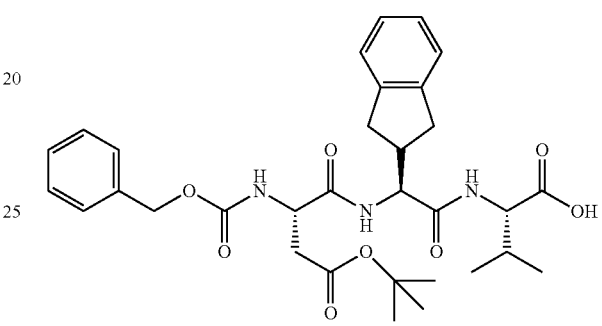

Z-Asp(O-tBu)-Indanylglycine-Val-(OAllyl) (0.102 g, 0.1611 mmol) was dissolved in THF (6 mL) and rotary evaporated to dryness, the sample was then redissolved in THF (6 mL) and vacuum aspirated (3*1 min of aspiration), followed by replacement of the atmosphere with Argon. $Pd(PPh_3)_4$ (0.017 g, 0.151 0.094 eq) was added in one shot, the flask was then evacued with Argon. Morpholine (0.06 mL, 4.28 eq) was added and the flask covered with a tin foil. The mixture was kept under stirring for 2.5 days under Argon. The sample was evaporated to dryness and the obtained residue was subjected to purification on $C_{18}$ using a gradient MeOH/solution of $H_2O$ at pH=3.5 (10 to 100%) to get 0.046 g of the desired compound.

NMR $^1H$ ($CD_3OD$, 400 MHz) δ: 7.4-7.23 (m, 5H); 7.18-7.03 (m, 4H); 5.20-5.0 (m, 2H); 4.58-4.50 (m, 2H); 4.3 (d, 1H, J=5.5 Hz); 3.0-2.7 (m, 6H); 2.6-2.50 (m, 1H); 1.4 (s, 9H); 0.97 (d, 3H, J=2.06 Hz); 0.96 (d, 3H, J=2.18 Hz).

Example 4

Synthesis of Compound 16
(Z-Asp(β-tert-butyl)-Phg-Val-OH)

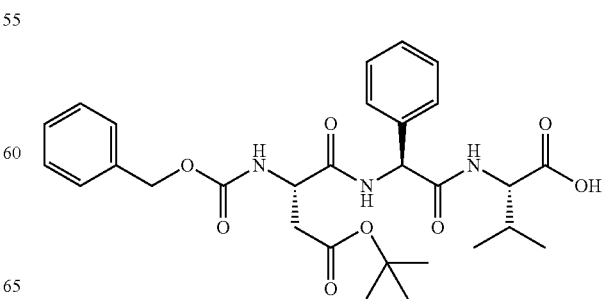

a) Fmoc-Phg-Val-OAllyl

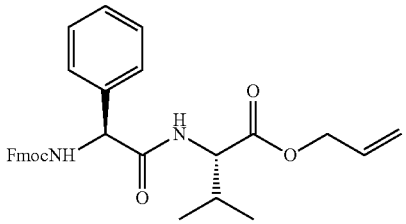

Fmoc-PhgOH (1 g, 2.678 mmol) was dissolved in a mix of anhydrous dichloromethane and DMF (9 ml/0.5 ml). Val (OAllyl)tosyl salt form (0.804 g, 2.44 mmol) in 1 ml of dichloromethane was added followed by diisopropylcarbodiimide (0.414 ml, 2.44 mmol) and N-methyl morpholine (0.270 ml, 2.44 mmol). The mixture was stirred for 2.20 hrs at RT, then filtered off on a path of celite (1 cm) and washed with dichloromethane. The filtrate was concentrated and the obtained residue was used as a crude material for the next step.

b) Phg-Val-OAllyl

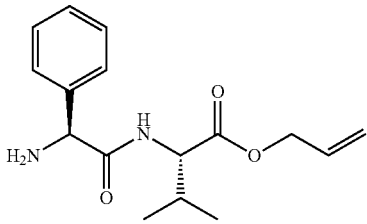 [SMILES: C=CCOC(=O)[C@@H](NC(=O)[C@@H](N)c1ccccc1)C(C)C]

1.45 g of the previous crude material (Fmoc-Phg-Val-OAllyl) was dissolved in a solution of 20% piperidine in dichloromethane (8.5 ml) and stirred at room temperature for 45 minutes. The mixture was then concentrated under vacuum, diluted with dichloromethane and filtered off through a path of celite (1 cm). The solvent was evaporated to dryness and then purified on silica gel, eluting first with ethyl acetate/hexane (20%) followed with a gradient of dichloromethane/methanol (0 to 10%) to get 0.72 g of the N-unprotected peptide Phg-Val-OAllyl.

c) Z-Asp(β-tert-Butyl)-Phg-Val-OAllyl

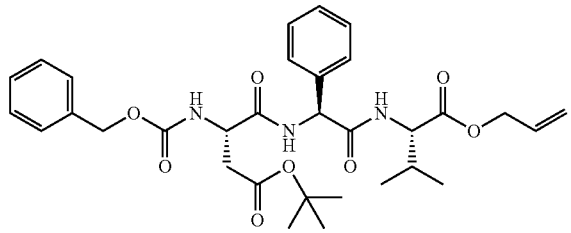 [SMILES: C=CCOC(=O)[C@@H](NC(=O)[C@@H](NC(=O)[C@H](CC(=O)OC(C)(C)C)NC(=O)OCc1ccccc1)c1ccccc1)C(C)C]

The Phg-Val-OAllyl (0.89 g, 2.74 mmol) was dissolved in anhydrous dichloromethane (7 ml). Then Z-Asp(β-tert-butyl)OH (0.89 g, 2.74 mmol) in dichloromethane (2 ml) was added followed by diisopropyl carbodiimide (0.424 ml, 2.74 mmol). The mixture was stirred at RT for 2.45 hrs and then diluted with dichloromethane. The organic phase was washed twice with brine and dried over anhydrous magnesium sulphate. The solvent was evaporated and the obtained residue was purified on silica gel (gradient: ethyl acetate/hexane) to afford 0.4 g of Z-Asp(OtBu)-Phg-Val-OAllyl.

d) Z-Asp(β-tert-Butyl)-Phg-Val-OH

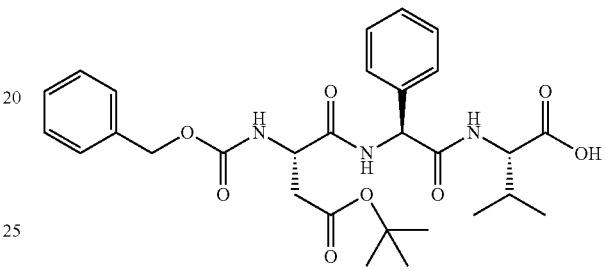

Z-Asp(β-tert-butyl)-Phg-Val-OAllyl (0.064 g; 0.107 mmol) was dissolved under argon in dry THF (3 ml, inhibitor free). The solvent was degassed three times under argon before adding morpholine (28 ul, 3 eq), followed by Tetrakis (13 mg). The mixture was stirred for 3.5 days at room temperature. The mixture was then concentrated under vacuum (12 mbar) and purified on silica gel (gradient methanol/dichloromethane: 1 to 14%) to afford 46 mg of the desired Z-Asp(β-tert-Butyl)-Phg-Val-OH.

NMR $^1$H (CD$_3$OD, 400 MHz) δ 7.43 (m, 2H); 7.34-7.26 (m, 8H); 5.57 (s, 1H); 5.10 (s, 2H); 4.60 (dd, J=8.28; 5.57 Hz, 1H); 4.24 (s, 1H); 2.81 (m, 1H); 2.58 (m, 1H); 1.41 (s, 9H); 0.96 (t, J=6 Hz, 6H).

LCMS negative (M-H)=554.2

Example 5

Synthesis of Compound 20
Cbz-Asp(O-tBu)-Glu(O-tBu)-Val-OH

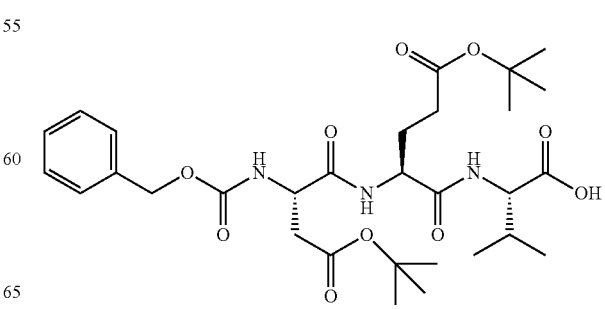

a) Fmoc-Glu(O-tBu)-Val-OAllyl

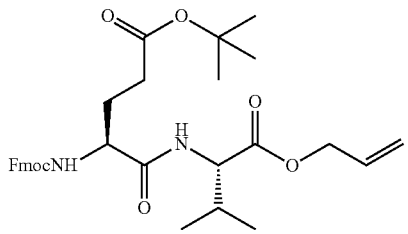

Fmoc-Glu (O-tBu)-OH (0.549 g, 1.292 mmol) was solvated in CH₂Cl₂ (5 mL) followed by addition of L-Val-allyl ester toluene-4-sulfonate (0.426 g, 1 eq), 4-methylmorpholine (0.145 mL, 1.02 eq), DMAP (11.53 mg, 0.13 eq) and finally EDC (0.252 g, 1.02 eq). The EDC vial was washed with CH₂Cl₂ (0.5 mL*2) and added to the reaction mixture. After 1 hour 10 min of stirring, the reaction mixture was extracted with CH₂Cl₂ (30 mL)/brine (5 mL). The organic layer was dried over MgSO₄, filtered off and concentrated. The obtained residue was purified on silica using a gradient Hex/EtOAc (0 to 40%) to get 0.396 g of the desired compound.

b) Glu(O-tBu)-Val-OAllyl

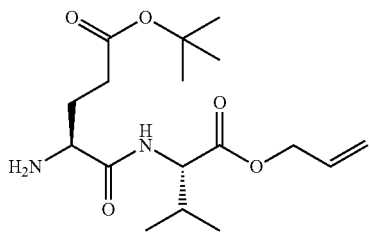 [SMILES: C=CCOC(=O)[C@@H](NC(=O)[C@@H](N)CCC(=O)OC(C)(C)C)C(C)C]

Fmoc-Glu(O-tBu)-Val(OAllyl) (0.394 g, 0.698 mmol) was solvated in CH₂Cl₂ (4 mL) followed by addition of piperidine (0.550 mL, 7.98 eq). After 40 min, the mixture was evaporated to dryness and co-evaporated with CH₂Cl₂ (20 mL*2) followed with high vacuum for 10 min to remove the excess of piperidine. The sample was purified on silica with a gradient of MeOH/CH₂Cl₂ (0 to 7%) to get 0.191 g of the desired compound.

c) Cbz-Asp(O-tBu)-Glu(O-tBu)-Val-OAllyl

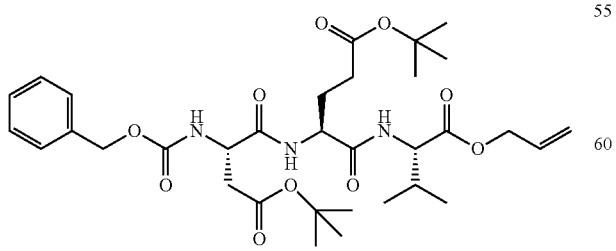

Glu-Val(OAllyl) (0.189 g, 0.55 mmol) was solvated in CH₂Cl₂ (2.5 ml) followed addition of Z-Asp (OtBu)-OH (0.187 g, 1.05 eq), DMAP (5.98 mg, 0.088 eq) and 4-methylmorpholine (0.065 ml, 1.07 eq), then EDC (0.109 g, 1.03 eq. The vial was rinsed with 0.5 ml of dichloromethane). The mixture was stirred for 2 hour at room temperature. Then it was extracted using CH₂Cl₂/brine. The organic layer was dried over MgSO₄, filtered off and concentrated. The obtained residue was purified on silica using a gradient EtOAc/Hex (10 to 100%) to get 0.300 g of the desired compound.

d) Cbz-Asp(O-tBu)-Glu(O-tBu)-Val-OH

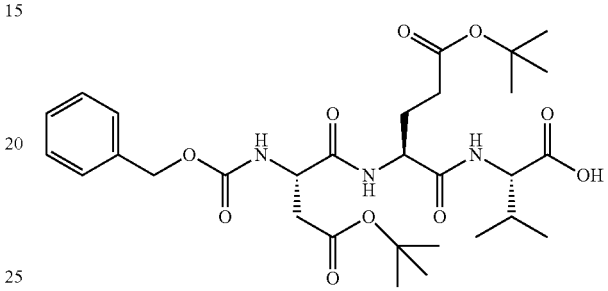

Cbz Asp(O-tBu)-Glu(OtBu)-Val-(OAllyl) (0.298 g, 0.46 mmol) was dissolved in THF (10 mL) and rotary evaporated to dryness, the sample was then redissolved in THF (10 mL) and vacuum aspirated (3*1 min of aspiration), followed by replacement of the atmosphere with Argon. Pd(PPh₃)₄ (0.052 g, 0.1 eq) was added in one shot, the flask was then evacued with Argon. Morpholine (0.14 mL, 3.49 eq) was added and the flask covered with a tin foil. The mixture was kept under stirring for 2.5 days under Argon. The sample was evaporated to dryness and the obtained residue was subjected to purification on C₁₈ using a gradient MeOH/solution of H₂O at pH=3.5 (10 to 100%) to get 0.150 g of the desired compound.

NMR ¹H (CD₃OD, 400 MHz) δ: 7.4-7.25 (m, 5H); 5.20-5.05 (m, 2H); 4.6-4.05 (m, 1H); 4.47-4.38 (m, 1H); 4.25-4.18 (m, 1H); 2.88-2.75 (m, 1H); 2.68-2.55 (m, 1H); 2.42-2.25 (m, 2H); 2.22-2.08 (m, 2H); 1.96-1.80 (m, 1H); 1.45 (2 s, 18H); 0.93 (t, 6H).

Example 6

Synthesis of Compound 23
(Asp(β-tert-butyl)Chlorovinyl-methyl Vinyl Sulfone Tosyl Salt)

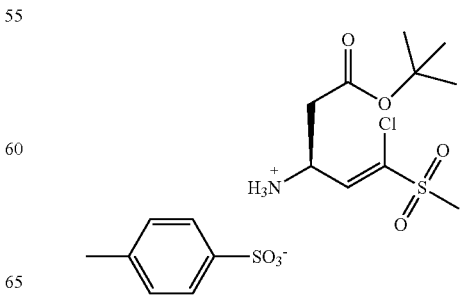

a) Diethyl chloro(methylsulfone)methylphosphonate

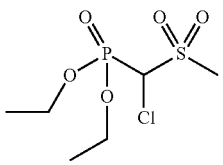

Method A
a) Treatment of Diethyl(methylthio)methylphosphonate (5 g) with NCS (1.1 eq) in CCl4 (41 ml; O0C/RT 3 h) gave after filtration and evaporation of solvent 5 g of Diethyl chloro(methylthio)methylphosphonate (Shankaran, eEROS, 2001)
b) In a flask equipped with a cold reflux condenser, Diethyl chloro(methylthio)methylphosphonate (5 g, 19.01 mmol) was solvated in acetic acid (19 ml) followed by addition of hydrogen peroxide (7.9 ml). The sample was heated to 70° C. for 30 minute (vigour evolution of gaz shortly observed upon heating: The flask was allowed to get out of the oil bath for 4 minutes, the time the boiling and evolution of the gaz ceased, then heated to 70 C). After 30 min the mixture was allowed to reach room temperature (10 minutes). The acetic acid was evaporated to dryness, the residue was diluted with ethyl acetate (100 ml), followed with the addition of NaHCO$_3$ 5% (50 ml). The organic layer was dried over MgSO$_4$ and purified twice on silica using a gradient EtOAc/Hexane (20 to 60%; 50 g Biotage column) to get 0.9 g of the desired compound.

NMR $^1$H (CDCl$_3$, 400 MHz) δ: 4.68 (dd, 1H, J=13.3; 0.8 Hz); 4.36-4.29 (m, 4H); 3.26 (s, 3H); 1.42-1.34 (m, 6 h).

Method B

Diethyl(methylsulfone)methylphosphonate (0.15 g, 0.65 mmol) in dry THF (2.35 ml) was shilled at ° C. NaH (19 mg, 95%, 1.1 eq, pre-cleaned with dry ether) in THF (0.5 ml) was added in a dropwise manner to the solution. The reaction was stirred for 20 min at O° C. before adding a solution of N-chlorosuccinimide (88 mg, 1 eq) in THF (2 ml). The solution was stirred for 1 h 20 at RT, it was then quenched with a saturated NH$_4$Cl (2 ml) and extracted with ethylacetate (3*8 ml). The organic layer was dried over MgSO$_4$ and purified on silica using a gradient EtOAc/Hexane (20 to 100%) to get 40 mg of the desired compound.

b) Boc-Asp(β-tert-butyl)achlorovinyl Methylsulfone

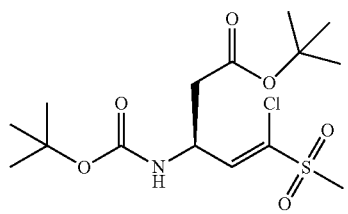 [SMILES: CC(C)(C)OC(=O)C[C@@H](/C=C(\Cl)S(C)(=O)=O)NC(=O)OC(C)(C)C]

Diethyl chloro(methylsulfone)methylphosphonate (0.327 g, 1.24 mmol) was solvated in THF (5 mL) and the solution was allowed to reach −78° C. NaH 60% (0.0519 g, 1.04 eq), which had been washed with Ether anhydrous (3*0.9 mL), was then added in suspension in THF (1.5 mL). The vial containing NaH in suspension was washed with THF (0.4 mL*2) and it was added to the solution. The mixture was stirred for 25 min, then Boc Asp(O-tBu)-H (0.326 g, 1 eq) solvated in THF (3 mL) was added dropwise to the solution over 1 min. The vial was rinsed with THF (0.3 mL*2) and added to the reaction mixture. After 3 hours of stirring, the solution was quenched with a solution of saturated ammonium chloride (5 mL) and extracted with EtOAc (30 mL). The organic layer was washed with brine, dried over MgSO$_4$, filtered and concentrated. The residue was purified on silica using a gradient of EtOAc/Hex (0 to 40%) to get first the cis isomer and then 0.183 g of the trans isomer compound.

NMR $^1$H (CDCl$_3$, 400 MHz) δ: 7.1 (d, 1H, J=8.06 Hz); 5.5 (m, 1H); 4.8 (m, 1H); 3.05 (s, 3H); 2.62 (m, 2H); 1.45 (2 s, 18H).

c) Asp(β-tert-butyl)achlorovinyl Methylsulfone Tosyl Salt

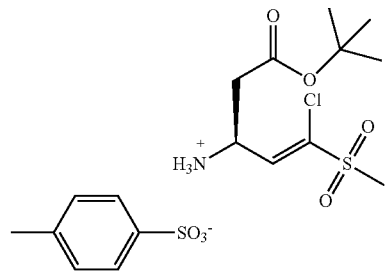

Boc-Asp(β-tert-butyl)Chlorovinyl-methyl vinyl sulfone (0.182 g, 0.4937 mmol) was solvated in CH$_2$Cl$_2$ (0.7 mL) followed by the addition of Et$_2$O (0.7 mL). p-Toluene sulfonic Acid monohydrate (0.101 g, 1.07 eq) was added in one shot. After 15 hours of stirring at room temperature, it was then diluted with Ether (8 mL) and filtered off. The while solid was then dried over vacuum, 0.12 g of the desired compound was obtained.

NMR $^1$H (DMSO, 400 MHz) δ: 8.2 (bs, 3H, NH$_3$); 7.48 (d, 2H, J=8.04 Hz); 7.12 (d, 2H, J=7.89 Hz); 7.02 (d, 1H, J=9.4 Hz); 4.4-4.3 (m, 1H); 3.2 (s, 3H); 2.85 (dd, 1H, J=16.39 Hz, J=5.55 Hz); 2.75 (dd, 1H, J=16.47 Hz, J=7.63 Hz); 2.28 (s, 3H); 1.42 (s, 9H).

Example 7

Synthesis of Compound 26
(Asp(6-tert-butyl)achlorovinyl Phenylsulfone Tosyl Salt)

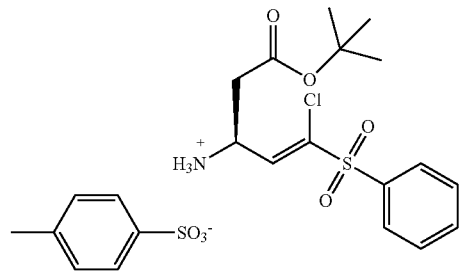

a) Diethyl chloro(phenylsulfone)methylphosphonate

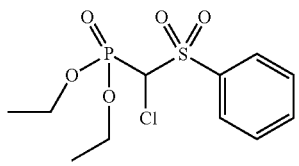 [SMILES: CCOP(=O)(OCC)C(Cl)S(=O)(=O)c1ccccc1]

Diethyl chloro(phenylthio)methylphosphonate (0.919 g, 3.12 mmol) was solvated in acetic acid (1.8 mL), followed by addition of hydrogen peroxide (0.78 mL, 2.8 eq). The sample was then placed in a oil bath preheated to 70° C. An additional portion of hydrogen peroxide (0.21 mL) was added after 5 min. After 30 min the reaction was allowed to reach room temperature. The sample was extracted with AcOEt/5% NaHCO$_3$ (30/5 mL). The organic layer was dried over MgSO$_4$, filtered and concentrated. The residue was purified on silica using a gradient EtOAc/Hexane (10 to 80%) to get 0.627 g of the desired compound.

b) Asp(β-tert-butyl)achlorovinyl Phenylsulfone

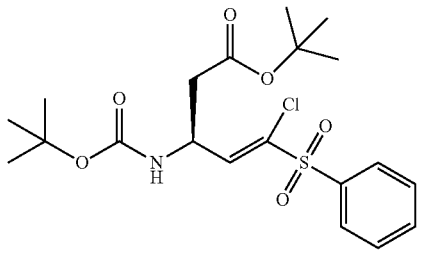 [SMILES: CC(C)(C)OC(=O)C[C@@H](/C=C(\Cl)S(=O)(=O)c1ccccc1)NC(=O)OC(C)(C)C]

Diethyl chloro(phenylsulfone)methylphosphonate (0.458 g, 1.03 eq) was solvated in THF (3 mL) and the solution was allowed to reach −78° C. NaH 60% (0.016 g, 1.11 eq), which had been washed with Ether anhydrous (3*0.9 mL), was then added in suspension in THF (1.5 mL). The vial containing NaH in suspension was washed with THF (0.4 mL*2) and added to the solution. The mixture was stirred for 25 min, then BocAsp(OtBu)-H (0.372 g, 1.36 mmol) solvated in THF (0.5 mL) was added dropwise to the solution over 1 min. The vial was rinsed with THF (2*0.5 ml) and added to the reaction mixture. After 45 min of stirring, the solution was quenched with a solution of ammonium chloride saturated (5 mL) and extracted with EtOAc (30 mL). The organic layer was washed with brine, dried over MgSO$_4$, filtered and concentrated. The residue was purified on silica using a gradient of Hex/EtOAc (0 to 30%), repurified using a gradient of MeOH/CH$_2$Cl$_2$ (0 to 3%) to elute first the cis product and then the trans product. Finally, a small amount of the desired compound was obtained.

NMR $^1$H (CDCl$_3$, 400 MHz) δ: 8.13 (m, 2H); 7.67 (t, 1H, J=7.42 Hz); 7.57 (t, 2H); 6.55 (d, 1H, J=9.19 Hz); 5.75 (bs, 1H); 5.64 (bs, 1H); 2.86-2.77 (m, 2H); 1.47 (s, 9H); 1.45 (s, 9H).

c) Asp(β-tert-butyl)achlorovinyl Phenylsulfone Tosyl Salt

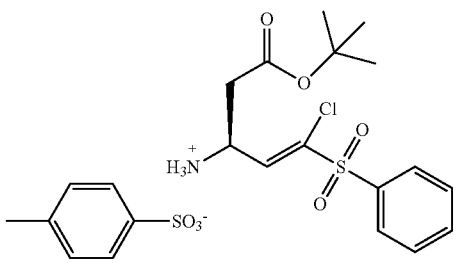

Asp(β-tert-butyl)achlorovinyl phenylsulfone (0.018 g, 0.04 mmol) was solvated in CH$_2$Cl$_2$ (0.1 mL) followed by the addition of Et$_2$O (0.1 mL). p-Toluene sulfonic Acid monohydrate (0.05 g, 0.1 eq) was added in one shot. After 15 hours of stirring at room temperature, it was then evaporated to dryness without heating to get 18 mg of the desired compound.

NMR $^1$H (DMSO, 400 MHz) δ: 8.3 (s, 3H, NH$_3$); 8.08-8.02 (m, 2H); 7.8 (t, 1H, J=7.46 Hz); 7.76 (t, 2H, J=8.08 Hz); 7.48 (d, 2H, J=8.06 Hz); 7.1 (d, 2H, J=7.81 Hz); 6.73 (d, 1H, J=10.09 Hz); 5.3 (m, 1H); 2.87 (dd, 1H, J=16.67 Hz, J=6.13 Hz); 2.78 (dd, 1H, J=16.77 Hz, J=7.01 Hz); 2.28 (s, 3H); 1.43 (s, 9H).

Example 8

Synthesis of Compound 30 (Asp(βMethyl)methyl Vinyl Sulfone Tosyl Salt)

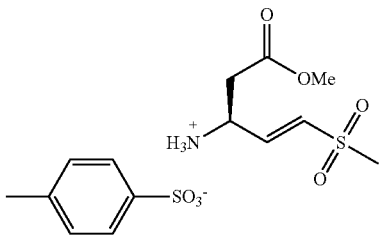

a) Boc-Aspartimol(β-Methyl)

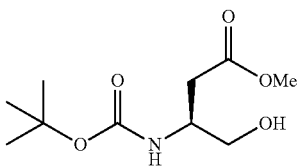 [SMILES: COC(=O)C[C@@H](CO)NC(=O)OC(C)(C)C]

a-Boc-L-Asp(β-Methyl)-OH (2.5 g, 0.0101 mol) was solvated in ethyl acetate (12.5 ml) and shilled at 0° c. N-hydroxysuccinimide (1.163 g, 1 eq) was added, followed with a dropwise addition of DCC (10.1 ml, 1 eq, 1M in CH$_2$Cl$_2$). The mixture was allowed to reach room temperature overnight (20 h), it was then diluted with ethyl acetate and filtered off on celite and washed with ethyl acetate (80 ml total volume). The organic layer was washed with 5% NaHCO3 (2*15 ml), brine (2*25 ml), dried over MgSO$_4$ and concentrated to dryness to get 3.58 g of the desired compound.

b-Boc-L-Asp(β-Methyl)-N-hydroxysuccinimide (1.81 g, 0.00526 mol) was dissolved in 24 mL of anhydrous THF under Argon. The mixture was chilled to 0° C., NaBH$_4$ (0.5 g, 2.51 eq) was added portion wise over a period of 25 min. The mixture was allowed to reach room temperature, and stirred for an extra 4 hours. A solution of ice water/brine (1/1, 15 mL) was added dropwise at 0° C. followed by caution addition of citric acid (0.5 M, 40 mL). The biphasic mixture was stirred and the product was extracted with EtOAc (4*40 mL). The combined organic layer were washed with 5% NaHCO$_3$ (15 mL) and brine (15 mL), dried over MgSO$_4$, filtered off and concentrated under vacuum. The crude material was then purified on silica with a gradient of CH$_2$Cl$_2$/MeOH (0 to 5%) to get 0.7 g of the desired compound.

NMR $^1$H (CDCl$_3$, 400 MHz) δ: 5.20 (bs, 1H); 4.02-3.95 (m, 1H); 3.88-3.64 (m, 2H); 3.70 (s, 3H); 2.63 (d, 2H, J=5.86 Hz); 2.0 (bs, 1H, OH); 1.44 (s, 9H).

b) Boc-Asp(β-Methyl)-H

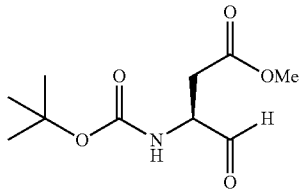 [SMILES: COC(=O)C[C@@H](C=O)NC(=O)OC(C)(C)C]

Oxalyl chloride 2M in CH$_2$Cl$_2$ (1.242 mL, 1.7 eq) dissolved in CH$_2$Cl$_2$ (2.4 mL) was cooled to −65° C. A solution of DMSO (0.4 mL, 3.9 eq) in CH$_2$Cl$_2$ (0.92 mL) was added dropwise over 20 min at −65° C. Boc Asp(OCH$_3$)—CH$_2$OH in CH$_2$Cl$_2$ (0.34 g, 2.6 mL) was added dropwise over a period of 20 min and the reaction was stirred for an extra 15 min at −65° C. TEA (1.33 mL, 6.54 eq) in CH$_2$Cl$_2$ (1.42 mL) was added dropwise over 20 min. The reaction was left for an extra 55 min at −65° C./−70° C. then quenched at this temperature with ether/0.5 N KHSO$_4$ (30/6 mL). The organic layer was washed 3 times with 0.5N KHSO$_4$ (3*6 mL) then brine, dried over MgSO$_4$, filtered off and concentrate, to get 0.29 g of the desired compound.

NMR $^1$H (CDCl$_3$, 400 MHz) δ: 9.65 (s, 1H); 5.61 (d, 1H, J=7.04 Hz); 4.38-4.35 (q, 1H, J=4.3 Hz); 3.70 (s, 3H); 3.01 (dd, 1H, J=17.41 Hz, J=4.49 Hz); 2.83 (dd, 1H, J=17.41 Hz, J=4.69 Hz); 1.46 (s, 9H).

c) Boc-Asp(β-Methyl)methyl Vinyl Sulfone

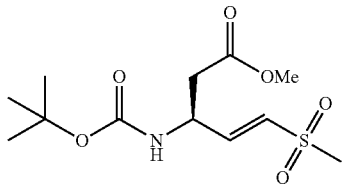 [SMILES: COC(=O)C[C@@H](/C=C/S(C)(=O)=O)NC(=O)OC(C)(C)C]

NaH 95% (0.038 g, 1.2 eq), which had been washed with Ether anhydrous (3*0.9 mL), was suspended in THF (1 mL). The NaH solution was added dropwise at 0° C. to Diethyl (methylsulfone)methylphosphonate (0.280 g, 1.08 eq) which was dissolved in a solution of THF (10 mL). The mixture was stirred for 20 min, then Boc Asp(OMethyl)-H (0.290 g, 1.255 mmol) solvated in THF (2.5 mL) was added dropwise to the solution over 1 min. After 15 min at 0° C., the reaction was allowed to reach room temperature. After 1 hour of stirring, the solution was quenched with a solution of saturated ammonium chloride (10 mL) and extracted with EtOAc (30 mL). The organic layer was washed with brine (20 mL), dried over MgSO$_4$, filtered and concentrated. The residue was purified on silica using a gradient of EtOAc/Hex (10 to 80%) to elute first the cis isomer then the trans isomer (0.174 g).

d) Boc-Asp(β-Methyl)methyl Vinyl Sulfone Tosyl Salt

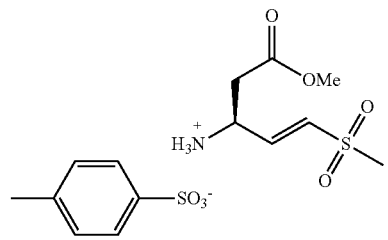

Boc-Asp(β-Methyl)methyl vinyl sulfone (0.172 g, 0.56 mmol) was solvated in CH$_2$Cl$_2$ (0.44 mL) followed by the addition of Et$_2$O (0.44 mL). p-Toluene sulfonic Acid monohydrate (0.19 g, 1.04 eq) was added in one shot. After 15 hours of stirring at room temperature, it was then diluted with Ether (2 mL) and filtered off. The while solid was then dried over vacuum, 0.140 g of the desired compound was obtained.

NMR $^1$H (DMSO, 400 MHz) δ: 8.20 (bs, 3H, NH$_3$); 7.47-7.45 (m, 2H); 7.11 (dd, 2H, J=8.41 Hz, J=0.58 Hz); 7.03 (dd, 1H, J=15.45 Hz, J=1.17 Hz); 6.73 (dd, 1H, J=15.45 Hz, J=6.26 Hz); 4.34 (q, 1H, J=6.45 Hz); 3.66 (s, 3H); 3.05 (s, 3H); 2.92-2.82 (m, 2H); 2.28 (s, 3H).

Example 9

Synthesis of Compound 33 (Asp(β-tert-butyl)methyl Vinyl Sulfone Tosyl Salt)

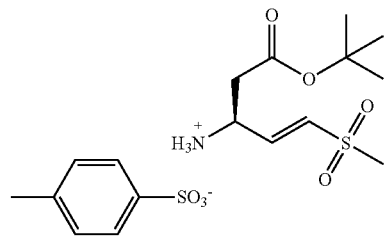

a) Diethyl(methylsulfone)methylphosphonate

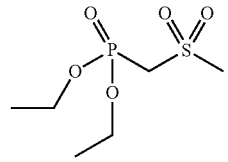

Diethyl(methylthio)methylphosphonate (4.0180 g, 20.3 mmol) was solvated in acetic acid (14 mL, 12 eq) follow by dropwise addition (10 min) of hydrogen peroxide (5.9 mL, 2.56 eq). The sample was then heated to 70° C., vigour evolution of gaz shortly followed. After 25 min the reaction was allowed to reach room temperature. Then NaHCO$_3$ was added in a small portion until the pH become neutral. The sample was then vacuum aspirated followed by extraction with Ether. The organic layer was then washed with 20% of citric acid (5 mL) and then brine (2*10 mL). The organic layer was dried over MgSO$_4$ and purified on silica using a gradient EtOAc/Hexane (10 to 100%) to get 3.237 g of the desired compound.

NMR $^1$H (DMSO, 400 MHz) δ: 4.18 (d, 2H, J=16.62 Hz); 4.10-4.03 (m, 4H); 3.10 (s, 3H); 1.23 (t, 6H, J=7.04 Hz).

b) Boc-Asp(β-tert-butyl)methyl Vinyl Sulfone

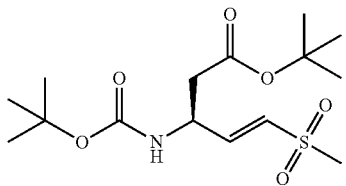 [SMILES: CC(C)(C)OC(=O)C[C@@H](/C=C/S(C)(=O)=O)NC(=O)OC(C)(C)C]

NaH 60% (0.087 g, 1.11 eq), which had been washed with Ether anhydrous (3*0.9 mL), was suspended in THF (1 mL). The NaH solution was added dropwise to Diethyl (methylsulfone)methylphosphonate (0.485 g, 1.08 eq) which was dissolved in a 0° C. solution of THF (20 mL). The mixture was stirred for 20 min, then Boc Asp(OtBu)-H (0.537 g, 1 eq) solvated in THF (2 mL) was added dropwise to the solution over 1 min. After 10 min at 0° C., the reaction was allowed to reach room temperature. After 1 hour of stirring, the solution was quenched with a solution of ammonium chloride saturated (45 mL) and extracted with EtOAc (100 mL). The organic layer was washed with brine (20 mL), dried over MgSO$_4$, filtered and concentrate. The residue was purified on silica using a gradient of Hex/EtOAc (10 to 80%) to elute 0.05 g of the cis compound and 0.480 g of the trans compound.

NMR $^1$H (CDCl$_3$, 400 MHz) δ: 6.86 (dd, 1H, J=15.08 Hz, J=4.60 Hz); 6.51 (dd, 1H, J=15.14 Hz, J=1.38 Hz); 5.41 (bs, 1H); 4.7 (bs, 1H); 2.91 (s, 3H); 2.64-2.52 (qd, 2H); 1.43 (s, 18H).

c) Asp(β-tert-butyl)methyl Vinyl Sulfone Tosyl Salt

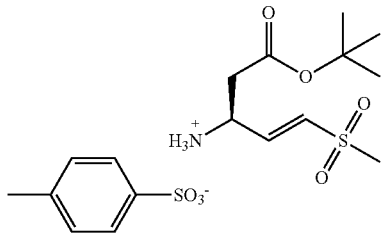

Boc-Asp(β-tert-butyl)methyl vinyl sulfone (0.158 g, 0.4534 mmol) was solvated in CH$_2$Cl$_2$ (0.7 mL) followed by the addition of Et$_2$O (0.7 mL). p-Toluene sulfonic Acid monohydrate (0.0878 g, 1.02 eq) was added in one shot. The use of excess of PTSA hydrate cleaves both boc and tert-butyl groups unlike what was reported by Palmer. After 15 hours of stirring at room temperature, it was then diluted with Ether (5 mL) and filtered off. The while solid was then dried over vacuum, 0.121 g of the desired compound was obtained.

NMR $^1$H (DMSO, 400 MHz) δ: 8.18 (bs, 3H, NH$_3$); 7.47 (d, 2H, J=8.14 Hz); 7.10 (d, 2H, J=7.85 Hz); 7.02 (d, 1H, J=15.42 Hz); 6.70 (dd, 1H, J=15.40 Hz, J=6.61 Hz); 4.27 (q, 1H, J=6.3 Hz); 3.04 (s, 3H); 2.81-2.70 (qd, 2H); 2.28 (s, 3H); 1.42 (s, 9H).

Example 10

Synthesis of Compound 37 (Asp-vinyl Phenyl Sulfone Salt Form)

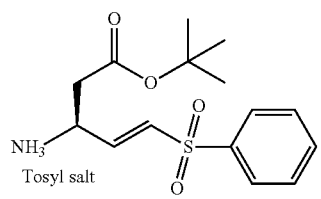 [SMILES: CC(C)(C)OC(=O)C[C@H](N)/C=C/S(=O)(=O)c1ccccc1]

The commercially available N-tBoc-L-Asp(β-tert-Butyl)-O-succinimide was reduced to the corresponding alcohol in the presence of sodium borohydride in THF, as described in the literature (Ramond J. Begeron et al., 1999)

a) Boc-Asp(β-tert-Butyl)-H

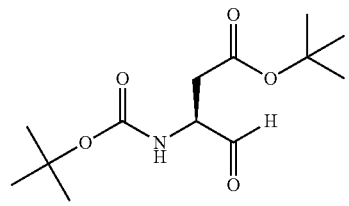 [SMILES: CC(C)(C)OC(=O)C[C@@H](C=O)NC(=O)OC(C)(C)C]

The alcohol is then oxidized to the corresponding Boc-L-Asp(β-tert-Butyl)-H in the presence of oxalyl chloride, DMSO and TEA in dichloromethane at −70° C. as described in the literature (William R. Ewing et al., 1999; Won Bum Jang. 2004 and Mancuso A et al., 1981)

b) Diethyl phenylsulfonylmethylphosphonate

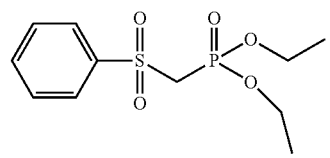 [SMILES: CCOP(=O)(CS(=O)(=O)c1ccccc1)OCC]

The precursor of phenyl vinyl sulfone was obtained in one step from benzenesulfonyl fluoride and triethyl phosphorane in the presence of lithium hexamethyldisilazide at −78° C. to get diethyl phenylsulfonylmethylphosphonate as described in the literature (Won Bum Jang et al., 1998).

Boc-Asp(β-tert-Butyl)-vinyl phenyl sulfone (Gang Wang et al., 2003; Marion G. Gotz et al., 2004; Palmer, James T et al., 1995).

c) Boc-Asp-vinyl Phenyl Sulfone

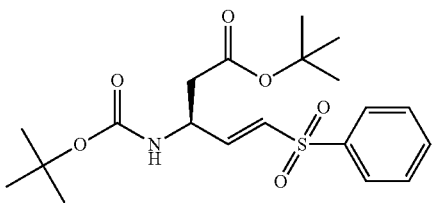 [SMILES: CC(C)(C)OC(=O)C[C@@H](/C=C/S(=O)(=O)c1ccccc1)NC(=O)OC(C)(C)C]

Sodium hydride (40 mg (60%), 1.09 eq) was added to a solution of diethyl phenylsulfonylmethylphosphonate (0.279 g, 1.09 eq) in dry THF (5.6 ml) at 0° C. The mixture was stirred for 20 minutes before adding, drop-wise, a solution of Boc-L-Asp(O-t-Bu)-H (0.24 g, 0.876 mmol) in 1.6 ml of THF. The mixture was stirred for 1.15 h at RT, then poured into a mix of ethyl acetate and ammonium chloride saturated solution (45/15 ml). The organic layer was dried over magnesium sulfate and the solvent was evaporated to dryness. The crude material was purified on silica gel (gradient: ethyl acetate/hexane) to make the desired compound with a high chemical yield.

NMR $^1$H (CD$_3$OD, 400 MHz) δ 7.87 (d, J=7.62 Hz, 2H); 7.61 (t, J=7.35 Hz, 1H); 7.53 (t, J=7.68 Hz, 2H); 6.92 (dd, J=15.08 and 4.28 Hz, 1H); 6.46 (d, J=15.12 Hz, 1H); 5.34 (m, 1H); 4.68 (m, 1H); 2.63-2.52 (m, 2H); 1.40 (s, 18H).

d) Asp Vinyl Phenyl Sulfone Tosyl Salt

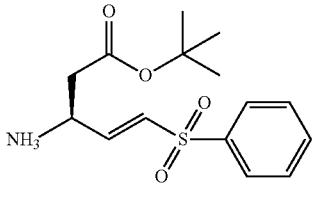

Tosyl salt

Boc-L-Asp(β-tert-Butyl)-Vinyl phenyl sulfone (0.1 g, 0.243 mmol) was dissolved in a mix of dichloromethane and ether (0.7/0.7 ml), then PTSA hydrate (1 eq) was added. The use of excess of PTSA hydrate cleaves both boc and tert-butyl groups unlike what was reported by Palmer. The mixture was stirred at room temperature overnight. Then, it was diluted with ether (8 ml). The white precipitate was filtered off and dried to yield to the desired compound as a white powder.

Example 11

Synthesis of Compound 40
(Asp(β-tert-butyl)phenoxy Vinylsulfone Tosyl Salt)

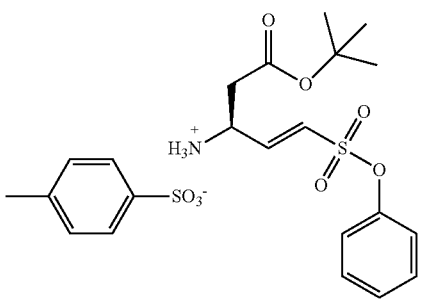

To a solution of phenol (1.62 g, 17.2 mmol) in Et$_2$O (50 mL) at −10° C. was added TEA (3.6 mL, 1.5 eq). After 15 min a solution of methanesulfonylchloride (1.6 mL, 1.2 eq) in Et$_2$O (4 mL) was added dropwise over 50 min. Then the solution was allowed to warm at room temperature and an additional portion of Et$_2$O (5 mL) was added. The reaction was quenched by addition of 1N HCl (12 mL, 4° C.), the organic layer was then washed with saturated NaHCO$_3$, brine and dried over MgSO$_4$, filtered off and concentrated to give an oil which was recristallised for CH$_2$Cl$_2$/Hex (1/1). The resulting solid was filtered and the residual solvent removed.

a) Diethyl(phenoxysulfone)methylphosphonate

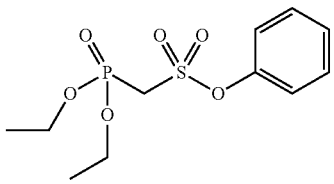 [SMILES: CCOP(=O)(CS(=O)(=O)Oc1ccccc1)OCC]

To a solution of methanesulfonyl phenoxy (1.938 g, 11.25 mmol) in THF (8 mL) at −78° C., was added dropwise a solution of potassium bis(trimethylsilyl)amide (2.36 g, 1 eq) in 11 mL of THF over a period of 40 min. Then the reaction was stirred for an extra 5 min. Diethyl chlorophosphonate (0.95 mL, 0.59 eq) was added dropwise over 7 min. After 1 hour, the reaction was quenched by dropwise addition of a solution of Acetic Acid (0.645 mL, 0.59 eq) over 5 min. The solution was allowed to warm to room temperature and the solvent was removed in vacuum. The product was extract with CH$_2$Cl$_2$ (30 mL) and H$_2$O (10 mL), dried over MgSO$_4$, filtered off and concentrate. The residue was purified on silica using a gradient EtOAc/Hexane (12 to 100%) to get 1.046 g of the desired compound.

NMR $^1$H (CDCl$_3$, 400 MHz) δ: 7.44-7.41 (m, 2H); 7.36-7.32 (m, 3H); 4.31-4.25 (m, 4H); 3.81 (d, 2H, J=17.14 Hz); 1.38 (t, 6H, J=7.11 Hz).

b) Asp(β-tert-butyl)phenoxy Vinyl Sulfone

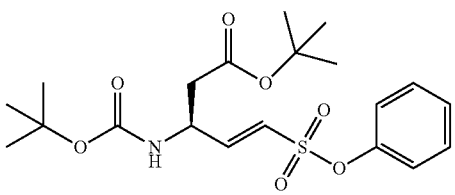 [SMILES: CC(C)(C)OC(=O)C[C@@H](/C=C/S(=O)(=O)Oc1ccccc1)NC(=O)OC(C)(C)C]

Diethyl(phenoxysulfone)methylphosphonate (0.36 g, 1.07 mmol) was solvated in THF (10 mL) and the solution was allowed to reach −0° C. NaH 60% (0.0539 g, 1.22 eq), which had been washed with Ether anhydrous (3*0.9 mL), was then added in suspension in THF (1 mL). The vial containing NaH in suspension was washed with THF (1 mL) and it was added to the solution. The mixture was stirred for 20 min, then Boc Asp(O-tBu)-H (0.30 g, 1 eq) solvated in THF (2 mL) was added dropwise to the solution over 1 min. The vial was rinsed with THF (1 mL) and added to the reaction mixture. After 2 hours of stirring at room temperature, the solution was quenched with a solution of ammonium chloride saturated (5 mL) and extracted with EtOAc (30 mL). The organic layer was washed with brine, dried over MgSO₄, filtered off and concentrated. The residue was purified on silica using a gradient of EtOAc/Hexane (0 to 30%, 30 to 80%) to get 0.359 g of the desired compound.

NMR ¹H (CDCl₃, 400 MHz) δ: 7.38 (t, 2H, J=7.96 Hz); 7.29 (t, 1H, J=7.46 Hz); 7.23-7.21 (m, 2H); 6.79 (dd, 1H, J=15.14 Hz, J=4.67 Hz); 6.49 (dd, 1H, J=15.18 Hz, J=1.31 Hz); 5.37 (bs, 1H); 4.65 (bs, 1H); 2.60 (dd, 1H, J=16.04 Hz, J=5.46 Hz); 2.50 (dd, 1H, J=16.04 Hz, J=5.63 Hz); 1.46 (s, 9H); 1.43 (s, 9H).

c) Asp(β-tert-butyl)phenoxy Vinyl Sulfone Tosyl Salt

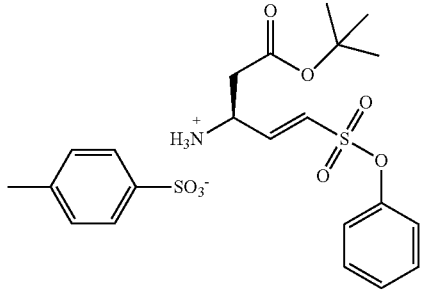

Asp(β-tert-butyl)phenoxy vinyl sulfone (0.187 g, 0.444 mmol) was solvated in CH₂Cl₂ (0.7 mL) followed by the addition of Et₂O (0.7 mL). p-Toluene sulfonic Acid monohydrate (0.084 g, 1.01 eq) was added in one shot. After 15 hours of stirring at room temperature, it was then diluted with Ether (8 mL) and filtered off. The while solid was then dried over vacuum to get the desired compound.

NMR ¹H (DMSO, 400 MHz) δ: 8.25 (bs, 3H, NH₃); 7.49-7.46 (m, 4H); 7.39 (t, 1H, J=7.4 Hz); 7.31-7.29 (m, 2H); 7.22-7.17 (m, 1H); 7.10 (d, 2H, J=7.88 Hz); 6.82 (dd, 1H, J=15.41 Hz, J=6.15 Hz); 4.35 (m, 1H); 2.82-2.73 (m, 2H); 2.28 (s, 3H); 1.41 (s, 9H).

Example 12

Synthesis of Compound 43
(Asp(β-tert-butyl)isopropyl Vinyl Sulfone Tosyl Salt)

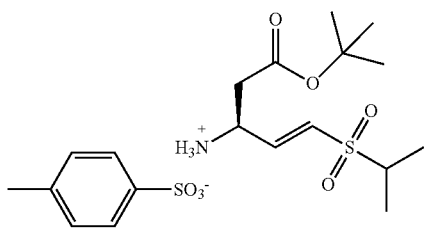

a) Diethyl(isopropylthio)methylphosphonate

Chloromethyl isopropylsulfide (12.54 g, 100.6 mmol) was heated to 110° C. follow by dropwise addition of triethylphosphonyl (21 mL, 1.10 eq). After stirring for 8 hours, the reaction was allowed to reach room temperature. The sample was purified by distillation (110° C./6 mmbar) to get 4.7 g of Diethyl(isopropylthio)methylphosphonate.

NMR ¹H (CDCl₃, 400 MHz) δ: 4.21-4.13 (m, 4H); 3.19-3.14 (m, 1H); 2.76 (d, 2H, J=14.35 Hz); 1.34-1.27 (m, 12H).

b) Synthesis of Compound 41
(Diethyl(isopropylsulfone)methylphosphonate)

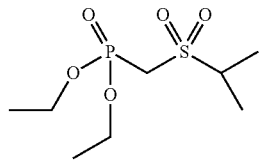

Diethyl(isopropylthio)methylphosphonate (4.746 g, 0.02 mol) was solvated in acetic acid (14.5 mL, 12.06 eq) followed by dropwise addition over 5 min of hydrogen peroxide (6 mL, 2.52 eq). The sample was then heated to 70° C., vigor evolution of gaz shortly followed. After 30 min the reaction was allowed to reach room temperature. Then NaHCO₃ was added in a small portion until the pH become neutral. The sample was then vacuum aspirated followed by extraction with Ether (30 mL). The organic layer was then washed with 20% of citric acid (5 mL) and then brine (2*10 mL). The organic layer was combined and extract with CH₂Cl₂/water, dried over MgSO₄ and purified on silica using a gradient EtOAc/Hexane (20 to 100%) to get 4.689 g of the desired compound.

NMR ¹H (CDCl₃, 400 MHz) δ: 4.23-4.50 (m, 4H); 3.67-3.63 (m, 1H); 3.53 (d, 2H, J=16.82 Hz); 1.37-1.30 (m, 12H).

c) Synthesis of Compound 42
(BocAsp(β-tert-butyl)isopropyl Vinyl Sulfone)

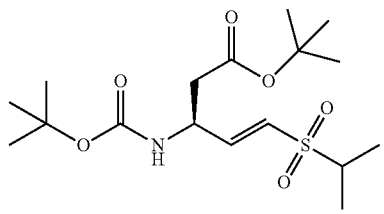 [SMILES: CC(C)S(=O)(=O)/C=C/[C@H](CC(=O)OC(C)(C)C)NC(=O)OC(C)(C)C]

Diethyl(isopropylsulfone)methylphosphonate (0.036 g, 0.1427 mmol) was solvated in THF (0.2 mL) and the solution was allowed to reach 0° C. NaH 60% (5.38 mg, 1.05 eq), which had been washed with Ether anhydrous (3*0.9 mL), was then added in suspension in THF (1.2 mL). The mixture was stirred for 25 min, then Boc Asp(O-tBu)-H (0.0351 g, 1 eq) solvated in THF (0.6 mL) was added dropwise to the solution over 1 min. After 45 min of stirring, the solution was quenched with a solution of ammonium chloride saturated (2 mL) and extracted with EtOAc (10 mL). The organic layer was washed with brine, dried over MgSO₄, filtered and concentrated. The residue was purified on silica using a gradient of EtOAc/Hexane (5 to 60%) to get 29.3 mg of the desired compound.

NMR ¹H (CDCl₃, 400 MHz) δ: 6.82 (dd, 1H, J=15.24 Hz, J=4.78 Hz); 6.38 (dd, 1H, J=15.17 Hz, J=1.41 Hz); 5.43 (m,

1H); 4.67 (s, 1H); 3.07-3.0 (m, 1H); 2.64 (dd, 1H, J=16.07 Hz, J=5.5 Hz); 2.57 (dd, 1H, J=16.12 Hz, J=5.52 Hz); 1.48-1.32 (m, 24H).

d) Synthesis of Compound 43
(Asp(β-tert-butyl)isopropyl Vinyl Sulfone Tosyl Salt)

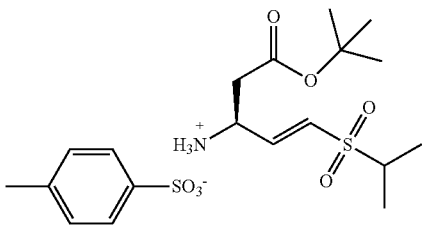

Boc-Asp(β-tert-butyl)isopropyl vinyl sulfone (0.028 g, 0.0741 mmol) was solvated in CH₂Cl₂ (0.2 mL) followed by the addition of Et₂O (0.2 mL). p-Toluene sulfonic Acid monohydrate (0.0154 g, 1.09 eq) was added in one shot. After 15 hours of stirring at room temperature, it was then diluted with Ether (8 mL) and filtered off. The while solid was then dried over vacuum, 11 mg of the desired compound was obtained.

NMR ¹H (DMSO, 400 MHz) δ: 8.21 (bs, 3H, NH₃); 7.46 (d, 2H, J=7.81 Hz); 7.10 (d, 2H, J=7.85 Hz); 6.92-6.85 (m, 1H); 6.71 (dd, 1H, J=15.42 Hz, J=6.34 Hz); 4.30 (m, 1H); 3.23-3.13 (m, 1H); 2.85-2.72 (m, 2H); 2.28 (s, 3H); 1.42 (s, 9H); 1.21 (m, 6H).

Example 13

Synthesis of Compound 46
(Asp(δ-tert-butyl)morpholine Vinyl Sulfone Tosyl Salt)

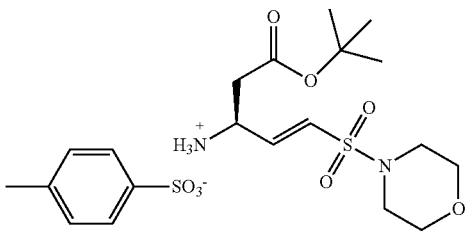

To a solution of morpholine (1.4 mL, 16.07 mmol) in CH₂Cl₂ (30 mL) at −10° C. was added TEA (3.4 mL, 1.5 eq). After 15 min a solution of methanesulfonylchloride (1.5 mL, 1.2 eq) in CH₂Cl₂ (4 mL) was added dropwise over 40 min. Then the solution was allowed to warm at room temperature and an additional portion of Et₂O (5 mL) was added. The reaction was quenched by addition of 1N HCl (12 mL, 4 C), the organic layer was then washed with saturated NaHCO₃, brine and dried over MgSO4, filtered off and concentrate to give an oil which was purified on silica using a gradient of MeOH/CH₂Cl₂ (0 to 5%) to get 0.831 g of Diethyl(morpholinethio)methylphosphonate.

a) Synthesis of Compound 44
(Diethyl(morpholinesulfone)methylphosphonate)

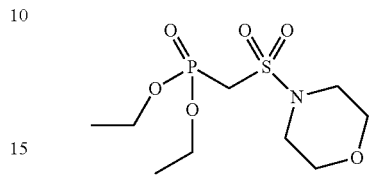

To a solution of methane sulfonyl morpholine (0.719 g, 4.356 mmol) in THF (4 mL) at −78° C., was added dropwise a solution of potassium bis(trimethylsilyl)amide (0.748 g, 0.86 eq) in 11 mL of THF over a period of 40 min. Then the reaction was stirred for an extra 5 min. Diethyl chloromethylphosphonate (0.37 mL, 0.57 eq) was added dropwise over 7 min. After 1 hour, the reaction was quenched by dropwise addition of a solution of Acetic Acid (0.226 mL, 0.77 eq) over 5 min. The solution was allowed to warm to room temperature and the solvent was removed in vacuum. The product was extract with CH₂Cl₂ (30 mL) and H₂O (10 mL), dried over MgSO₄, filtered off and concentrate. The residue was purified on silica using a gradient MeOH/CH₂Cl₂ (0 to 4%) to get 0.247 g of the desired compound.

NMR ¹H (CDCl₃, 400 MHz) δ: 4.26-4.20 (m, 4H); 3.76 (t, 4H, J=4.6 Hz); 3.51 (d, 2H, J=17.33 Hz); 3.34 (t, 4H, J=4.74 Hz); 1.37 (t, 6H, J=7.11 Hz).

b) Synthesis of Compound 45
(Boc-Asp(β-tert-butyl)morpholine Vinyl Sulfone)

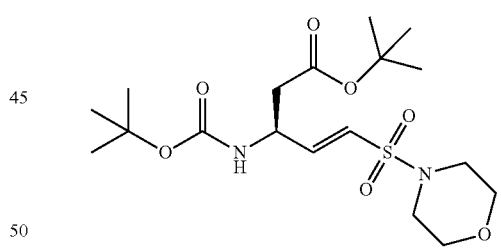

Diethyl(morpholinesulfone)methylphosphonate (0.103 g, 1.07 mmol) was solvated in THF (1 mL) and the solution was allowed to reach −10° C. NaH 60% (0.013 g, 1.04 eq), which had been washed with Ether anhydrous (3*0.9 mL), was then added in suspension in THF (1 mL). The vial containing NaH in suspension was washed with THF (0.5 mL) and it was added to the solution. The mixture was stirred for 20 min, then Boc Asp(OtBu)-H (0.208 g, 1 eq) solvated in THF (1.5 mL) was added dropwise to the solution over 1 min, the vial was washed with DMF (0.5 ml) and added to the solution. After 3 hours of stirring at room temperature, the solution was quenched with a solution of ammonium chloride saturated (5 mL) and extracted with EtOAc (30 mL). The organic layer was washed with brine, dried over MgSO4, filtered off and concentrated. The residue was purified on silica using a gradient of first Hex/EtOAc (5 to 80%) then CH$_2$Cl$_2$/MeOH (0 to 10%) to get 0.075 g of the desired compound.

c) Synthesis of Compound 46 (Asp(β-tert-butyl)morpholine Vinyl Sulfone Tosyl Salt)

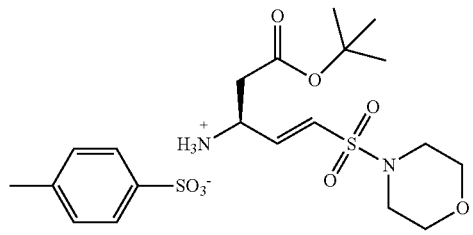

Boc-Asp(β-tert-butyl)morpholine vinyl sulfone (0.075 g, 0.178 mmol) was solvated in CH$_2$Cl$_2$ (0.2 mL) followed by the addition of Et$_2$O (0.2 mL). p-Toluene sulfonic Acid monohydrate (0.034 g, 1.0 eq) was added in one shot. After 15 hours of stirring at room temperature, it was then diluted with Ether (0.5 mL) and filtered off. The while solid was then dried over vacuum, 0.045 g of the desired compound was obtained.

NMR $^1$H (DMSO, 400 MHz) δ: 8.20 (bs, 3H, NH$_3$); 7.47 (d, 2H, J=7.9 Hz); 7.10 (d, 2H, J=7.89 Hz); 6.88 (d, 1H, J=15.33 Hz); 6.60 (dd, 1H, J=15.00 Hz, J=6.36 Hz); 4.28 (s, 1H); 3.65 (t, 4H, J=4.43 Hz); 3.02 (m, 4H); 2.84-2.76 (m, 2H); 2.28 (s, 3H); 1.42 (s, 9H).

Example 14

Synthesis of Compound 47 (Z-Asp(β-tert-Butyl)-Ala (2'-quinolyl)-Val-Asp(β-tert-Butyl)achlorovinyl Methylsulfone)

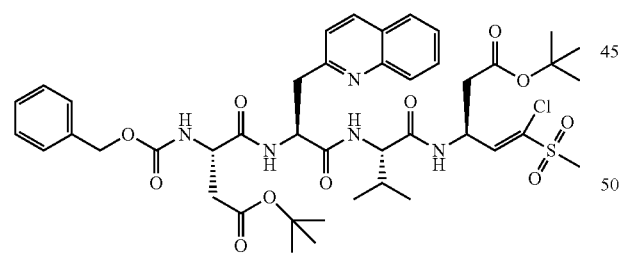

The Z-Asp(β-tert-Butyl)-Ala(2'-quinolyl)-Val-OH (18 mg, 0.029 mmol) is dissolved in a mix of dichloromethane and DMF (0.39 ml/0.13 ml). The mixture was allowed to reach −15/−20° C. before adding N-methyl morpholine (8 μl) followed 3 min latter with isobutyl chloroformate (7 μl). The mixture was stirred at −15° C. for 10 minutes. Next, Asp(β-tert-butyl)achloromethyl-methylsulfone tosyl salt (13 mg, 1 eq) was added in one shot, followed by N-methyl morpholine (8 μl). The mixture was stirred 35 minutes at −15/−20° C. and then diluted with 5 ml of dichloromethane and quenched with 1.5 ml of a saturated solution of sodium bicarbonate. The organic layer was dried over magnesium sulphate, the solvent was evaporated to dryness. The obtained residue was purified on silica gel (gradient: ethyl acetate/hexane: 5 to 100%) to afford 12 mg of the desired compound.

Example 15

Synthesis of Compound 48 (Z-Asp-Ala(2'-quinolyl)-Val-Asp-achlorovinyl Methylsulfone)

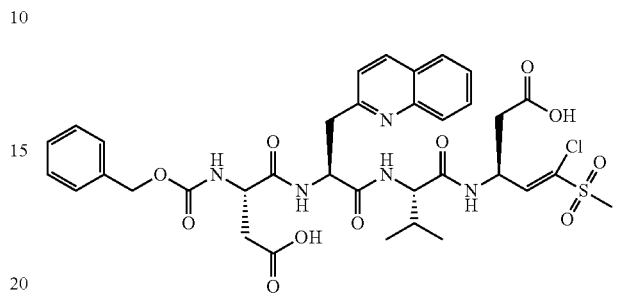

Z-Asp(β-tert-Butyl)-Ala(2'-quinolyl)-Val-Asp(β-tert-Butyl)-achlorovinyl methylsulfone (11.7 mg) was dissolved in dichloromethane (0.24 ml), followed by addition of trifluoroacetic acid (0.35 ml). The mixture was stirred at room temperature overnight (15 h). It was then quenched with diethyl ether (5 ml), the solvent was removed under vacuum. The obtained residue was diluted again with ether (5 ml) and the process was repeated twice. The precipitate was washed with 2*1 ml of ether, dried to give 9 mg of the desired compound.

NMR $^1$H (CD$_3$OD, 400 MHz) δ: 8.6-7.25 (m, 11H); 7.07 (d, 1H, J=8.61 Hz); 5.03-4.06 (m, 4H); 4.45-4.42 (m, 1H); 4.09-4.05 (m, 1H); 3.65-3.49 (m, 2H); 3.07 (s, 3H); 2.84-2.7 (m, 2H); 2.71-2.66 (m, 2H); 2.00 (m, 1H); 0.85 (t, 6H, J=8.2 Hz). LCMS (M-H+)=772.4.

Example 16

Synthesis of Compound 49 (Ts-Ala(2'quinolyl)-Val-Asp(β-tert-Butyl)-achlorovinyl Methylsulfone)

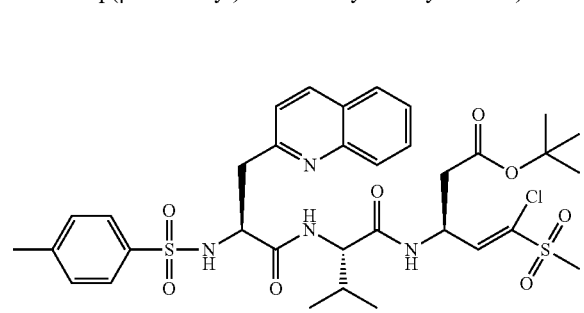

The Ts-Ala(2'-quinolyl)-OH (5.6 mg, 0.0123 mmol) was dissolved in a mix of CH$_2$Cl$_2$/DMF (0.15/0.13 mL). The mixture was allowed to reach −15° C./−20° C. (ice MeOH bath) before adding NMM (0.004 mL) followed 3 min later with isobutylchloroformate (0.004 mL). The mixture was stirred for 10 min at −15° C. before adding Asp(β-tert-butyl) Chlorovinyl-methyl vinyl sulfone tosyl salt (6.3 mg, 1 eq) in one shot, followed with 4-methylmorpholine (0.004 mL). The mixture was stirred at −15° C./−20° C. for 30 min, it was then diluted with CH$_2$Cl$_2$ (5 mL), then water (2 mL) and the mixture was allowed to reach room temperature, extracted.

The organic layer was dried over MgSO₄, concentrated and purified by silica using Hex/EtOAc (15 to 100%) to get 6 mg of the desired compound.

Example 17

Synthesis of Compound 50 (Ts-Ala(2'quinolyl)-Val-Asp-achlorovinyl Methylsulfone)

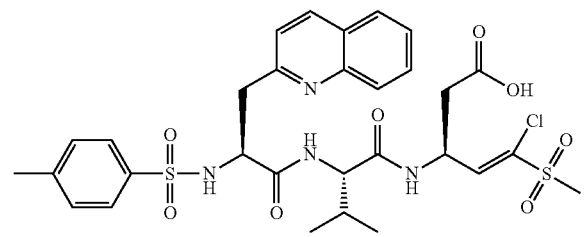

Ts-Ala(2'quinolyl)-Val-Asp(β-tert-Butyl)-achlorovinyl methylsulfone (6 mg) was dissolved in dichloromethane (0.15 ml), followed by addition of trifluoroacetic acid (0.2 ml). The mixture was stirred at room temperature overnight (15 h). It was then quenched with diethyl ether (5 ml) and the solvent was removed under vacuum. The obtained residue was diluted again with ether and the process was repeated twice. The precipitate was washed with 2*1 ml of ether, dried to give 4 mg of the desired compound.

NMR ¹H (CD₃OD, 400 MHz) δ: 8.37 (m, 1H); 8.01-7.99 (m, 1H); 7.96-7.94 (m, 1H); 7.90-7.94 (m, 1H); 7.90-7.88 (m, 1H); 7.71-7.63 (m, 1H); 7.46 (m, 1H); 7.37 (d, 2H, J=8.22 Hz); 7.08 (d, 1H, J=8.46 Hz); 6.88 (d, 2H, J=8.0 Hz); 5.04-5.01 (m, 1H); 4.37-4.34 (m, 1H); 4.08-4.07 (m, 1H); 3.44-3.4 (m, 1H); 3.2 (m, 1H); 3.08 (s, 3H); 2.83-2.78 (m, 1H); 2.73-2.684 (m, 1H); 2.17 (s, 3H); 2.07-2.03 (m, 1H); 0.91-0.89 (m, 6H).

Example 18

Synthesis of Compound 51 (Z-Asp(β-methyl)-Indanylglycine-Val-Asp(β-methyl)methyl Vinyl Sulfone)

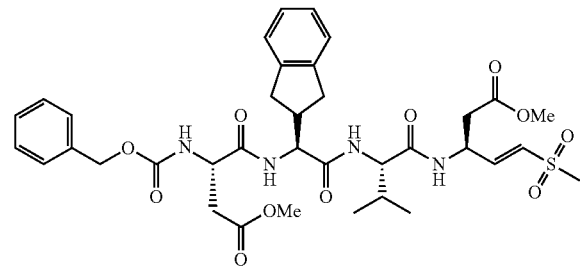 [SMILES: COC(=O)C[C@@H](/C=C/S(C)(=O)=O)NC(=O)[C@@H](NC(=O)[C@@H](NC(=O)[C@H](CC(=O)OC)NC(=O)OCc1ccccc1)C1Cc2ccccc2C1)C(C)C]

a) Cbz-Asp(β-methyl)-Indanylglycine-Val-OAllyl

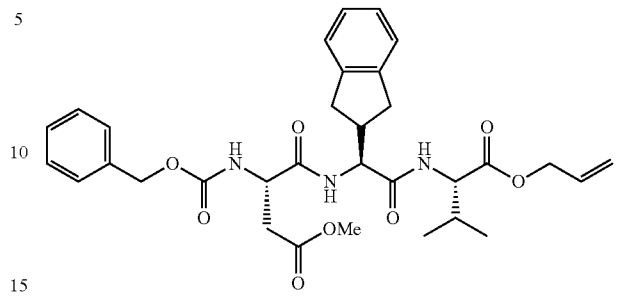

It was synthesized from Cbz-Asp(β-methyl)-indanylglycine-Val-OAllyl as described for Cbz-Asp(β-methyl)-phenylglycine-Val-OAllyl b) Cbz-Asp(β-methyl)Indanylglycine-Val-OH

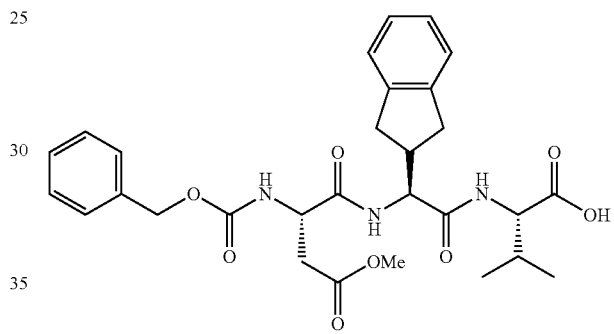

It was synthesized from Indanylglycine-Val-OAllyl and Z-L-Asp(β-methyl)-OH as described for Cbz-Asp(β-methyl) Phenylglycine-Val-OH.

c) Synthesis of Compound 51 (Z-Asp(β-methyl)-Indanylglycine-Val-Asp(β-methyl)methyl Vinyl Sulfone)

The Z-Asp(β-methyl)-Indanylglycine-Val-OH (16.7 mg, 0.0301 mmol) is dissolved in a mix of THF and DMF (0.5 ml/0.1 ml). The mixture was allowed to reach −15/−20° C. before adding N-methyl morpholine (9 μl) followed 3 min latter with isobutyl chloroformate (8 μl). The mixture was stirred at −15° C. for 10 minutes. Next, Asp(β-methyl)methyl vinyl sulfone tosyl salt (12 mg, 1 eq) was added in one shot, the vial was washed with THF (0.1 ml) and added to the solution, followed by the addition of N-methyl morpholine (9 μl). The mixture was stirred 35 minutes at −15/−20° C. and then diluted with 7 ml of dichloromethane and quenched with 1.5 ml of a saturated solution of sodium bicarbonate. After that, the organic layer was dried over magnesium sulphate. The solvent was evaporated to dryness. The obtained residue was purified on silica gel (ethyl acetate/hexane: 40% then dichloromethane/methanol: 5 to 15%) to afford 14 mg of Z-Asp(β-methyl)-Indanylglycine-Val-Asp(β-methyl)-methyl vinyl sulfone.

NMR ¹H (DMSO, 400 MHz) δ: 8.31 (d, NH, J=7.82 Hz); 8.11 (d, NH, J=8.8 Hz); 7.93 (d, NH, J=8.21 Hz); 7.69 (d, NH, J=8.02 Hz); 7.37-7.08 (m, 9H); 6.74 (dd, 1H, J=15.45 Hz,

J=4.30 Hz); 6.67 (d, 1H, J=15.59 Hz); 5.05 (s, 2H); 4.99 (m, 1H); 4.44 (m, 2H); 4.11 (m, 1H); 3.57 (s, 6H); 2.98 (s, 3H); 2.95-2.5 (m, 9H); 2.00-1.94 (m, 1H); 0.84 (t, 6H, J=6.06 Hz).

Example 19

Synthesis of Compound 52 (Z-Asp(β-tert-Butyl)-Phg-Val-Asp(β-tert-Butyl)methyl Vinyl Sulfone)

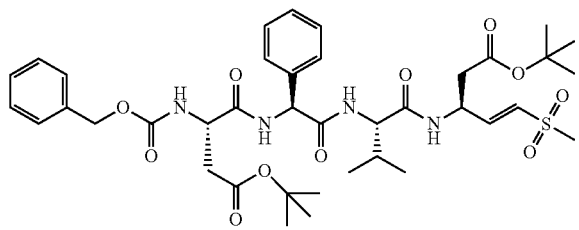 [SMILES: CC(C)[C@H](NC(=O)[C@@H](NC(=O)[C@H](CC(=O)OC(C)(C)C)NC(=O)OCc1ccccc1)c1ccccc1)C(=O)N[C@H](/C=C/S(C)(=O)=O)CC(=O)OC(C)(C)C]

The Z-Asp(β-tert-Butyl)-Phg-Val-OH (17 mg, 0.0306 mmol) is dissolved in a mix of dichloromethane and DMF (0.39 ml/0.13 ml). The mixture was allowed to reach −15/−20° C. before adding N-methyl morpholine (8 μl) followed 3 min latter with isobutyl chloroformate (8 μl). The mixture was stirred at −15° C. for 10 minutes. Next, Asp(β-tert-butyl) methyl vinyl sulfone tosyl salt (12 mg, 1 eq) was added in one shot, followed by N-methyl morpholine (8 μl). The mixture was stirred 35 minutes at −15/−20° C. and then diluted with 5 ml of dichloromethane and quenched with 1.5 ml of a saturated solution of sodium bicarbonate. The organic layer was dried over magnesium sulphate. The solvent was evaporated to dryness. The obtained residue was purified on silica gel (gradient: ethyl acetate/hexane: 5 to 100%) to afford 8 mg of Z-Asp(β-tert-Butyl)-Phg-Val-Asp(β-tert-butyl)-methyl vinyl sulfone.

Example 20

Synthesis of Compound 53 (Z-Asp-Phg-Val-Asp-methyl Vinyl Sulfone)

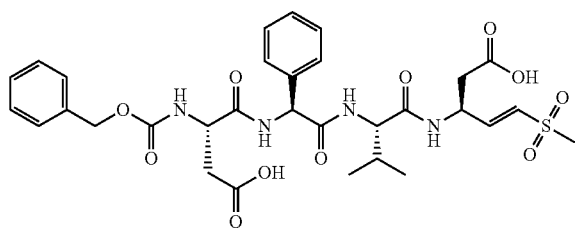 [SMILES: CC(C)[C@H](NC(=O)[C@@H](NC(=O)[C@H](CC(=O)O)NC(=O)OCc1ccccc1)c1ccccc1)C(=O)N[C@H](/C=C/S(C)(=O)=O)CC(=O)O]

Z-Asp(β-tert-Butyl)-Phg-Val-Asp(β-tert-butyl)methyl vinyl sulfone (6.2 mg) was dissolved in dichloromethane (0.16 ml), followed by addition of trifluoroacetic acid (0.22 ml). The mixture was stirred at room temperature overnight (15 h). It was then quenched with diethyl ether (5 ml), then the solvent was removed under vacuum. The obtained residue was diluted again with ether (5 ml) and the process was repeated twice. The crude material was diluted once more with ether, the filtrate was removed and the precipitate was washed with 2*1 ml of ether, dried to give 5 mg of the desired compound.

NMR ¹H (CD₃OD, 400 MHz) δ: 7.46-7.29 (m, 10H); 6.83 (dd, 1H, J=15.22 Hz, J=4.60 Hz); 6.68 (dd, 1H, J=15.229 Hz, J=1.36 Hz); 5.38 (s, 1H); 5.10 (q, 2H, J=12.73 Hz); 4.94-4.90 (m, 1H); 4.56 (t, 1H, J=6.75 Hz); 4.10 (d, 1H, J=7.07 Hz); 2.95 (s, 3H); 2.98-2.88 (m, 1H); 2.76-2.60 (m, 3H); 2.21-2.12 (m, 1H); 0.98 (t, 6H, J=6.3 Hz). LCMS (M-H⁺)=673.7

Example 21

Synthesis of Compound 54 (Z-Asp(β-tert-Butyl)-Al (2'-quinolyl)-Val-Asp(β-tert-Butyl)methyl Vinyl Sulfone)

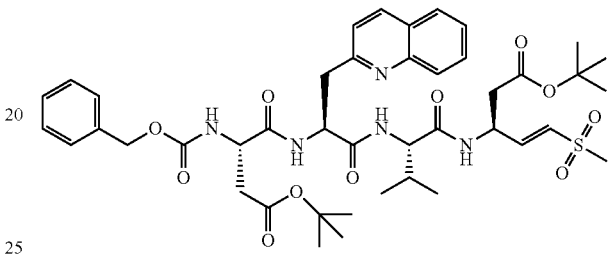

The Z-Asp(β-tert-Butyl)-Al(2'-quinolyl)-Val-OH (19 mg, 0.0306 mmol) is dissolved in a mix of dichloromethane and DMF (0.4 ml/0.14 ml). The mixture was allowed to reach −15/−20° C. before adding N-methyl morpholine (9 μl) followed 3 min latter with isobutyl chloroformate (9 μl). The mixture was stirred at −15° C. for 10 minutes. Next, Asp(β-tert-butyl)methyl vinyl sulfone tosyl salt (13.1 mg, 1 eq) was added in one shot, followed by N-methyl morpholine (9 μl). The mixture was stirred 35 minutes at −15/−20° C. and then diluted with 5 ml of dichloromethane and quenched with 1.5 ml of a saturated solution of sodium bicarbonate. After that, the organic layer was washed with sodium bicarbonate and dried over magnesium sulphate. The solvent was evaporated to dryness. The obtained residue was purified on silica gel (gradient: ethyl acetate/hexane: 5 to 100%) to afford 13.1 mg of Z-Asp(β-tert-Butyl)-Al(2'-quinolyl)-Val-Asp(β-tert-butyl)-methyl vinyl sulfone.

Example 22

Synthesis of Compound 55 (Z-Asp-Ala(2'-quinolyl)-Val-Aspmethyl Vinyl Sulfone)

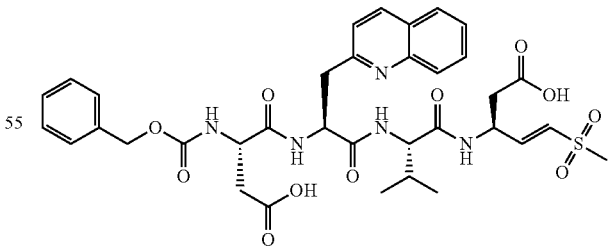

Z-Asp(β-tert-Butyl)-Phg-Val-Asp(β-tert-butyl)methyl vinyl sulfone (13.1 mg) was dissolved in dichloromethane (0.32 ml), followed by addition of trifluoroacetic acid (0.44 ml). The mixture was stirred at room temperature overnight (15 h). It was then quenched with diethyl ether (5 ml), then the solvent was removed under vacuum. The obtained residue was diluted again with ether and the process was repeated twice. The precipitate was washed with 2*1 ml of ether, dried to give 12 mg of the desired compound.

NMR $^1$H (CD$_3$OD, 400 MHz) δ: 8.68 (m, 1H); 8.17 (d, 1H, J=8.9 Hz); 8.1 (d, 1H, J=8.2 Hz); 7.93 (t, 1H, J=7.85 Hz); 7.78 (m, 2H); 7.34-7.29 (m, 5H); 6.88 (dd, 1H, J=15.20 and 4.75 Hz); 6.7 (d, 1H, J=15.20 Hz); 5.03-4.83 (m, 4H); 4.44 (t, 1H, J=6.45 Hz); 4.1 (d, 1H, J=7.15 Hz); 3.70 (m, 1H); 3.52 (m, 1H); 2.98 (s, 3H); 2.90-2.68 (m, 4H); 0.92 (d, 3H, J=6.9 Hz), 0.89 (d, 3H, J=6.7 Hz). LCMS (M-H$^+$)=738.3

Example 23

Synthesis of Compound 56 (Z-Asp(β-tert-Butyl)-Indanylglycine-Val-Asp(β-tert-Butyl)methyl Vinyl Sulfone)

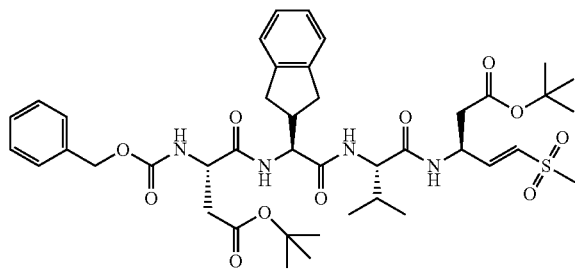 [SMILES: CC(C)[C@H](NC(=O)[C@@H](NC(=O)[C@H](CC(=O)OC(C)(C)C)NC(=O)OCc1ccccc1)C1Cc2ccccc2C1)C(=O)N[C@H](/C=C/S(C)(=O)=O)CC(=O)OC(C)(C)C]

The Z-Asp(β-tert-Butyl)-Indanylglycine-Val-OH (21 mg, 0.0353 mmol) is dissolved in a mix of dichloromethane and DMF (0.44 ml/0.15 ml). The mixture was allowed to reach −15/−20° C. before adding N-methyl morpholine (10 µl) followed by isobutyl chloroformate (9 µl). The mixture was stirred at −15° C. for 10 minutes. Next, Asp(β-tert-butyl) methyl vinyl sulfone tosyl salt (15 mg, 1 eq) was added in one shot, followed by N-methyl morpholine (10 µl). The mixture was stirred 35 minutes at −15/−20° C. and then diluted with 5 ml of dichloromethane and quenched with 1.5 ml of a saturated solution of sodium bicarbonate. After that, the organic layer was washed with sodium bicarbonate and dried over magnesium sulphate. The solvent was evaporated to dryness. The obtained residue was purified on silica gel (ethyl acetate/hexane: 40% then dichloromethane/methanol: 5 to 15%) to afford 10 mg of Z-Asp(β-tert-Butyl)-indanylglycine-Val-Asp (β-tert-butyl)-methyl vinyl sulfone.

Example 24

Synthesis of Compound 57
(Z-Asp-Indanylglycine-Val-Aspmethyl Vinyl Sulfone)

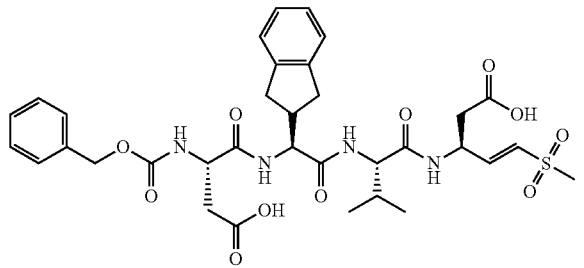 [SMILES: CC(C)[C@H](NC(=O)[C@@H](NC(=O)[C@H](CC(=O)O)NC(=O)OCc1ccccc1)C1Cc2ccccc2C1)C(=O)N[C@H](/C=C/S(C)(=O)=O)CC(=O)O]

Z-Asp(β-tert-Butyl)-Indanylglycine-Val-Asp(β-tert-butyl)-methyl vinyl sulfone (11 mg) was dissolved in dichloromethane (0.26 ml), followed by addition of trifluoroacetic acid (0.36 ml). The mixture was stirred at room temperature overnight (15 h). It was then quenched with diethyl ether (5 ml) and the solvent was removed under vacuum. The obtained residue was diluted again with ether and the process was repeated twice. The precipitate was washed with 2*1 ml of ether, dried to give 9 mg of the desired compound.

NMR $^1$H (DMSO, 400 MHz) δ: 12.35 (bs, 2H, 2*CO$_2$H); 8.21 (d, 1H, J=7.78 Hz); 8.06 (m, 1H); 7.89 (d, 1H, J=7.34 Hz); 7.61 (d, 1H, J=7.10 Hz); 7.34-7.31 (m, 5H); 7.17-6.95 (m, 4H); 6.75 (dd, 1H, J=15.33 Hz, J=4.8 Hz); 6.64 (d, 1H, J=15.58 Hz); 4.99 (s, 2H); 4.81 (m, 1H); 4.46-4.40 (m, 2H); 4.12 (t, 1H, J=6.28 Hz); 2.97 (s, 3H); 2.82-2.44 (m, 9H); 0.85 (t, 6H, J=5.95 Hz).

Example 25

Synthesis of Compound 58 (Z-Asp(β-tert-Butyl)-Glu (βtert-Butyl)-Val-Asp(β-tert-Butyl)methyl Vinyl Sulfone)

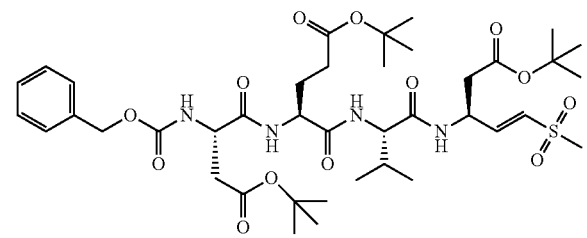 [SMILES: CC(C)[C@H](NC(=O)[C@H](CCC(=O)OC(C)(C)C)NC(=O)[C@H](CC(=O)OC(C)(C)C)NC(=O)OCc1ccccc1)C(=O)N[C@H](/C=C/S(C)(=O)=O)CC(=O)OC(C)(C)C]

The Z-Asp(β-tert-Butyl)-Glu(β-tert-Butyl)-Val-OH (18 mg, 0.029 mmol) is dissolved in a mix of dichloromethane and DMF (0.39 ml/0.13 ml). The mixture was allowed to reach −15/−20° C. before adding N-methyl morpholine (8 µl) followed 3 min latter with isobutyl chloroformate (7 µl). The mixture was stirred at −15° C. for 10 minutes. Next, Asp(β-tert-butyl)methyl vinyl sulfone tosyl salt (13 mg) was added in one shot, followed by N-methyl morpholine (8 µl). The mixture was stirred 35 minutes at −15/−20° C. and then diluted with 5 ml of dichloromethane and quenched with 1.5 ml of a saturated solution of sodium bicarbonate. After that, the organic layer was dried over magnesium sulphate. The solvent was evaporated to dryness. The obtained residue was purified on silica gel (ethyl acetate/hexane: 40% then dichloromethane/methanol: 5 to 15%) to afford 24 mg of the desired compound.

Example 26

Synthesis of Compound 59
(Z-Asp-Glu-Val-Aspmethyl Vinyl Sulfone)

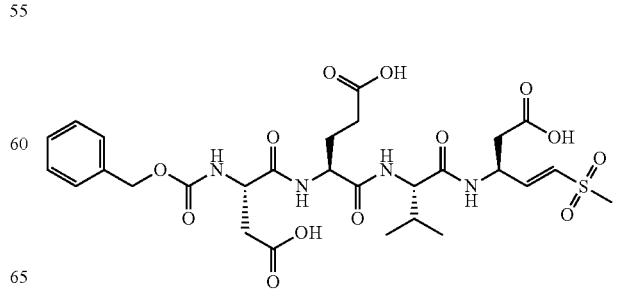

Z-Asp(β-tert-Butyl)-Glu(β-tert-Butyl)-Val-Asp(β-tert-butyl)-methyl vinyl sulfone (22.7 mg) was dissolved in dichloromethane (0.55 ml), followed by addition of trifluoroacetic acid (0.7 ml). The mixture was stirred at room temperature overnight (15 h). It was then quenched with diethyl ether (7 ml) and the solvent was removed under vacuum. The obtained residue was diluted again with ether (5 ml) and the process was repeated twice. The precipitate was washed with 2*1 ml of ether, dried to give 19 mg of the desired compound.

Example 27

Synthesis of Compound 60
Z-Val-Asp(β-tert-Butyl)methyl Vinyl Sulfone

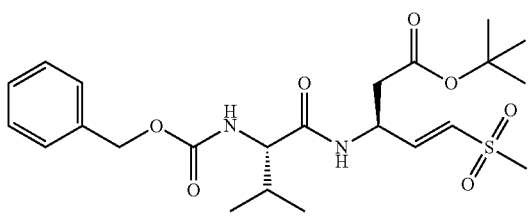 [SMILES: CC(C)[C@H](NC(=O)OCc1ccccc1)C(=O)N[C@H](/C=C/S(C)(=O)=O)CC(=O)OC(C)(C)C]

The Z-Val-OH (15 mg, 0.059 mmol) is dissolved in a mix of dichloromethane and DMF (0.5 ml/0.2 ml). The mixture was allowed to reach −15/−20° C. before adding N-methyl morpholine (10 μl) followed by isobutyl chloroformate (9 μl). The mixture was stirred at −15° C. for 10 minutes. Next, Asp(β-tert-butyl)methyl vinyl sulfone tosyl salt (25 mg, 1 eq) was added in one shot, followed by N-methyl morpholine (10 μl). The mixture was stirred 35 minutes at −15/−20° C. and then diluted with 5 ml of dichloromethane and quenched with 1.5 ml of a saturated solution of sodium bicarbonate. After that, the organic layer was dried over magnesium sulphate. The solvent was evaporated to dryness. The obtained residue was purified on silica gel (gradient: methanol/dichloromethane: 0 to 15%) to afford 24 mg of Z-Val-Asp-methyl vinyl sulfone.
NMR $^1$H (CD$_3$OD, 400 MHz) δ: 7.38-7.29 (m, 5H); 6.82 (m, 1H); 6.69 (m, 1H); 5.10 (m, 2H); 4.96 (m, 1H); 3.91 (m, 1H); 2.94 (s, 3H); 2.8-2.6 (m, 2H); 2.1-2.0 (m, 1H); 1.43 (s, 9H); 0.95 (t, 6H, J=6.7 Hz).

Example 28

Synthesis of Compound 61 (Z-Val-Asp-methyl Vinyl Sulfone)

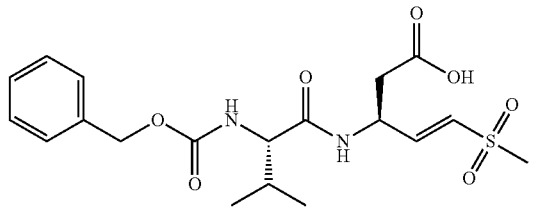 [SMILES: CC(C)[C@H](NC(=O)OCc1ccccc1)C(=O)N[C@H](/C=C/S(C)(=O)=O)CC(=O)O]

Z-Val-Asp(βtert-butyl)-methyl vinyl sulfone (25 mg) was dissolved in dichloromethane (0.6 ml), followed by addition of trifluoroacetic acid (0.45 ml). The mixture was stirred at room temperature overnight (15 h). It was then quenched with diethyl ether (7 ml), the solvent was removed under vacuum. The obtained residue was diluted again with ether and the process was repeated twice. The precipitate was washed with 2*1 ml of ether, dried to give 22 mg of the desired compound.
NMR $^1$H (CD$_3$OD, 400 MHz) δ: 7.38-7.27 (m, 5H); 6.86 (m, 1H); 6.68 (m, 1H); 5.11 (m, 2H); 5.03 (m, 1H); 3.92 (m, 1H); 2.94 (s, 3H); 2.88-2.59 (m, 2H); 2.09-2.01 (m, 1H); 0.95 (t, 6H, J=6.49 Hz).

Example 29

Synthesis of Compound 62 (Z-Asp(β-tert-Butyl)-Ala(2'-quinolyl)Val-Asp(β-tert-Butyl)phenyl Vinyl Sulfone)

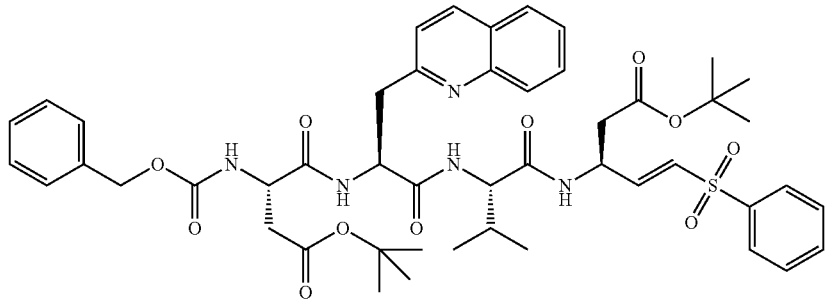 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(=O)(=O)c1ccccc1)CC(=O)OC(C)(C)C]

The Z-Asp(β-tert-Butyl)-Ala(2'-quinolyl)-Val-OH (19 mg, 0.0306 mmol) is dissolved in a mix of dichloromethane and DMF (0.39 ml/0.13 ml). The mixture was allowed to reach −15/−20° C. before adding N-methyl morpholine (8 μl) followed by isobutyl chloroformate (7 μl). The mixture was stirred at −15° C. for 10 minutes. Next, Asp(β-tert-butyl) phenyl vinyl sulfone tosyl salt (11 mg) was added in one shot, followed by N-methyl morpholine (8 μl). The mixture was stirred 35 minutes at −15/−20° C. and then diluted with 5 ml of dichloromethane and quenched with 1.5 ml of a saturated solution of sodium bicarbonate. After that, the organic layer was dried over magnesium sulphate. The solvent was evaporated to dryness. The obtained residue was purified on silica gel (gradient: ethyl acetate/hexane: 5 to 100%) to afford 13.7 mg of the desired compound.

Example 30

Synthesis of Compound 63
(Z-Asp-Ala(2'-quinolyl)-Val-Aspphenyl Vinyl Sulfone)

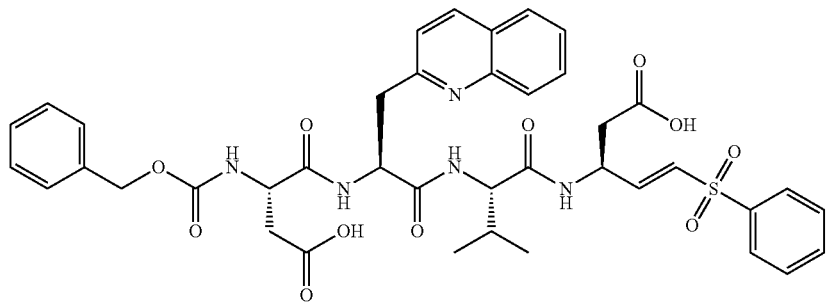 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(=O)(=O)c1ccccc1)CC(=O)O]

Z-Asp(β-tert-Butyl)-Ala(2'-quinolyl)-Val-Asp(β-tert-Butyl)-phenyl vinyl sulfone (13.7 mg) was dissolved in dichloromethane (0.3 ml), followed by addition of trifluoroacetic acid (0.4 ml). The mixture was stirred at room temperature overnight (15 h). It was then quenched with diethyl ether (5 ml), the solvent was removed under vacuum. The obtained residue was diluted again with ether and the process was repeated twice. The precipitate was washed with 2*1 ml of ether, dried to give 10 mg of the desired compound.

NMR $^1$H (CD$_3$OD, 400 MHz) δ: 8.58 (m, 1H); 8.11 (d, 1H, J=8.75 Hz); 8.04 (d, 1H, J=7.99 Hz); 7.85 (d, 3H, J=7.25 Hz); 7.72-7.6 (m, 3H); 7.56 (t, 2H, J=7.83 Hz); 7.31-7.28 (m, 5H); 6.93 (dd, 1H, J=15.24 Hz, J=5.15 Hz); 6.65 (d, 1H, J=14.87 Hz); 4.97-4.80 (m, 4H); 4.40 (m, 1H); 4.21-4.02 (m, 1H); 3.63-3.50 (m, 1H); 3.47-3.44 (m, 1H); 2.82-2.6 (m, 4H); 2.15-1.98 (m, 1H); 0.81 (t, 6H, J=6.38 Hz). LCMS (M-H+)=800.5

Example 31

Synthesis of Compound 64 (Z-Asp(β-tert-Butyl)-Ala(2'-quinolyl)-Val-Asp(β-tert-Butyl)phenoxy Vinyl Sulfone)

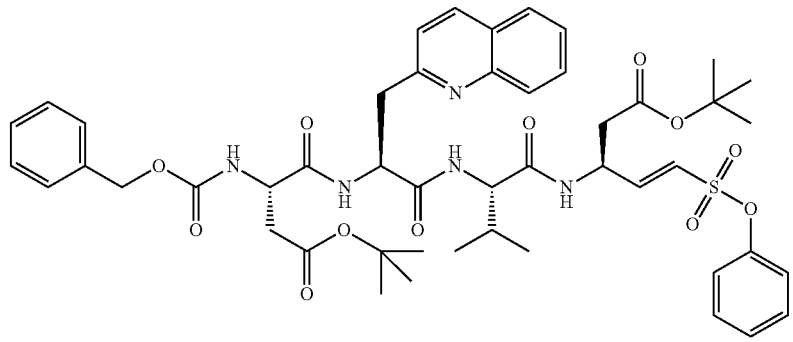 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(=O)(=O)Oc1ccccc1)CC(=O)OC(C)(C)C]

The Z-Asp(β-tert-Butyl)-Al(2'-quinolyl)-Val-OH (10 mg, 0.016 mmol) is dissolved in a mix of dichloromethane and DMF (0.24 ml/0.080 ml). The mixture was allowed to reach −15/−20° C. before adding N-methyl morpholine (5 μl) followed 3 min latter with isobutyl chloroformate (5 μl). The mixture was stirred at −15° C. for 10 minutes. Next, Asp(β-tert-butyl)phenoxy vinyl sulfone tosyl salt (11.3 mg, 0.023 mmol) was added in one shot, the vial was washed with DMF (0.04 ml), followed by the addition of N-methyl morpholine (5 μl). The mixture was stirred 35 minutes at −15/−20° C. and then diluted with 5 ml of dichloromethane and quenched with 1.5 ml of a saturated solution of sodium bicarbonate. After that, the organic layer was dried over magnesium sulphate. The solvent was evaporated to dryness. The obtained residue was purified on silica gel (gradient: ethyl acetate/hexane: 12 to 100%) to afford 4.7 mg of the desired compound.

Example 32

Synthesis if Compound 65
(Z-Asp-Ala(2'-quinolyl)-Val-Aspphenoxy Vinyl Sulfone)

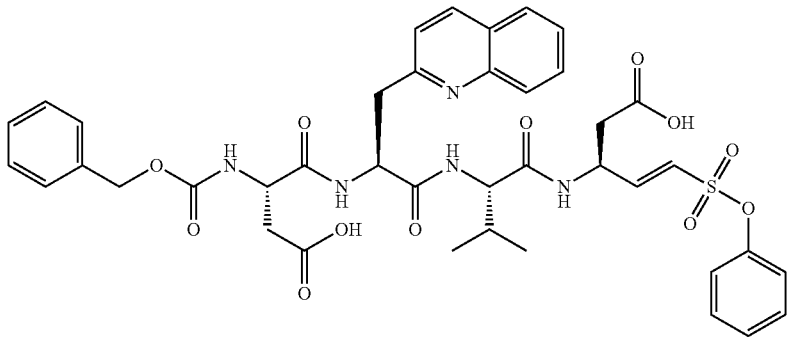 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(=O)(=O)Oc1ccccc1)CC(=O)O]

Z-Asp(β-tert-Butyl)-Ala(2'-quinolyl)-Val-Asp(β-tert-Butyl)-phenoxy vinyl sulfone (4.7 mg) was dissolved in dichloromethane (0.15 ml), followed by addition of trifluoroacetic acid (0.2 ml). The mixture was stirred at room temperature overnight (15 h). It was then quenched with diethyl ether (5 ml) and the solvent was removed under vacuum. The obtained residue was diluted again with ether (5 ml) and the process was repeated twice. The precipitate was washed with 2*1 ml of ether, dried to give 4 mg of the desired compound.

NMR $^1$H (CD$_3$OD, 400 MHz) δ: 8.25 (d, 1H, J=7.9 Hz); 8.05 (d, 1H, J=8.66 Hz); 7.88 (d, 1H, J=8.25 Hz); 7.63 (d, 1H, J=6.82 Hz); 7.53 (t, 1H, J=7.46 Hz); 7.45-7.33 (m, 3H); 7.33-7.20 (m, 8H); 6.75 (dd, 1H, J=15.33 Hz, J=4.33 Hz); 6.65 (d, 1H, J=15.55 Hz); 5.1-4.8 (m, 4H); 4.49 (t, 1H, J=6.17 Hz); 4.06 (d, 1H, J=6.45 Hz); 3.6-3.4 (m, 2H); 2.9 (dd, 1H, J=17.02 Hz, J=5.39 Hz); 2.73 (dd, 1H, J=16.57 Hz, J=6.53 Hz); 2.59 (d, 2H, J=6.97 Hz); 2.08 (m, 1H); 0.75 (m, 6H).

Example 33

Synthesis of Compound 66 (Z-Asp(β-tert-Butyl)-Ala(2'-quinolyl)-Val-Asp(β-tert-Butyl)morpholine Vinyl Sulfone)

Z-Asp(β-tert-Butyl)-Ala(2'-quinolyl)-Val-OH (13 mg, 0.0209 mmol) is dissolved in a mix of dichloromethane and DMF (0.28/0.094 ml). The mixture was allowed to reach −15/−20° C. before adding N-methyl morpholine (6 μl) followed by isobutyl chloroformate (5 μl). The mixture was stirred at −15° C. for 10 minutes. Next, Asp(β-tert-butyl) morpholine vinyl sulfone tosyl salt (10.2 mg, 1 eq) was added in one shot, followed by N-methyl morpholine (6 μl). The mixture was stirred 35 minutes at −15/−20° C. and then diluted with 5 ml of dichloromethane and quenched with 1.5 ml of a saturated solution of sodium bicarbonate. After that, the organic layer was washed with sodium bicarbonate and dried over magnesium sulphate. The solvent was evaporated to dryness. The obtained residue was purified on silica gel (gradient: ethyl acetate/hexane: 12 to 100%) to afford 10 mg of the desired compound.

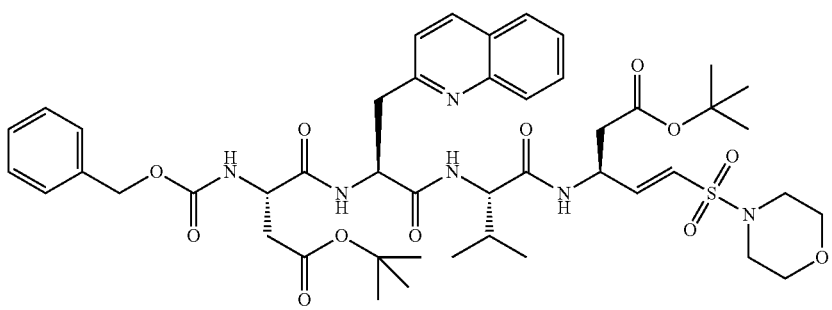 [SMILES: CC(C)[C@H](NC(=O)[C@H](Cc1ccc2ccccc2n1)NC(=O)[C@H](CC(=O)OC(C)(C)C)NC(=O)OCc1ccccc1)C(=O)N[C@H](/C=C/S(=O)(=O)N1CCOCC1)CC(=O)OC(C)(C)C]

Example 34

Synthesis of Compound 67
(Z-Asp-Ala(2'-quinolyl)-Val-Aspmorpholine Vinyl Sulfone)

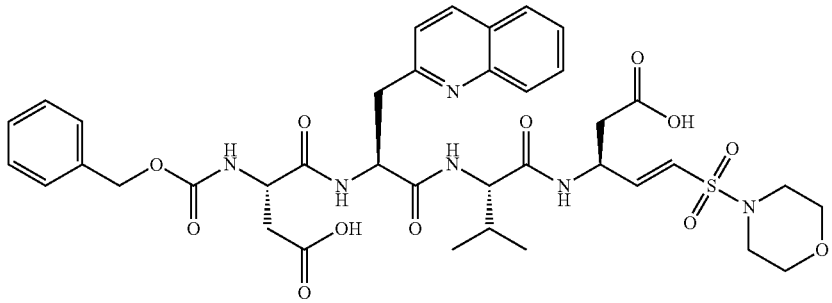 [SMILES: CC(C)[C@H](NC(=O)[C@H](Cc1ccc2ccccc2n1)NC(=O)[C@H](CC(=O)O)NC(=O)OCc1ccccc1)C(=O)N[C@H](/C=C/S(=O)(=O)N1CCOCC1)CC(=O)O]

Z-Asp(β-tert-Butyl)-Al(2'-quinolyl)-Val-Asp(β-tert-Butyl)-morpholine vinyl sulfone (4.7 mg) was dissolved in dichloromethane (0.15 ml), followed by addition of trifluoroacetic acid (0.2 ml). The mixture was stirred at room temperature overnight (15 h). It was then quenched with diethyl ether (5 ml) and the solvent was removed under vacuum. The obtained residue was diluted again with ether and the process was repeated twice. The precipitate was washed with 2*1 ml of ether, dried to give 4 mg of the desired compound.

NMR $^1$H (CD$_3$OD, 400 MHz) δ: 8.39 (s, 1H); 8.08 (d, 1H, J=8.56 Hz); 7.94 (d, 1H, J=8.29 Hz); 7.74 (m, 1H); 7.66-7.55 (m, 2H); 7.31-7.29 (m, 5H); 6.69 (dd, 1H, J=14.98 Hz, J=4.59 Hz); 6.41 (d, 1H, J=14.86 Hz); 5.0-4.7 (m, 4H); 4.45 (m, 1H); 4.05 (d, 1H, J=6.65 Hz); 3.70-3.64 (m, 4H); 3.55-3.44 (m, 2H); 3.16-3.08 (m, 4H); 2.89-2.70 (m, 4H); 2.17-2.07 (m, 1H); 0.85-0.81 (m, 6H). LCMS (M-H+)=809.6

Example 35

Synthesis of Compound 68
(Z-Asp-Indanylglycine-Val-Aspisopropyl Vinyl Sulfone)

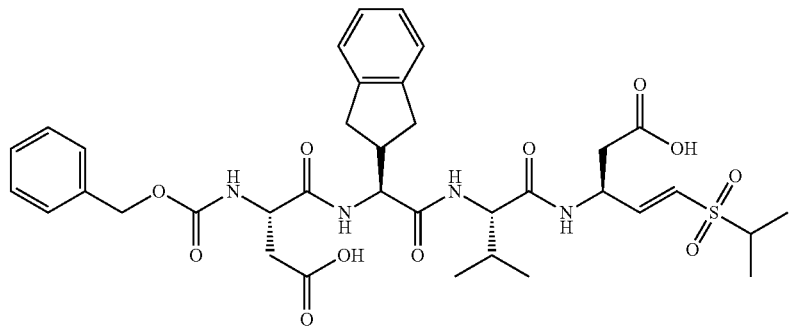 [SMILES: CC(C)[C@H](NC(=O)[C@@H](NC(=O)[C@H](CC(=O)O)NC(=O)OCc1ccccc1)C1Cc2ccccc2C1)C(=O)N[C@H](/C=C/S(=O)(=O)C(C)C)CC(=O)O]

This compound was synthesized from Asp(β-tert-butyl) isopropyl vinyl sulfone tosyl salt (43) and Cbz-Asp(O-tBu) Indanylglycine-Val-OH (12) via anhydride mixte method as for Z-Asp-Indanylglycine-Val-Aspmethyl vinyl sulfone (57).

Example 36

Synthesis of Compound 69
(Z-Asp-Phg-Val-Asp-phenyl Vinylsulfone)

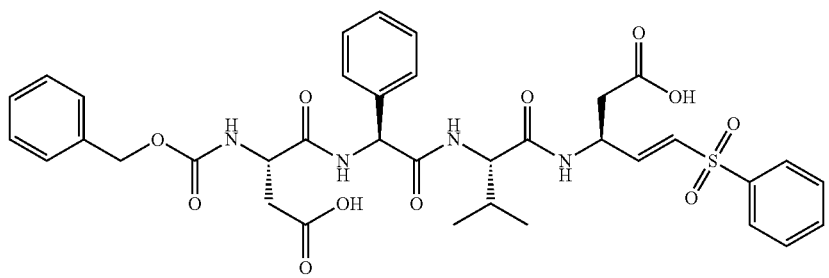 [SMILES: CC(C)[C@H](NC(=O)[C@@H](NC(=O)[C@H](CC(=O)O)NC(=O)OCc1ccccc1)c1ccccc1)C(=O)N[C@H](/C=C/S(=O)(=O)c1ccccc1)CC(=O)O]

This compound was synthesized from Z-Asp(β-tert-Butyl)-Phg-Val-OH (16) and Asp(OtBu)-Vinyl phenyl sulfone tosyl salt (37) via anhydride mixte method as for Z-Asp-Ala (2'-quinolyl)-Val-Aspphenyl vinyl sulfone (63).

Example 37

Synthesis of Compound 70 (Z-Asp-(D,L Ala(2'-quinolyl))-Val-Aspphenyl Vinylsulfone)

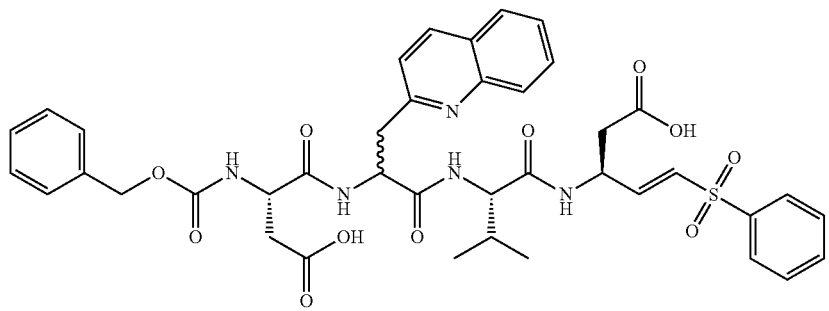 [SMILES: CC(C)[C@H](NC(=O)C(Cc1ccc2ccccc2n1)NC(=O)[C@H](CC(=O)O)NC(=O)OCc1ccccc1)C(=O)N[C@H](/C=C/S(=O)(=O)c1ccccc1)CC(=O)O]

This compound was synthesized as the corresponding Z-Asp-Ala(2'-quinolyl)-Val-Asp-phenyl vinyl sulfone (63).

Example 38

Synthesis of Compound 71 (Z-Asp-(D,L Ala(2'-quinolyl))-Val-Aspmethyl Vinylsulfone)

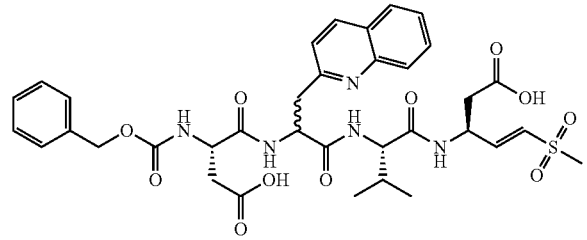 [SMILES: CC(C)[C@H](NC(=O)C(Cc1ccc2ccccc2n1)NC(=O)[C@H](CC(=O)O)NC(=O)OCc1ccccc1)C(=O)N[C@H](/C=C/S(C)(=O)=O)CC(=O)O]

This compound was synthesized as the corresponding Z-Asp-Ala(2'-quinolyl)-Val-Aspmethyl vinyl sulfone (55).

Example 39

Synthesis of Compound 76
(Z-Asp-Tyr-Val-Aspmethyl Vinyl Sulfone)

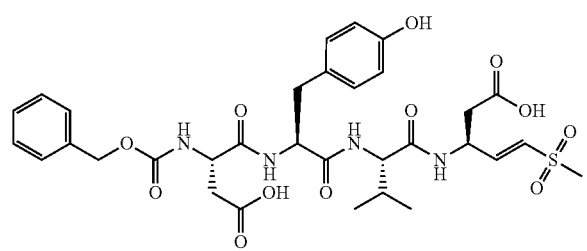 [SMILES: CC(C)[C@H](NC(=O)[C@H](Cc1ccc(O)cc1)NC(=O)[C@H](CC(=O)O)NC(=O)OCc1ccccc1)C(=O)N[C@H](/C=C/S(C)(=O)=O)CC(=O)O]

This compound was synthesized from Z-Asp-Tyr(OtBu)-Val-OH (75) and Asp(OtBu)-Vinyl methy sulfone tosyl salt (33) via anhydride mixte method as for Z-Asp-Phg-Val-Aspmethyl vinyl sulfone (53).

Z-Asp-Tyr(OtBu)-Val-OH was synthesized as Cbz-Asp(O-tBu)-Glu(O-tBu)-Val-OH (20).

Example 40

Synthesis of Compound 82
(Z-Tyr-Glu-Val-Aspmethyl Vinyl Sulfone)

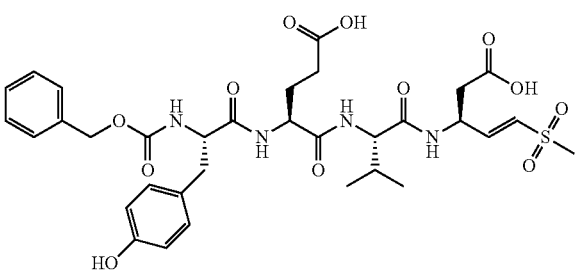 [SMILES: CC(C)[C@H](NC(=O)[C@H](CCC(=O)O)NC(=O)[C@H](Cc1ccc(O)cc1)NC(=O)OCc1ccccc1)C(=O)N[C@H](/C=C/S(C)(=O)=O)CC(=O)O]

This compound was synthesized from Z-Tyr(OtBu)-Glu(OtBu)-Val-OH (80) and Asp(OtBu)-Vinyl methy sulfone tosyl salt (33) via anhydride mixte method as for Z-Asp-Phg-Val-Aspmethyl vinyl sulfone (53).

Z-Tyr(OtBu)-Glu(OtBu)-Val-OH (80) was synthesized as Cbz-Asp(O-tBu)-Glu(O-tBu)-Val-OH (20).

Example 41

Synthesis of Compound 88
(Z-Asp-Trp-Val-Aspmethyl Vinyl Sulfone)

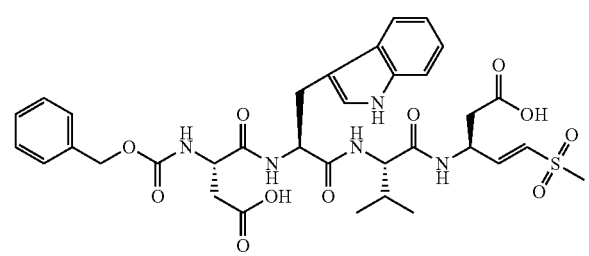 [SMILES: CC(C)[C@H](NC(=O)[C@H](Cc1c[nH]c2ccccc12)NC(=O)[C@H](CC(=O)O)NC(=O)OCc1ccccc1)C(=O)N[C@H](/C=C/S(C)(=O)=O)CC(=O)O]

This compound was synthesized from Z-Asp(OtBu)-Trp-Val-OH (86) and Asp(OtBu)-Vinyl methy sulfone tosyl salt (33) via anhydride mixte method as for Z-Asp-Phg-Val-Asp-methyl vinyl sulfone (53).

Example 42

Synthesis of Compound 85
(Z-Asp-Ala(2'-pyridyl)-Val-Aspmethyl Vinylsulfone)

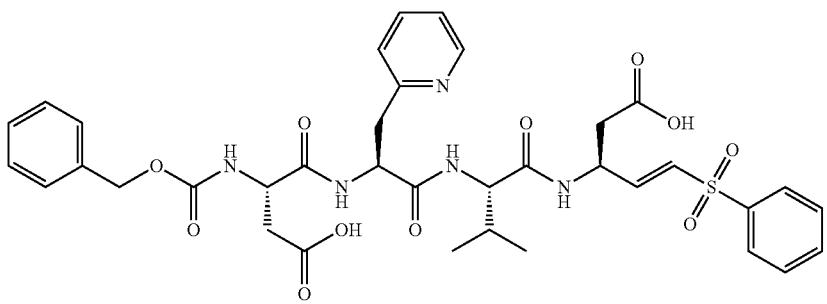 [SMILES: CC(C)[C@H](NC(=O)[C@H](Cc1ccccn1)NC(=O)[C@H](CC(=O)O)NC(=O)OCc1ccccc1)C(=O)N[C@H](/C=C/S(=O)(=O)c1ccccc1)CC(=O)O]

This compound was synthesized from Z-Asp(OtBu)-Ala(2'-pyridyl)-Val-OH (83) and Asp(OtBu)-Vinyl phenyl sulfone tosyl salt (37) via anhydride mixte method as for Z-Asp-Ala(2'-quinolyl)-Val-Aspphenyl vinyl sulfone (63).

Example 43

Synthesis of Compound 98 (2-Quinaldic Acid-Asp-methyl Vinyl Sulfone)

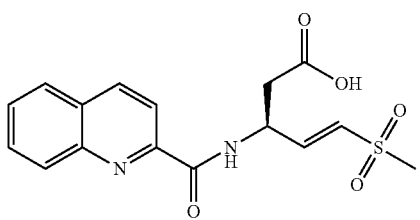 [SMILES: CS(=O)(=O)/C=C/[C@H](CC(=O)O)NC(=O)c1ccc2ccccc2n1]

2-Quinaldic Acid-Asp(β-tert-Butyl)methyl Vinyl Sulfone

The Quinaldic acid (5 mg, 0.028 mmol) is dissolved in a mix of THF and DMF (0.4 ml/0.1 ml). The mixture was allowed to reach −15/−20° C. before adding N-methyl morpholine (8 μl) followed 3 min latter with isobutyl chloroformate (6 μl). The mixture was stirred at −15° C. for 10 minutes.

Next, Asp (β-tert-butyl)methyl vinyl sulfone tosyl salt (12 mg) was added in one shot, followed by N-methyl morpholine (8 μl). The mixture was stirred 35 minutes at −15/−20° C. and then diluted with 5 ml of dichloromethane and quenched with 1.5 ml of a saturated solution of sodium bicarbonate. The organic layer was dried over magnesium sulphate. The solvent was evaporated to dryness. The obtained residue was purified on silica gel (ethyl acetate/hexane: 40%, then dichloromethane/methanol: 5 to 15%) to afford 9.5 mg of the desired compound.

b) 2-Quinaldic Acid-Aspmethyl Vinyl Sulfone

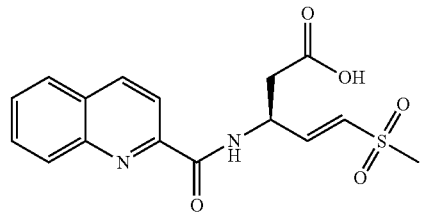

2-Quinaldic acid-Asp(β-tert-Butyl)-methyl vinyl sulfone (5.7 mg) was dissolved in dichloromethane (0.14 ml), followed by addition of trifluoroacetic acid (0.18 ml). The mixture was stirred at room temperature overnight (15 h). It was then quenched with diethyl ether (7 ml) and the solvent was removed under vacuum. The obtained residue was diluted again with ether (5 ml) and the process was repeated twice. The precipitate was washed with 2*1 ml of ether, dried to give 4 mg of the desired compound.

NMR $^1$H (DMSO-$d_6$, 400 MHz) δ: 9.24 (d, 1H, J=8.8 Hz); 8.54 (d, 1H, J=8.0 Hz); 8.11 (m, 2H); 8.05 (d, 1H, J=8.0 Hz); 7.85 (t, 1H, J=8 Hz); 7.71 (m, 1H); 6.84-6.76 (m, 2H); 5.17 (m, 1H); 2.95 (s, 3H); 2.86-2.8 (m, 2H).

Example 44

Syntheses of Compound 90:
Asp(β-Methyl)achlorovinyl Methyl Vinyl Sulfone Tosyl Salt

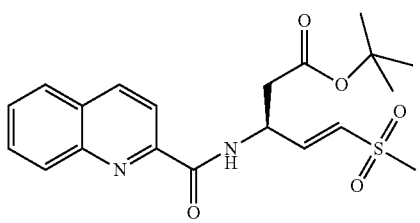 [SMILES: CC(C)(C)OC(=O)C[C@@H](/C=C/S(C)(=O)=O)NC(=O)c1ccc2ccccc2n1]

a) Boc-Asp(β-Methyl)achlorovinyl Methyl Vinyl Sulfone

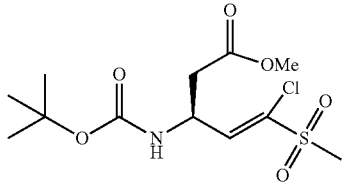 [SMILES: COC(=O)C[C@@H](/C=C(\Cl)S(C)(=O)=O)NC(=O)OC(C)(C)C]

Diethyl chloro(methylsulfone)methylphosphonate (0.43 g, 1.04 eq) was solvated in THF (6.6 mL) and the solution was allowed to reach −78° C. NaH 95% (0.048 g, 1.1 eq), which had been washed with Ether anhydrous (1.2 mL), was then added in suspension in THF (2 mL). The vial containing NaH in suspension was washed with THF (0.5 mL) and added to the solution. The mixture was stirred for 25 min, then Boc-Asp(β-Methyl)-H (0.37 g, 1.01 mmol) solvated in THF (4 mL) was added dropwise to the solution over 1 min. The vial was rinsed with THF (2*0.4 ml) and added to the reaction mixture. After 3 h of stirring, the solution was quenched with a solution of ammonium chloride saturated (5 mL) and extracted with EtOAc (30 mL). The organic layer was washed with brine, dried over MgSO$_4$, filtered and concentrated. The residue was purified on silica using a gradient of ethyl acetate/hexane (0 to 40%) to elute first the cis product and then the trans product (121 mg).

NMR $^1$H (CDCl$_3$, 400 MHz) δ: 7.13 (d, 1H, J=8.02 Hz); 5.51 (m, 1H); 4.87 (m, 1H); 3.72 (s, 3H); 3.04 (s, 3H); 2.74 (m, 2H); 1.44 (s, 9H).

b) Asp(β-Methyl)achlorovinyl Methyl Vinyl Sulfone Tosyl Salt

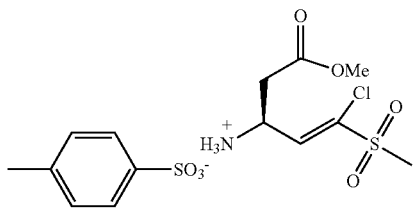

Boc-Asp(β-Methyl)achlorovinyl methyl vinyl sulfone (0.121 g, 0.354 mmol) was solvated in CH$_2$Cl$_2$ (0.44 mL) followed by the addition of Et$_2$O (0.44 mL). p-Toluene sulfonic Acid monohydrate (0.07 g, 1.04 eq) was added in one shot. After 15 hours of stirring at room temperature, it was then diluted with Ether (2 mL) and filtered off. The while solid was then dried over vacuum, 0.105 g of the desired compound was obtained. NMR $^1$H (DMSO, 400 MHz) δ: 8.3 (bs, 3H, NH$_3$); 7.46 (d, 2H, J=7.63 Hz); 7.11 (d, 2H, J=8.02 Hz); 7.05 (d, 1H, J=9.39 Hz); 4.4 (s, 1H); 3.65 (s, 3H); 3.23 (s, 3H); 2.92 (m, 2H); 2.28 (s, 3H).

Example 45

Synthesis of Compound 101 (Z-Asp(β-methyl)-phenylglycine-Val-Asp(β-methyl)methyl Vinyl Sulfone)

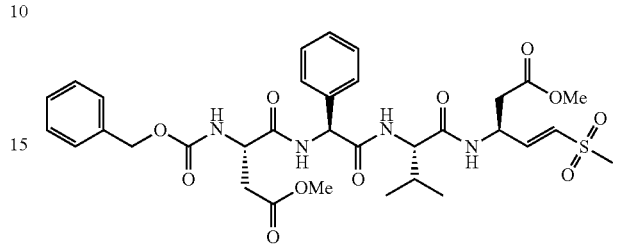

a) Cbz-Asp(β-methyl)-phenylglycine-Val-OAllyl

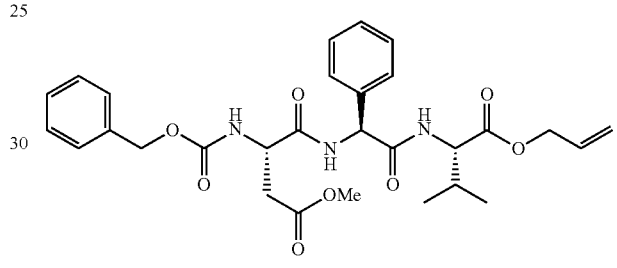

Phg-Val-OAllyl (0.737 g, 0.214 mmol) and Z-L-Asp(β-methyl)-OH (0.81 g, 1.1 mmol) were solvated in CH$_2$Cl$_2$ (5 mL) followed by addition of DMAP (11.6 mg, 0.13 eq), 4-methylmorpholine (0.85 mL, 1.16 eq), then EDC (0.818 g, 1.12 eq). The mixture was stirred for 2 hours at RT. Then it was extracted using CH$_2$Cl$_2$/water. The organic layer was dried over MgSO$_4$, concentrated and purified on silica using a gradient of EtOAc/Hexane (0 to 80%) to get 0.39 g of the desired compound.

NMR $^1$H (CD$_3$OD, 400 MHz) δ: 7.43 (m, 2H); 7.42-7.26 (m, 8H); 5.86-5.76 (m, 1H); 5.26-5.09 (m, 4H); 4.6 (m, 1H); 4.58-4.52 (m, 2H); 4.34 (d, 1H, J=6.26 Hz); 3.64 (s, 3H); 2.87 (dd, 1H, J=16.62 Hz, J=5.87 Hz); 2.70 (dd, 1H, J=16.6 Hz, J=7.63 Hz); 2.17 (m, 1H); 0.96 (T, 6H, J=6.7 Hz).

b) Cbz-Asp(β-methyl)Phenylglycine-Val-OH

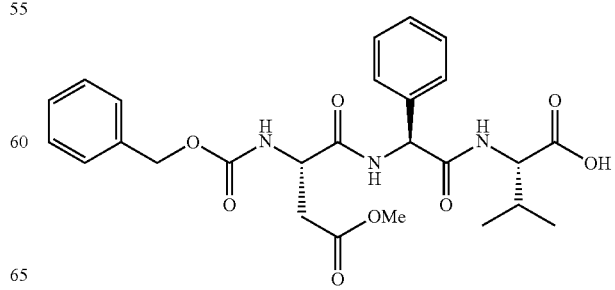

Z-Asp(β-methyl)-phenylglycine-Val-(OAllyl) (0.703 g, 0.89 mmol) was dissolved in THF (15 mL) and rotary evaporated to dryness, the sample was then redissolved in THF (20 mL) and vacuum aspirated (3*1 min of aspiration), followed by replacement of the atmosphere with Argon. Pd(PPh₃)₄ (0.077 g, 0.11 eq) was added in one shot, the flask was then evacued with Argon. Morpholine (0.249 mL, 4.07 eq) was added and the flask covered with a tin foil. The mixture was kept under stirring for 45 hours. The sample was evaporated to dryness, then coevaporated with dichloromethane (2*10 ml) and the obtained residue was subjected to purification on $C_{18}$ using a gradient MeOH/solution of $H_2O$ at pH=3.5 (10 to 100%) to get 141 mg of the desired compound.

NMR ¹H (CD₃OD, 400 MHz) δ 7.45-7.43 (m, 2H); 7.34-7.26 (m, 8H); 5.53 (m, 1H); 5.08 (m, 2H); 4.65-4.61 (m, 1H); 4.18 (d, 1H, J=5.0 Hz); 3.64 (s, 3H); 2.9-2.62 (m, 2H); 2.17 (m, 1H); 0.93 (t, 6H, J=7.82 Hz).

c) Z-Asp(β-methyl)-phenylglycine-Val-Asp(β-methyl)methyl Vinyl Sulfone)

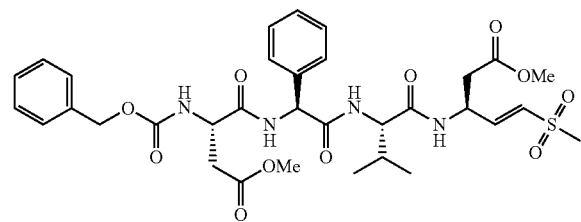 [SMILES: COC(=O)C[C@@H](/C=C/S(C)(=O)=O)NC(=O)[C@@H](NC(=O)[C@@H](NC(=O)[C@H](CC(=O)OC)NC(=O)OCc1ccccc1)c1ccccc1)C(C)C]

The Z-Asp(β-methyl)-phenylglycine-Val-OH (28.5 mg, 0.055 mmol) is dissolved in a mix of THF and DMF (0.8 ml/0.18 ml). The mixture was allowed to reach −15/−20° C. (ice/MeOH bath) before adding N-methyl morpholine (13 μl) followed 3 min latter with isobutyl chloroformate (11 μl). The mixture was stirred at −15° C. for 10 minutes. Next, Asp(β-methyl)methyl vinyl sulfone tosyl salt (20.6 mg, 1 eq) was added in one shot, followed by addition of N-methyl morpholine (13 μl). The mixture was stirred for 35 minutes at −15/−20° C., then diluted with 7 ml of dichloromethane and quenched with 1.5 ml of a saturated solution of sodium bicarbonate. The organic layer was dried over magnesium sulphate and the solvent was evaporated to dryness. The obtained residue was purified on silica gel (ethyl acetate/hexane: 40% then dichloromethane/methanol: 0 to 14%) to afford 29 mg of Z-Asp(β-methyl)-phenylglycine-Val-Asp(β-methyl)methyl vinyl sulfone.

NMR ¹H (DMSO, 400 MHz) δ: 8.8-8.4 (m, 3*NH); 7.43-7.38 (m, 1*NH); 7.8-7.4 (m, 10H); 6.67 (dd, 1H, J=15.23 Hz, J=4.5 Hz); 6.6 (dd, 1H); 5.53 (d, 1H, J=7.63); 5.01 (s, 2H); 4.77-4.75 (m, 1H); 4.48-4.46 (m, 1H); 4.13-4.09 (m, 1H); 3.55 (s, 3H); 3.45 (s, 3H); 2.98 (s, 3H); 2.8-2.6 (m, 4H); 1.98 (m, 1H); 0.86-0.81 (m, 6H).

Example 46

Syntheses of Compound 104 Z-Asp(β-methyl)-phenylglycine-Val-Asp(β-methyl)achlorovinyl Methylsulfone

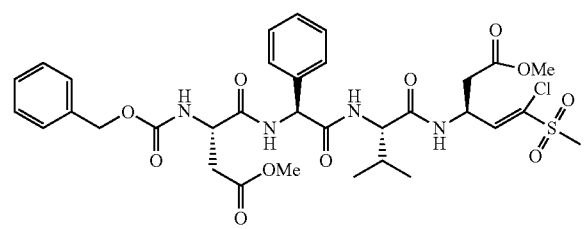 [SMILES: COC(=O)C[C@@H](/C=C(\Cl)S(C)(=O)=O)NC(=O)[C@@H](NC(=O)[C@@H](NC(=O)[C@H](CC(=O)OC)NC(=O)OCc1ccccc1)c1ccccc1)C(C)C]

The Z-Asp(β-methyl)-phenylglycine-Val-OH (20 mg, 0.039 mmol) is dissolved in a mix of THF and DMF (0.58 ml/0.13 ml). The mixture was allowed to reach −15/−20° C. (ice/MeOH bath) before adding N-methyl morpholine (11 μl) followed 3 min latter with isobutyl chloroformate (9 μl). The mixture was stirred at −15° C. for 10 minutes. Next, Asp(β-methyl))achlorovinyl methylsulfone tosyl salt (15 mg, 1 eq) was added in one shot, followed by addition of N-methyl morpholine (11 μl). The mixture was stirred for 30 minutes at −15/−20° C., then diluted with 7 ml of dichloromethane and quenched with 1.5 ml of water. The organic layer was dried over magnesium sulphate and the solvent was evaporated to dryness. The obtained residue was purified on silica gel (ethyl acetate/hexane: 40% then dichloromethane/methanol: 0 to 14%) to afford 16.7 mg of desired compound.

NMR ¹H (DMSO-d₆, 400 MHz) δ: 8.34-7.6 (m, NH); 7.34-7.20 (m, 10H); 6.86 (d, 1H, J=8.8 Hz); 5.5 (m, 1H); 4.98 (m, 2H); 4.8 (m, 1H); 4.42 (m, 1H); 4.02 (m, 1H); 3.52 (s, 3H); 3.48 (s, 3H); 3.08 (s, 3H); 2.76-2.42 (m, 4H); 1.84 (m, 1H); 0.76 (m, 6H).

Example 47

Syntheses of Compound 105: Z-Asp(β-methyl)-indanylglycine-Val-Asp(β-methyl)achlorovinyl Methylsulfone

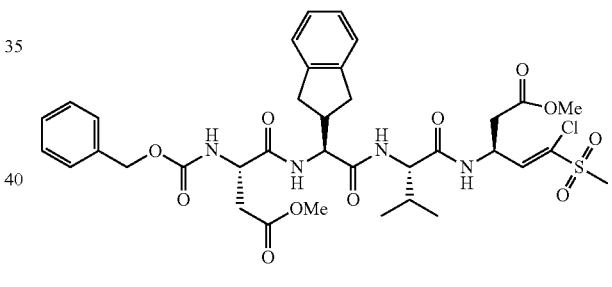

The Z-Asp(β-methyl)-Indanylglycine-Val-OH (20 mg, 0.036 mmol) is dissolved in a mix of THF and DMF (0.54 ml/0.16 ml). The mixture was allowed to reach −15/−20° C. (ice/MeOH bath) before adding N-methyl morpholine (10 μl) followed 3 min latter with isobutyl chloroformate (8 μl). The mixture was stirred at −15° C. for 10 minutes. Next, Asp(β-methyl)) achlorovinyl methylsulfone tosyl salt (14 mg, 1 eq) was added in one shot, followed by addition of N-methyl morpholine (10 μl). The mixture was stirred for 30 minutes at −15/−20° C., then diluted with 7 ml of dichloromethane and quenched with 1.5 ml of water. The organic layer was dried over magnesium sulphate and the solvent was evaporated to dryness. The obtained residue was purified on silica gel (ethyl acetate/hexane: 40% then dichloromethane/methanol: 0 to 14%) to afford 17 mg of desired compound.

NMR ¹H (DMSO-d₆, 400 MHz) δ: 8.41-7.6 (m, NH); 7.33-7.0 (m, 9H); 6.93 (d, 1H, J=8.4 Hz); 5.0-4.8 (m, 3H); 4.4

(m, 2H); 4.0 (m, 1H); 3.53 (s, 3H); 3.51 (s, 3H); 3.10 (s, 3H); 2.8-2.5 (m, 9H); 1.84 (m, 1H); 0.77 (m, 6H).

Example 48

Synthesis of Compound 111 (Z-Asp-3-(1-naphtyl)-L-alanine-Val-Asp Methyl Vinyl Sulfone)

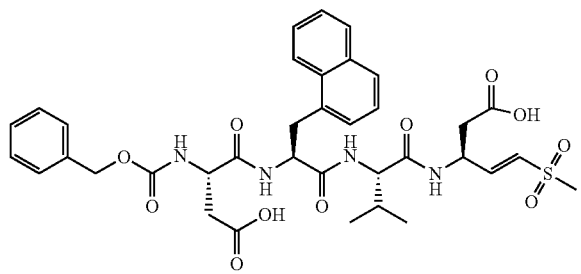 [SMILES: CC(C)[C@H](NC(=O)[C@H](Cc1cccc2ccccc12)NC(=O)[C@H](CC(=O)O)NC(=O)OCc1ccccc1)C(=O)N[C@H](/C=C/S(C)(=O)=O)CC(=O)O]

a) Fmoc-3-(1-naphtyl)-L-alanine-Val-OAllyl

Fmoc-3-(1-naphtyl)-L-alanine-OH (0.515 g, 1.01 eq) was solvated in CH$_2$Cl$_2$ (1.5 mL) and DMF (3 ml) followed by addition of L-Val-allyl ester toluene-4-sulfonate (0.382 g, 1.162 mmol), DMAP (14.51 mg, 0.12 eq); 4-methylmorpholine (0.135 mL, 1.06 eq), and finally EDC (0.224 g, 1.01 eq). The EDC vial was washed with CH$_2$Cl$_2$ (0.5 mL) and added to the reaction mixture. After 2 hours of stirring, the reaction mixture was extracted with CH$_2$Cl$_2$ (20 mL)/brine (5 mL). The organic layer was dried over MgSO$_4$, filtered off and concentrated.

b) 3-(1-naphtyl)-L-alanine-Val-OAllyl

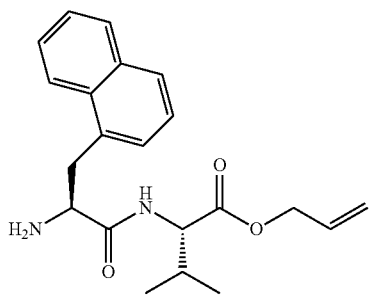 [SMILES: C=CCOC(=O)[C@@H](NC(=O)[C@@H](N)Cc1cccc2ccccc12)C(C)C]

Fmoc-3-(1-naphtyl)-L-alanine-Val-OAllyl (0.67 g, 1.16 mmol) was solvated in CH$_2$Cl$_2$ (5 mL) followed by addition of piperidine (0.920 mL). After 45 min, the mixture was evaporated to dryness and co-evaporated with CH$_2$Cl$_2$ (20 mL*2) followed with high vacuum (without heating) for 10 min to remove the excess of piperidine. The sample was purified on silica with a gradient of MeOH/CH$_2$Cl$_2$ (0 to 5%) to get 0.396 g of the desired compound.

c) Cbz-Asp(O-tBu)-3-(1-naphtyl)-L-alanine-Val-OAllyl

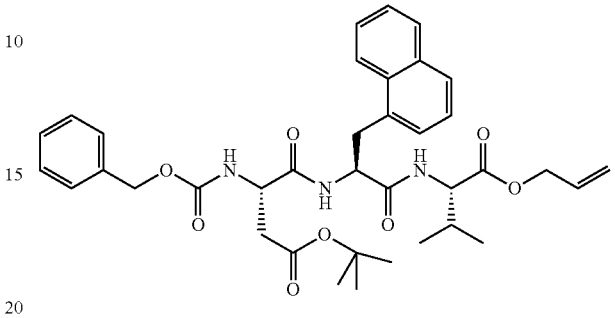

3-(1-naphtyl)-L-alanine-Val-OAllyl (0.394 g, 1.11 mmol) was solvated in CH$_2$Cl$_2$ (1.5 mL) and DMF (3 ml) followed addition of Z-Asp(OtBu)-OH (0.369 g, 1.03 eq), DMAP (14.8 mg, 0.11 eq) and 4-methylmorpholine (0.125 ml, 1.02 eq), then EDC (0.221 g, 1.04 eq). The vial was rinsed with 0.5 ml of dichloromethane. The mixture was stirred for 2 hours at room temperature. Then it was extracted using CH$_2$Cl$_2$/brine. The organic layer was dried over MgSO$_4$, filtered off and concentrated. The obtained residue was purified on silica using a gradient EtOAc/Hex (0 to 80%) to get 0.516 g of the desired compound.

NMR $^1$H (CD$_3$OD, 400 MHz) δ: 8.15 (d, 1H, J=8.4 Hz); 7.84 (d, 1H, J=8.09 Hz); 7.72 (t, 1H, J=4.52 Hz); 7.53 (t, 1H, J=6.98 Hz); 7.45 (t, 1H, J=7.14 Hz); 7.4-7.25 (m, 7H); 5.95-5.85 (m, 1H); 5.32 (dd, 1H, J=17.25 Hz, J=1.36 Hz); 5.22 (dd, 1H, J=10.49 Hz, J=1.16 Hz); 5.06 (q, 2H, J=12.57 Hz); 4.8 (m, 1H); 4.55 (m, 2H); 4.45 (m, 1H); 4.3 (d, 1H, J=6.41 Hz); 3.63 (m, 1H); 3.38 (m, 1H); 2.66 (dd, 1H, J=16.31 Hz, J=5.81 Hz); 2.45 (dd, 1H, J=16.31 Hz, J=8.16 Hz); 2.1 (m, 1H); 1.4 (s, 9H); 0.9 (dd, 6H, J=12.63 and 10.44 Hz).

d) Cbz-Asp(O-tBu)-3-(1-naphtyl)-L-alanine-Val-OH

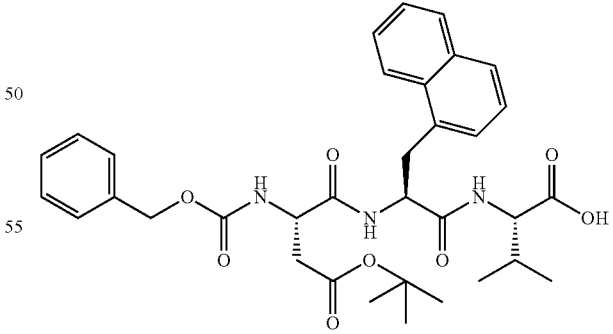

Cbz-Asp(O-tBu)-3-(1-naphtyl)-L-alanine-Val-OAllyl (0.312 g, 0.47 mmol) was dissolved in THF (13 mL) and rotary evaporated to dryness, the sample was then redissolved in THF (13 mL) and vacuum aspirated (3*1 min of aspiration), followed by replacement of the atmosphere with Argon. Pd(PPh$_3$)$_4$ (0.060 g, 0.11 eq) was added in one shot, the flask was then evacued with Argon. Morpholine (0.267 mL, 4.42 eq) was added and the flask covered with a tin foil. The mixture was kept under stirring for 3 days under Argon. The sample was evaporated to dryness and the obtained residue was subjected to purification on $C_{18}$ using a gradient of MeOH/solution of $H_2O$ at pH=3.5 (10 to 100%) to get 0.18 g of the desired compound.

NMR $^1$H (CD$_3$OD, 400 MHz) δ: 8.2 (d, 1H, J=8.5 Hz); 7.85 (d, 1H, J=8.0 Hz); 7.74 (dd, 1H, J=6.85 Hz; 2.7 Hz); 7.56-7.52 (m, 1H); 7.48 (t, 1H, J=7.15 Hz); 7.37-7.26 (m, 7H); 5.09 (q, 2H, J=12.55 Hz); 4.8 (m, 1H); 4.45 (m, 1H); 4.29 (d, 1H, J=5.6 Hz); 3.68 (dd, 1H, J=14.45 Hz; 5.75 Hz); 3.4-3.3 (m, 1H); 2.66 (dd, 1H, J=16.25; 5.6 Hz); 2.45 (dd, 1H, J=16.21 Hz, J=8.2 Hz); 2.15 (m, 1H); 1.4 (s, 9H); 0.96 (t, 6H, J=5 Hz).

e) -Z-Asp(β-tert-Butyl)-3-(1-naphtyl)-L-alanine-Val-Asp(β-tert-Butyl)methyl Vinyl Sulfone

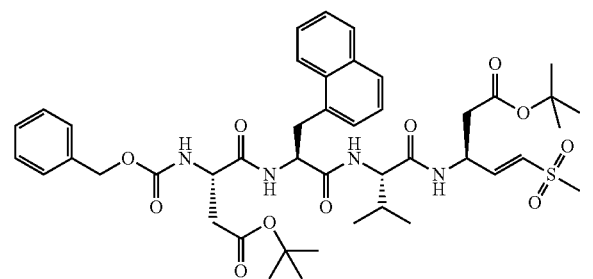 [SMILES: CC(C)[C@H](NC(=O)[C@H](Cc1cccc2ccccc12)NC(=O)[C@H](CC(=O)OC(C)(C)C)NC(=O)OCc1ccccc1)C(=O)N[C@H](/C=C/S(C)(=O)=O)CC(=O)OC(C)(C)C]

The Cbz-Asp(O-tBu)-3-(1-naphtyl)-L-alanine-Val-OH (20.7 mg, 0.033 mmol) is dissolved in a mix of THF and DMF (0.5 ml/0.1 ml). The mixture was allowed to reach −15/−20° C. (ice/MeOH bath) before adding N-methyl morpholine (10 μl) followed 3 min latter with isobutyl chloroformate (8 μl). The mixture was stirred at −15° C. for 10 minutes. Next, Asp(β-tert-Butyl)-methylvinylsulfone tosyl salt (14 mg, 1 eq) was added in one shot, followed by addition of N-methyl morpholine (10 μl). The mixture was stirred for 30 minutes at −15/−20° C., then diluted with 7 ml of dichloromethane and quenched with 1.5 ml of a saturated solution of sodium bicarbonate. The organic layer was dried over magnesium sulphate and the solvent was evaporated to dryness. The obtained residue was purified on silica gel (ethyl acetate/hexane: 40% then dichloromethane/methanol: 0 to 14%) to afford 21 mg of desired compound.

f) -Z-Asp-3-(1-naphtyl)-L-alanine-Val-Asp Methyl Vinyl Sulfone

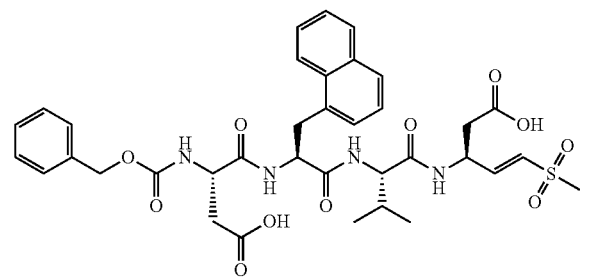 [SMILES: CC(C)[C@H](NC(=O)[C@H](Cc1cccc2ccccc12)NC(=O)[C@H](CC(=O)O)NC(=O)OCc1ccccc1)C(=O)N[C@H](/C=C/S(C)(=O)=O)CC(=O)O]

Z-Asp(β-tert-Butyl)-3-(1-naphtyl)-L-alanine-Val-Asp(β-tert-Butyl)methyl vinyl sulfone (0.02 g) was solvated in CH$_2$Cl$_2$ (0.5 mL) followed by the addition of TFA (0.65 mL). The mixture was stirred at room temperature overnight (15 h). It was then quenched with diethyl ether (7 ml), the solvent was removed under vacuum. The obtained residue was diluted again with ether and the process was repeated twice. The precipitate was washed with 2*1 ml of ether, dried to give 15 mg of the desired compound.

NMR $^1$H (CD$_3$OD, 400 MHz) δ: 8.14 (d, 1H, J=8.24 Hz); 7.81 (d, 1H, J=7.7 Hz); 7.68 (m, 1H); 7.51 (m, 1H); 7.45 (m, 1H); 7.33-7.28 (m, 7H); 6.8 (dd, 1H, J=15.2 Hz, J=4.56 Hz); 6.66 (dd, 1H, J=15.2 Hz, J=4.5 Hz); 5.0 (m, 2H); 4.95 (m, 1H); 4.65 (m, 1H); 4.39 (m, 1H); 4.02 (d, 1H, J=7.32 Hz); 3.8-3.18 (m, 2H); 2.92 (s, 3H); 2.8-2.44 (m, 4H); 2.02 (m, 1H); 0.88 (d, 6H, J=6.78 Hz).

Example 50

Synthesis of Compound 113 (Z-Asp-3-(1-naphtyl)-L-alanine-Val-Asp Achlorovinyl Methylsulfone

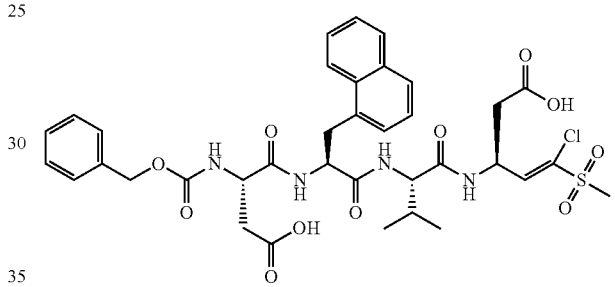

a) -Z-Asp(β-tert-Butyl)-3-(1-naphtyl)-L-alanine-Val-Asp(β-tert-Butyl)achlorovinyl Methylsulfone

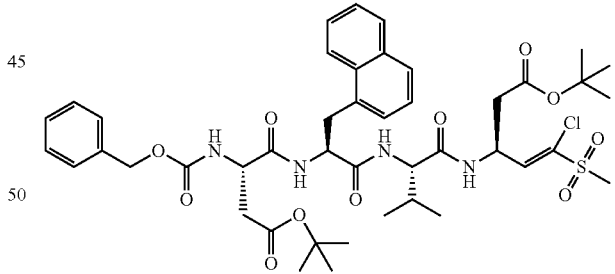

The Cbz-Asp(O-tBu)-3-(1-naphtyl)-L-alanine-Val-OH (20.7 mg, 0.033 mmol) is dissolved in a mix of THF and DMF (0.5 ml/0.1 ml). The mixture was allowed to reach −15/−20° C. (ice/MeOH bath) before adding N-methyl morpholine (10 μl) followed 3 min latter with isobutyl chloroformate (8 μl). The mixture was stirred at −15° C. for 10 minutes. Next, Asp(β-tert-Butyl)-achlorovinyl methylsulfone tosyl salt (15.2 mg, 1 eq) was added in one shot (the vial was rinsed with THF (0.1 ml) followed by addition of N-methyl morpholine (10 μl). The mixture was stirred for 30 minutes at −15/−20° C., then diluted with 7 ml of dichloromethane and quenched with 1.5 ml of water. The organic layer was dried over magnesium sulphate and the solvent was evaporated to dryness.

205

The obtained residue was purified on silica gel (ethyl acetate/hexane: 40% then dichloromethane/methanol: 0 to 14%) to afford 16 mg of desired compound.

b) -Z-Asp-3-(1-naphtyl)-L-alanine-Val-Asp Achlorovinyl Methylsulfone

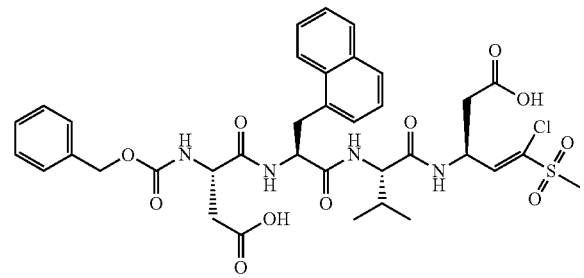 [SMILES: CC(C)[C@H](NC(=O)[C@H](Cc1cccc2ccccc12)NC(=O)[C@H](CC(=O)O)NC(=O)OCc1ccccc1)C(=O)N[C@H](/C=C(\Cl)S(C)(=O)=O)CC(=O)O]

Z-Asp(β-tert-Butyl)-3-(1-naphtyl)-L-alanine-Val-Asp(β-tert-Butyl)methylvinyl sulfone (0.016 g) was solvated in CH$_2$Cl$_2$ (0.37 mL) followed by the addition of TFA (0.48 mL). The mixture was stirred at room temperature overnight (15 h). It was then quenched with diethyl ether (7 ml), the solvent was removed under vacuum. The obtained residue was diluted again with ether and the process was repeated twice. The precipitate was washed with 2*1 ml of ether, dried to give 15 mg of the desired compound.

NMR $^1$H (CD$_3$OD, 400 MHz) δ: 8.19 (d, 1H, J=8.35 Hz); 7.86 (d, 1H, J=8.05 Hz); 7.75 (m, 1H); 7.56 (m, 1H); 7.50 (m, 1H); 7.38-7.3 (m, 7H); 6.82 (dd, 1H, J=15.0; 4.3 Hz); 6.68 (dd, 1H, J=15.1; 4.3 Hz); 5.08-4.97 (m, 3H); 4.76 (m, 1H); 4.46 (m, 1H); 4.08 (d, 1H, J=7.4 Hz); 3.8-3.3 (m, 2H); 3.08 (s, 3H); 2.85-2.55 (m, 4H); 2.03 (m, 1H); 0.91 (d, 6H, J=6.8 Hz).

Example 51

Synthesis of Compound 121 (Z-Asp-Val-Asp-methyl Vinyl Sulfone)

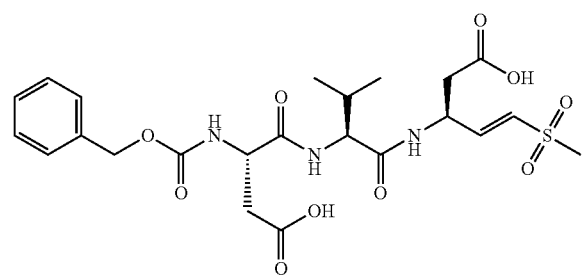 [SMILES: CC(C)[C@H](NC(=O)[C@H](CC(=O)O)NC(=O)OCc1ccccc1)C(=O)N[C@H](/C=C/S(C)(=O)=O)CC(=O)O]

Z-Asp-Val-Asp-methyl vinyl sulfone was synthesized from Z-Asp(β-tert-Butyl)-Val-OH (119) and Asp(β-tert-Butyl)-methyl vinyl sulfone tosyl salt (33) as for Z-Asp-3-(1-naphtyl)-L-alanine-Val-Asp methyl vinyl sulfone (111).

Z-Asp(β-tert-Butyl)-Val-OH (119) was synthesized from z-Asp(β-tert-Butyl)-OH and Val-O-Allyl tosyl salt followed with allyl deprotection as for Cbz-Asp(O-tBu)-3-(1-naphtyl)-L-alanine-Val-OH (109).

206

Scale-Up and Optimization of Short Peptide Synthesis

Example 52

Synthesis of Compound 16
(Z-Asp(β-tert-butyl)-Phg-Val-OH)

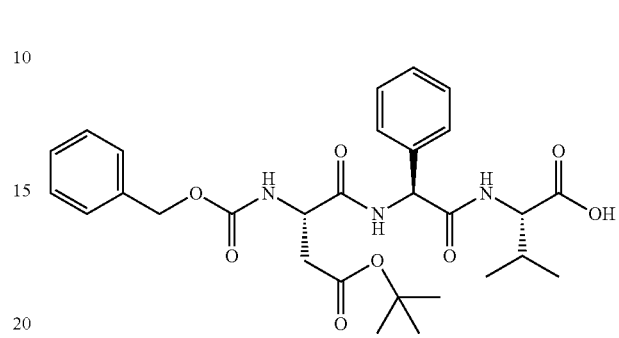

a) Boc-Phg-Val-OAllyl

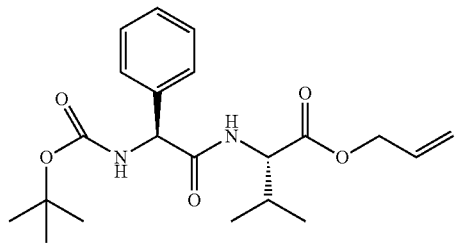 [SMILES: C=CCOC(=O)[C@@H](NC(=O)[C@@H](NC(=O)OC(C)(C)C)c1ccccc1)C(C)C]

To a solution of Tosyl valine(OAllyl) (1.31 g, 1 eq) in DMF (5.2 ml) was added N,N-diisopropyl ethyl amine (0.69 ml, 1 eq) and the mixture was stirred for 4 min, then added to a solution of Boc-Phg-OH (1.0 g, 3.98 mmol) in 3.5 ml of DMF. The mixture was chilled at 0° C. HOBT anhydrous (0.53 g, 1 eq) was added followed with EDC (0.83 g; 1.09 eq) in DMF (2.6 ml, as a suspension), The vial of EDC was washed with DMF (2.5 ml) and added to the solution. The mixture was stirred for 22 h (0° C. to RT). It was then diluted with EtOAc (50 ml), the organic layer was washed with H$_2$SO$_4$ 2M (3*5 ml), then K$_2$CO$_3$ (7.5% w/w) (3*10 ml), then Brine (1*10 ml). The organic layer was dried with MgSO4, filtered off and the solvent was evaporated to dryness to get 1.5 g of the desired compound which was used for the next step as a crude material.

b) Phg-Val-OAllyl TFA Salt

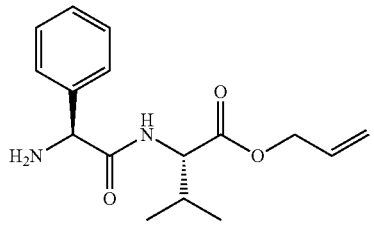

1.5 g (3.84 mmol) of the previous crude material (BocPhg-Val-OAllyl) was solvated in a solution of dichloromethane (7.5 ml) and TFA (7.5 ml). The mixture was stirred at room temperature for 3 hours. It was then evaporated to dryness, then it was kept under higher vacuum for 20 minutes. The product crystallized with ether (5 ml). The white solid was filtered off and washed with ether (4 ml+2+2) to get 1.044 g of Phg-Val-Oallyl TFA salt. NMR $^1$H (DMSO, 500 MHz) δ 8.81 (d, 1H, J=8.0 Hz); 8.61 (s, 3H); 7.51-7.43 (m, 5H); 5.8-5.72 (m, 1H); 5.22-5.16 (m, 2H); 5.16 (m, 1H); 4.51-4.49 (m, 2H); 4.29-4.26 (m, 1H); 2.12-2.08 (m, 1H); 0.93 (d, 6H, J=6.85 Hz).

c) Z-Asp(β-tert-Butyl)-Phg-Val-OAllyl

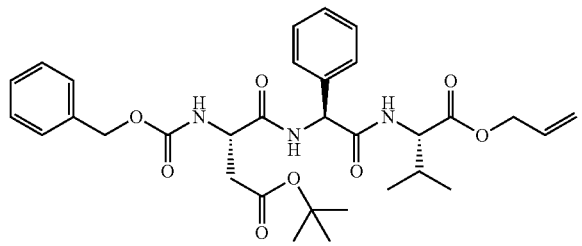 [SMILES: C=CCOC(=O)[C@@H](NC(=O)[C@@H](NC(=O)[C@H](CC(=O)OC(C)(C)C)NC(=O)OCc1ccccc1)c1ccccc1)C(C)C]

A solution of Phg-Val-OAllyl TFA salt (1.022 g, 1 eq) in DMF (3.6 ml) was added N,N-diisopropyl ethyl amine (0.44 ml, 1 eq) and the mixture was stirred for 4 min, then added to a solution of Z-Asp(β-tert-butyl)-OH (0.817 g, 2.529 mmol) in 2.4 ml of DMF. The mixture was chilled at 0° C. HOBT anhydrous (0.342 g, 1 eq) was added followed with EDC (0.53 g; 1.1 eq) in DMF (1.8 ml, as a suspension), The vial of EDC was washed with DMF (2*1.3 ml) and was added to the solution. The mixture was stirred for 22 h (0° C. to RT). It was then diluted with EtOAc (50 ml), the organic layer was washed with citric acid 0.5 M (3*10 ml), then K$_2$CO$_3$ (7.5% w/w) (3*10 ml), then Brine (1*10 ml). The organic layer was dried with MgSO$_4$, filtered off and the solvent was evaporated to dryness to get 1.1 g of the desired and clean compound, which was used for the next step as a crude compound. NMR $^1$H (DMSO, 500 MHz) δ 8.60 (d, NH, J=7.98 Hz); 8.25 (d, NH, J=8.15 Hz); 7.68 (d, NH, J=8.31 Hz); 7.42-7.27 (m, 10H); 5.81-5.75 (m, 1H); 5.63 (d, 1H, J=8.17 Hz); 5.25 (dd, 1H, J=3.38; 1.65 Hz); 5.21 (dd, 1H; J=3.16; 1.55 Hz); 5.17 (s, 2H); 4.51-4.46 (m, 3H); 4.21 (t, 1H, J=1.65 Hz); 2.68-2.64 (m, 1H); 2.47-2.42 (m, 1H); 2.10-2.06 (m, 1H); 1.37 (s. 9H); 0.91 (dd, 6H, J=6.85; 3.75 Hz).

d) Z-Asp(β-tert-Butyl)-Phg-Val-OH

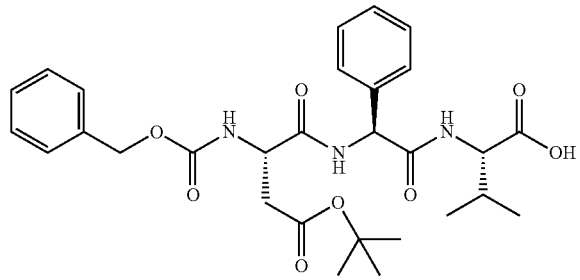 [SMILES: CC(C)[C@H](NC(=O)[C@@H](NC(=O)[C@H](CC(=O)OC(C)(C)C)NC(=O)OCc1ccccc1)c1ccccc1)C(=O)O]

Z-Asp(β-tert-butyl)-Phg-Val-OAllyl (0.9 g; 1.51 mmol) was co-evaporated with THF to dryness (2*10 ml), then dissolved under argon in dry THF (18 ml, inhibitor free). The solvent was degassed three times under argon (3 min+2+2) before adding dropwise addition of morpholine (0.658 ml, 5 eq) followed with addition of Tetrakis in one shot (174 mg, 0.1 eq). The mixture was purged under argon for 3 min. the reaction was carried out in the absence of light and at room temperature for 30 minutes. It was then diluted with ether (18 ml) followed with citric acid 0.5M (18 ml). The mixture was stirred for 3 minutes, then extracted. The aqueous layer was washed with ether (3*18 ml). The combined organic layers were dried with MgSO$_4$. The solvent was evaporated to dryness. The crude was purified on C-18 column 50 g (pH: 3.5; gradient: 10 to 100% MeOH/Water; 4 ml methanol injection volume) to get 0.75 g of the desired product (second pic). NMR $^1$H (CD$_3$OD, 400 MHz) δ 7.46-7.29 (m, 10H); 5.61 (s, 1H); 5.12 (s, 2H); 4.63-4.40 (m, 1H); 4.34 (d, 1H, J=5.70 Hz); 2.84 (dd, 1H, J=16.3; 5.80 Hz); 2.60 (dd, 1H, J=16.2; 8.30 Hz); 2.22-2.15 (m, 1H); 2.15 (m, 1H); 1.44 (s, 9H); 1.0 (d, 6H; J=6.8 Hz).

Example 53

Synthesis of Compound 109 Cbz-Asp(O-tBu)-3-(1-naphtyl)-L-alanine-Val-OH

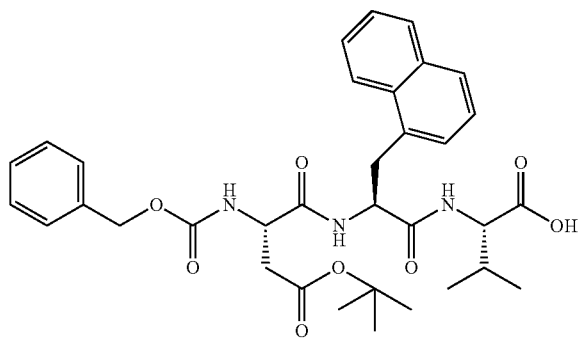 [SMILES: CC(C)[C@H](NC(=O)[C@H](Cc1cccc2ccccc12)NC(=O)[C@H](CC(=O)OC(C)(C)C)NC(=O)OCc1ccccc1)C(=O)O]

a) Boc-3-(1-naphtyl)-L-alanine-Val-OAllyl

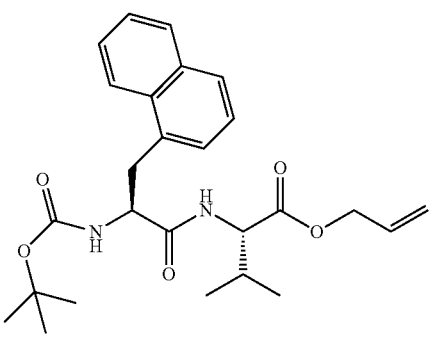 [SMILES: C=CCOC(=O)[C@@H](NC(=O)[C@H](Cc1cccc2ccccc12)NC(=O)OC(C)(C)C)C(C)C]

To a solution of Tosyl valine (OAllyl) (1.567 g, 1 eq) in DMF (6.2 ml) was added N,N-diisopropyl ethyl amine (0.828 ml, 1 eq) and the mixture was stirred for 5 min, then added to a solution of Boc-3-(1-naphtyl)-(1.5 g, 4.75 mmol) in 4.2 ml of DMF. The mixture was chilled at 0° C. HOBT anhydrous (0.643 g, 1 eq) was added followed with EDC (1.003 g; 1.09 eq) in DMF (2.4 ml, as a suspension), The vial of EDC was washed with DMF (3 ml) and was added to the solution. The mixture was stirred for 22 h (0° C. to RT). It was then diluted with EtOAc (70 ml), the organic layer was washed with H₂SO₄ 2M (3*6 ml), then K₂CO₃ (7.5% w/w) (3*12 ml), then Brine (1*12 ml). The organic layer was dried with MgSO₄, filtered off and the solvent was evaporated to dryness to get 2.02 g of the desired and clean compound, which was used as a crude material for the next step.

b) 3-(1-naphtyl)-L-alanine-Val-OAllyl TFA Salt

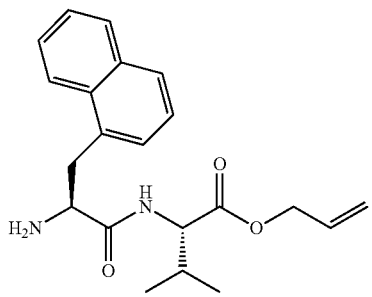 [SMILES: C=CCOC(=O)[C@@H](NC(=O)[C@@H](N)Cc1cccc2ccccc12)C(C)C]

2.02 g (4.44 mmol) of the previous crude material (Boc3-(1-naphtyl)-L-alanine-Val-OAllyl) was solvated was solvated in a solution of dichloromethane (8.8 ml) and TFA (8.8 ml). The mixture was stirred at room temperature for 3 hours (TLC). The solvent was evaporated to dryness then it was kept under higher vacuum for 20 minutes. The product crystallized with isopropyl ether (5 ml). The white solid was filtered off and washed with isopropyl ether to get 1.515 g of 3-(1-naphtyl)-L-alanine-Val-Oallyl TFA salt. NMR ¹H (DMSO, 500 MHz) δ NMR ¹H (DMSO, 500 MHz) δ 8.68 (d, 1H, J=8.1 Hz); 8.33 (s, 3H); 8.19 (d, 1H, J=8.45 Hz); 7.99 (d, 1H, J=8.0 Hz); 7.89 (d, 1H, J=8.05 Hz); 7.64-7.55 (m, 2H); 7.45-7.38 (m, 2H); 5.93-5.85 (m, 1H); 5.37-5.32 (m, 1H); 5.27-5.23 (m, 1H); 4.59-4.50 (m, 2H); 4.25-4.22 (m, 2H); 3.5-3.3 (m, 2H); 2.04-1.91 (m, 1H); 0.89 (t, 6H, J=6.90 Hz).

c) Cbz-Asp(O-tBu)-3-(1-naphtyl)-L-alanine-Val-OAllyl

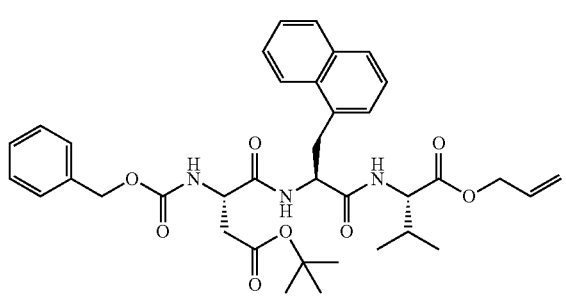 [SMILES: C=CCOC(=O)[C@@H](NC(=O)[C@H](Cc1cccc2ccccc12)NC(=O)[C@H](CC(=O)OC(C)(C)C)NC(=O)OCc1ccccc1)C(C)C]

A solution of 3-(1-naphtyl)-L-alanine-Val-OAllyl TFA salt (1.515 g, 1 eq) in DMF (4.6 ml) was added N,N-diisopropyl ethyl amine (0.56 ml, 1 eq) and the mixture was stirred for 5 min, then added to a solution of Z-Asp(β-tert-butyl)-OH (1.045 g, 3.23 mmol) in 3 ml of DMF. The mixture was shilled at 0° C. HOBT anhydrous (0.437 g, 1 eq) was added followed with EDC (0.682 g; 1.1 eq) in DMF (2.3 ml, as a suspension), The vial of EDC was washed with DMF (2*1.6 ml) and was added to the solution. The mixture was stirred for 22 h (0° C. to RT). It was then diluted with EtOAc (60 ml), the organic layer was washed with citric acid 0.5 M (3*10 ml), then K₂CO₃ (7.5% w/w) (3*10 ml), then Brine (1*10 ml). The organic layer was dried with MgSO₄, filtered off and the solvent was evaporated to dryness to get 1.88 g of the desired and clean compound, which was used for the next step as a crude compound.

d) Cbz-Asp(O-tBu)-3-(1-naphtyl)-L-alanine-Val-OH

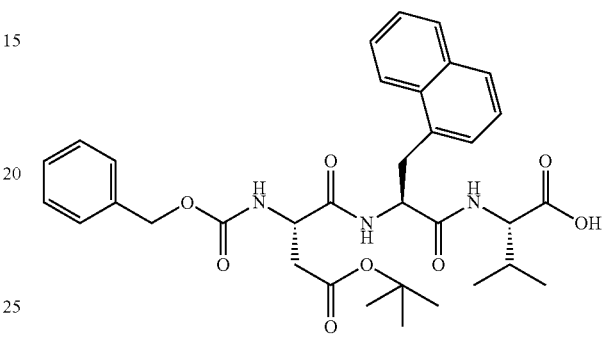

Cbz-Asp(O-tBu)-3-(1-naphtyl)-L-alanine-Val-OAllyl (1 g; 1.51 mmol) was co-evaporated with THF to dryness (2*10 ml), then dissolved under argon in dry THF (18 ml, inhibitor free). The solvent was degassed three times under argon (3 min+2+2) before dropwise addition of morpholine (0.658 ml, 5 eq) followed with addition of Tetrakis in one shot (174 mg, 0.1 eq). The mixture was purged under argon for 3 min. the reaction was carried out in the absence of light and at room temperature for 30 minutes. It was then diluted with ether (18 ml) followed with citric acid 0.5M (18 ml). The mixture was stirred for 3 minutes, then extracted. The aqueous layer was washed with ether (3*18 ml) then combined, dried with MgSO₄. The solvent was evaporated to dryness. The crude was purified on C-18 column 50 g (pH: 3.5; gradient: 10 to 100° A) MeOH/Water; 4 ml methanol injection volume) to get 0.75 g of the desired product (second pic). NMR ¹H (CD₃OD, 500 MHz) δ 8.20 (d, 1H, J=8.5 Hz); 7.85 (d, 1H, J=8.1 Hz); 7.75-7.72 (m, 1H); 7.56-7.46 (m, 2H); 7.37-7.27 (m, 7H); 5.09 (q, 2H, J=12.35 Hz); 4.85 (m, 1H); 4.47-4.44 (m, 1H); 4.30 (d, 1H, J=5.8 Hz); 3.68 (dd, 1H, J=14.10; 5.80 Hz); 3.43-3.37 (m, 1H); 2.66 (dd, 1H, J=16.30; 5.9 Hz); 2.46 (dd, 1H, J=16.20; 8.1 Hz); 2.19-2.12 (m. 1H); 1.41 (s, 9H); 0.96 (d, 6H, J=6.80 Hz).

Example 54

Scale-Up Synthesis of Compound 53
(Z-Asp-Phg-Val-Aspmethyl Vinyl Sulfone)

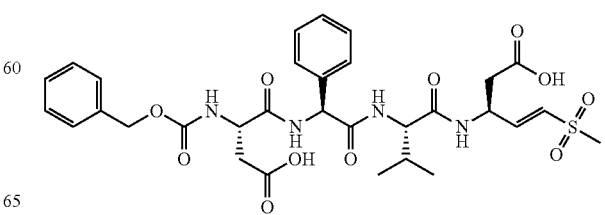

a) Synthesis of (Z-Asp(β-tert-Butyl)-Phg-Val-Asp(β-tert-Butyl)methyl Vinyl Sulfone)

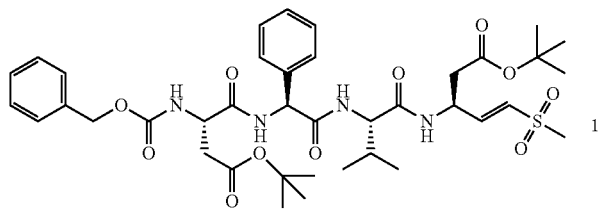

The Z-Asp(β-tert-Butyl)-Phg-Val-OH (204 mg, 3.67 mmol) is dissolved in a mix of THF and DMF (2.5 ml/0.52 ml). The mixture was allowed to reach −18° C. (ice/MeOH bath) before dropwise addition of N-methyl morpholine (42 µl) followed 3 min later with dropwise addition of isobutyl chloroformate (50 µl). The mixture was stirred for 10 minutes (the ice bath was changed after 8 minutes when the temperature of the bath dropped −13° C.). Next, Asp(β-tert-butyl) methyl vinyl sulfone tosyl salt (159 mg, 1 eq) was added in one shot, followed by dropwise addition of N-methyl morpholine (42 µl). The mixture was stirred for 35 minutes, then diluted with 8 ml of dichloromethane and quenched with dropwise addition of saturated solution of sodium bicarbonate (3 ml) at −12° C. The mixture was stirred 2 minutes at −12° C. and 5 minutes at RT. The mixture was transferred in a separatory funnel and it was diluted with dichloromethane (23 ml). The aqueous layer was washed with dichloromethane (2*17 ml). The combined organic layer was dried over magnesium sulphate. The solvent was evaporated to dryness. The obtained residue was solubilized in a minimum of dichloromethane at 44° C., then added to the samplet of Biotage column (25 g). The purification is carried out first with ethyl acetate/hexane (40%, 12 CV), then dichloromethane/methanol (0 to 15%, 10 CV) to afford 245 mg of Z-Asp(β-tert-Butyl)-Phg-Val-Asp(β-tert-butyl)-methyl vinyl sulfone, obtained as E-isomer. NMR $^1$H (CD$_3$OD, 500 MHz) δ: 7.45-7.31 (m, 10H); 6.81 (dd, 1H, J=15.20, J=5 Hz); 6.68 (dd, 1H, J=15.20; 1.45 Hz); 5.46 (s, 1H); 5.14 (s, 2H); 4.93 (m, 1H); 4.58 (m, 1H); 4.14 (d, 1H, J=7.10 Hz); 2.96 (s, 3H); 2.88-2.82 (m, 1H); 2.66-2.54 (m, 3H); 2.17 (m, 1H); 1.45 (s, 9H); 1.42 (s, 9H); 0.99 (t, 6H, J=4.55 Hz).

b) Synthesis of (Z-Asp-Phg-Val-Asp-methyl Vinyl Sulfone)

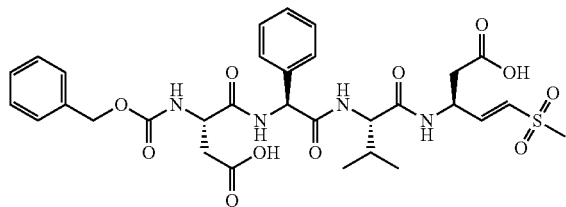 [SMILES: CC(C)[C@H](NC(=O)[C@@H](NC(=O)[C@H](CC(=O)O)NC(=O)OCc1ccccc1)c1ccccc1)C(=O)N[C@H](/C=C/S(C)(=O)=O)CC(=O)O]

Z-Asp(β-tert-Butyl)-Phg-Val-Asp(β-tert-butyl)-methyl vinyl sulfone (245 mg) was dissolved in dichloromethane (4 ml) for 4 min, followed by quick addition of trifluoroacetic acid (5 ml). The mixture was stirred at room temperature overnight (15 h). It was then quenched with diethyl ether (12 ml) and the solvent was removed under vacuum. The obtained residue was diluted again with ether (12 ml) and the process was repeated twice. The obtained solid was washed with ether (3*1 ml). The filtrate was removed and the precipitate was dried to give 200 mg of the desired compound. NMR $^1$H (CD$_3$OD, 500 MHz) δ: 7.48-7.30 (m, 10H); 6.86 (dd, 1H, J=15.28, J=4.60 Hz); 6.72 (dd, 1H, J=15.30; 1.65 Hz); 5.40 (s, 1H); 5.13 (q, 2H, J=12.35 Hz); 4.96-4.90 (m, 1H); 4.59 (t, 1H, J=6.75 Hz); 4.12 (d, 1H, J=7.15 Hz); 2.97 (s, 3H); 2.96-2.60 (m, 4H); 2.24-2.19 (m, 1H); 1.0 (t, 6H, J=5.88 Hz).

Example 55

Scale-Up Synthesis of Compound 111 (Z-Asp-3-(1-naphtyl)-L-alanine-Val-Asp Methyl Vinyl Sulfone)

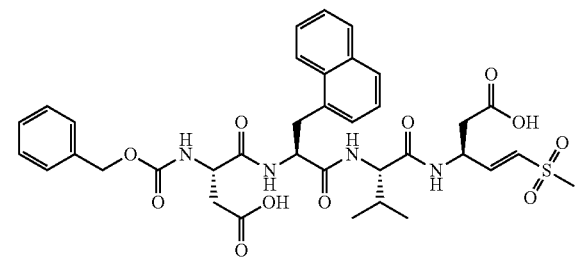 [SMILES: CC(C)[C@H](NC(=O)[C@H](Cc1cccc2ccccc12)NC(=O)[C@H](CC(=O)O)NC(=O)OCc1ccccc1)C(=O)N[C@H](/C=C/S(C)(=O)=O)CC(=O)O]

A—The Cbz-Asp(O-tBu)-3-(1-naphtyl)-L-alanine-Val-OH (226 mg, 3.66 mmol) is dissolved in a mix of THF and DMF (2.5 ml/0.52 ml). The mixture was allowed to reach −18° C. (ice/MeOH bath) before dropwise addition of N-methyl morpholine (41 µl) followed 3 min later with isobutyl chloroformate (49 µl). The mixture was stirred for 10 minutes (the ice bath was changed after 8 minutes when the temperature of the bath dropped to −13° C.). Next, Asp(β-tert-butyl) methyl vinyl sulfone tosyl salt (158 mg, 1 eq) was added in one shot, followed by dropwise addition of N-methyl morpholine (41 µl). The mixture was stirred 35 minutes then diluted with 8 ml of dichloromethane and quenched with dropwise addition of 3 ml of a saturated solution of sodium bicarbonate at −12° C. The mixture was stirred 2 minutes at −12° C. and 5 minutes at RT. The mixture was transferred in a separatory funnel and was diluted with dichloromethane (23 ml). The aqueous layer was washed with dichloromethane (2*17 ml). The combined organic layer was dried over magnesium sulphate. The solvent was evaporated to dryness. The obtained residue was solubilized in a minimum of dichloromethane at 45° C., then added to the samplet of Biotage column (25 g). The purification is carried out first with ethyl acetate/hexane (40%, 12 CV), then dichloromethane/methanol (0 to 15%, 10 CV) to afford 266 mg of Z-Asp(β-tert-butyl)-3-(1-naphtyl)-L-alanine-Val-Asp(β-tert-butyl)methyl vinyl sulfone, obtained as E-isomer. NMR $^1$H (CD$_3$OD, 500 MHz) δ: 8.2 (d, 1H, J=8.65 Hz); 7.87 (d, 1H, J=7.75 Hz); 7.76 (t, 1H, J=4.7 Hz); 7.56 (m, 1H); 7.49 (m, 1H); 7.38-7.32 (m, 7H); 6.84 (dd, 1H, J=15.20; 4.85 Hz); 6.74 (d, 1H, J=15.25 Hz); 5.07 (q, 2H; J=12.45 Hz); 4.92 (m, 1H); 4.77 (m, 1H); 4.41 (t, 1H, J=2.1 Hz); 4.09 (d, 1H, J=7.0 Hz); 3.74 (dd, 1H, J=14.8; 5.25 Hz); 3.45-3.33 (m, 1H); 2.98 (s, 3H); 2.69-2.65 (m, 3H); 2.48 (dd, 1H, J=16.60; 8.30 Hz); 2.10 (m, 1H); 1.45 (s, 9H); 1.40 (s, 9H); 0.94 (dd, 6H, J=6.8; 3.7 Hz).

B Z-Asp(β-tert-butyl)-3-(1-naphtyl)-L-alanine-Val-Asp (β-tert-butyl)methyl vinyl sulfone (266 mg) was dissolved in dichloromethane (4 ml) for 4 min, followed by quick addition of trifluoroacetic acid (5 ml). The mixture was stirred at room temperature overnight (15 h). It was then quenched with diethyl ether (9 ml) and the solvent was removed under vacuum. The obtained residue was diluted again with ether (9 ml) and the process was repeated twice. The obtained solid was washed with ether (3*1 ml). The filtrate was removed and the precipitate was dried to give 220 mg of the desired compound. NMR $^1$H (CD$_3$OD, 500 MHz) δ: 8.2 (d, 1H, J=8.4 Hz); 7.87 (d, 1H, J=8.0 Hz); 7.76 (d, 1H, J=2.35 Hz); 7.57 (m, 1H); 7.51 (m, 1H); 7.38-7.32 (m, 7H); 6.87 (dd, 1H, J=15.20; 4.6 Hz); 6.73 (dd, 1H, J=15.20; 1.6 Hz); 5.09-5.03 (m, 2H); 4.97 (m, 1H); 4.75 (m, 1H); 4.45 (t, 1H, J=6.85 Hz); 4.08 (d, 1H, J=7.25 Hz); 3.78 (dd, 1H, J=14.10; 4.65 Hz); 3.46-3.34 (m, 1H); 2.98 (s, 3H); 2.88-2.58 (m, 4H); 2.14-2.09 (m, 1H); 0.94 (dd, 6H, J=7.05; 1.05 Hz).

Example 56

Scale-Up Synthesis of Compound 123 (Z-Asp-phenylglycine-Val-Asp-achlorovinyl Methylsulfone)

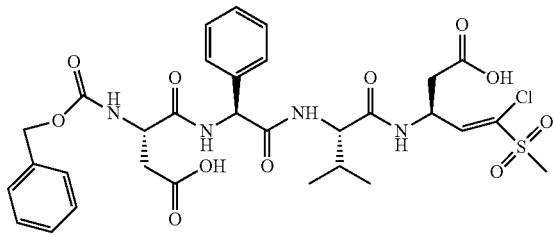 [SMILES: CC(C)[C@H](NC(=O)[C@@H](NC(=O)[C@H](CC(=O)O)NC(=O)OCc1ccccc1)c1ccccc1)C(=O)N[C@H](/C=C(\Cl)S(C)(=O)=O)CC(=O)O]

a) Synthesis of (Z-Asp(β-tert-Butyl)-Phg-Val-Asp(β-tert-Butyl)achlorovinyl Methyl Sulfone)

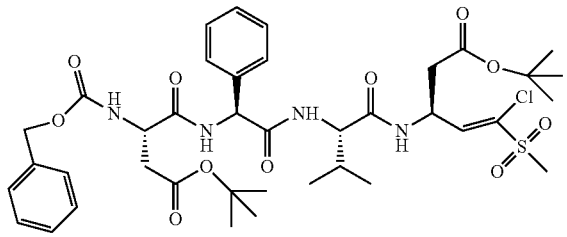 [SMILES: CC(C)[C@H](NC(=O)[C@@H](NC(=O)[C@H](CC(=O)OC(C)(C)C)NC(=O)OCc1ccccc1)c1ccccc1)C(=O)N[C@H](/C=C(\Cl)S(C)(=O)=O)CC(=O)OC(C)(C)C]

The Z-Asp(β-tert-Butyl)-Phg-Val-OH (204 mg, 3.67 mmol) is dissolved in a mix of THF and DMF (2.5 ml/0.52 ml). The mixture was allowed to reach −18° C. (ice/MeOH bath) before dropwise addition of N-methyl morpholine (42 µl) followed 3 min later with dropwise addition of isobutyl chloroformate (50 µl). The mixture was stirred for 10 minutes (the ice bath was changed after 8 minutes when the temperature of the bath dropped −13° C.). Next, Asp(β-tert-butyl) achlorovinyl methyl sulfone tosyl salt (171 mg, 1 eq) was added in one shot, followed by dropwise addition of N-methyl morpholine (42 µl). The mixture was stirred for 35 minutes, then diluted with 8 ml of dichloromethane and quenched with dropwise addition of saturated solution of sodium bicarbonate (3 ml) at −12° C. The mixture was stirred 2 minutes at −12° C. and 5 minutes at RT. The mixture was transferred in a separatory funnel and it was diluted with dichloromethane (23 ml). The aqueous layer was washed with dichloromethane (2*17 ml). The combined organic layer was dried over magnesium sulphate. The solvent was evaporated to dryness. The obtained residue was solubilized in dichloromethane at 44° C., then added to the samplet of Biotage column (25 g). The purification is carried out first with ethyl acetate/hexane (40%, 12 CV), then dichloromethane/methanol (0 to 15%, 10 CV) to afford 229 mg of Z-Asp(β-tert-Butyl)-Phg-Val-Asp(β-tert-Butyl)achlorovinyl methyl sulfone, obtained as E-isomer.

NMR $^1$H (CD$_3$OD, 500 MHz) δ: 7.44-7.30 (m, 10H); 7.03 (d, 1H, J=8.55 Hz); 5.48 (s, 1H); 5.13 (s, 2H); 5.01-4.9 (m, 1H); 4.59 (dd, 1H, J=5.8; 8.05 Hz); 4.12 (d, 1H, J=7.65 Hz); 3.07 (s, 3H); 2.84 (dd, 1H, J=15.9; 5.7 Hz); 2.68-2.55 (m, 3H); 2.09 (m, 1H); 1.45 (s, 9H); 1.42 (s, 9H); 0.98-0.92 (dd, 6H, J=6.6; 12.85 Hz).

b) Synthesis of (Z-Asp-Phg-Val-Asp-methyl Achlorovinyl Sulfone)

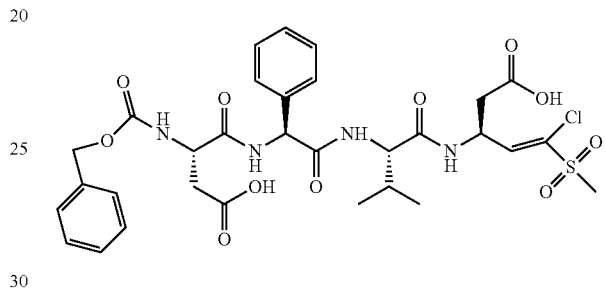

Z-Asp(β-tert-Butyl)-Phg-Val-Asp(β-tert-Butyl)achlorovinyl methyl sulfone (123 mg) was dissolved in dichloromethane (2 ml) for 4 min, followed by quick addition of trifluoroacetic acid (2.5 ml). The mixture was stirred at room temperature overnight (15 h). It was then quenched with diethyl ether (8 ml) and the solvent was removed under vacuum. The obtained residue was diluted again with ether (8 ml) and the process was repeated twice. The obtained solid was washed with ether (3*1 ml). The filtrate was removed and the precipitate was dried to give 108 mg of the desired compound. NMR $^1$H (CD$_3$OD, 500 MHz) δ: 7.47-7.30 (m, 10H); 7.08 (d, 1H, J=8.4 Hz); 5.45 (s, 1H); 5.12 (q, 2H, J=12.9 Hz); 5.04-4.97 (m, 1H); 4.60 (t, 1H, J=6.9 Hz); 4.14 (d, 1H, J=6.15 Hz); 3.08 (s, 3H); 2.95-2.89 (m, 1H); 2.79-2.73 (m, 2H); 2.69-2.64 (m, 1H); 2.16 (m, 1H); 0.97 (dd, 6H, J=6.8; 12.3 Hz).

Example 57

Selectivity of Exemplary Compounds for Caspase-3 Relative to Caspase-1, Caspase-5, Caspase-7, and Caspase-9

Selectivity of compound 55, compound 63, compound 48, compound 57, compound 88 toward caspase-1 (pro-inflammatory group), caspase-5 (group I), caspase-9 (group II) and caspase-3 and caspase-7 (group III) was evaluated by using fluorometric methods using the Caspase-1, -3, -5, -7, -9 Inhibitor Drug Screening Kit™ (Catalog #: K151-100, K153-100, K155-100/K157-100, K159-100 respectively, BioVision™). Briefly, using instructions of the manufacturer, a wide range of different concentrations of the compound: 3333, 1000, 333, 100, 33, 10, 3, and 1 nM (final concentration) was added directly to the reaction mixtures containing the substrate and the enzyme in a final volume of 10 µl. After a 30-minute incubation at 37° C., the liberation of AFC was measured as an endpoint assay using the Flexstation3™ (Molecular Devices) with an excitation wavelength of 400 nm and an emission wavelength of 505 nm. The level of inhibition of caspase-1, -3, -5, -7, -9 activity was determined by comparison of the relative fluorescence intensity in samples with or without the compound. Results are summarized in Table 3 herein after.

As shown in Table 3, Compound 55 showed an inhibitory effect on both caspase-3 and -7 activity. However, based on the IC50 values calculated, it was about 200 fold more selective of Caspase-3 over Caspase-7 (see Table 3). No significant inhibitory activity of the compound was observed for caspase-1, -5, and -9 at the tested dose-range. Inhibition of Caspase-1, -5, and -9 was achieved (25%, 21%, and 57% respectively) but at extremely high concentration (about 10,000 nM).

Similar to Compound 55, Compound 63 also showed high selectivity in caspase-3 activity inhibition relative to caspase-1, -5, -7, and -9. Compound 63 also showed an inhibitory effect on caspase-3 and -7, with about a 50 fold selectivity of caspase-3 over caspase-7. No significant inhibitory activity was observed for caspase-1, -5, and -9 at the tested dose-range of Compound 63. The data indicates that both Compound 55 and Compound 63 are highly potent and selective compounds for caspase-3 activity inhibition.

Compound 48 was able to inhibit specific groups of caspases. The compound was able to inhibit caspase-3, -7, and -9 with IC50 values of about 8-30 nM, 0.4-0.9 uM and 1-1.8 uM respectively. Thus Compound 48 shows inhibition of Group III caspases (caspase-3 and -7) with high potency, and inhibition of Group II caspase (caspase-9) with a lower yet significant efficacy.

From the inhibition profile of Compound 57 on caspase-1, -3, -5, -7, and -9 activity, it can be appreciated that Compound 57 is a potent inhibitor of Group III caspases (caspase-3 and -7). Compound 57 inhibited caspase-3 and -7 activities with IC50 values of about 30-90 nM and about 180-300 nM respectively. Therefore, data indicates that Compound 48 and Compound 57 are not specific inhibitors for caspase-3 activity, but are in fact inhibitors targeted at specific groups of caspases.

Compound 88 has a dual inhibition effect on both caspase-1 and caspase-3 activity. It is a potent inhibitor of caspase-3 activity, with an IC50 value of about 30-90 nM. It also inhibits caspase-1 activity with an IC50 value of about 0.6-1.2 uM.

Example 58

In Vitro Inhibitory Activity of Caspase-3 Inhibitors

To test the efficacy of caspase-3 inhibitors at the cellular level, the ability of selected compounds to inhibit the proteolytic cleavage of PARP (poly ADP-ribose polymerase) was evaluated in live Hela cells.

Briefly, in this assay Hela cells are seeded in 96 well plates and incubated for 4 hours with staurosporine, a well characterized inducer of apoptosis, alone or together with different concentrations of compound (50, 25, 10 and 3 uM). After formaldehyde-based fixation, the cells are stained with a fluorescein-labeled anti-cleaved PARP antibody (Cell signaling, Cat#: 9547) and counterstained with Hoechst33342 (Invitrogen, Cat#: H3570) to mark all nuclei. Fluorescence images are taken on a Cellomics™ microscope system (Thermo Scientific, Pittsburgh, USA) with the Hoechst stain in the blue channel and the cleaved PARP antibody stain in the green channel. The percentage of cleaved PARP positive cells is determined by calculating the ratio between nuclei with a cleaved PARP antibody staining above a certain threshold and all (Hoechst positive) nuclei. The efficacy of caspase-3 inhibition is determined by calculating the ratio between cleaved PARP positive cells after staurosporine incubation together with compounds and staurosporine incubation without compounds. Results are summarized in Table 3.

As shown in Table 3, results of this assay show that compounds that inhibited Caspase-3 activity in the enzymatic assay with an IC50 below 100 nM were generally also effective in inhibiting PARP cleavage in vitro, although a major factor contributing to a compound's activity/effectivity in this assay is the compound's cell membrane permeability coefficient (the higher the permeability coefficient, the greater the amount of the compound in the media reaching inside the cell). Certain modifications in the molecular composition of the compounds improved the inhibitory activity

TABLE 3

Activity assays for caspase inhibitors.

| | | Caspase enzymatic activity, IC50 (uM) | | | | | % inhibition of PARP cleavage at 50 uM | % inhibition of PARP cleavage at 50 uM DEVDFMK (positive control) | % of inhibition with compound relative to DEVDFMK | IC50 (uM) Glo3/7 |
|---|---|---|---|---|---|---|---|---|---|---|
| No | Name | Caspase 1 | Caspase 3 | Caspase 5 | Caspase 7 | Caspase 9 | | | | |
| 48 | Z-Asp-Ala(2'-quinolyl)-Val-Asp alpha chlorovinyl methylsulfone | >3.33 | 0.01 | >3.33 | 0.4 | 1.2 | 45 | 70 | 65 | 0.1 |
| 50 | Tosyl-Ala(2'-quinolyl)-Val-Asp alpha chlorovinyl methylsulfone | >3.33 | >3.33 | >3.33 | >3.33 | >3.33 | 0 | 60 | 0 | 40 |
| 36 | Boc-Asp(O-tBu)VSphenyl | >3.33 | >2 | >3.33 | >3.33 | >3.33 | | | | >50 |
| 37 | Asp(O-tBu)VSphenyl salt | >3.33 | >2 | >3.33 | >3.33 | >3.33 | 20 | 60 | 35 | >50 |
| 16 | Z-Asp(O-tBu)-Phg-Val-OH | >3.33 | >2 | >3.33 | >3.33 | >3.33 | 13 | 57 | 23 | >50 |
| 51 | Z-Asp(O-Methyl)-Indanylglycine-Val-Asp(O-Methyl)VSmethyl | >3.0 | 1 | >3.0 | >3.0 | >3.0 | 65 | 80 | 80 | >50 |
| 53 | Z-Asp-Phg-Val-AspVSmethyl | 2 | 0.06 | >10 | 0.8 | >10 | 55 | 70 | 80 | 0.1 |
| 93 | AspVSmethyl salt | >3.33 | >10 | >3.33 | >3.33 | >3.33 | 15 | 60 | 25 | >50 |
| 33 | Asp(O-tBu)VSmethyl salt | >3.33 | >10 | >3.33 | >3.33 | >3.33 | 30 | 60 | 50 | >50 |
| 71 | Z-Asp-d,l Ala(2'-quinolyl)-Val-AspVSmethyl | >10 | 0.1 | >10 | 8.9 | >10 | 20 | 60 | 35 | 0.3 |

TABLE 3-continued

Activity assays for caspase inhibitors.

| Compound | | Caspase enzymatic activity, IC50 (uM) | | | | | % inhibition of PARP cleavage at 50 uM compound | % inhibition of PARP cleavage at 50 uM DEVDFMK (positive control) | % of inhibition with compound relative to DEVDFMK | IC50 (uM) Glo3/7 |
|---|---|---|---|---|---|---|---|---|---|---|
| No | Name | Caspase 1 | Caspase 3 | Caspase 5 | Caspase 7 | Caspase 9 | | | | |
| 55 | Z-Asp-Ala(2'-quinolyl)-Val-AspVSmethyl | >10 | 0.01 | >10 | 1.4 | >3.33 | 40 | 65 | 60 | 0.1 |
| 65 | Z-Asp-Ala(2'-quinolyl)-Val-AspVSphenoxy | 1.2 | 0.01 | >3.33 | 0.4 | 0.3 | 30 | 75 | 40 | 0.2 |
| 70 | Z-Asp-d,l Ala(2'-quinolyl)-Val-AspVSphenyl | >3.33 | 0.3 | >10 | >10 | >10 | | | | 20 |
| 63 | Z-Asp-Ala(2'-quinolyl)-Val-AspVSphenyl | >3.33 | 0.04 | >3.33 | 1.8 | >3.33 | 10 | 70 | 15 | 0.9 |
| 66 | Z-Asp-Ala(2'-quinolyl)-Val-AspVSmorpholine | >3.33 | 0.2 | >3.33 | >3.33 | >3.33 | 25 | 75 | 35 | 1.4 |
| 85 | Z-Asp-Ala(2'-pyridyl)-Val-AspVSphenyl | >3.33 | 0.03 | >3.33 | 1.0 | >3.33 | 40 | 90 | 45 | 0.3 |
| 69 | Z-Asp-Phg-Val-AspVSphenyl | >3.33 | 0.1 | >10 | 1.8 | >3.33 | 20 | 60 | 35 | 1.4 |
| 76 | Z-Asp-Tyr-Val-AspVSmethyl | >3.33 | 0.03 | >3.33 | 0.7 | >3.33 | 55 | 90 | 60 | 0.04 |
| 57 | Z-Asp-Indanylglycine-Val-AspVSmethyl | 0.9 | 0.03 | >3.33 | 0.2 | >3.33 | 65 | 90 | 70 | 0.1 |
| 88 | Z-Asp-Trp-Val-AspVSmethyl | 0.7 | 0.04 | >3.33 | 1.1 | >3.33 | 45 | 90 | 50 | 0.7 |
| 59 | Z-Asp-Glu-Val-AspVSmethyl | 1.4 | 0.02 | >3.33 | 0.04 | 0.5 | 45 | 65 | 70 | 0.09 |
| 61 | Z-Val-AspVSmethyl | >3.33 | >3.33 | >3.33 | >3.33 | >3.33 | 5 | 70 | 5 | 50 |
| 68 | Z-Asp-Indanylglycine-Val-AspVSisopropyl | >3.33 | 0.2 | >3.33 | 1.5 | >3.33 | 30 | 60 | 50 | 1.1 |
| 96 | Z-Tyr-Val-Ala-AspVSphenyl | 1.3 | >10 | >3.33 | >10 | >10 | 1 | 60 | 2 | >50 |
| 82 | Z-Tyr-Glu-Val-AspVSmethyl | 0.5 | 0.3 | >3 | >5 | 1.6 | 15 | 90 | 15 | 3.7 |
| 101 | Z-Asp(β-methyl)-phenylglycine-Val-Asp(β-methyl)methyl vinyl sulfone | >3.33 | >3.33 | >3.33 | >3.33 | >3.33 | 40 | 90 | 45 | 20 |

Values given are approximations of the average values obtained from the assays.

further; for example Compound 51, Compound 53, Compound 57, and Compound 76 reduced the percentage of PARP positive cells after staurosporine treatment by more than 50%, with Compound 51 and Compound 57 being the most effective compounds reaching values of about 65% inhibition, and Compound 53 also being highly effective relative to DEVD-fmk (positive control compound with low caspase-3 selectivity but highly cell membrane permeable with general caspase inhibitory activity), and Compounds 48, 55, and 59 also showing effectivity especially relative to DEVD-fmk. These results indicate that inhibitory compounds identified in a primary enzymatic assay screen retain their activity in a cellular environment and that molecular modifications allow to further improve their activity as caspase-3 inhibitors.

Example 59

Treatment of Neurodegeneration with Compounds

The aim of this study was to verify the effectiveness of compounds in a chronic mouse animal model of EAE. EAE is a good proof-of-principle model of neurodegeneration since it encompasses degeneration or destruction of practically all the cells in the central nervous system, includes most major immunomodulatory components, and is able to maintain normal innate regenerative functions in the animal. This is a standard model (Antel J P et al., J Neurosci Res. 1997, 50: 345-353) used mainly to mimic the course evolution of Multiple Sclerosis (MS) in humans, and is commonly used for studying disease mechanisms and testing potential therapies. EAE is induced by immunization with myelin proteins, leading to development of myelin-specific T cells. These autoreactive T cells traffic into CNS parenchyma where they initiate an inflammatory cascade through recruitment of other cells such as monocytes and neutrophils. Accumulation of immune cells within CNS leads to myelin damage, axonal loss and clinical deficit in affected animals. EAE can be induced in a variety of species and strains of animals [mice, Rat, marmoset monkey, rhesus macaques] using various CNS antigens [Myelin Oligodendrocyte Glycoprotein (MOG), proteolipid protein (PLP) and myelin basic protein (MBP)]. Seven to 8 week old female C57BL/6 mice were purchased from Charles River Laboratories, and housed at MISPRO™ animal facility for one week before experimentation for adaptation to the new environment. All proper animal experimentation and ethics approvals were obtained prior to the start of any experiments. Mice were immunized subcutaneously with 100 μg of $MOG_{35-55}$ (Sheldon Biotechnology Centre, McGill University) in CFA containing 5 mg/ml of desiccated (killed and dried) *Mycobacterium tuberculosis* H37Ra (Difco, Inc), at two sites on the back. The mice were then injected with 200 ng of pertussis toxin (List Biological Laboratories, Inc) in PBS intraperitoneally on days 0 and 2 using 25 gauge needles and scored daily using an EAE clinical scale as detailed below (Touil T et al., J Neurol Sci. 2008, 271:191-202; Antel J P et al., 1997, supra; Owens T et al., Curr Pharm Des. 2005, 1:1031-1037).

EAE was clinically assessed throughout the experiments by daily scoring using a scale from 0 to 5 as follows: partial limp tail, 0.5; full limp tail, 1; limp tail and waddling gait, 1.5; paralysis of one hind limb, 2; paralysis of one hind limb and partial paralysis of other hind limb, 2.5; paralysis of both hind limbs, 3; ascending paralysis, 3.5; paralysis of trunk, 4; moribund, 4.5; death, 5. In all the EAE models a body weight loss is always associated with the clinical signs. This body weight loss is associated with the loss of the function and the paralysis of the muscle (atrophy inducing loss of weight). For animals showing a clinical sign of 2 or more, the food and the water were presented inside the cage to facilitate eating and drinking.

At the onset of clinical signs of EAE, the mice were treated with 200 μl of Compound 51, 53, 57, 59, 101, 104, 105, 111 or 123 dissolved in 2.5% Dimethyl sulfoxide (DMSO) in PBS, while placebo groups were treated with 2.5% Dimethyl sulfoxide (DMSO) in PBS only, by intraperitoneal injection at different time of the clinical evolution. Each group had 7 mice, and the average score of the 7 mice in each group is shown in FIGS. 1-4. Doses used of each compound, and the general results of treatment with each compound are presented in Table 4 and Table 5.

In a study comparing the effects of Compounds 53, 111, and Z-DEVD-FMK in ameliorating disease progression in the EAE model by administration of the compounds for 15 days after the start of clinical symptoms of the disease (see FIG. 4), and comparing these results to the inhibitory activity towards Caspase-1 to -10 in an enzymatic assay (see Example 59 and FIG. 5), some of the mechanisms of these compounds were unveiled. Z-DEVD-FMK delayed the onset and reduced the severity of the disease, especially for the first 10 days of compound treatment after which it started to lose these effects—this seems at least partially to be due to the high inhibitory activity towards the initiator caspases (see Example 59 and FIG. 5) strongly reducing disease progression in the beginning but an inability to sustain this due to lack of inhibitory activity towards the effector caspases. Compound 53, on the other hand, did not reduce the severity of the

TABLE 4

Amount of compound administered to each mouse per day.

| Cpd # | Experiment 1 | | Experiment 2 | | Experiment 3 | | Experiment 4 | |
|---|---|---|---|---|---|---|---|---|
| | mg/mouse/day | mM/mouse/day | mg/mouse/day | mM/mouse/day | mg/mouse/day | mM/mouse/day | mg/mouse/day | mM/mouse/day |
| 51 | 0.279 | 0.000376 | | | | | | |
| 53 | 0.2719 | 0.000403 | 0.2476 | 0.000367 | 0.5444 | 0.000807 | 0.675 | 0.001 |
| 57 | 0.260 | 0.000364 | | | | | | |
| 59 | | | | | 0.201 | 0.0003 | | |
| 101 | | | 0.2499 | 0.000356 | 0.209 | 0.000298 | | |
| 104 | | | 0.2598 | 0.000353 | | | | |
| 105 | | | 0.2731 | 0.000352 | | | | |
| 111 | | | | | 0.2214 | 0.0003 | 0.7388 | 0.001 |
| 123 | | | | | 0.2113 | 0.00029 | | |

TABLE 5

Average overall effects of tested compounds on the EAE model.

| | Delay in onset of the disease | Reduction in severity of the disease | Reduction in body weight loss |
|---|---|---|---|
| Compound 51 | ++ | ++ | +++ |
| Compound 53 | +++ | +++ | +++ |
| Compound 57 | + | + | + |
| Compound 59 | ++ | ++ | ++ |
| Compound 101 | + | + | ++ |
| Compound 104 | ++ | + | − |
| Compound 105 | ++ | + | ++ |
| Compound 111 | + | ++ | ++ |
| Compound 123 | + | ++ | +++ |

+++: high level improvement;
++: moderate improvement;
+: small improvement;
−: no improvement At the end of the study, the mice were sacrificed by $CO_2$ euthanasia. The blood was then recovered by cardiac puncture using 2 ml sterile syringe with needle and the mouse perfused transcardially with 0.1 M PBS (pH 7.4). The spleen and the lymph node (LN) were removed and stored in 10% FBS (fetal bovine serum) RPMI media at 4° C. One third of the spinal cord was removed and saved in Trizol™ (Sigma) to be later analyzed using real-time PCR, while one third of the spinal cord was removed and kept on PBS for cell culture studies. The perfusion was completed by transcardial perfusion with 4% paraformaldehyde solution and the brain and spinal cord were removed and stored in 4% PFA solution for histological analysis.

disease as much as Z-DEVD-FMK in the very beginning (potentially due to lack of initiator caspase inhibitory activity, see Example 59 and FIG. 5), but then began to reverse the effects of the disease and reduced the severity of the disease continuously (even after several days after the end of compound administration) more significantly that Z-DEVD-FMK which must be (at least partially) due to its high inhibitory activity towards effector caspases (Caspase-3 and -7). Compound 111 with its high Caspase-3 inhibitory activity (but no initiator caspase inhibitory activity, see Example 59 and FIG. 5) also did not reduce the severity of the disease as much as Z-DEVD-FMK in the beginning (but also not as much as Compound 53, potentially due to either lacking strong Caspase-7 inhibitory activity like Compound 53 or lacking pro-inflammatory caspase inhibitory activity like compound 53 and Z-DEVD-FMK which most likely slowed down the progression of the disease), but then was able to start reversing the effects of the disease and reduced the severity of the disease for the rest of the period of compound administration. Thus, inhibition of effector caspases, especially Caspase-3, could reverse the progression of a neurodegenerative disease (as well as potentially some other types of degenerative diseases). Loss of body weight in all compound treated groups was less than placebo, especially for compound 53 (see FIG. 4B).

Example 60

Inhibitory Activity of Compounds #53, #111 and #123 and Z-DEVD Towards Caspase-1 to -10

The inhibition of the activity of Caspase-1 to -10 by four different compounds (#53, #111, #123 & Z-DEVD-FMK used as a prodrug: z-D(OMe)E(OMe)VD(OMe)FMK (comparison control compound, SM Biochemicals LLC, Cat# SMFMK003)) and their respective $IC_{50}$ values were determined using a fluorometric enzymatic assay (Active Recombinant Caspase Set IV™ (BioVision, Cat# K233-10-25) and Caspase Fluorometric Substrate Set II Plus (BioVision, Cat# K137-9-25)) on a Flexstation 3™ (Molecular Devices). In brief, each compound was serially diluted for a final test concentration range of 0.1 nM to 3.3 µM (10-point titration). Each active recombinant Caspase (Active Recombinant Caspase Set IV™ (BioVision, Cat# K233-10-25)) was added to the respective wells of the 96-well High Efficiency™ plates (Molecular Devices, Cat#75-000-0005), followed by the addition of the diluted test compounds. DMSO (Final=1%) or Z-VAD-FMK (Caspase-Family Inhibitor, Z-VAD-FMK (BioVision, Cat#1010-100), Final concentration=20 uM) was added in the designated wells as a background control or positive inhibitor control respectively. Each dilution of the test compounds was tested in duplicates, whereas the DMSO or Z-VAD-FMK controls were tested in triplicates. The synthetic peptide substrate specific for each Caspase (BioVision) was then added to the respective wells, which when cleaved by the active caspase releases free AFC that can be quantified by fluorometry. After a 30-minute incubation at 37° C., the plates were read using the Flexstation 3™ with a 400 nm excitation filter and a 505 nm emission filter (cutoff at 495 nm). The inhibition efficiency and the $IC_{50}$ values of the test compounds were then determined by comparing the fluorescence intensity (FI) of the test compounds with that of the DMSO control.

The SoftMax Pro Software™ (v5.2 rev C, Molecular Devices) was used for data analysis. The % Inhibition is calculated by: % Inhibition=[FI(DMSO)–FI(test sample)/FI (DMSO)]×100. The % Inhibition vs. Log(concentration) was plotted, and the curve was fitted using the 5-parameter fit of the software. The $IC_{50}$ values for each compound were then interpolated from the fitted curves and are shown in Table 5.

FIGS. 5A-J demonstrate the inhibition curves of the activity of Caspase-1 through -10 by the 4 tested compounds. The graphs are plotted using GraphPad Prism™ (Prism 5 for Mac OS X™, Version 5.0c).

Compounds #53 and #123 exhibited high inhibitory activity towards the effector (executioner) caspases Caspase-3 and -7, but compound #53 also exhibited inhibitory activity towards the pro-inflammatory caspases Caspase-1 and -4 while compound #123 exhibited inhibitory activity towards the initiator caspases Caspase-9 and -10. Compound #111 exhibited high inhibitory activity only towards Caspase-3. Z-DEVD-FMK exhibited inhibitory activity towards the pro-inflammatory caspases Caspase-1 and -4 as well as the initiator caspases Caspase-8, -9 and -10.

Compound #53 inhibits Caspase-3 and -7 with $IC_{50}$ values of 0.09 µM and 0.8 µM respectively. It inhibits Caspase-1 and -4 activity to a lesser extent ($IC_{50}$=2.1 µM and 2.8 µM). It shows much less inhibition towards the other caspases.

Compound #111 inhibits Caspase-3 activity similarly to that of #53, with an $IC_{50}$ value of 0.08 µM. However, its effect on all other caspases is negligible ($IC_{50}$>3.33 µM).

Compound #123 inhibits Caspase-3 activity similarly to the two compounds above (#53 and #111), with an $IC_{50}$ of 0.06 µM. It inhibits Caspase-7 activity with an $IC_{50}$ value of 0.5 µM. Weak inhibition towards Caspase-9 and -10 is also observed ($IC_{50}$=2.8 µM and 2.0 µM respectively). Much less inhibition is observed towards the other caspases tested.

Z-DEVD shows a stronger inhibition for Caspase-1, -8 and -9 compared to the other test compounds, with $IC_{50}$ values of 0.7 µM, 1.6 µM and 0.6 µM respectively. In comparison, it shows less inhibition towards Caspase-3 and -7 ($IC_{50}$>3.33 µM). Its effect on Caspase-4 and -10 is weak ($IC_{50}$=2.5 µM and 2.7 µM) and is negligible for Caspase-2, -5 and -6.

Inhibitory activity towards Caspase-2, -5 and -6 was negligible for all four compounds. It should be noted that when comparing the results between this experiment and previous examples, there are small discrepancies in the $IC_{50}$ values for some caspases (e.g. Caspase-3 and -7). The supplier of the kits (BioVision) claims that both sets of data are valid since the Z-VAD-FMK (positive inhibitor control) showed >50% inhibition for all experiments. Therefore the difference in results is due to the variation in the sensitivity of the kits from lot to lot. For this experiment, all 10 active caspases and their substrates were from the same lot; therefore the results are comparable between each other for all 10 caspases.

TABLE 5

$IC_{50}$ values (µM) of the four compounds tested (#53, #111, #123 and Z-DEVD-FMK as a prodrug: z-D(OMe)E(OMe)VD(OMe)FMK) for inhibition of Caspase-1 through -10.

| | $IC_{50}$ values (µM) of the compounds tested | | | |
|---|---|---|---|---|
| | #53 | #111 | #123 | Z-DEVD |
| Caspase-1 | 2.1 | >3.33 | >3.33 | 0.7 |
| Caspase-2 | >3.33 | >3.33 | >3.33 | >3.33 |
| Caspase-3 | 0.09 | 0.08 | 0.06 | >3.33 |
| Caspase-4 | 2.8 | >3.33 | >3.33 | 2.5 |
| Caspase-5 | >3.33 | >3.33 | >3.33 | >3.33 |
| Caspase-6 | >3.33 | >3.33 | >3.33 | >3.33 |
| Caspase-7 | 0.8 | >3.33 | 0.5 | >3.33 |
| Caspase-8 | >3.33 | >3.33 | >3.33 | 1.6 |
| Caspase-9 | >3.33 | >3.33 | 2.8 | 0.6 |
| Caspase-10 | >3.33 | >3.33 | 2.0 | 2.7 |

As shown in Table 5, Compounds #53 and #123 exhibited high inhibitory activity towards the effector (executioner) caspases Caspase-3 and -7, but compound #53 also exhibited inhibitory activity towards the pro-inflammatory caspases Caspase-1 and -4 while compound #123 exhibited inhibitory activity towards the initiator caspases Caspase-9 and -10. Compound #111 exhibited high inhibitory activity only towards Caspase-3. Z-DEVD-FMK exhibited inhibitory activity towards the pro-inflammatory caspases Caspase-1 and -4 as well as the initiator caspases Caspase-8, -9 and -10.

Headings are included herein for reference and to aid in locating certain sections. These headings are not intended to limit the scope of the concepts described therein under, and these concepts may be applicable in other sections throughout the entire specification. Thus, the present invention is not intended to be limited to the embodiments shown herein but is to be accorded the widest scope consistent with the principles and novel features disclosed herein.

As used herein and in the appended claims, the singular forms "a", "an", and "the" include plural referents unless the context clearly indicates otherwise. Thus, for example, reference to "a compound" includes one or more of such compounds, and reference to "the method" includes reference to equivalent steps and methods known to those of ordinary skill in the art that could be modified or substituted for the methods described herein.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

We claim:

1. A compound according to Formula I:

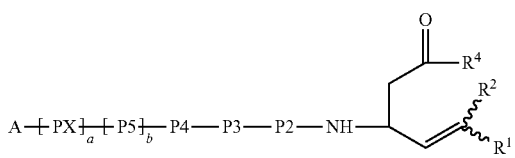

I wherein a is 0 or 1;
wherein b is 0 or 1 provided that when b is 0, a is 0;
wherein A is selected from the group consisting of H, $C_1$-$C_6$ alkyl, aryl, heteroaryl, heterocyclyl, $R^3$—OC(O)—, $R^3$—$CH_2OC(O)$—, and $R^3$—$S(O)_2$—;
wherein P2, P3, P4, and, when present, P5 and PX are each independently any (D) or (L) natural or non-natural amino acid residue;
wherein the line "-" when located between P2, P3, P4, P5, or PX represents a peptide bond or a peptidomimetic bond selected from the group consisting of $CH_2$—NH, CO—$CH_2$, azapeptide, and retro-inverso bonds;
wherein the wavy line represents either cis or trans orientation of $R^1$ and $R^2$;
wherein $R^1$ is selected from the group consisting of aryl, heteroaryl, heterocyclyl, $C_2$-$C_6$ alkene-$R^{20}$, $SO_2R^5$, $SO_3R^5$, $SOR^5$, $SONHR^5$, $SO_2NHR^5$, CN, $CO_2R^5$, $COR^5$, $PO_3R^5$, $PO(OR^5)_2$, and $PO(OR^5)$, in which the aryl, heteroaryl, or heterocyclyl is optionally substituted with one or more $R^{30}$;
wherein $R^2$ is selected from the group consisting of $R^1$, H, halogen, haloalkyl, $C_1$-$C_6$ alkyl, $C_2$-$C_6$ alkene, $C_3$-$C_7$ cycloalkyl, $OR^9$, $SR^9$, $N^+(R^4)_3$, $OCOR^6$, $OCO_2R^6$, $NR^7R^8$, $NHSO_2R^6$, $NHCOR^6$, aryl, heteroaryl, and heterocyclyl;
wherein $R^3$ is selected from the group consisting of $C_1$-$C_6$ alkyl, aryl-$C_1$-$C_6$ alkyl, heteroaryl, and heterocyclyl;
wherein each $R^4$ is independently selected from the group consisting of OH and $OC_1$-$C_6$ alkyl;
wherein each $R^5$ is independently selected from the group consisting of H, $C_1$-$C_6$ alkyl, $C_2$-$C_6$ alkene, $C_3$-$C_7$ cycloalkyl, haloalkyl, aryl, heteroaryl, heterocyclyl, $NHCH_2C(O)OH$, and (D) or (L) natural or non-natural amino acid optionally protected with an amino acid protecting group;
wherein each $R^6$ is independently selected from the group consisting of any (D) or (L) amino acid residue, $C_1$-$C_6$ alkyl, $C_3$-$C_7$ cycloalkyl, aryl, heteroaryl, and heterocyclyl, in which the alkyl or cycloalkyl is optionally substituted with one or more $R^{10}$ substituents, and in which the aryl, heteroaryl, or heterocyclyl is optionally substituted with one or more $R^{20}$ substituents;
wherein $R^7$ and $R^8$ are independently selected from the group consisting of H, $C_1$-$C_6$ alkyl, $C_3$-$C_7$ cycloalkyl, haloalkyl, aryl, heteroaryl, and heterocyclyl, in which the alkyl or cycloalkyl is optionally substituted with one or more $R^{10}$ substituents, and in which the aryl, heteroaryl, or heterocyclyl is optionally substituted with one or more $R^{20}$ substituents;
wherein $R^9$ is selected from the group consisting of H, $C_1$-$C_6$ alkyl, $C_3$-$C_7$ cycloalkyl, aryl, heteroaryl, and heterocyclyl, in which the alkyl or cycloalkyl is optionally substituted with one or more $R^{10}$ substituents, and in which the aryl, heteroaryl, or heterocyclyl is optionally substituted with one or more $R^{20}$ substituents;
wherein each $R^{10}$ is independently selected from the group consisting of halogen, $C_1$-$C_6$ alkyl, $C_3$-$C_7$ cycloalkyl, haloalkyl, aryl, heteroaryl, heterocyclyl, $OR^9$, $S(O)_mR^9$, $NR^7R^8$, $COR^9$, $C(O)OR^9$, $OC(O)R^9$, $SC(O)R^9$, $CONR^7R^8$, and $S(O)_2NR^7R^8$, wherein m is an integer of 0, 1, or 2;
wherein each $R^{20}$ is independently selected from the group consisting of halogen, $NO_2$, CN, $C_1$-$C_6$ alkyl, haloalkyl, $C_3$-$C_7$ cycloalkyl, $OR^7$, $NR^7R^8$, $SR^7$, aryl, heteroaryl, heterocyclyl, $SO_2R^5$, $SO_3R^5$, $SOR^5$, $SONHR^5$, $SO_2NHR^5$, $PO_3R^5$, $PO(OR^5)_2$, $PO(OR^5)$, $COR^5$, $COR^7$, $CO_2R^7$, $S(O)_mR^7$, $CONR^7R^8$, $S(O)_2NR^7R^8$, in which the alkyl or cycloalkyl is optionally substituted with one or more $R^6$ substituents, and in which the aryl, heteroaryl, or heterocyclyl is optionally substituted with one or more $R^{30}$, wherein m is an integer of 0, 1, or 2; and
wherein each $R^{30}$ is independently selected from the group consisting of $NO_2$, $C_2$-$C_6$ alkene-$R^{20}$, $SO_2R^5$, $SOR^5$, $SONHR^5$, $SO_2NHR^5$, CN, $CO_2R^5$, $COR^5$, $PO_3R^5$, $PO(OR^5)_2$, and $PO(OR^5)$;
or a pharmaceutically acceptable salt or ester thereof, or the compound is labeled with a detectable label or an affinity tag thereof, or combinations thereof wherein the compound is not one of the following compounds:

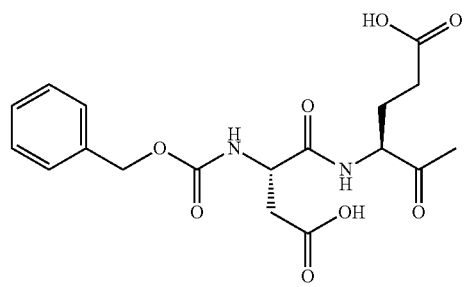

-continued
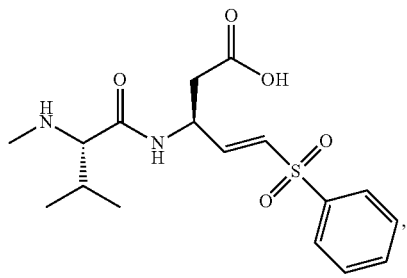
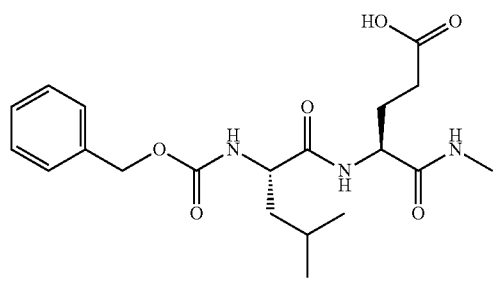
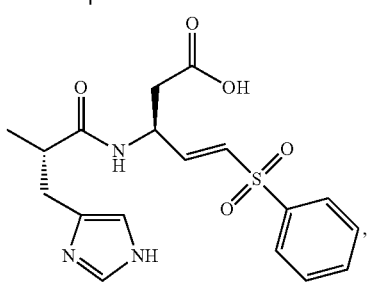
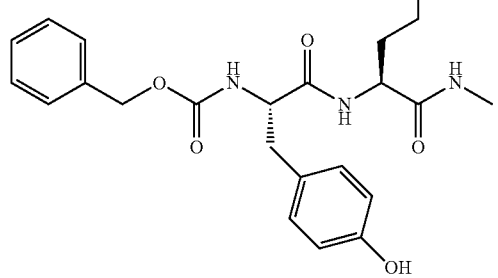
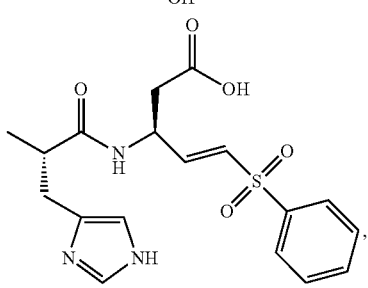
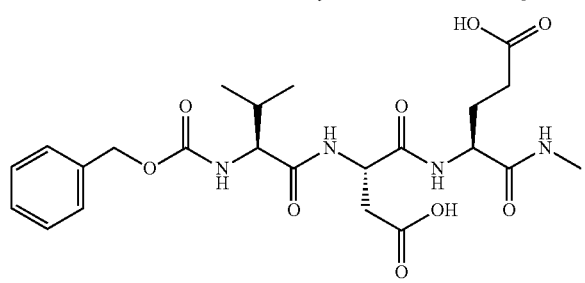

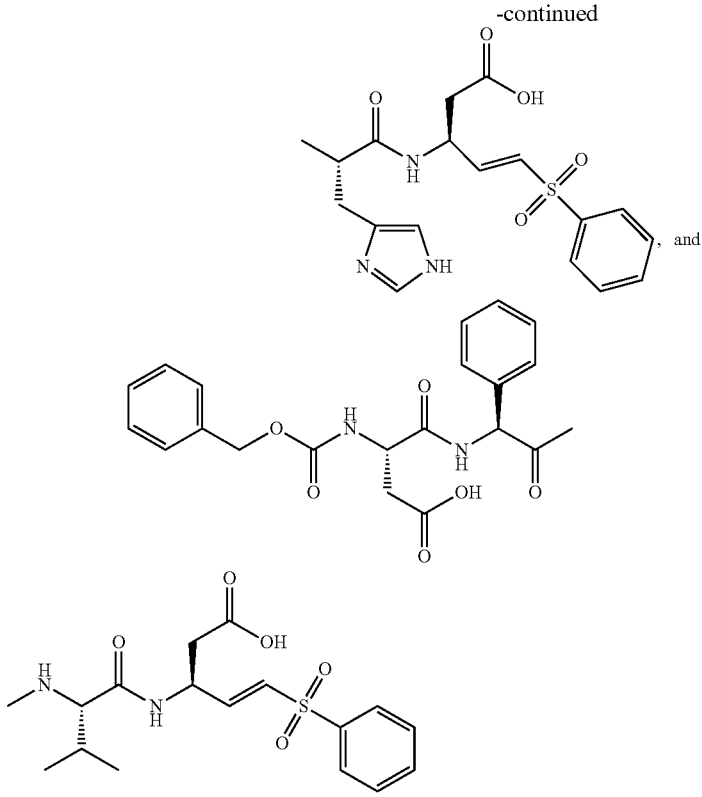
, and

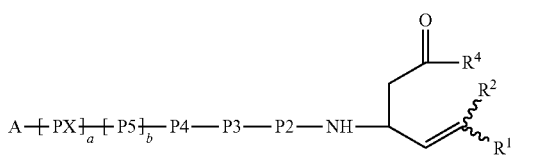

2. The compound of claim 1, wherein $R^1$ is selected from the group consisting of $SO_2R^5$, $SO_3R^5$, and $SOR^5$, and wherein $R^5$ is selected from the group consisting of $C_1$-$C_6$ alkyl, aryl, and heterocyclyl.

3. The compound of claim 1, wherein $R^2$ is selected from the group consisting of H, halogen, haloalkyl, $C_1$-$C_6$ alkyl, and $C_3$-$C_7$ cycloalkyl.

4. A compound according to Formula I:

$$A\text{---}(PX)_a\text{---}(P5)_b\text{---}P4\text{---}P3\text{---}P2\text{---}NH\text{---}\underset{R^1}{\overset{R^2}{\diagdown}}$$

I wherein a is 0 or 1;
wherein b is 0 or 1 provided that when b is 0, a is 0;
wherein A is selected from the group consisting of H, $C_1$-$C_6$ alkyl, aryl, heteroaryl, heterocyclyl, $R^3$—OC(O)—, $R^3$—CH$_2$OC(O)—, and $R^3$—S(O)$_2$—;
wherein P2, P3, P4, and, when present, P5 and PX are each independently any (D) or (L) natural or non-natural amino acid residue;
wherein the line "-" when located between P2, P3, P4, P5, or PX represents a peptide bond or a peptidomimetic bond selected from the group consisting of CH$_2$—NH, CO—CH$_2$, azapeptide, and retro-inverso bonds;
wherein the wavy line represents either cis or trans orientation of $R^1$ and $R^2$;

wherein $R^1$ is selected from the group consisting of aryl, heteroaryl, heterocyclyl, $C_2$-$C_6$ alkene-$R^{20}$, $SO_2R^5$, $SO_3R^5$, $SOR^5$, $SONHR^5$, $SO_2NHR^5$, CN, $CO_2R^5$, $COR^5$, $PO_3R^5$, $PO(OR^5)_2$, and $PO(OR^5)$, in which the aryl, heteroaryl, or heterocyclyl is optionally substituted with one or more $R^{30}$;

wherein $R^2$ is selected from the group consisting of $R^1$, H, halogen, haloalkyl, $C_1$-$C_6$ alkyl, $C_2$-$C_6$ alkene, $C_3$-$C_7$ cycloalkyl, $OR^9$, $SR^9$, $N^+(R^4)_3$, $OCOR^6$, $OCO_2R^6$, $NR^7R^8$, $NHSO_2R^6$, $NHCOR^6$, aryl, heteroaryl, and heterocyclyl;

wherein $R^3$ is selected from the group consisting of $C_1$-$C_6$ alkyl, aryl-$C_1$-$C_6$ alkyl, heteroaryl, and heterocyclyl;

wherein each $R^4$ is independently selected from the group consisting of OH and $OC_1$-$C_6$ alkyl;

wherein each $R^5$ is independently selected from the group consisting of H, $C_1$-$C_6$ alkyl, $C_2$-$C_6$ alkene, $C_3$-$C_7$ cycloalkyl, haloalkyl, aryl, heteroaryl, heterocyclyl, NHCH$_2$C(O)OH, and (D) or (L) natural or non-natural amino acid optionally protected with an amino acid protecting group;

wherein each $R^6$ is independently selected from the group consisting of any (D) or (L) amino acid residue, $C_1$-$C_6$ alkyl, $C_3$-$C_7$ cycloalkyl, aryl, heteroaryl, and heterocyclyl, in which the alkyl or cycloalkyl is optionally substituted with one or more $R^{10}$ substituents, and in which the aryl, heteroaryl, or heterocyclyl is optionally substituted with one or more $R^{20}$ substituents;

wherein $R^7$ and $R^8$ are independently selected from the group consisting of $C_1$-$C_6$ alkyl, $C_3$-$C_7$ cycloalkyl, haloalkyl, aryl, heteroaryl, and heterocyclyl, in which the alkyl or cycloalkyl is optionally substituted with one or more $R^{10}$ substituents, and in which the aryl, heteroaryl, or heterocyclyl is optionally substituted with one or more $R^{20}$ substituents;

wherein $R^9$ is selected from the group consisting of H, $C_1$-$C_6$ alkyl, $C_3$-$C_7$ cycloalkyl, aryl, heteroaryl, and heterocyclyl, in which the alkyl or cycloalkyl is optionally substituted with one or more $R^{10}$ substituents, and in which the aryl, heteroaryl, or heterocyclyl is optionally substituted with one or more $R^{20}$ substituents;

wherein each $R^{10}$ is independently selected from the group consisting of halogen, $C_1$-$C_6$ alkyl, $C_3$-$C_7$ cycloalkyl, haloalkyl, aryl, heteroaryl, heterocyclyl, $OR^9$, $S(O)_mR^9$, $NR^7R^8$, —$COR^9$, $C(O)OR^9$, $OC(O)R^9$, $SC(O)R^9$, $CONR^7R^8$, and $S(O)_2NR^7R^8$, wherein m is an integer of 0, 1, or 2;

wherein each $R^{20}$ is independently selected from the group consisting of halogen, $NO_2$, CN, $C_1$-$C_6$ alkyl, haloalkyl, $C_3$-$C_7$ cycloalkyl, $OR^7$, $NR^7R^8$, $SR^7$, aryl, heteroaryl, heterocyclyl, $SO_2R^5$, $SO_3R^5$, $SOR^5$, $SONHR^5$, $SO_2NHR^5$, $PO_3R^5$, $PO(OR^5)_2$, $PO(OR^5)$, $COR^5$, $COR^7$, $CO_2R^7$, $S(O)_mR^7$, $CONR^7R^8$, $S(O)_2NR^7R^8$, in which the alkyl or cycloalkyl is optionally substituted with one or more $R^6$ substituents, and in which the aryl, heteroaryl, or heterocyclyl is optionally substituted with one or more $R^{30}$, wherein m is an integer of 0, 1, or 2; and wherein each $R^{30}$ is independently selected from the group consisting of $NO_2$, $C_2$-$C_6$ alkene-$R^{20}$, $SO_2R^5$, $SOR^5$, $SONHR^5$, $SO_2NHR^5$, CN, $CO_2R^5$, $COR^5$, $PO_3R^5$, $PO(OR^5)_2$, and $PO(OR^5)$;

or a pharmaceutically acceptable salt or ester thereof, or the compound is labeled with a detectable label or an affinity tag thereof, or any combinations thereof; and wherein the compound is not one of the following compounds

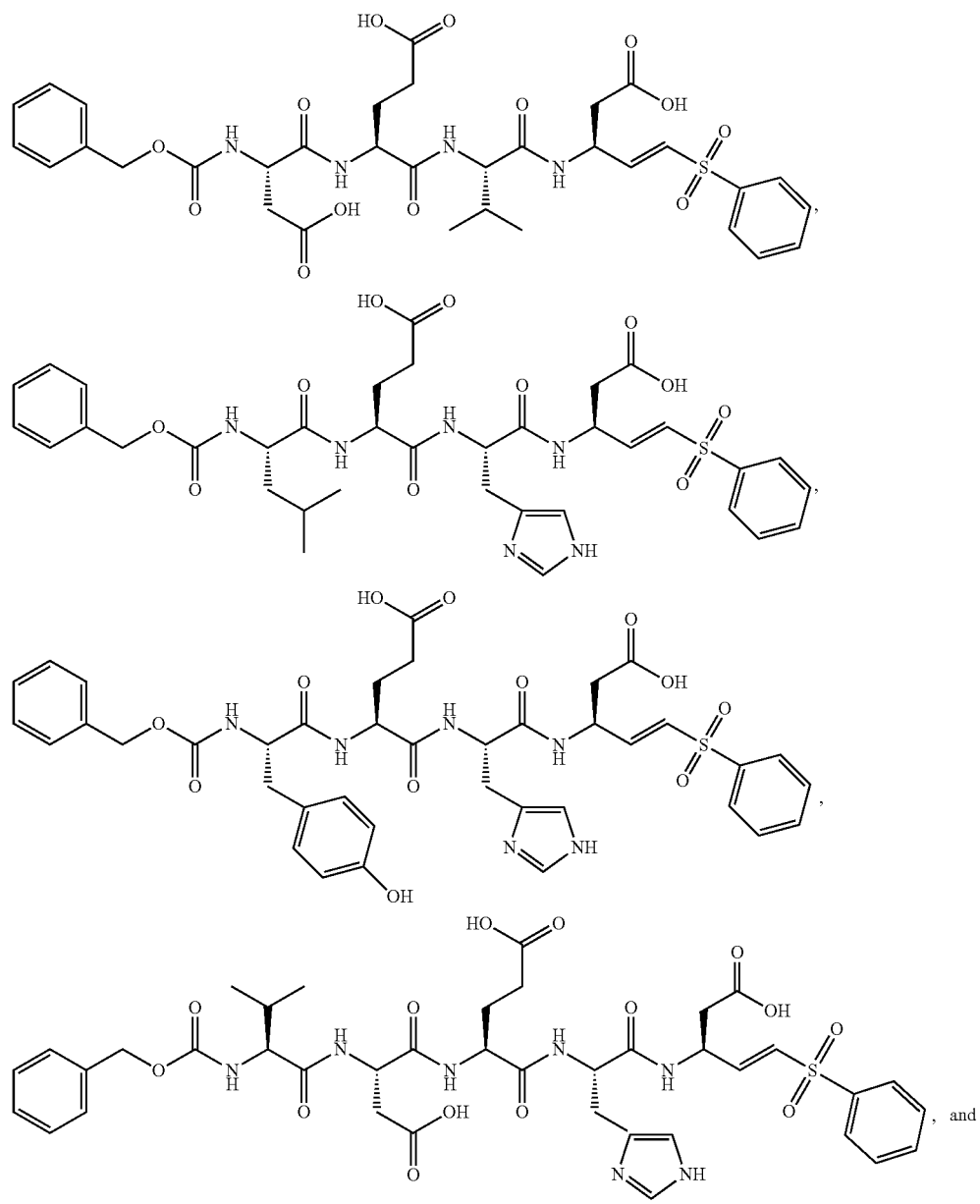

-continued
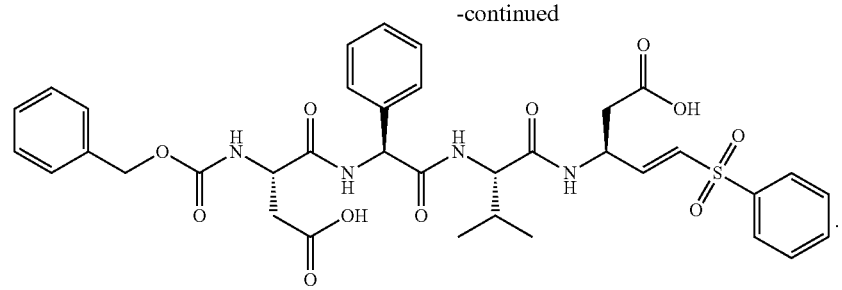
* * * * *